US012697308B2

(12) United States Patent
Bett et al.

(10) Patent No.: US 12,697,308 B2
(45) Date of Patent: Aug. 4, 2026

(54) THERMOSTABLE LIPID NANOPARTICLE AND METHODS OF USE THEREOF

(71) Applicant: Merck Sharp & Dohme LLC, Rahway, NJ (US)

(72) Inventors: Andrew Bett, Lansdale, PA (US); Izzat T. Raheem, Doylestown, PA (US); Jason W. Skudlarek, Abdubon, PA (US)

(73) Assignee: Merck Sharp & Dohme LLC, Rahway, NJ (US)

(*) Notice: Subject to any disclaimer, the term of this patent is extended or adjusted under 35 U.S.C. 154(b) by 860 days.

(21) Appl. No.: 17/820,417

(22) Filed: Aug. 17, 2022

(65) Prior Publication Data

US 2023/0118665 A1 Apr. 20, 2023

Related U.S. Application Data

(60) Provisional application No. 63/235,014, filed on Aug. 19, 2021.

(51) Int. Cl.

| | |
|---|---|
| ***A61K 9/51*** | (2006.01) |
| ***A61K 39/00*** | (2006.01) |
| ***A61K 39/12*** | (2006.01) |
| ***A61K 39/39*** | (2006.01) |
| ***A61P 31/20*** | (2006.01) |
| ***A61P 37/04*** | (2006.01) |
| ***C08G 65/333*** | (2006.01) |
| ***C12N 7/00*** | (2006.01) |

(52) U.S. Cl.

CPC .......... *A61K 9/5123* (2013.01); *A61K 9/5146* (2013.01); *A61K 39/12* (2013.01); *A61K 39/39* (2013.01); *A61P 31/20* (2018.01); *A61P 37/04* (2018.01); *C08G 65/33396* (2013.01); *C12N 7/00* (2013.01); *A61K 2039/5258* (2013.01); *A61K 2039/545* (2013.01); *A61K 2039/55555* (2013.01); *C12N 2710/20023* (2013.01); *C12N 2710/20034* (2013.01); *C12N 2710/20071* (2013.01)

(58) Field of Classification Search

None

See application file for complete search history.

(56) References Cited

U.S. PATENT DOCUMENTS

| | | | |
|---|---|---|---|
| 5,208,036 | A | 5/1993 | Eppstein et al. |
| 5,264,618 | A | 11/1993 | Felgner et al. |
| 5,279,833 | A | 1/1994 | Rose |
| 5,283,185 | A | 2/1994 | Epand et al. |
| 5,437,951 | A | 8/1995 | Lowy et al. |
| 5,820,870 | A | 10/1998 | Joyce et al. |
| 6,599,508 | B1 | 7/2003 | Gissmann et al. |
| 6,890,557 | B2 | 5/2005 | Huang et al. |
| 7,250,170 | B2 | 7/2007 | Bryan et al. |
| 7,276,243 | B2 | 10/2007 | Jansen et al. |
| 7,482,428 | B2 | 1/2009 | Jansen et al. |
| 7,498,036 | B2 | 3/2009 | Bryan et al. |
| 7,700,103 | B2 | 4/2010 | Bryan et al. |
| 7,744,892 | B2 | 6/2010 | Bryan et al. |
| 7,976,848 | B2 | 7/2011 | Bryan et al. |
| 8,952,955 | B2 | 2/2015 | Yokoyama et al. |
| 9,669,097 | B2 | 6/2017 | Stanton et al. |
| 2006/0240554 | A1 | 10/2006 | Chen et al. |
| 2008/0020058 | A1 | 1/2008 | Chen et al. |
| 2008/0057080 | A1 | 3/2008 | Luke et al. |
| 2008/0085870 | A1 | 4/2008 | Hermanson et al. |
| 2008/0248062 | A1* | 10/2008 | Bryan ..................... A61P 31/12 424/204.1 |
| 2009/0263407 | A1 | 10/2009 | Dande et al. |
| 2009/0285881 | A1 | 11/2009 | Dande et al. |
| 2010/0055168 | A1 | 3/2010 | Dande et al. |
| 2010/0055169 | A1 | 3/2010 | Dande et al. |
| 2010/0063135 | A1 | 3/2010 | Dande et al. |
| 2010/0076055 | A1 | 3/2010 | Dande et al. |
| 2010/0099738 | A1 | 4/2010 | Hansen et al. |
| 2010/0104629 | A1 | 4/2010 | Dande et al. |
| 2013/0017239 | A1 | 1/2013 | Petit et al. |
| 2016/0361411 | A1 | 12/2016 | Gindy et al. |
| 2018/0296662 | A1* | 10/2018 | Ciaramella ............. A61P 31/14 |

FOREIGN PATENT DOCUMENTS

| | | | |
|---|---|---|---|
| WO | 2006114312 | A2 | 11/2006 |
| WO | 2007068907 | A2 | 6/2007 |
| WO | 2009132131 | A1 | 10/2009 |
| WO | 2010/021865 | A1 | 2/2010 |

(Continued)

OTHER PUBLICATIONS

Baylor, N. W., Aluminum salts in vaccines—US perspective, Vaccine, 2002, S18-S23, 20.

Bryan, Janine T., Developing an HPV vaccine to prevent cervical cancer and genital warts, Vaccine, 2007, 3001-3006, 25.

Chan, Chee Kai et al., Human Papillomavirus Infection and Cervical Cancer: Epidemiology, Screening, and Vaccination-Review of Current Perspectives, Journal of Oncology, 2019, 1-11, Article ID 3257939.

Harper, Diane M. et al., Efficacy of a bivalent L1 virus-like particle vaccine in prevention of infection with human papillomavirus types 16 and 18 in young women: a randomised controlled trial, Lancet, 2004, 1757-1765, 364.

(Continued)

*Primary Examiner* — Bethany P Barham
*Assistant Examiner* — Peter Anthopolos
(74) *Attorney, Agent, or Firm* — Matthew A. Leff; Emily K. Sauter

(57) ABSTRACT

The present disclosure provides, among other things, a lipid nanoparticle adjuvant composition. The present disclosure provides pharmaceutical compositions that include a stable lipid nanoparticle adjuvant and human papillomavirus (HPV) virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82.

2 Claims, 47 Drawing Sheets

(56) References Cited

FOREIGN PATENT DOCUMENTS

| | | | | |
|---|---|---|---|---|
| WO | 2010042877 A1 | | 4/2010 | |
| WO | 2010105209 A1 | | 9/2010 | |
| WO | 2010146740 A1 | | 12/2010 | |
| WO | 2011022460 A1 | | 2/2011 | |
| WO | 2011076807 A2 | | 6/2011 | |
| WO | WO-2012040184 A2 | * | 3/2012 | A61P 43/00 |
| WO | 2015094928 A1 | | 6/2015 | |
| WO | 2015130584 A2 | | 9/2015 | |
| WO | 2021163002 A1 | | 8/2021 | |

OTHER PUBLICATIONS

Kirii, Yasuyuki, et al., Human Papillomavirus Type 58 DNA Sequence, Virology, 1991, 424-427, 185.

Klein, J. et al., Analysis of Aluminum Hydroxyphosphate Vaccine Adjuvants by 27 A1 MAS NMR, Journal of Pharmaceutical Sciences, 2000, 311-21, 89(3).

Li, Zhihai et al., Rational design of a triple-type human papillomavirus vaccine by compromising viral-type specificity, Nature, 2018, 1-15, 9:5360.

McMurray, H.R. et al., Viruses and Cancer—Biology of human papillomaviruses, Int. J. Exp. Pathol., 2001, 15-33, 82(1).

Nygård, Mari et al., Evaluation of the Long-Term Anti-Human Papillomavirus 6 (HPV6), 11, 16, and 18 Immune Responses Generated by the Quadrivalent HPV Vaccine, Clinical and Vaccine Immunology, 2015, 943-948, 22(8).

Schiller, John T. et al., Developing HPV virus-like particle vaccines to prevent cervical cancer: a progress report, Journal of Clinical Virology, 2000, 67-74, 19.

Shi, L. et al., Gardasil: Prophylactic Human Papillomavirus Vaccine Development—From Bench Top to Bed-side, Clinical Pharmacology and Therapeutics, 2007, 259-264, 81(2).

Villa, Luisa L. et al., Immunologic responses following administration of a vaccine targeting human papillomavirus Types 6, 11, 16, and 18, Vaccine, 2006, 5571-5583, 24.

* cited by examiner

Freshly field mixed

Imaged after 7.5 months of storage at 2-8C

Freshly field mixed

Imaged after 6 months at 25C and 1.5 months 2-8C

THERMOSTABLE LIPID NANOPARTICLE AND METHODS OF USE THEREOF

CROSS-REFERENCE TO RELATED APPLICATIONS

This application claims the benefit of U.S. Provisional Application No. 63/235,014, filed Aug. 19, 2021, the contents of which are hereby incorporated by reference in their entirety.

FIELD OF THE INVENTION

The invention relates generally to the prevention of human papillomavirus (HPV) infection. More specifically, the invention relates to pharmaceutical compositions and formulations comprising virus-like particles (VLPs) of HPV and an LNP adjuvant, which can be administered as a single-dose vaccine. The present disclosure provides, among other things, a single-dose vaccine composition that includes an LNP adjuvant and an HPV vaccine, where a single administration of the vaccine composition provides a comparable or enhanced immune response in comparison to multiple administrations of the same HPV vaccine formulated without an LNP adjuvant. Further provided are methods of using the disclosed compositions and formulations.

BACKGROUND

Human papillomaviruses (HPVs) are small, double-stranded DNA viruses that infect the skin and internal squamous mucosal epithelia of men and women. HPVs are classified based on their carcinogenic properties. HPVs include major (L1) and minor (L2) capsid proteins. Over 200 distinct HPV genotypes have been identified (Li et al., "Rational design of a triple-type human papillomavirus vaccine by compromising viral-type specificity," Nature, 9:5360 (2018)), many of which have been associated with pathologies ranging from benign proliferative warts to malignant carcinomas of the cervix (for review, see McMurray et al., Int. J. Exp. Pathol. 82(1): 15-33 (2001)). Those labeled as "high-risk" include HPV types 16, 18, 31, 33, 35, 39, 45, 51, 52, 56, 58, 68, and 59. (Chan et al., "Human Papillomavirus Infection and Cervical Cancer: Epidemiology, Screening, and Vaccination-Review of Current Perspectives," Journal of Oncology, vol. 2019, Article ID 3257939, 11 pages, 2019.)

HPV is the primary etiological agent in cervical cancer, one of the most common cancer in women, as well as squamous cell carcinomas of the anus, tonsil, tongue, vulva, vagina, and penis. HPV16 and HPV18 are well known as the most virulent of the high-risk HPV types as they cause approximately 70% of all invasive cervical cancer in the world.

Papillomaviruses are small (50-60 mm diameter), nonenveloped, icosahedral DNA viruses that encode early (E1-E7) and late (L1-L2) genes. The L1 protein is the major capsid protein and has a molecular weight of 55-60 kDa. Expression of the L1 protein or a combination of the L1 and L2 proteins in yeast, insect cells, mammalian cells or bacteria leads to self-assembly of virus-like particles (VLPs) (for review, see Schiller and Roden, in Papillomavirus Reviews: Current Research on Papillomaviruses; Lacey, ed. Leeds, UK: Leeds Medical Information, pp 101-12 (1996)).

VLPs are morphologically similar to authentic virions and are capable of inducing high titers of neutralizing antibodies upon administration into animals or humans. Because VLPs do not contain the potentially oncogenic viral genome, they present a safe alternative to the use of live virus in HPV vaccine development (for review, see Schiller and Hidesheim, J Clin. Virol. 19: 67-74 (2000)). For this reason, the L1 and L2 genes have been identified as immunological targets for the development of prophylactic and therapeutic vaccines for HPV infection and disease.

VLP-based vaccines have proven to be effective at inducing immune responses in human patients vaccinated with bivalent HPV 16 and 18 VLP-based vaccines (Harper et al. Lancet 364(9447): 1757-65 (2004)), quadrivalent HPV 6, 11, 16, and 18 VLP-based vaccines (Villa et al. Vaccine 24: 5571-5583 (2006)) and multi-valent HPV 6, 11, 16, 18, 31, 33, 45, 52 and 58 VLP-based vaccines. Three approved VLP-based vaccines against HPV are administered according to 2 or 3 dose regimens. CERVARIX® (GlaxoSmithKline Biologics, Rixensart, Belgium) is a bivalent vaccine protective against HPV 16 and 18. GARDASIL® and GARDASIL®9 (Merck & Co., Inc., Rahway, NJ, USA) protect against two and seven additional HPV types, respectively, and prevent additional HPV-related anogenital diseases, including wart formation. The additional five high risk strains in GARDASIL®9 over GARDASIL® increase protection against from about 70% to about 90% of anogenital malignancies. (Id., M. Nygard, et al., "Evaluation of the long-term anti-human papillomavirus 6 (HPV6), 11, 16, and 18 immune responses generated by the quadrivalent HPV vaccine," Clinical and Vaccine Immunology, vol. 22, no. 8, pp. 943-948, 2015.)

Though improving, worldwide HPV vaccination rates remain suboptimal. The worldwide coverage of HPV vaccination rates can be improved by reducing the number of healthcare practitioner visits required for the vaccination, increasing education on HPV disease prophylaxis, and alleviating the social stigma associated with vaccination. The proportion of adolescents in the Americas and in Europe completing a two dose vaccination series is estimated to be under 50%. Accordingly, it is desirable to improve HPV vaccination rates by generating improved vaccines that can generate immunity against HPV through a single administration that provides a comparable immune response to existing HPV vaccines that require 2 or more doses. Further, there is a need for thermostable single dose vaccine formulations to assist in the distribution of the vaccine while providing comparable immune response to existing HPV vaccines that require 2 or more doses.

There is a need for an HPV vaccine that can be administered as a single injection and provide comparable or enhanced initial anti-HPV immune response when compared to the standard multi-dose HPV vaccine.

SUMMARY

The present invention provides a PEG-lipid having the structure set forth in Formula I:

(I)

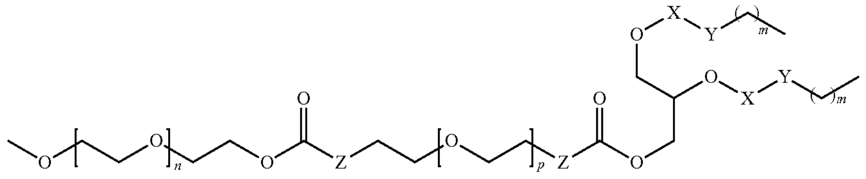

wherein, each m is independently from 5-20; n is from 20-60; p is 0, 1, or 2; each X is independently $CH_2$, CHR, $CR_2$, or C═O; each Y is independently $CH_2$, CHR, $CR_2$, or NH; each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl.

The present invention also provides a lipid nanoparticle comprising: a PEG-lipid having the structure set forth in Formula I:

(I)

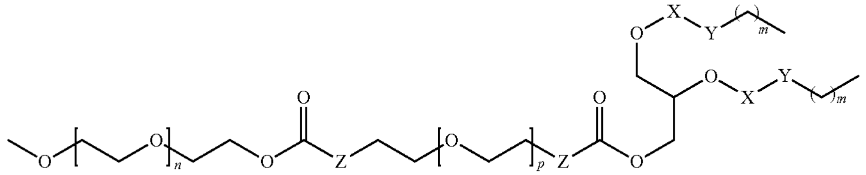

wherein, each m is independently from 5-20; n is from 20-60; p is 0, 1, or 2; each X is independently $CH_2$, CHR, $CR_2$, or C═O; each Y is independently $CH_2$, CHR, $CR_2$, or NH; each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and a phospholipid.

The present invention also provides a pharmaceutical composition comprising:

virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 69, 70, 73, and 82, a PEG-lipid having the structure set forth in Formula I:

(I)

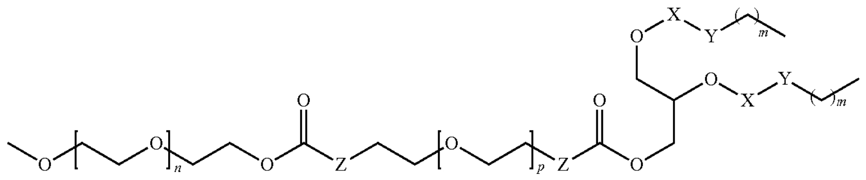

wherein, each m is independently from 5-20; n is from 20-60; p is 0, 1, or 2; each X is independently $CH_2$, CHR, $CR_2$, or C═O; each Y is independently $CH_2$, CHR, $CR_2$, or NH; each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl, and a pharmaceutically acceptable carrier.

The present invention also provides a pharmaceutical composition comprising:

(a) virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 69, 70, 73, and 82, (b) a phospholipid having the structure set forth in Formula III (III)

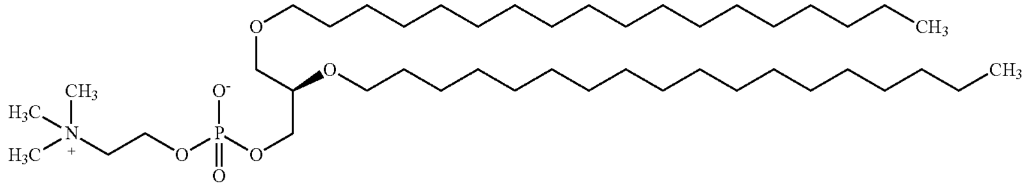

or the structure set forth in Formula IIIa (IIIa)

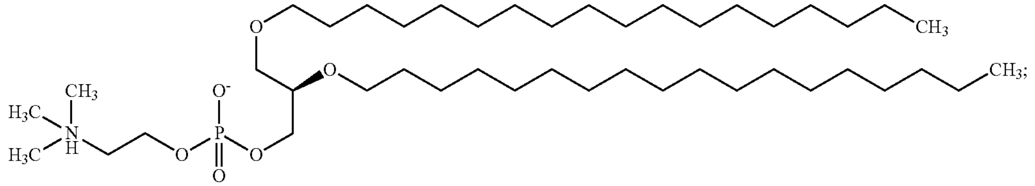

and (c) a pharmaceutically acceptable carrier.

The present invention also provides a pharmaceutical composition comprising:

(a) virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 69, 70, 73, and 82;

(b) a lipid nanoparticle (LNP), wherein the LNP comprises:

(i) a PEG-lipid having the structure set forth in Formula I:

(I)

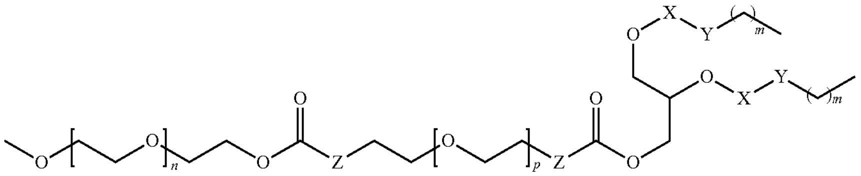

wherein, each m is independently from 5-20; n is from 20-60; p is 0, 1, or 2; each X is independently $CH_2$, CHR, $CR_2$, or C═O; each Y is independently $CH_2$, CHR, $CR_2$, or NH; each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and (ii) a phospholipid having the structure set forth in Formula III:

(III)

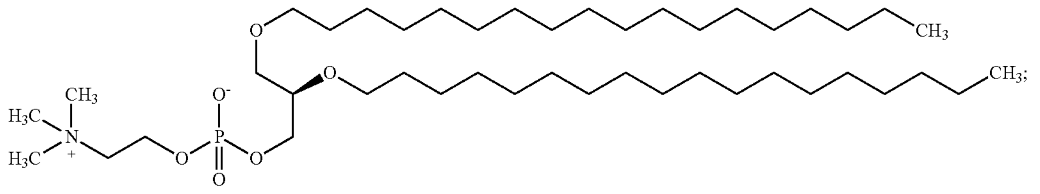

and (c) a pharmaceutically acceptable carrier.

The present invention also provides a single-dose vaccine composition comprising: virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82;

a PEG-lipid having the structure set forth in Formula I:

(I)

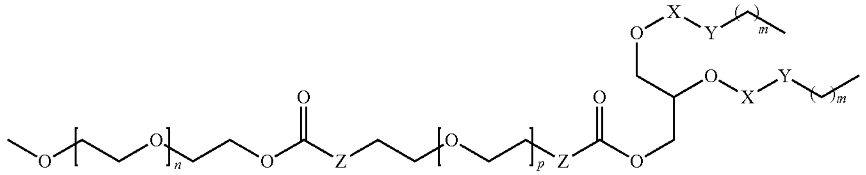

wherein, each m is independently from 5-20; n is from 20-60; p is 0, 1, or 2; each X is independently $CH_2$, CHR, $CR_2$, or C═O; each Y is independently $CH_2$, CHR, $CR_2$, or NH; each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and a phospholipid having the structure set forth in Formula III:

(III)

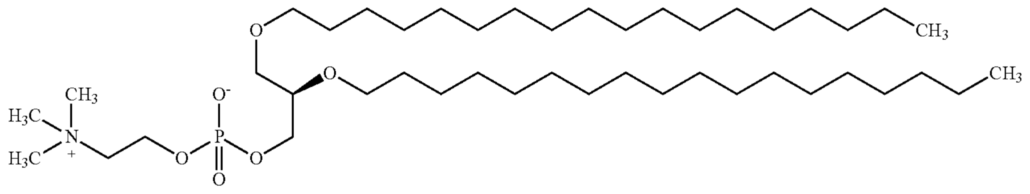

and a pharmaceutically acceptable carrier; wherein the single-dose vaccine composition provides an elevated or comparable anti-HPV immune response relative to multiple doses of the same composition formulated without a lipid nanoparticle adjuvant.

The present invention also provides a method of inducing an immune response to one or more human papillomaviruses (HPVs) in a human patient comprising co-administering to the patient (a) a pharmaceutical composition comprising virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82 and (b) a lipid nanoparticle comprising:

(i) a PEG-lipid having the structure set forth in Formula I:

(I)

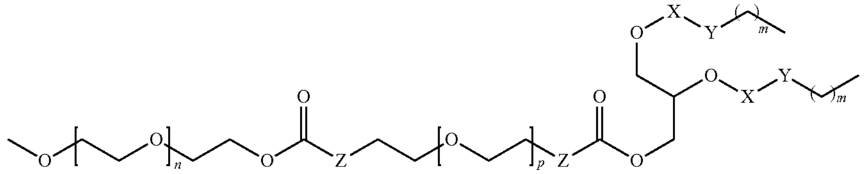

wherein, each m is independently from 5-20; n is from 20-60; p is 0, 1, or 2; each X is independently $CH_2$, CHR, $CR_2$, or C═O; each Y is independently $CH_2$, CHR, $CR_2$, or NH; each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and (ii) a phospholipid having the structure set forth in Formula III:

(III)

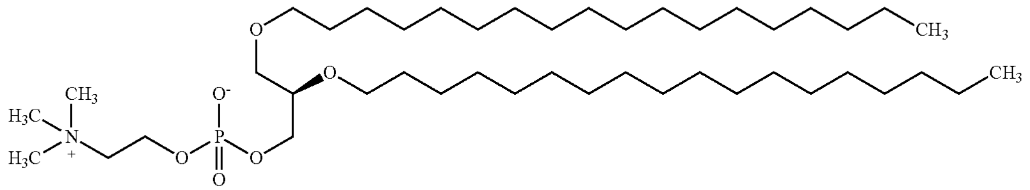

and (c) a pharmaceutically acceptable carrier.

The present invention also provides a method of preventing infection of or reducing the likelihood of infection of a human patient by a human papillomavirus (HPV) comprising co-administering to the patient (a) a pharmaceutical composition comprising virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82 and (b) a lipid nanoparticle comprising:

a PEG-lipid having the structure set forth in Formula I:

(I)

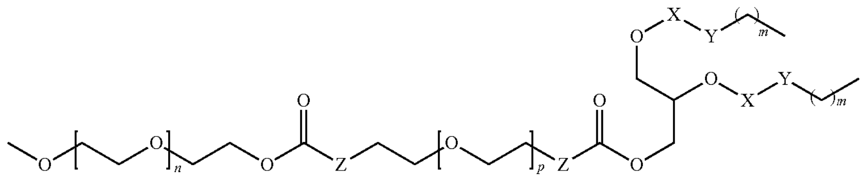

wherein, each m is independently from 5-20; n is from 20-60; p is 0, 1, or 2; each X is independently $CH_2$, CHR, $CR_2$, or C═O; each Y is independently $CH_2$, CHR, $CR_2$, or NH; each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; a phospholipid having the structure set forth in Formula III:

(III)

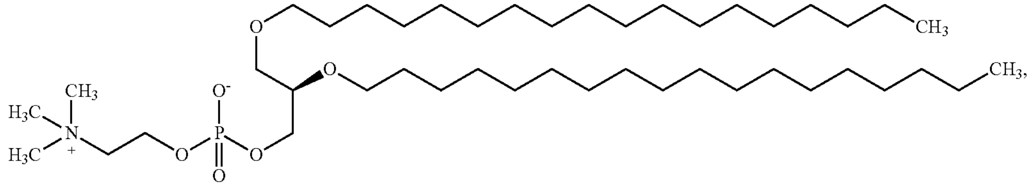

and a pharmaceutically acceptable carrier.

The present invention also provides a kit comprising: (a) a human papilloma virus (HPV) vaccine; and (b) a lipid nanoparticle comprising: a PEG-lipid having the structure set forth in Formula I:

(I)

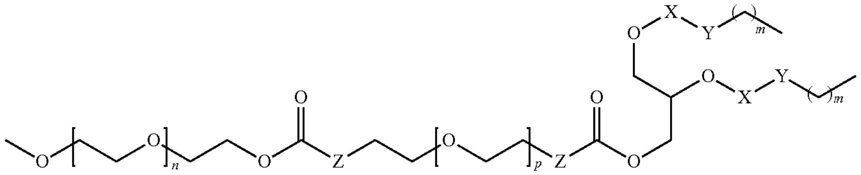

wherein, each m is independently from 5-20; n is from 20-60; p is 0, 1, or 2; each X is independently $CH_2$, CHR, $CR_2$, or C═O; each Y is independently $CH_2$, CHR, $CR_2$, or NH; each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and a phospholipid having the structure set forth in Formula (III)

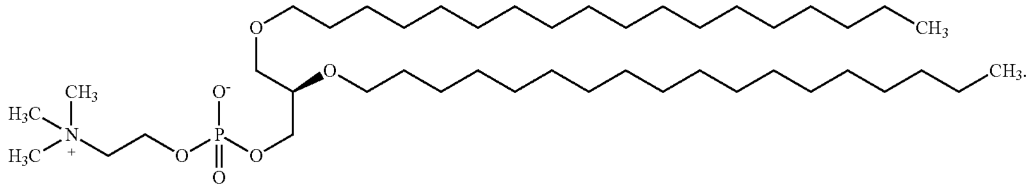

The present invention also provides a method of delivering a pharmaceutical composition to a subject that induces a neutralizing titer against an HPV antigen in the subject comprising: administering to the subject a pharmaceutical composition comprising: a lipid nanoparticle adjuvant comprising: a PEG-lipid having the structure set forth in Formula I:

(I)

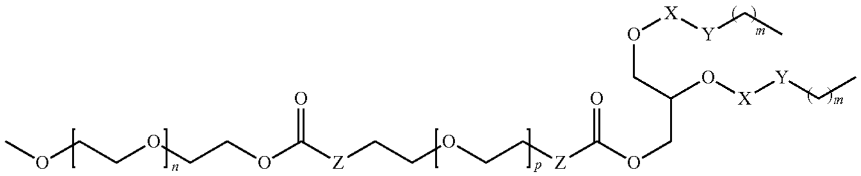

wherein, each m is independently from 5-20; n is from 20-60; p is 0, 1, or 2; each X is independently $CH_2$, CHR, $CR_2$, or C═O; each Y is independently $CH_2$, CHR, $CR_2$, or NH; each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and a phospholipid having the structure set forth in Formula III:

(III)

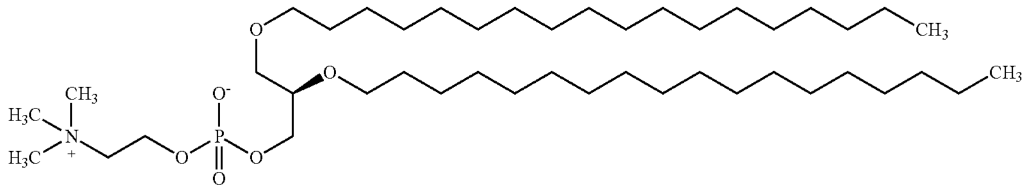

and a pharmaceutically acceptable carrier; and virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82, whereby the administration of the pharmaceutical composition induces a neutralizing titer against the HPV antigen in the subject, wherein a single dose of the pharmaceutical composition provides enhanced or comparable neutralizing titers when compared to multiple doses of the same pharmaceutical composition when the same composition is formulated without a lipid nanoparticle adjuvant.

In some embodiments, the present invention provides a formulation comprising virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82; and a PEG-lipid having the structure set forth in Formula I:

(I)

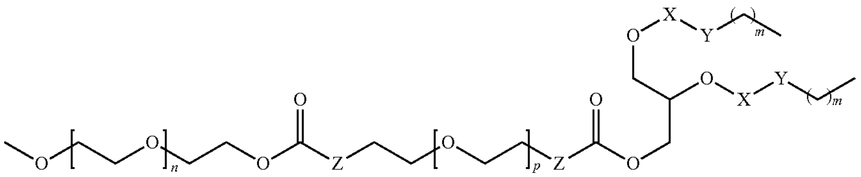

wherein, each m is independently from 5-20; n is from 20-60; p is 0, 1, or 2; each X is independently $CH_2$, CHR, $CR_2$, or C═O; each Y is independently $CH_2$, CHR, $CR_2$, or NH; each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl.

In some embodiments, the present invention also provides a formulation comprising: virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82; and a phospholipid having the structure set forth in Formula III:

(III)

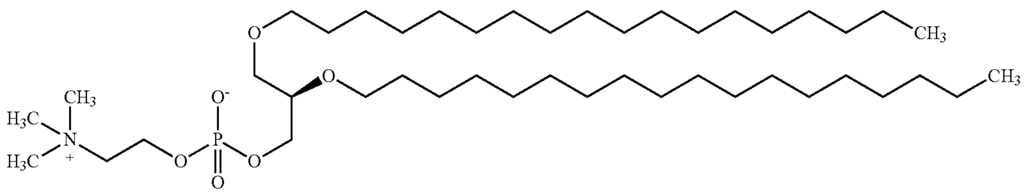

and a pharmaceutically acceptable carrier comprising a buffer.

The present invention also provides a formulation comprising virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82; and a PEG-lipid having the structure set forth in Formula I:

(I)

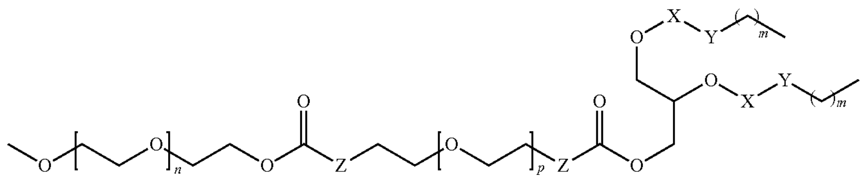

wherein: each m is independently from 5-20; n is from 20-60; p is 0, 1, or 2; each X is independently $CH_2$, CHR, $CR_2$, or C═O; each Y is independently $CH_2$, CHR, $CR_2$, or NH; each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl;

a phospholipid having the structure set forth in Formula III:

(III)

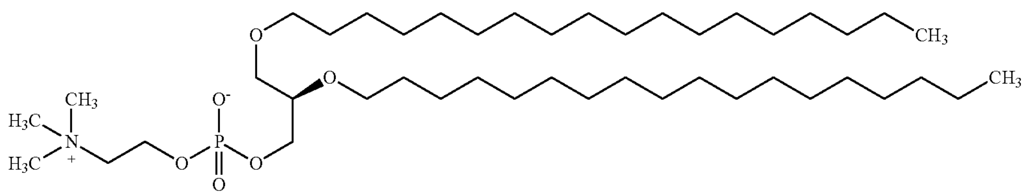

and a pharmaceutically acceptable carrier.

Definitions

As used throughout the specification and in the appended claims, the singular forms "a," "an," and "the" include the plural reference unless the context clearly dictates otherwise.

As used throughout the specification and appended claims, the following definitions and abbreviations apply:

AAHS: As used herein, the term "AAHS" refers to an amorphous aluminum hydroxyphosphate sulfate adjuvant.

About: As used herein, the term "about," when used herein in reference to a value, refers to a value that is the same as or, in context, is similar to the referenced value. In general, those skilled in the art, familiar with the context, will appreciate the absolute amount and/or relative degree of difference encompassed by "about" in that context. For example, in some embodiments, the term "about" can encompass a range of values that within 25%, 20%, 19%, 18%, 17%, 16%, 15%, 14%, 13%, 12%, 11%, 10%, 9%, 8%, 7%, 6%, 5% 4%, 3%, 2%, 1%, or less of the referenced value.

Adjuvant: As used herein, the term "adjuvant" refers to a composition or compound that is capable of enhancing the immune response against an antigen of interest. Adjuvants are substances or combinations of substances that are used in conjunction with a vaccine antigen to enhance (e.g., increase, accelerate, prolong and/or possibly target) the specific immune response to the vaccine antigen or modulate to a different type (e.g., switch a Th1 immune response to a Th2 response, or a humoral response to a cytotoxic T cell response) in order to enhance the clinical effectiveness of the vaccine. In some embodiments, the adjuvant modifies (Th1/Th2) the immune response. In some embodiments, the adjuvant boosts the strength and longevity of the immune response. In some embodiments, the adjuvant broadens the immune response to a concomitantly administered antigen. In some embodiments, the adjuvant is capable of inducing strong antibody and T cell responses. In some embodiments, the adjuvant is capable of increasing the polyclonal ability of the induced antibodies. In some embodiments, the adjuvant is used to decrease the amount of antigen necessary to provoke the desired immune response and provide protection against the disease. In some embodiments, the adjuvant is used to decrease the number of injections needed in a clinical regimen to induce a durable immune response and provide protection against the disease. Adjuvant containing formulations described herein may demonstrate enhancements in humoral and/or cellular immunogenicity of vaccine antigens, for example, subunit vaccine antigens. Adjuvants of the present invention are not used to deliver antigens, antibodies, active pharmaceutical ingredients (APIs), or VLPs.

Administration: As used herein, the term "administration" refers to the act of providing an active agent, composition, or formulation to a subject. Exemplary routes of administration to the human body can be through the eyes (ophthalmic), mouth (oral), skin (transdermal), nose (nasal), lungs (inhalant), rectal, vaginal, oral mucosa (buccal), ear, by injection (e.g., intravenously (IV), subcutaneously, intratumorally, intraperitoneally, intramuscular (IM), intradermal (ID) etc. and the like.

Agent: As used herein, the term "agent" refers to a particle, compound, molecule, or entity of any chemical class including, for example, a VLP, a small molecule, polypeptide (e.g., a protein), polynucleotide (e.g., a DNA polynucleotide or an RNA polynucleotide), saccharide, lipid, or a combination or complex thereof. In some embodiments, the term "agent" can refer to a compound, molecule, or entity that includes a polymer, or a plurality thereof.

Alkyl and Alkenyl: As used herein, the term "alkyl" refers to a straight chain, cyclic or branched saturated aliphatic hydrocarbon having the specified number of carbon atoms. A numerical range, which refers to the chain length in total, may be given. For example, $C_1$-$C_6$ heteroalkyl has a chain length of 1 to 6 atoms. As used herein, the term "alkenyl" means a straight chain, cyclic or branched unsaturated aliphatic hydrocarbon having the specified number of carbon atoms including but not limited to diene, triene and tetraene unsaturated aliphatic hydrocarbons.

Antibody: As used herein, the term "antibody" (or "Ab") refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized antibodies, fully human antibodies, and chimeric antibodies.

Antigen: As used herein, the term "antigen" refers to any antigen that can generate one or more immune responses. The antigen may be a protein (including recombinant proteins), VLP, polypeptide, or peptide (including synthetic peptides). In certain embodiments, the antigen is a lipid or a carbohydrate (polysaccharide). In certain embodiments, the antigen is a protein extract, cell (including tumor cell), or tissue. The antigen may be one that generates a humoral and/or CTL immune response.

API: As used herein, the term "API" refers to an active pharmaceutical ingredient, e.g., HPV VLP, which is a component of the compositions or formulations disclosed herein that is biologically active (e.g. capable of inducing an appropriate immune response) and confers a therapeutic or prophylactic benefit to a person or animal in need thereof. As used herein, an API is a vaccine active ingredient.

Aryl: As used herein, the term "aryl" refers to a carbocycle aromatic monocyclic or bicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. Non-limiting examples of aryl groups include phenyl and naphthyl. In one embodiment, an aryl group is phenyl. Unless otherwise indicated, an aryl group is unsubstituted.

Cationic lipid: As used herein, the term "cationic lipid" refers to a lipid species that carries a net positive charge at a selected pH, such as physiological pH. Those of skill in the art will appreciate that a cationic lipid can include, but are not limited to those disclosed in U.S. Patent Application Publication Nos. US 2008/0085870, US 2008/0057080, US 2009/0263407, US 2009/0285881, US 2010/0055168, US 2010/0055169, US 2010/0063135, US 2010/0076055, US 2010/0099738, US 2010/0104629, US 2013/0017239, and US 2016/0361411, International Patent Application Publication Nos. WO2011/022460 A1; WO2012/040184, WO2011/076807, WO2010/021865, WO 2009/132131, WO2010/042877, WO2010/146740, WO2010/105209, and in U.S. Pat. Nos. 5,208,036, 5,264,618, 5,279,833, 5,283,185, 6,890,557, and 9,669,097.

Co-administration: As used herein, the term "co-administration" or "co-administering" refers to administration of an LNP adjuvant and a pharmaceutical formulation (e.g., an HPV vaccine) concurrently, i.e., simultaneously in time, or sequentially, i.e., administration of an HPV vaccine followed by administration of the LNP adjuvant (or vice versa). That is, after administration of the HPV vaccine (or LNP adjuvant), the LNP adjuvant (or HPV vaccine) can be administered substantially immediately after the HPV vaccine (or LNP adjuvant) or the LNP adjuvant (or the HPV vaccine) can be administered after an effective time period after the HPV vaccine (or LNP adjuvant); the effective time period is generally within 1, 2, 3, 5, 10, 15, 20, 25, 30, 45, or 60 minutes.

Dose: As used herein, the term "dose" means a quantity of an agent, API, formulation, or pharmaceutical composition administered or recommended to be administered at a particular time.

Heteroalkyl: As used herein, the term "heteroalkyl" refers to means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical.

The heteroalkyl groups may be substituted. Unless otherwise stated in the specification, heteroalkyl groups may be substituted at carbon atoms in the radicals with one or more substituents which independently are oxo, fluoro, $C_1$-$C_3$ alkyl, $C_1$-$C_3$ fluoroalkyl, amino, or hydroxy. In some embodiments, the heteroalkyl groups have 1-3 heteroatoms selected from nitrogen, sulfur and oxygen atoms in the atom chain. In other embodiments, the heteroalkyl groups have 1-2 heteroatoms selected from nitrogen, sulfur and oxygen atoms in the atom chain. In some embodiments, the heteroalkyl groups have 1 heteroatom selected from nitrogen, sulfur and oxygen atoms in the atom chain. In some embodiments, the heteroatoms are selected from O, S, S(O), $S(O)_2$, and —NH—, —N(alkyl)-. Non-limiting examples include ethers, thioethers, amines, hydroxymethyl, 3-hydroxypropyl, 1,2-dihydroxyethyl, 2-methoxyethyl, 2-aminoethyl, 2-dimethylaminoethyl, and the like, and an aliphatic group containing a heteroatom.

Heteroaryl: As used herein, the term "heteroaryl" refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

HPV and PV: As used herein, the terms "HPV" and "PV" refer to human papillomavirus and papillomavirus, respectively.

Lipid: As used herein, the term "lipid" refers to any of a group of organic compounds that are esters of fatty acids and are characterized by being insoluble in water or having low solubility in water but may be soluble in many organic solvents. Lipids can be divided into at least three classes: (1) "simple lipids," which include, e.g., fats and oils as well as waxes; (2) "compound lipids," which include, e.g., phospholipids and glycolipids; and (3) "derived lipids," which include, e.g., steroids.

Lipid nanoparticle: As used herein, the term "lipid nanoparticle" (or "LNP") refers to a lipid composition that forms a particle having a length or width measurement (e.g., a maximum length or width measurement) between 10 and 1000 nanometers. In some embodiments, the LNP may be used as an adjuvant to increase or enhance the immune response against an antigen of interest when used as a component of a vaccine. In some embodiments, a lipid nanoparticle can be used as an adjuvant or used in combination with non-LNP adjuvants.

Multiple-dose: As used herein, the term "multiple-dose" refers to a vaccine composition, or pharmaceutical composition, that requires more than one dose or administration or injection of the components therein in a clinical regimen to induce a durable immune response and provide protection from a pathogen or disease. One of skill in the art would understand how to determine a durable immune response, e.g., by measuring antibody titers over a specified period of time.

Neutral lipid: As used herein, the term "neutral lipid" refers to a lipid species that exists either in an uncharged or neutral zwitterionic form at a selected pH. At physiological pH, such lipids include, for example, diaeylphosphatidylcholine, diacylphosphatidyletbanolamine, ceramide, sphingomyelin, cephalin, cholesterol, cerebrosides and diacylglycerols.

Patient: As used herein, the term "patient" refers to any human being that is to receive the HPV vaccines, or pharmaceutical compositions, described herein. As defined herein, "patient" includes those already infected with one or more types of HPV as well as those in which infection with one or more types of HPV is to be prevented.

Pharmaceutically acceptable: As used herein with respect to a carrier, diluent, or excipient of a pharmaceutical composition, the term "pharmaceutically acceptable" indicates that a carrier, diluent, or excipient must be compatible with the other ingredients of the composition and not deleterious to the recipient thereof.

Pharmaceutical composition: As used herein, the term "pharmaceutical composition," refers to a composition containing an active pharmaceutical or biological ingredient, along with one or more additional components, e.g., a composition in which an active agent is formulated together with one or more pharmaceutically acceptable carriers. As used herein, the terms "pharmaceutical formulation" and "formulation" are used interchangeably with "pharmaceutical composition." In some embodiments, the active agent is present in a unit dose amount appropriate for administration in a therapeutic regimen that shows a statistically significant probability of achieving a predetermined therapeutic effect when administered to a relevant population. The pharmaceutical compositions or formulations can be liquid or solid (e.g., lyophilized). Additional components that may be included as appropriate include pharmaceutically acceptable excipients, additives, diluents, buffers, sugars, amino acids, chelating agents, surfactants, polyols, bulking agents, stabilizers, lyo-protectants, solubilizers, emulsifiers, salts, adjuvants, tonicity enhancing agents, delivery vehicles, and anti-microbial preservatives. The pharmaceutical compositions or formulations are nontoxic to recipients at the dosages and concentrations employed. In some embodiments, a pharmaceutical composition can be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces. In some embodiments, the term formulation refers to a single-dose of vaccine, which can be included in any volume suitable for injection.

Ring System Substituent: As used herein, the term "ring system substituent," refers to a substituent group attached to an aromatic or non-aromatic ring system which, for example, replaces an available hydrogen on the ring system. Ring system substituents may be the same or different, and are each independently selected. Examples of ring system substituents include alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O— haloalkyl, -alkylene-O-alkyl, —O-aryl, —O-alkylene-aryl, acyl, —C(O)-aryl, halo, —NO2, —CN, —$SF_5$, —C(O)OH, —C(O)O-alkyl, —C(O)O-aryl, —C(O)O-alkylene-aryl, —S(O)-alkyl, —$S(O)_2$-alkyl, —S(O)-aryl, —$S(O)_2$-aryl, —S(O)-heteroaryl, —$S(O)_2$-heteroaryl, —S-alkyl, —S-aryl, —S-heteroaryl, —S— alkylene-aryl, —S-alkylene-heteroaryl, —$S(O)_2$-alkylene-aryl, —$S(O)_2$-alkylene-heteroaryl, —Si$(alkyl)_2$, —$Si(aryl)_2$, —$Si(heteroaryl)_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)— cycloalkyl, —C(═N—CN)—$NH_2$, —C(═NH)—$NH_2$, —C(═NH)—NH(alkyl), —N(Y1)(Y2), -alkylene-N($Y_1$)(Y2), —C(O)N(Y1)(Y2) and —$S(O)_2$N(Y1)(Y2), wherein $Y_1$ and Y2 can be the same or different and are independently selected from the group consisting of hydrogen, alkyl, aryl, cycloalkyl, and -alkylene-aryl.

Single-dose: As used herein, the term "single-dose" refers to a vaccine composition that only requires one administration or injection in a clinical regimen to induce a durable immune response and provide protection from a pathogen or disease. One of skill in the art would understand how to determine a durable immune response, e.g., by measuring antibody titers over a specified period of time.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutically Effective Amount: As used herein, the term "therapeutically effective amount" refers to an amount of the active ingredient (e.g. therapeutic protein, vaccine, or antibody) sufficient to produce the desired therapeutic effect in a human or animal, e.g., the amount necessary to elicit an immune response, treat, cure, prevent, or inhibit development and progression of a disease or the symptoms thereof and/or the amount necessary to ameliorate symptoms or cause regression of a disease. Therapeutically effective amount may vary depending on the structure and potency of the active ingredient and the contemplated mode of administration. One of skill in the art can readily determine a therapeutically effective amount of a given antibody or therapeutic protein or vaccine antigen.

Vaccine: As used herein, the term "vaccine" or "immunogenic composition" refers to a substance or preparation used to stimulate the production of antibodies and provide immunity against one or several diseases, prepared from the causative agent of a disease, its products, or a synthetic substitute, treated to act as an antigen without inducing the disease. A vaccine composition may include at least one antigen or HPV VLP in a pharmaceutically acceptable vehicle useful for inducing an immune response in a subject. The vaccine composition is administered by doses and techniques known to those skilled in the pharmaceutical or veterinary fields, taking into account factors such as the age, sex, weight, species, and condition of the recipient animal and the route of administration.

Valent: As used herein, the term "valent" refers to the presence of a specified number of antigens in a vaccine. For example, the terms bi-valent, bivalent, 2 valent, or 2 valent refer to two different antigens. Similarly, the terms quadrivalent, 4 valent, or 4 valent refer to four different antigens and the terms nonavalent, 9 valent or 9-valent refer to nine different antigens.

Virus Like Particles: As used herein, the term "virus like particles" or "VLPs" refers to agents that are morphologically similar to authentic virions or provide an arrayed display of an antigen and are capable of inducing high antibody neutralization ratings after administration in an animal. VLPs lack the viral genetic material of the authentic virions and are thus non-infectious.

Abbreviations

The following abbreviations are used herein:

Anh Anhydrous
Aq. aqueous
Bn benzyl
DIEA or DIPEA N,N-diisopropylethylamine
DMAP 4-dimethylaminopyridine
DMF N, N-dimethylformamide
DMP Dess-Martin periodinane
DMSO dimethyl sulfoxide
DSC bis(2,5-dioxopyrrolidin-1-yl) carbonate
EDTA ethylenediaminetetraacetic acid
ESI electrospray ionization
Et ethyl
$Et_2O$ diethyl ether
EtOH ethanol
EtOAc ethyl acetate
$Et_3N$ triethylamine
h hour
HPLC high-performance liquid chromatography
IM intramuscular
IPA isopropanol
iPr isopropyl
LC liquid chromatography
LCMS liquid chromatography mass spectrometry
MeOH methanol
mg milligrams
min minutes
mL microliters
mL milliliters
mmol millimoles
mN Number average molecular weight
NMR nuclear magnetic resonance spectroscopy
Pd polydispersity
Pet. ether petroleum ether
Ph phenyl
RT or rt room temperature
sat. saturated
SFC supercritical fluid chromatography
TBAI n-tetrabutylammonium iodide
TFA trifluoroacetic acid
THF tetrahydrofuran

DETAILED DESCRIPTION

Figure 1A:
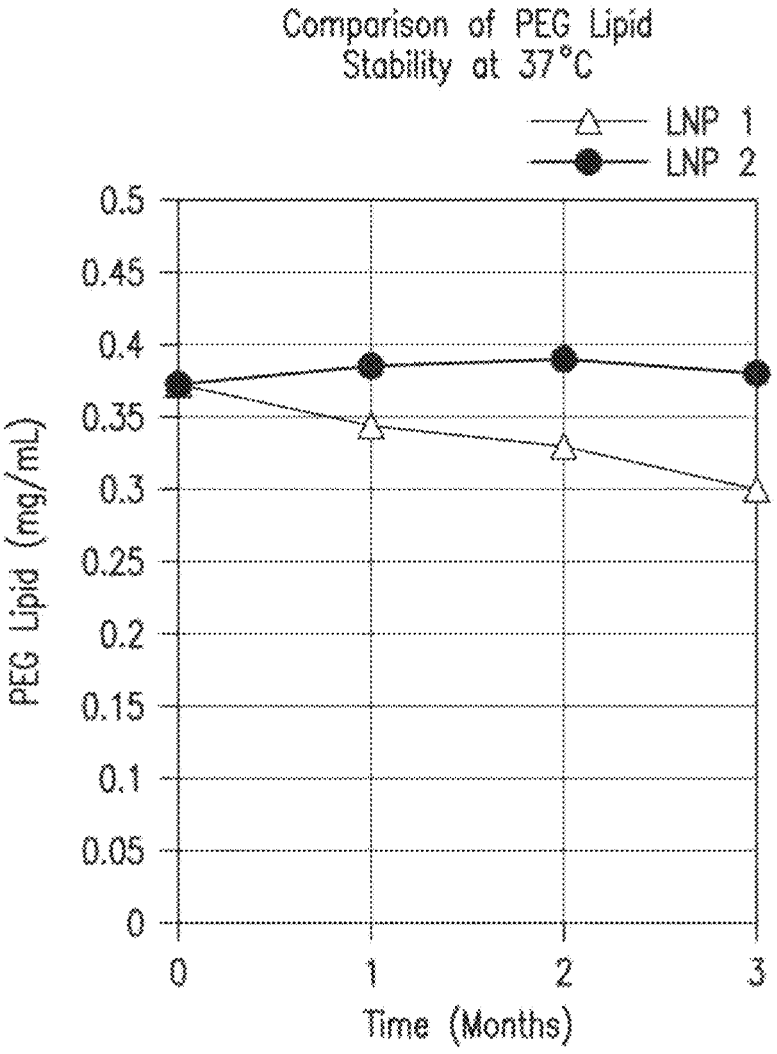
FIGS. 1A-1B depict graphical comparison of the different PEG and DSPC lipids over 3.5 months.

Currently, there are multiple approved HPV vaccines that are composed of virus like particles (VLPs) and are highly effective at protecting vaccinated patients against premalignant lesions and anogenital cancers and genital warts when administered prior to natural infection in subjects 9 years and older as multidose regimens. In accordance with this invention, it has been shown that a single-dose HPV vaccine composition that includes HPV VLPs of at least one HPV type ("targeted HPV types") and an LNP adjuvant are able to provide comparable or enhanced antibody titers to the same targeted HPV types when compared to multiple-doses of vaccine compositions that include VLPs of the targeted HPV types formulated, or administered, without an LNP adjuvant. The compositions of the present invention are intended to generate immunity against HPV subtypes through a single-injection regimen that is comparable to, at least, a 2-3 injection regimen of such HPV vaccine, including an approved two-, four-, or nine-valent HPV vaccine.

The PEG-Lipid

In some embodiments, PEG lipids of the present invention are synthesized via various intermediates. In some embodiments, 2,5-dioxopyrrolidin-1-yl (2-(2-methoxyethoxy)ethyl) carbonate (Intermediate 1) is synthesized by the following scheme:

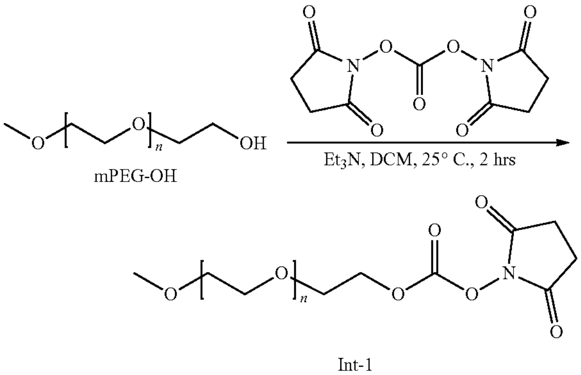

Int-1

In some embodiments, 2-bromoethyl phosphorodichloridate (Intermediate 2) is synthesized by the following scheme:

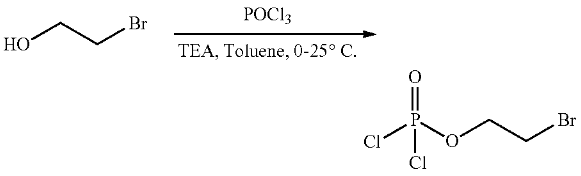

Int-2

In some embodiments, 1-isocyanatotridecane (Intermediate 3) is synthesized by the following scheme:

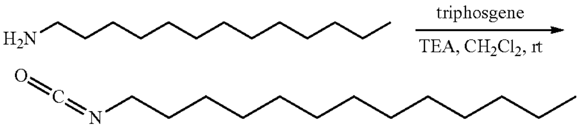

Int-3

In some embodiments, 2,2-dimethylpentadecanoyl chloride (Intermediate 4) is synthesized by the following scheme:

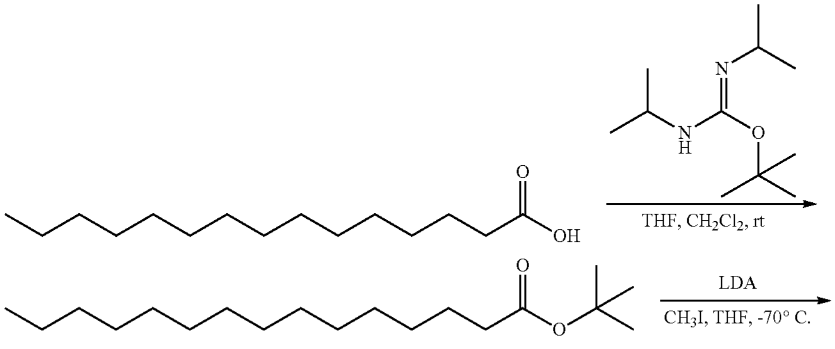

Int-4a

-continued
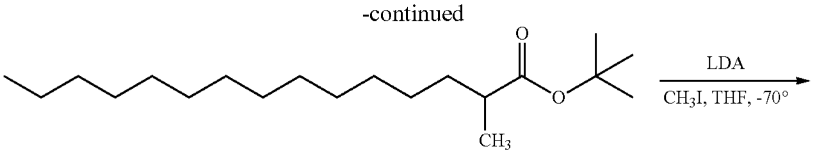
Int-4b
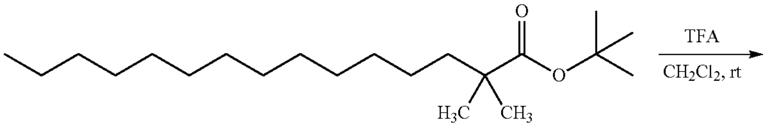
Int-4c
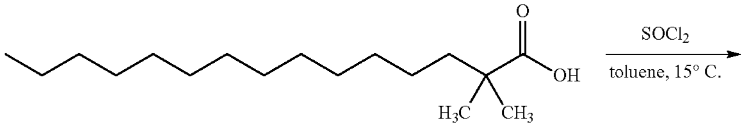
Int-4d
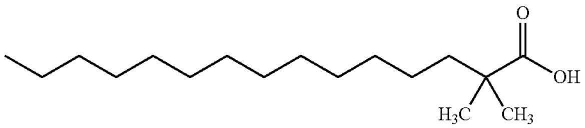
Int-4
In some embodiments, tert-butyl pentadecanoate (Int-4a) is synthesized by the following scheme:
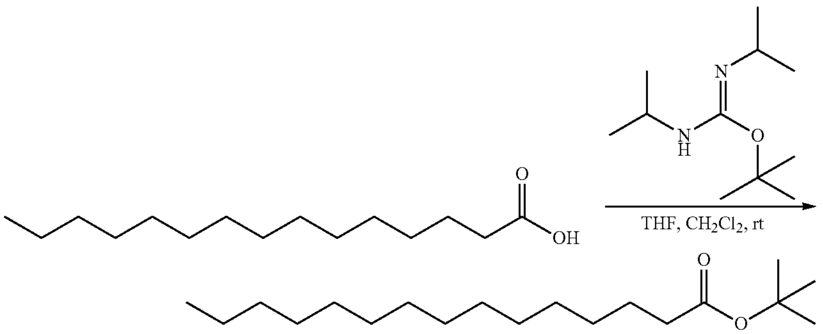
Int-4a
In some embodiments, tert-butyl 2-methylpentadecanoate (Int-4b) is synthesized by the following scheme:
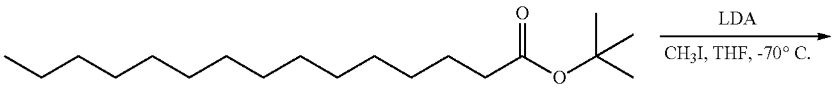
Int-4a
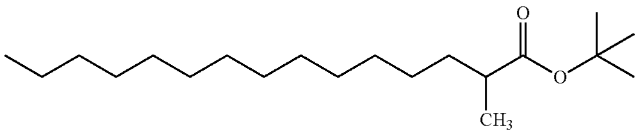
Int-4b In some embodiments, tert-butyl 2,2-dimethylpentadecanoate (Int-4c) is synthesized by the following scheme:

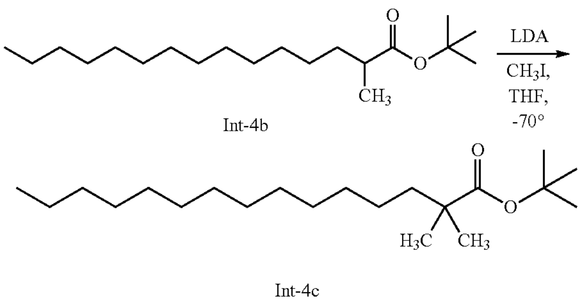

In some embodiments, 2,2-dimethylpentadecanoic acid (Int-4d) is synthesized by the following scheme:

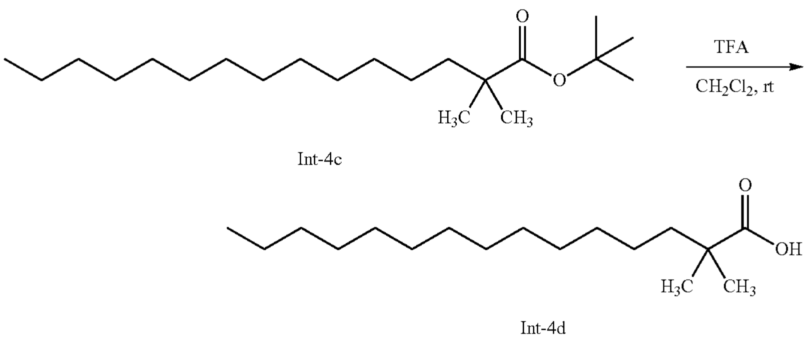

In some embodiments, 2,2-dimethylpentadecanoyl chloride (Int-4) is synthesized by the following scheme:

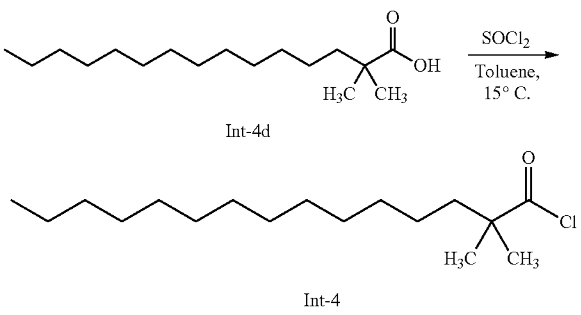

In some embodiments, (R)-2-methylpentadecanoyl chloride (Intermediate 5) is synthesized by the following scheme:

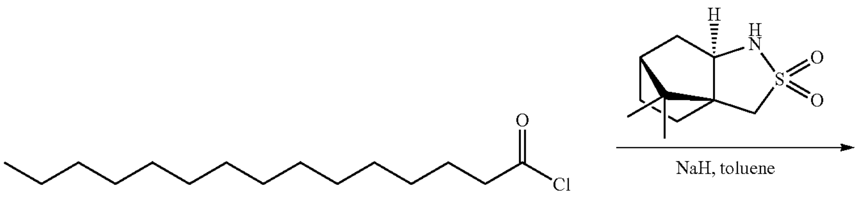

-continued
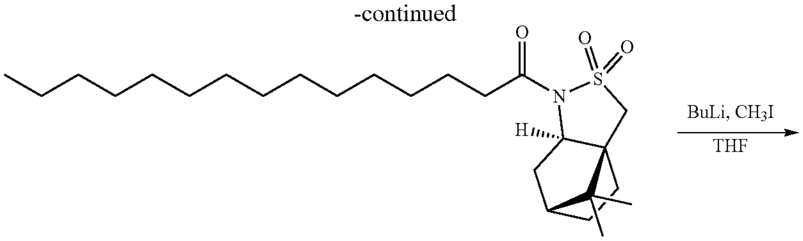
Int-5a
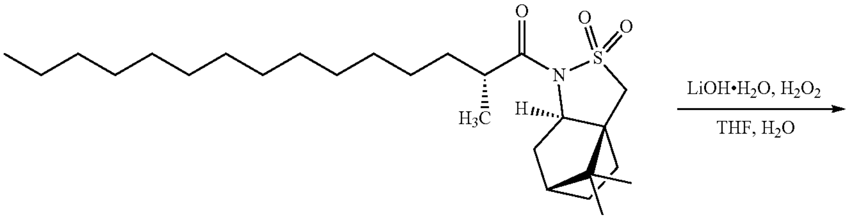
Int-5b
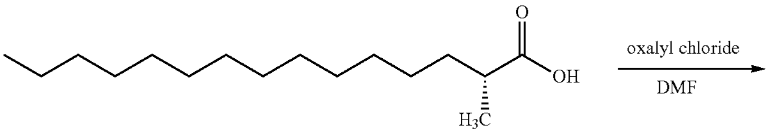
Int-5c
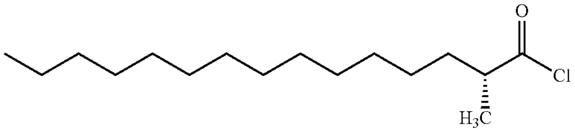
Int-5
In some embodiments, 1-((3aS,6R,7aR)-8,8-dimethyl-2,2-dioxidotetrahydro-3H-3a,6-methanobenzo[c]-isothiazol-1(4H)-yl)pentadecan-1-one (Int-5a) is synthesized by the following scheme:
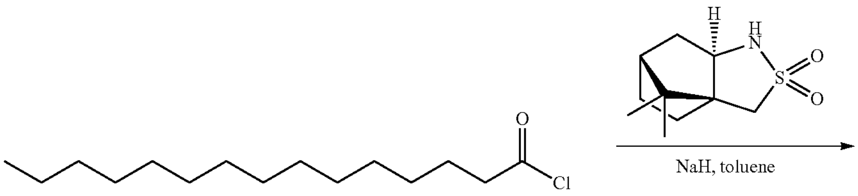
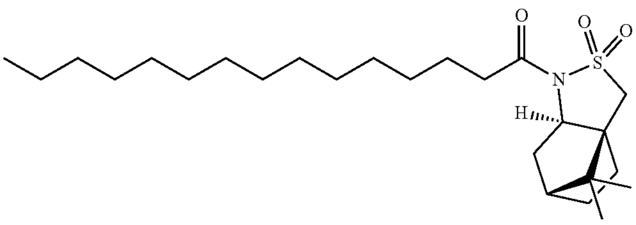
Int-5a In some embodiments, (R)-1-((3aS,6R,7aR)-8,8-dimethyl-2,2-dioxidotetrahydro-3H-3a,6-methanobenzo-[c]isothiazol-1(4H)-yl)-2-methylpentadecan-1-one (Int-5b) is synthesized by the following scheme:

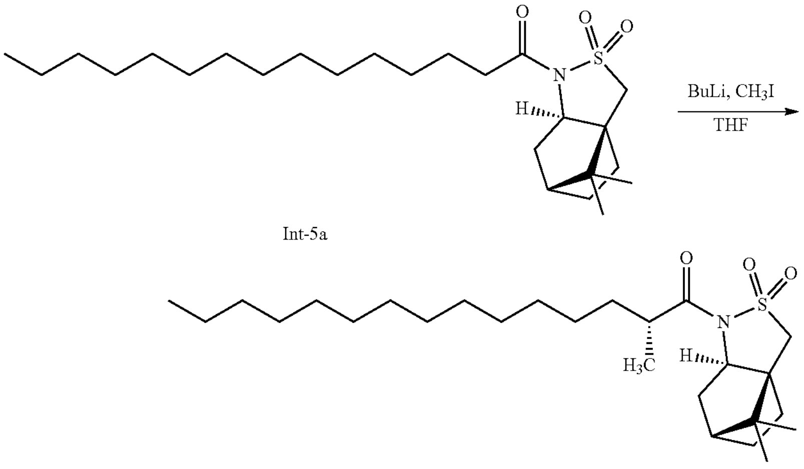

Int-5a

Int-5b

In some embodiments, (R)-2-methylpentadecanoic acid (Int-5c) is synthesized by the following scheme:

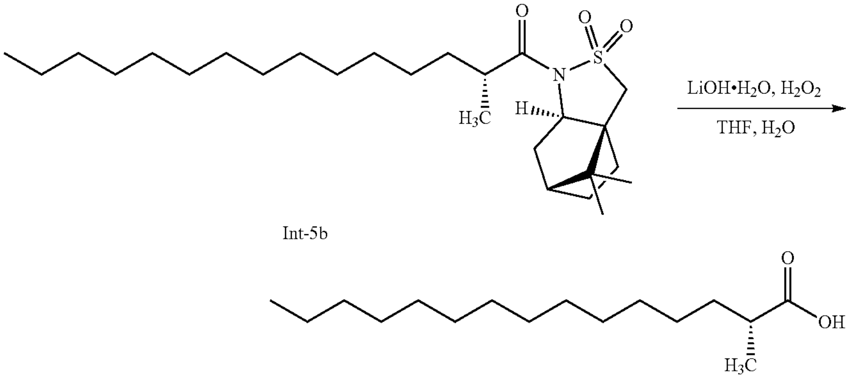

Int-5b

Int-5c

In some embodiments, (R)-2-methylpentadecanoyl chloride (Int-5) is synthesized by the following scheme

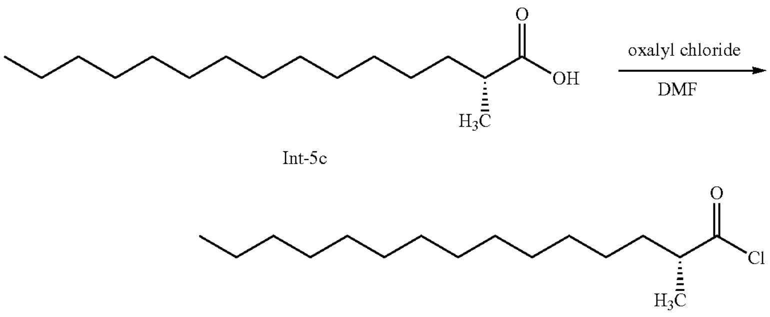

Int-5c

Int-5

In some embodiments, α-[(15R)-1,12-Dioxo-15-(tetradecyloxy)-5,8,13,17-tetraoxa-2,11-diazahentriacont-1-yl]-ω-methoxypoly(oxyethane-1,2-diyl (Compound 1) is synthesized according to the following scheme:
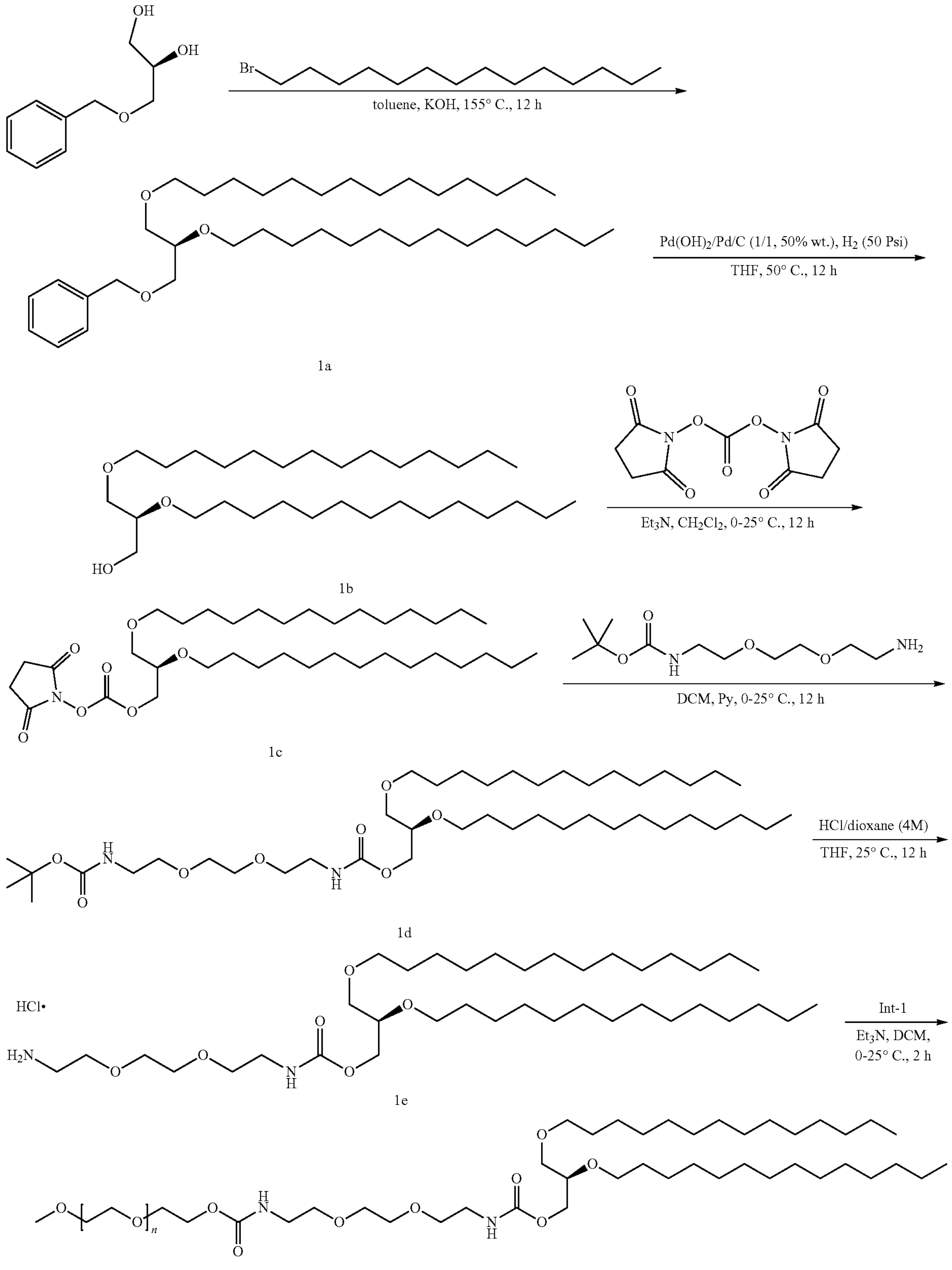
1a
1b
1c
1d
1e
Compound 1

In some embodiments, (R)-((2,3-bis(tetradecyloxy)propoxy)methyl)benzene (Compound 1a) is synthesized according to the following scheme:

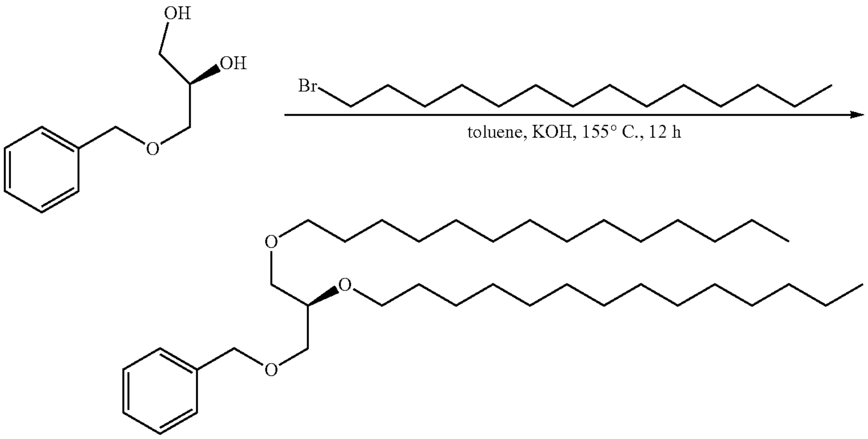

1a

In some embodiments, (S)-2,3-bis(tetradecyloxy)propan-1-ol (Compound 1b) is synthesized according to the following scheme:

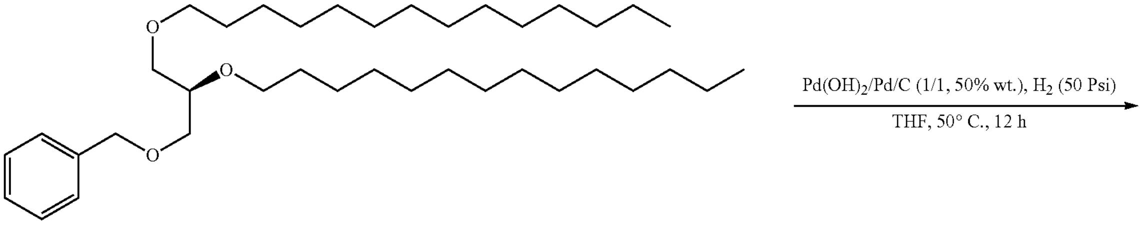

1a

1b

In some embodiments, (R)-2,3-bis(tetradecyloxy)propyl (2,5-dioxopyrrolidin-1-yl) carbonate (Compound 1c) is synthesized according to the following scheme:

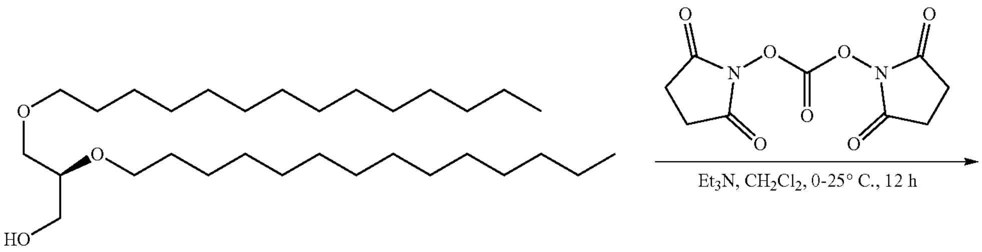

1b

-continued
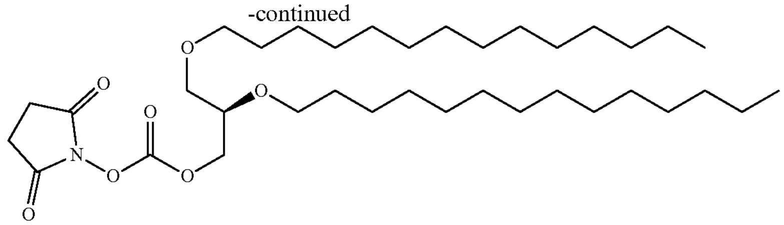
1c
In some embodiments, (R)-2,3-bis(tetradecyloxy)propyl (2,2-dimethyl-4-oxo-3,8,11-trioxa-5-azatridecan-13-yl)carbamate (Compound 1d) is synthesized according to the following scheme:
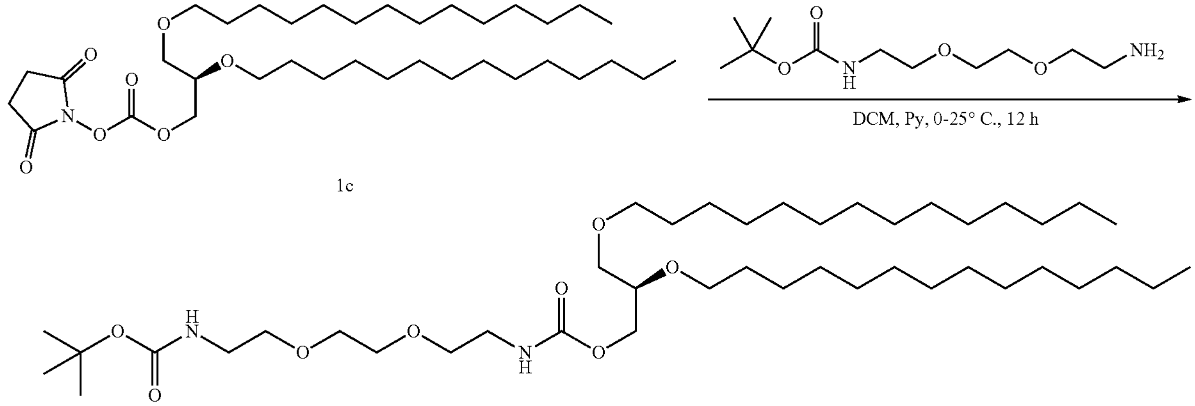
1c
1d
In some embodiments, (R)-2,3-bis(tetradecyloxy)propyl (2-(2-(2-aminoethoxy)ethoxy)ethyl)carbamate hydrochloride (Compound 1e) is synthesized according to the following scheme:
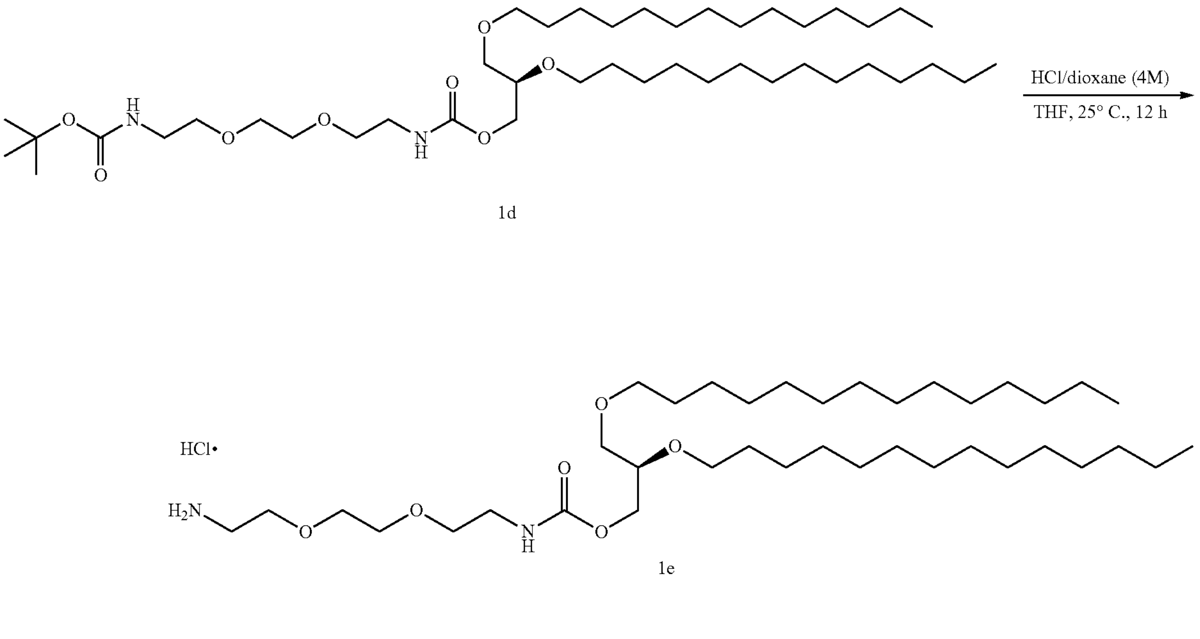
1d
1e In some embodiments, α-[(15R)-1,12-Dioxo-15-(tetradecyloxy)-5,8,13,17-tetraoxa-2,11-diazahentriacont-1-yl]-ω-methoxypoly(oxyethane-1,2-diyl) (Compound 1) is synthesized by the following scheme:

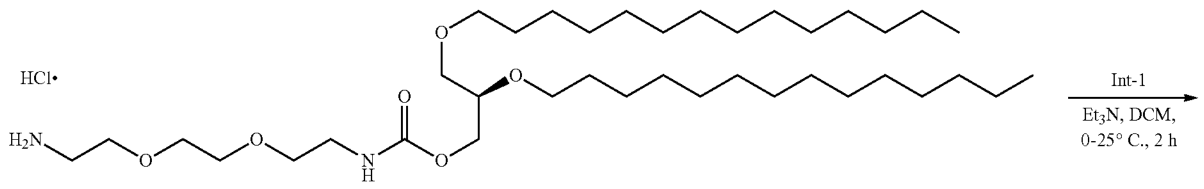

1e

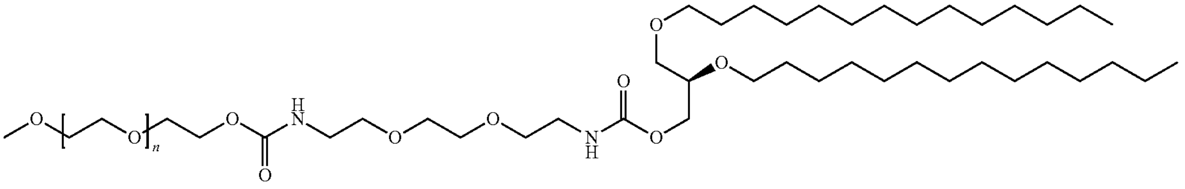

Compound 1

In some embodiments, the PEG-lipid includes α-[(15S)-1,12-Dioxo-15-(tetradecyloxy)-5,8,13,17-tetraoxa-2,11-diazahentriacont-1-yl]-ω-methoxypoly(oxyethane-1,2-diyl) (Compound 2), the structure of which is shown in Table 1 below. In some embodiments, the PEG-lipid includes t α-[(15S)-1,12-Dioxo-15 rac-α-[1,12-Dioxo-15-(tetradecyloxy)-5,8,13,17-tetraoxa-2,11-diazahentriacont-1-yl]-ω-methoxypoly(oxyethane-1,2-diyl) (Compound 3), the structure of which is shown in Table 1 below. In some embodiments, the PEG-lipid includes α-[(15R)-1,12,18-Trioxo-15-[(1-oxo-2-aza-tetradecyl)oxy]-5,8,13,17-tetraoxa-2,11,19-triazahentriacont-1-yl]-ω-methoxypoly-(oxyethane-1,2-diyl) (Compound 4), the structure of which is shown in Table 1 below. In some embodiments, the PEG-lipid includes α-[(15R)-1,12,18-Trioxo-19,19-dimethyl-15-[(1-oxo-2,2-dimethyl-tetradecyl)oxy]-5,8,13,17-tetraoxa-2,11-diazahentriacont-1-yl]-ω-methoxypoly-(oxyethane-1,2-diyl), the structure of which is shown in Table 1 below. In some embodiments, the PEG-lipid includes α-[(15R)-1,12,18-Trioxo-19,19-dimethyl-15-[(1-oxo-2,2-dimethyl-tetradecyl)oxy]-5,8,13,17-tetraoxa-2,11-diazahentriacont-1-yl]-ω-methoxypoly-(oxyethane-1,2-diyl), the structure of which is shown in Table 1 below.

In some embodiments, (2R)-2,3-bis(octadecyloxy)propyl 2-(trimethylazaniumyl)ethyl phosphate (Compound 7) is synthesized according to the following scheme:

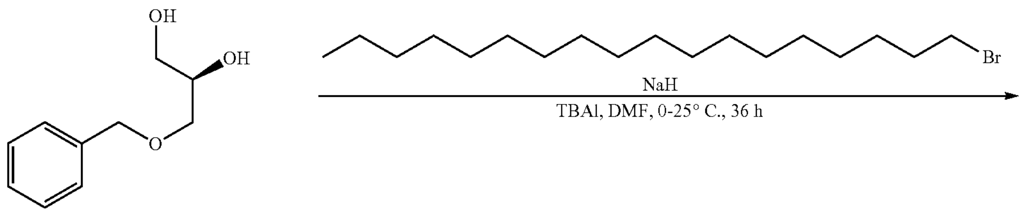

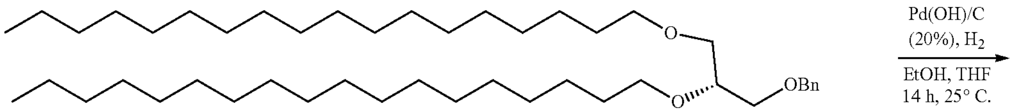

7a

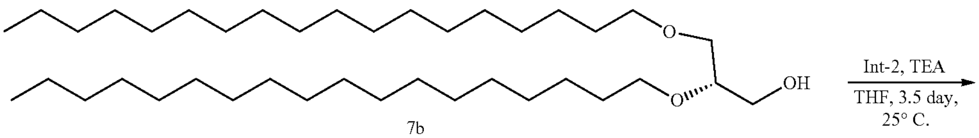

7b

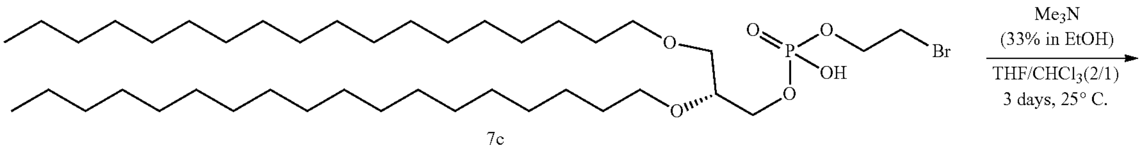

7c

-continued

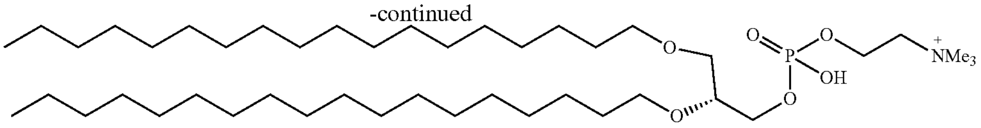

Compound 7

In some embodiments, (R)-((2,3-bis(octadecyloxy)propoxy)methyl)benzene (Compound 7a) is synthesized according to the following scheme:

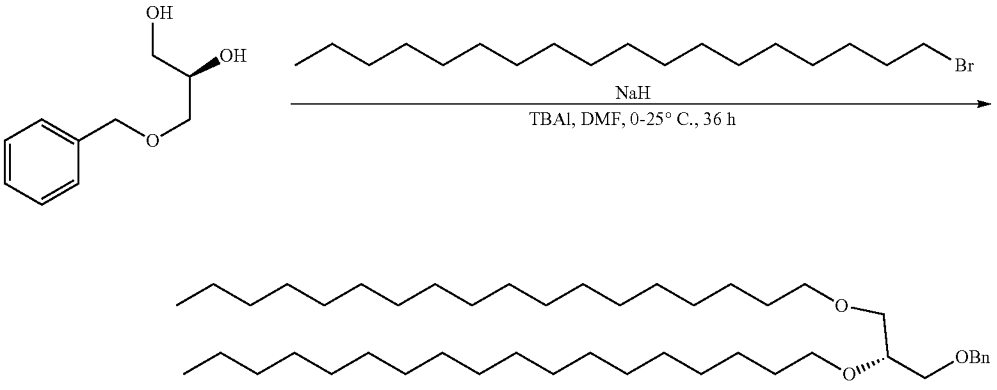

Compound 7a

In some embodiments, (S)-2,3-bis(octadecyloxy)propan-1-ol (Compound 7b) is synthesized according to the following scheme:

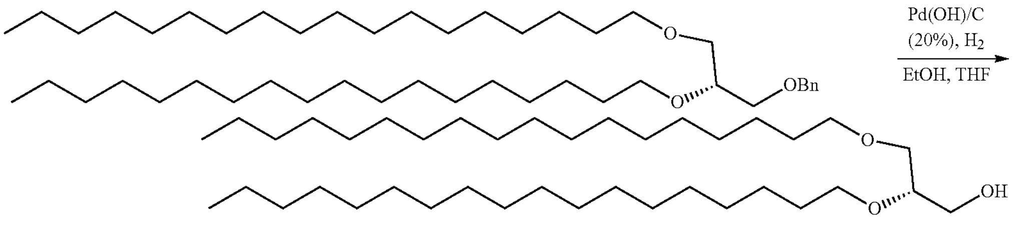

Compound 7b

In some embodiments, (R)-2,3-bis(octadecyloxy)propyl (2-bromoethyl)phosphate (Compound 7c) is synthesized according to the following scheme:

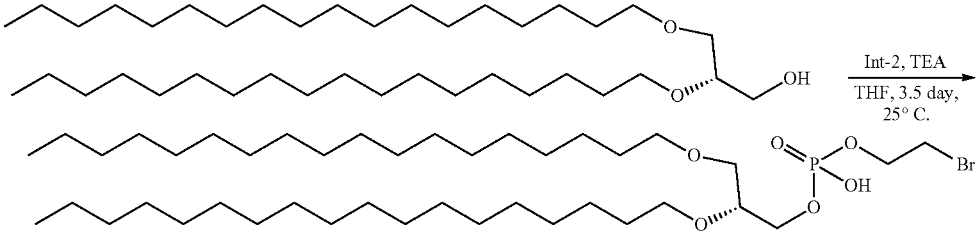

Compound 7c

In some embodiments, (2R)-2,3-bis(octadecyloxy)propyl 2-(trimethylazaniumyl)ethyl phosphate (Compound 7) is synthesized according to the following scheme:

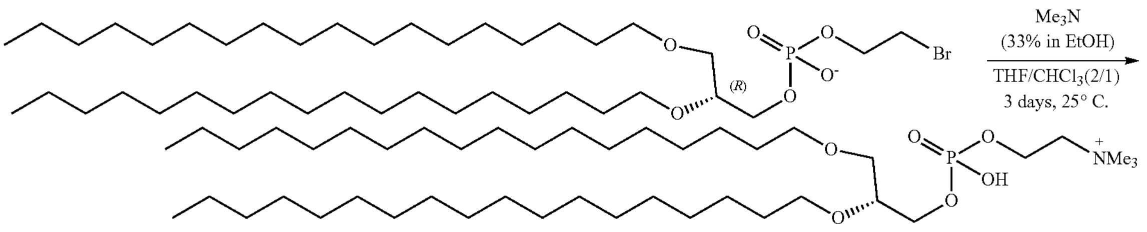

Compound 7

TABLE 1

| Compound | Structure<br>Name |
|---|---|
| 1 | 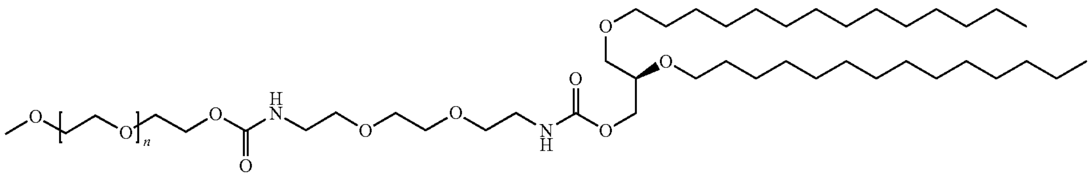<br>α-[(15R)-1,12-Dioxo-15-(tetradecyloxy)-5,8,13,17-tetraoxa-2,11-diazahentriacont-1-yl]-ω-methoxypoly(oxyethane-1,2-diyl |
| 2 | 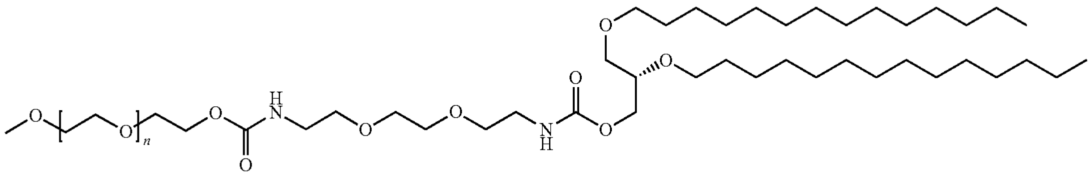<br>α-[(15S)-1,12-Dioxo-15-(tetradecyloxy)-5,8,13,17-tetraoxa-2,11-diazahentriacont-1-yl]-ω-methoxypoly(oxyethane-1,2-diyl) |
| 3 | 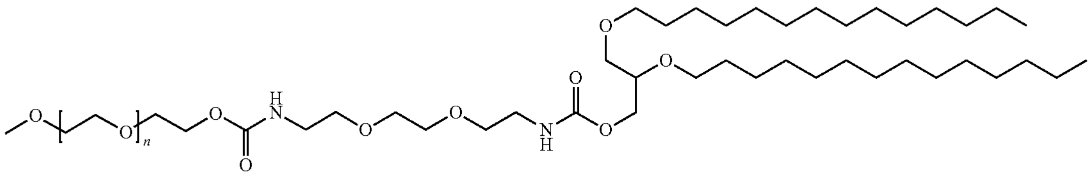<br>rac-α-[1,12-Dioxo-15-(tetradecyloxy)-5,8,13,17-tetraoxa-2,11-diazahentriacont-1-yl]-ω-methoxypoly(oxyethane-1,2-diyl) |
| 4 | 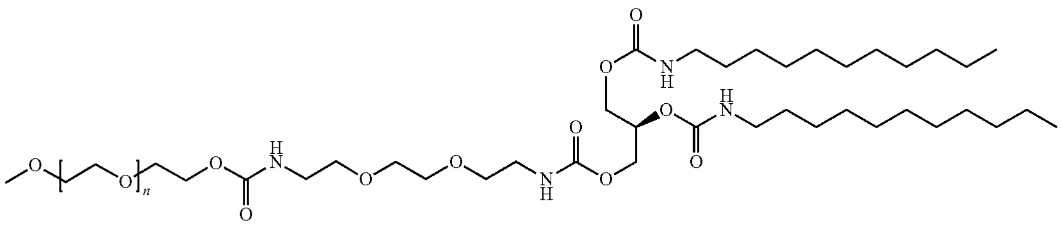<br>α-[(15R)-1,12,18-Trioxo-15-[(1-oxo-2-aza-tetradecyl)oxy]-5,8,13,17-tetraoxa-2,11,19-triazahentriacont-1-yl]-co-methoxypoly-(oxyethane-1,2-diyl) |

TABLE 1-continued

| Compound | Structure<br>Name |
|---|---|
| 5 | 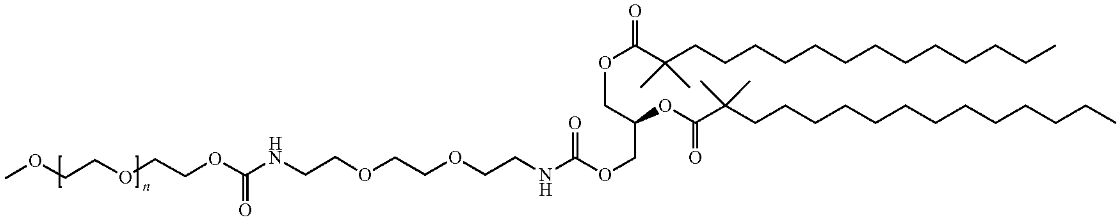<br>α-[(15R)-1,12,18-Trioxo-19,19-dimethyl-15-[(1-oxo-2,2-dimethyl-tetradecyl)oxy]-5,8,13,17-tetraoxa-2,11-diazahentriacont-1-yl]-ω-methoxypoly-(oxyethane-1,2-diyl) |
| 6 | 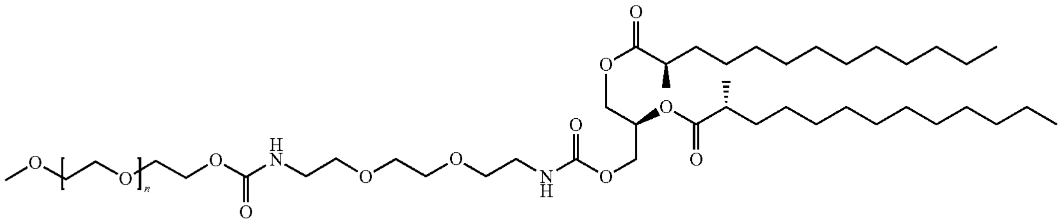<br>α-[(15R)-1,12,18-Trioxo-19R-methyl-15-[(1-oxo-2R-methyl-tetradecyl)oxy]-5,8,13,17-tetraoxa-2,11-diazahentriacont-1-yl]-ω-methoxypoly-(oxyethane-1,2-diyl) |
| 7 | 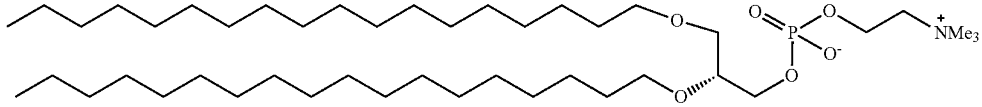<br>(2R)-2,3-bis(octadecyloxy)propyl 2-(trimethylazaniumyl)ethyl phosphate |

In some embodiments, the PEG-lipid of the present invention is represented by the structure set forth in Formula I:

(I)

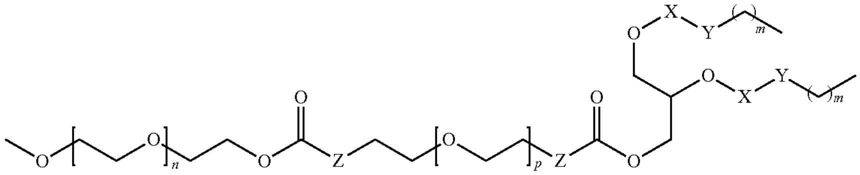

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently alkyl, aryl, heteroalkyl, or heteroaryl.

In some embodiments, the PEG-lipid of the present invention is represented by the structure set forth in Formula I, wherein each m is independently from 8-18. In some embodiments, the PEG-lipid of the present invention is represented by the structure set forth in Formula I, wherein each m is independently from 10-15. In some embodiments, the PEG-lipid of the present invention is represented by the structure set forth in Formula I, wherein each m is independently from 12-15. In some embodiments, the PEG-lipid of the present invention is represented by the structure set forth in Formula I, wherein each m is independently 10, 11, 12, 13, 14, 15, 16, 17, 18, 19, or 20.

In some embodiments, the PEG-lipid of the present invention is represented by the structure set forth in Formula I, wherein n is from 20-60. In some embodiments, the PEG-lipid of the present invention is represented by the structure set forth in Formula I, wherein n is from 20-50. In some embodiments, the PEG-lipid of the present invention is represented by the structure set forth in Formula I, wherein n is from 20-45. In some embodiments, the PEG-lipid of the present invention is represented by the structure set forth in Formula I, wherein n is from 30-60. In some embodiments, the PEG-lipid of the present invention is represented by the structure set forth in Formula I, wherein n is from 30-50. In some embodiments, the PEG-lipid of the present invention is represented by the structure set forth in Formula I, wherein n is from 30-45. In some embodiments, the PEG-lipid of the present invention is represented by the structure set forth in Formula I, wherein n is from 35-60. In some embodiments, the PEG-lipid of the present invention is represented by the structure set forth in Formula I, wherein n is from 35-50. In some embodiments, the PEG-lipid of the present invention is represented by the structure set forth in Formula I, wherein n is from 35-45. In some embodiments, the PEG-lipid of the present invention is represented by the structure set forth in Formula I, wherein n is from 40-60. In some embodiments, the PEG-lipid of the present invention is represented by the structure set forth in Formula I, wherein n is from 40-55. In some embodiments, the PEG-lipid of the present invention is represented by the structure set forth in Formula I, wherein n is from 40-50. In some embodiments, the PEG-lipid of the present invention is represented by the structure set forth in Formula I, wherein n is from 45-55.

In some embodiments, the PEG-lipid of the present invention is represented by the structure set forth in Formula I, wherein p is 0, 1, or 2. In some embodiments, the PEG-lipid of the present invention is represented by the structure set forth in Formula I, wherein p is 0. In some embodiments, the PEG-lipid of the present invention is represented by the structure set forth in Formula I, wherein p is 1. In some embodiments, the PEG-lipid of the present invention is represented by the structure set forth in Formula I, wherein p is 2.

In some embodiments, the PEG-lipid of the present invention is represented by the structure set forth in Formula I, wherein each X is independently $CH_2$, CHR, $CR_2$, or C═O and each R is independently alkyl, aryl, heteroalkyl, or heteroaryl. In some embodiments, the PEG-lipid of the present invention is represented by the structure set forth in Formula I, wherein each X is $CH_2$. In some embodiments, the PEG-lipid of the present invention is represented by the structure set forth in Formula I, wherein each X is CHR and wherein each R is independently alkyl, aryl, heteroalkyl, or heteroaryl. In some embodiments, the PEG-lipid of the present invention is represented by the structure set forth in Formula I, wherein each X is $CR_2$ and each R is independently alkyl, aryl, heteroalkyl, or heteroaryl.

In some embodiments, the PEG-lipid of the present invention is represented by the structure set forth in Formula I, wherein each Y is independently $CH_2$, CHR, $CR_2$, NH and wherein each R is independently alkyl, aryl, heteroalkyl, or heteroaryl. In some embodiments, the PEG-lipid of the present invention is represented by the structure set forth in Formula I, wherein each Y is $CH_2$. In some embodiments, the PEG-lipid of the present invention is represented by the structure set forth in Formula I, wherein each Y is CHR and wherein each R is independently alkyl, aryl, heteroalkyl, or heteroaryl. In some embodiments, the PEG-lipid of the present invention is represented by the structure set forth in Formula I, wherein each Y is $CR_2$ and each R is independently alkyl, aryl, heteroalkyl, or heteroaryl. In some embodiments, the PEG-lipid of the present invention is represented by the structure set forth in Formula I, wherein each Y is NH.

In some embodiments, the PEG-lipid of the present invention is represented by the structure set forth in Formula I, wherein each Z is independently absent, $CH_2$, or NH. In some embodiments, the PEG-lipid of the present invention is represented by the structure set forth in Formula I, wherein each Z is absent. In some embodiments, the PEG-lipid of the present invention is represented by the structure set forth in Formula I, wherein each Z is $CH_2$. In some embodiments, the PEG-lipid of the present invention is represented by the structure set forth in Formula I, wherein each Z is NH.

In some embodiments, the PEG-lipid of the present invention is represented by the structure set forth in Formula I, wherein each R is independently alkyl, aryl, heteroalkyl, or heteroaryl.

The LNP Adjuvant

Lipid nanoparticle (LNP) adjuvants of the present invention are used herein to boost the immunological response of the HPV vaccine. Generally, LNP adjuvants of the immunological compositions of the present invention include one or more cationic lipids, one or more polymer-lipid conjugates (e.g., a poly(ethylneglycol)-lipid (PEG-lipid)), one or more cholesterol, and one or more phospholipid.

In some embodiments, the LNP adjuvant includes any cationic lipid mentioned in U.S. Patent Application Publication Nos. US 2008/0085870, US 2008/0057080, US 2009/0263407, US 2009/0285881, US 2010/0055168, US 2010/0055169, US 2010/0063135, US 2010/0076055, US 2010/0099738, US 2010/0104629, US 2013/0017239, and US 2016/0361411, International Patent Application Publication Nos. WO2011/022460 A1; WO2012/040184, WO2011/076807, WO2010/021865, WO 2009/132131, WO2010/042877, WO2010/146740, WO2010/105209, and in U.S. Pat. Nos. 5,208,036, 5,264,618, 5,279,833, 5,283,185, 6,890,557, and 9,669,097.

In some embodiments, the LNP adjuvant includes a cationic lipid having the following structure, illustrated by Formula 1:

Formula 1

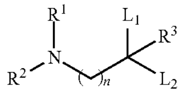

wherein:

$R^1$ and $R^2$ are each methyl;

$R^3$ is H;

n is 1 or 2;

$L_1$ is selected from $C_5$-$C_{24}$ alkyl and $C_5$-$C_{24}$ alkenyl; and $L_2$ is selected from $C_4$-$C_9$ alkyl and $C_4$-$C_9$ alkenyl;

or any pharmaceutically acceptable salt or stereoisomer thereof.

In some embodiments, the cationic lipid is an aminoalkyl lipid. In some embodiments, the cationic lipid is an asymmetric aminoalkyl lipid. In some embodiments, the cationic lipid is (13Z, 16Z)—N, N-dimethyl-3-nonyldocosa 13, 16-dien-1-amine (See, U.S. Pat. No. 9,669,097).

In some embodiments, the LNP adjuvant includes 30-65 mole % cationic lipid. In some embodiments, the LNP adjuvant includes 30-55 mole % cationic lipid. In some embodiments, the LNP adjuvant includes 30-45 mole % cationic lipid. In some embodiments, the LNP adjuvant includes 55-65 mole % cationic lipid. In some embodiments, the LNP adjuvant includes 58 mole % cationic lipid.

In some embodiments, the LNP adjuvant may include a neutral lipid selected from: phospholipids, diaeylphosphatidylcholine, diacylphosphatidyletbanolamine, ceramide, sphingomyelin, cephalin, cholesterol, cerebrosides, diacylglycerols, and combinations thereof. In some embodiments, the neutral lipid may include a phospholipid and cholesterol.

In some embodiments, the neutral lipid may include a sterol, such as cholesterol. In some embodiments, the neutral lipid includes cholesterol. In some embodiments, the LNP adjuvant includes 10-40 mole % cholesterol. In some embodiments, the LNP adjuvant includes 15-25 mole % cholesterol. In some embodiments, the LNP adjuvant includes 10-20 mole % cholesterol. In some embodiments, the LNP includes 20-30 mole % cholesterol. In some embodiments, the LNP adjuvant includes 10-15 mole % cholesterol. In some embodiments, the LNP adjuvant includes 25-35 mole % cholesterol. In some embodiments, the LNP adjuvant includes 30 mole % cholesterol.

In some embodiments, the LNP adjuvant may include a phospholipid selected from: phospholipids, aminolipids and sphingolipids. In some embodiments, the LNP may include a phospholipid selected from: phosphatidylcholine, phosphatidylethanolamine, phosphatidylserine, phosphatidylinositol, phosphatidic acid, palmitoyloleryl phosphatidylcholine, lysophosphatidylcholine, lysophosphatidylethanolamine, dipalmitoylphosphatidylcholine, dioleoylphospbatidylcholine, dstearoylphosphatidylcholine or dilinoleoylphosphatidylcholine. In some embodiments, the LNP adjuvant may include a neutral lipid selected from: sphingolipid, glycosphingolipid families, diacylglycerols and S-acyloxyacids. In some embodiments, the LNP may include a neutral lipid selected from: phosphatidylcholine (PC), phosphatidylethanolamine (PE), and phosphatidylglycerol (PG), phosphatidylserine (PS), phosphatidylinositol (PI), phosphatidic acid (phosphatidate) (PA), dipalmitoylphosphatidylcholine, monoacyl-phosphatidylcholine (lyso PC), 1-palmitoyl-2-oleoyl-sn-glycero-3-phosphocholine (POPC), N-acyl-PE, phosphoinositides, and phosphosphingolipids. In some embodiments, the LNP may include a neutral lipid selected from: phosphatidic acid (DMPA, DPPA, DSPA), phosphatidylcholine (DDPC, DLPC, DMPC, DPPC, DSPC, DOPC, POPC, DEPC), phosphatidylglycerol (DMPG, DPPG, DSPG, POPG), phosphatidylethanolamine (DMPE, DPPE, DSPE DOPE), and phosphatidylserine (DOPS). In some embodiments, the LNP may include a neutral lipid selected from: fatty acids include C14:0, palmitic acid (C16:0), stearic acid (C18:0), oleic acid (C18:1), linoleic acid (C18:2), linolenic acid (C18:3), arachidonic acid (C20:4), C20:0, C22:0 and lecithin. In some embodiments, the phospholipid may include 1,2-Distearoyl-sn-glycero-3-phosphocholine (DSPC). In some embodiments, the phospholipid may include a diether DSPC (e.g. (2R)-2,3-Bis(octadecyloxy)propyl 2-(trimethylazaniumyl)ethyl phosphate) In some embodiments, the phospholipid of the present invention is represented by the structure set forth in Formula 2, Formula 2

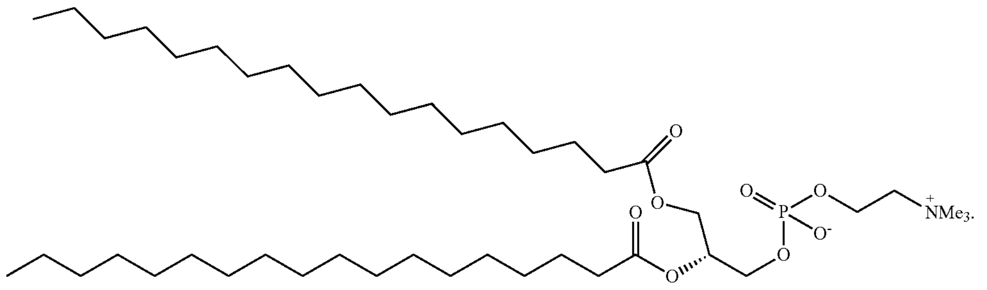

In some embodiments, the phospholipid of the present invention is represented by the structure set forth in Formula 3:

Formula 3

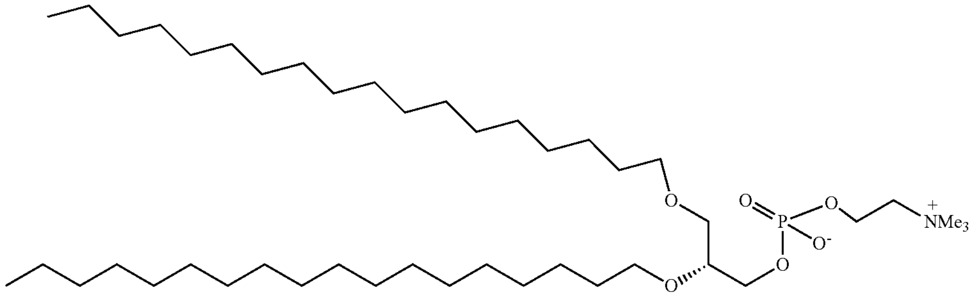

In some embodiments, the phospholipid of the present invention is represented by the structure set forth in Formula 4:

Formula 4

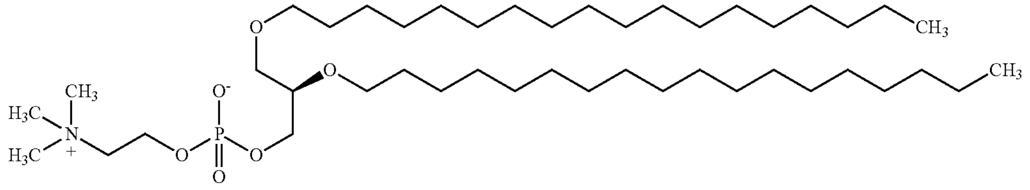

In some embodiments, the neutral lipid may include a phospholipid. In some embodiments, the LNP adjuvant includes 5-30 mole % phospholipid. In some embodiments, the LNP adjuvant includes 5-15 mole % phospholipid. In some embodiments, the LNP includes 10-20 mole % phospholipid. In some embodiments, the LNP adjuvant includes 20-30 mole % phospholipid. In some embodiments, the LNP adjuvant includes 10-15 mole % phospholipid. In some embodiments, the LNP adjuvant includes 25-30 mole % phospholipid. In some embodiments, the LNP adjuvant includes 10 mole % phospholipid.

In some embodiments, the polymer-lipid conjugate includes a PEG-lipid. In some embodiments the PEG is conjugated to the lipid via a direct linkage (see, e.g., cPEG2000-DMG described below) or is conjugated to the lipid via a linker (see, e.g., ePEG2000-DMG). In some embodiments, the PEG-lipid is conjugated to a diacylglycerol (a PEG-DAG). In some embodiments, the PEG is conjugated to DAG as described in, e.g., U.S. Patent Publication Nos. 2003/0077829 and 2005/008689. In one embodiment, the PEG-DAG conjugate is a PEG dimyristylglycerol (c14) conjugate. In some embodiments, the PEG-lipid is PEG-dimyristolglycerol (PEG-DMG).

In certain embodiments, the PEG-lipid is PEG conjugated to dimyristoylglycerol (PEG-DMG), e.g., as described in Abrams et al., 2010, Molecular Therapy 18(1):171, and U.S. Patent Application Publication Nos. US 2006/0240554 and US 2008/0020058.

In certain embodiments, the PEG-lipid comprises a polyethylene glycol having an average molecular weight ranging from about 500 daltons to about 10,000 daltons, from about 75 daltons to about 5,000 daltons, from about 1,000 daltons to about 5,000 daltons, from about 1,500 daltons to about 3,000 daltons or of about 2,000 daltons. In certain embodiments, the PEG-lipid comprises PEG1500, PEG2000 or PEG5000.

In some embodiments, the LNP includes 0.05-5 mole % polymer-lipid conjugate. In some embodiments, the LNP includes 1-4 mole % polymer-lipid conjugate. In some embodiments, the LNP includes 0.5-2 mole % polymer-lipid conjugate. In some embodiments, the LNP includes 1-4 mole % polymer-lipid conjugate. In some embodiments, the LNP includes 1-3 mole % polymer-lipid conjugate. In some embodiments, the LNP includes 1-2.5 mole % polymer-lipid conjugate. In some embodiments, the LNP includes 2 mole % polymer-lipid conjugate. In each case, it is expressed as total mole % of lipid in the particle.

In some embodiments, the LNP adjuvant includes 30-65 mole % cationic lipid, 10-30 mole % cholesterol, 5-30 mole % phospholipid, and 0.05-4 mole % PEG-lipid. In some embodiments, the LNP adjuvant includes 55-65 mole % cationic lipid, 25-35 mole % cholesterol, 5-15 mole % phospholipid, and 1-2.5 mole % PEG-lipid. In some embodiments, the LNP adjuvant includes 40-50 mole % cationic lipid, 15-20 mole % cholesterol, 18-20 mole % phospholipid, and 1.5-2.5 mole % PEG-lipid. In some embodiments, the LNP adjuvant includes 56-59 mole % cationic lipid, 15-20 mole % cholesterol, 18-20 mole % phospholipid, and 0.5-1.5 mole % PEG-lipid. In some embodiments, the LNP adjuvant includes 56-59 mole % cationic lipid, 28-32 mole % cholesterol, 8-12 mole % phospholipid, and 1-3 mole % PEG-lipid. In some embodiments, the LNP adjuvant includes 58 mole % cationic lipid, 30 mole % cholesterol, 10 mole % PEG-lipid and 2 mole % PEG-lipid.

In some embodiments, the LNP includes a PEG-lipid represented by the structure set forth in Formula:

(I)

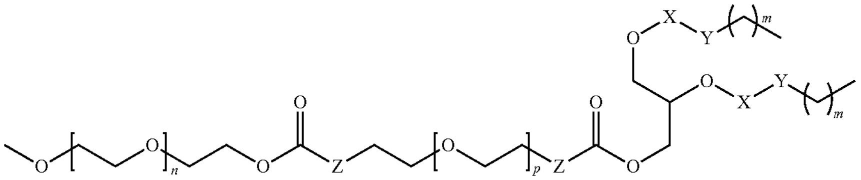

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently alkyl, aryl, heteroalkyl, or heteroaryl.

In some embodiments, the LNP includes a PEG-lipid represented by the structure set forth in Formula I, wherein each m is independently from 8-18. In some embodiments, the PEG-lipid of the present invention is represented by the structure set forth in Formula I, wherein each m is independently from 10-15. In some embodiments, the PEG-lipid of the present invention is represented by the structure set forth in Formula I, wherein each m is independently from 12-15. In some embodiments, the PEG-lipid of the present invention is represented by the structure set forth in Formula I, wherein each m is independently 10, 11, 12, 13, 14, 15, 16, 17, 18, 19, or 20.

In some embodiments, the LNP includes a PEG-lipid represented by the structure set forth in Formula I, wherein n is from 20-60. In some embodiments, the PEG-lipid of the present invention is represented by the structure set forth in Formula I, wherein n is from 20-50. In some embodiments, the PEG-lipid of the present invention is represented by the structure set forth in Formula I, wherein n is from 20-45. In some embodiments, the PEG-lipid of the present invention is represented by the structure set forth in Formula I, wherein n is from 30-60. In some embodiments, the PEG-lipid of the present invention is represented by the structure set forth in Formula I, wherein n is from 30-50. In some embodiments, the PEG-lipid of the present invention is represented by the structure set forth in Formula I, wherein n is from 30-45. In some embodiments, the PEG-lipid of the present invention is represented by the structure set forth in Formula I, wherein n is from 35-60. In some embodiments, the PEG-lipid of the present invention is represented by the structure set forth in Formula I, wherein n is from 35-50. In some embodiments, the PEG-lipid of the present invention is represented by the structure set forth in Formula I, wherein n is from 35-45. In some embodiments, the PEG-lipid of the present invention is represented by the structure set forth in Formula I, wherein n is from 40-60. In some embodiments, the PEG-lipid of the present invention is represented by the structure set forth in Formula I, wherein n is from 40-55. In some embodiments, the PEG-lipid of the present invention is represented by the structure set forth in Formula I, wherein n is from 40-50. In some embodiments, the PEG-lipid of the present invention is represented by the structure set forth in Formula I, wherein n is from 40-55.

In some embodiments, the LNP includes a PEG-lipid represented by the structure set forth in Formula I, wherein p is 0, 1, or 2. In some embodiments, the PEG-lipid of the present invention is represented by the structure set forth in Formula I, wherein p is 0. In some embodiments, the PEG-lipid of the present invention is represented by the structure set forth in Formula I, wherein p is 1. In some embodiments, the PEG-lipid of the present invention is represented by the structure set forth in Formula I, wherein p is 2.

In some embodiments, the LNP includes a PEG-lipid represented by the structure set forth in Formula I, wherein each X is independently $CH_2$, CHR, $CR_2$, or C═O and each R is independently alkyl, aryl, heteroalkyl, or heteroaryl. In some embodiments, the PEG-lipid of the present invention is represented by the structure set forth in Formula I, wherein each X is $CH_2$. In some embodiments, the PEG-lipid of the present invention is represented by the structure set forth in Formula I, wherein each X is CHR and wherein each R is independently alkyl, aryl, heteroalkyl, or heteroaryl. In some embodiments, the PEG-lipid of the present invention is represented by the structure set forth in Formula I, wherein each X is $CR_2$ and each R is independently alkyl, aryl, heteroalkyl, or heteroaryl.

In some embodiments, the LNP includes a PEG-lipid represented by the structure set forth in Formula I, wherein each Y is independently $CH_2$, CHR, $CR_2$, NH and wherein each R is independently alkyl, aryl, heteroalkyl, or heteroaryl. In some embodiments, the PEG-lipid of the present invention is represented by the structure set forth in Formula I, wherein each Y is independently $CH_2$. In some embodiments, the PEG-lipid of the present invention is represented by the structure set forth in Formula I, wherein each Y is CHR and wherein each R is independently alkyl, aryl, heteroalkyl, or heteroaryl. In some embodiments, the PEG-lipid of the present invention is represented by the structure set forth in Formula I, wherein each Y is $CR_2$ and each R independently is alkyl, aryl, heteroalkyl, or heteroaryl. In some embodiments, the PEG-lipid of the present invention is represented by the structure set forth in Formula I, wherein each Y is NH.

In some embodiments, the LNP includes a PEG-lipid represented by the structure set forth in Formula I, wherein each Z is independently absent, $CH_2$, or NH. In some embodiments, the PEG-lipid of the present invention is represented by the structure set forth in Formula I, wherein each Z is absent. In some embodiments, the PEG-lipid of the present invention is represented by the structure set forth in Formula I, wherein each Z is $CH_2$. In some embodiments, the PEG-lipid of the present invention is represented by the structure set forth in Formula I, wherein each Z is NH.

In some embodiments, the LNP includes a PEG-lipid represented by the structure set forth in Formula I, wherein each R is independently alkyl, aryl, heteroalkyl, or heteroaryl.

In some embodiments, the LNP includes a PEG-lipid represented by the structure set forth as Compound 1:

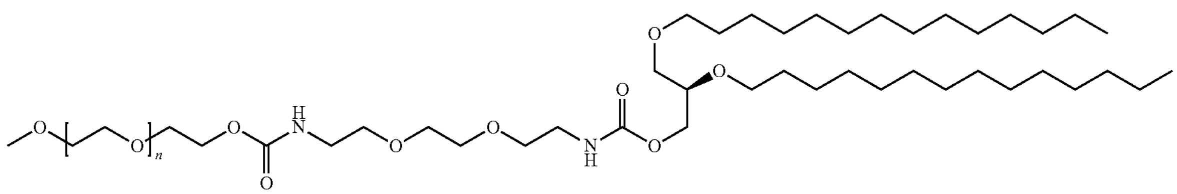

In some embodiments, the LNP includes a PEG-lipid represented by the structure set forth as Compound 2:

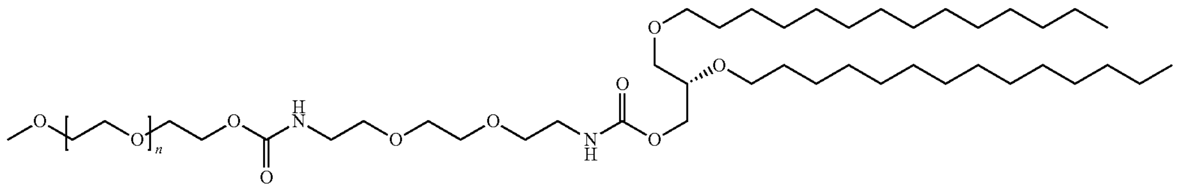

In some embodiments, the LNP includes a PEG-lipid represented by the structure set forth as Compound 3:

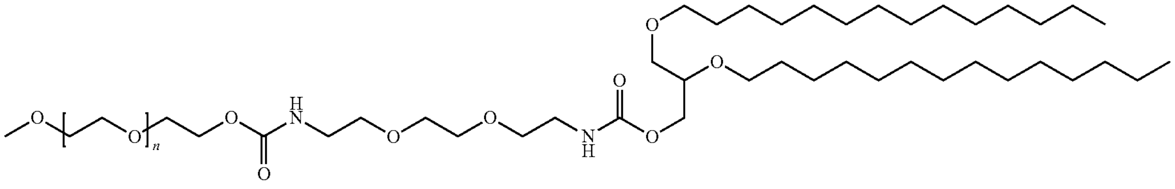

In some embodiments, the LNP includes a PEG-lipid represented by the structure set forth as Compound 4:

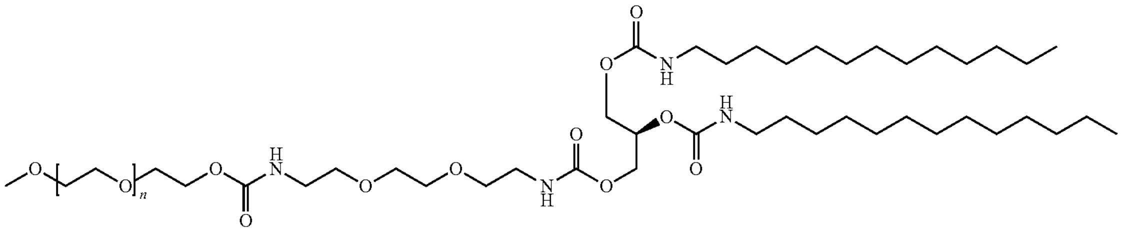

In some embodiments, the LNP includes a PEG-lipid represented by the structure set forth as Compound 5:

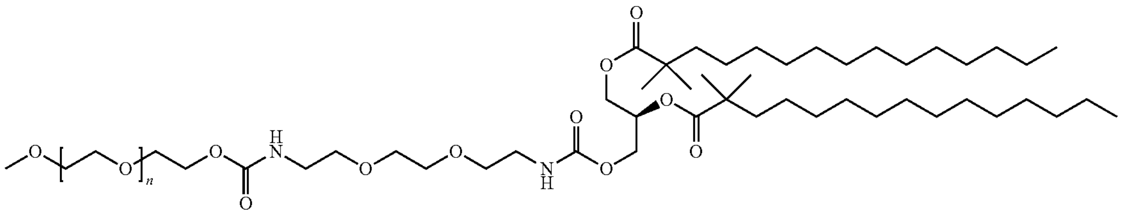

In some embodiments, the LNP includes a PEG-lipid represented by the structure set forth as Compound 6:

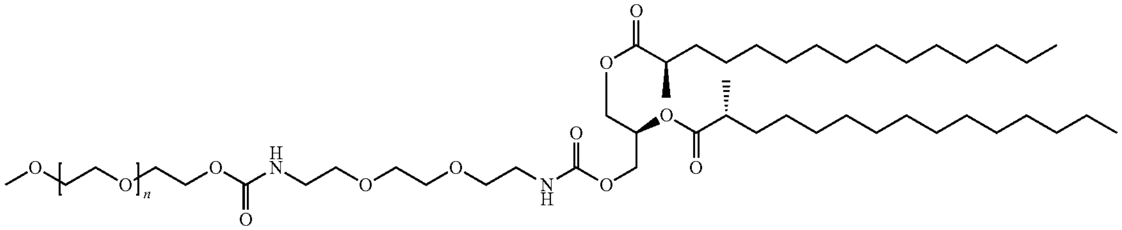

In some embodiments, the LNP includes a PEG-lipid represented by the structure set forth as Compound 7:

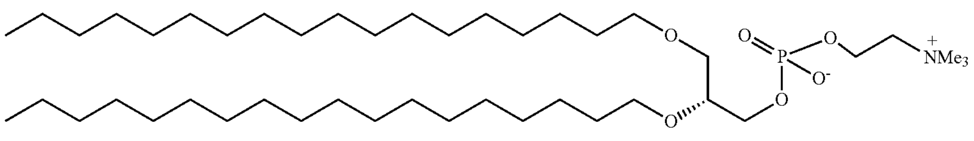

In some embodiments, the LNP adjuvant may include a buffer. In some embodiments, the buffer may be selected from any pharmaceutically acceptable buffer, including acetic acid, histidine, citrate, Bis-Tris, HEPES, phosphate, MES, and combinations thereof. In some embodiments, the buffer may be present in the amount of 1 mMol to about 100 mMol.

In some embodiments, the LNP adjuvant may include a tonicity modifier. In some embodiments, the tonicity modifier may be selected from any pharmaceutically acceptable tonicity modifier, such as sodium chloride, potassium chloride, sucrose, trehalose and combinations thereof. In some embodiments the tonicity modifier is present in the amount of 10 mM to 500 mM.

In some embodiments, the LNP adjuvant includes a cryoprotectant. In some embodiments, the cryoprotectant is selected from any pharmaceutically acceptable cryoprotectant, such as sucrose, trehalose, mannitol, glycerol, and the like, and combinations thereof. In some embodiments, the cryoprotectant is present in the amount of 0.1 to about 10% (w/v).

In some embodiments, LNP adjuvants of the present invention exhibit physical stability, (e.g. particle size is maintained) and chemical stability (e.g. lipids do not undergo hydrolysis) when subjected to various times and temperatures. In some embodiments, LNP formulations of the present invention exhibit physical stability for at least 1 month at 37° C. In some embodiments, LNP formulations of the present invention exhibit chemical stability for at least 1 month at 37° C. In some embodiments, LNP formulations of the present invention exhibit physical and chemical stability for at least 1 month at 37° C. In some embodiments, LNP formulations of the present invention exhibit physical stability for at least 6 months at 25° C. In some embodiments, LNP formulations of the present invention exhibit chemical stability for at least 6 months at 25° C. In some embodiments, LNP formulations of the present invention exhibit physical and chemical stability for at least 6 months at 25° C. In some embodiments, LNP formulations of the present invention exhibit physical stability for at least 3 years at 2-8° C. In some embodiments, LNP formulations of the present invention exhibit chemical stability for at least 3 years at 2-8° C. In some embodiments, LNP formulations of the present invention exhibit physical and chemical stability for at least 3 years at 2-8° C.

Methods of Making LNP Adjuvants

In some embodiments, the LNP adjuvants are formed, for example, by a rapid precipitation process that entails micromixing the lipid components dissolved in a lower alkanol solution (e.g. ethanol) with an aqueous solution using a confined volume mixing apparatus such as a confined volume T-mixer, a multi-inlet vortex mixer, microfluidics mixer devices, or other mixer. The lipid solution may include one or more cationic lipids, one or more neutral lipid (e.g., phospholipids, DSPC, cholesterol), and one or more polymer-lipid conjugate (e.g. cPEG2000-DMG, cPEG-2000-DMG(s), ePEG2000-DMG, ether-ePEG2000-DMG) at specific molar ratios in ethanol.

In some embodiments, the aqueous and organic solutions are optionally heated to a temperature in the range of 25° C.-45° C., preferably 30° C.-40° C., and then mixed in a confined volume mixer to form the LNP. When a confined volume T-mixer is used, the T-mixer may have an internal diameter range from 0.25 to 10.0 mm. In some embodiments, the alcohol and aqueous solutions are delivered to the inlet of the T-mixer using programmable syringe pumps, and with a total flow rate from 10 mL/min-600 L/minute. In some embodiments, the aqueous and alcohol solutions are combined in the confined-volume mixer with a ratio in the range of 1:1 to 4:1 vol: vol. In some embodiments, the aqueous and alcohol solutions are combined at a ratio in the range of 1.1:1 to 4:1, 1.2:1 to 4:1, 1.25:1 to 4:1, 1.3:1 to 4:1, 1.5:1 to 4:1, 1.6:1 to 4:1, 1.7:1 to 4:1, 1.8:1 to 4:1, 1.9:1 to 4:1, 2.0:1 to 4:1, 2.5:1 to 4:1, 3.0:1 to 4:1, and 3.5:1 to 4:1.

In some embodiments, the combination of ethanol volume fraction, solution flow rates, lipid(s) concentrations, mixer configuration and internal diameter, and mixer tubing internal diameter utilized at this mixing stage provide LNPs having a particle size between 30 and 300 nm. The resulting LNP suspension may be diluted into higher pH buffers in the range of 6-8. In some embodiments, the diluted suspension is further diluted with an additional buffer, such as phosphate buffered saline having a pH between 6-8.

In some embodiments, the LNPs are also concentrated and filtered via an ultrafiltration process to remove the alcohol. In some embodiments, the high pH buffer is also removed and exchanged for a final buffer solution. In some embodiments, the final buffer solution is selected from a phosphate buffered saline or any buffer system suitable for cryopreservation (for example, buffers containing sucrose, trehalose or combinations thereof). Following filtration, the vialed LNP product may be stored under suitable storage conditions (such as, 2° C.-8° C., or −80 to −20° C. if frozen) or may be lyophilized.

In some embodiments, the ultrafiltration process includes a tangential flow filtration format ("TFF") that utilizes a hollow fiber membrane nominal molecular weight cutoff range from 30-500 KD, targeting 500 KD. In some embodiments, the TFF retains the LNP in the retentate and the filtrate or permeate contains the alcohol and final buffer wastes. In some embodiments, the TFF provides an initial LNP concentration of 1-100 mg/mL. Following initial concentration, the LNP adjuvant may be diafiltered against the final buffer (for example, phosphate buffered saline "PBS") to remove the alcohol and perform buffer exchange. The material may then be concentrated via ultrafiltration to a final desired concentration.

In some embodiments, the concentrated LNP adjuvant is then filtered to reduce bioburden into a suitable container under aseptic conditions. In some embodiments, the bioburden reduced filtration (BRF) is accomplished by passing the LNP suspension through a pre-filter (Sartobran P 0.45μιη capsule) and a bioburden reduction filter (Sartobran P 0.2μιη capsule). Following filtration, the LNP adjuvant bulk intermediate (ABI) may be stored under suitable conditions.

The VLPs

As stated above, the pharmaceutical compositions and formulations of the present invention comprise at least one HPV VLP type, such as HPV 16 or 18. In particular embodiments of the compositions disclosed herein, the vaccine further comprises VLPs of at least one additional HPV type. In further embodiments, the at least one additional HPV type is selected from the group consisting of 6, 11, 16, 18, 26, 31, 33, 35, 39, 45, 51, 52, 53, 55, 56, 58, 59, 66, 68, 69, 70, 73, and 82. In some embodiments, the at least one additional HPV type includes HPV 16 and 18. In some embodiments, the at least one additional HPV type includes HPV 6, 11, 16, and 18. In some embodiments, the at least one additional HPV type includes HPV 6, 18, 52, and 58. In some embodiments, the at least one additional HPV type includes HPV 6, 11, 16, 18, 31, 45, 52, and 58. In some embodiments, the at least one additional HPV type includes HPV 6, 11, 16, 18, 33, 45, 52, and 58. In some embodiments, the at least one additional HPV type includes HPV 6, 11, 16, 18, 31, 33, 45, 52, and 58. In some embodiments, the at least one additional HPV type includes 6, 11, 16, 18, 31, 33, 45, 52, and 59. In some embodiments, the at least one additional HPV type includes HPV 6, 11, 16, 18, 31, 33, 45, 53, and 58. In some embodiments, the at least one additional HPV type includes HPV 6, 11, 16, 18, 31, 33, 45, 53, and 59. In some embodiments, the at least one additional HPV type includes HPV 6, 11, 16, 18, 31, 33, 35, 45, 52, and 58. In some embodiments, the at least one additional HPV type includes HPV 6, 11, 16, 18, 31, 33, 35, 45, 52, 58, and 59. In some embodiments, the at least one additional HPV type includes HPV 6, 11, 16, 18, 31, 33, 45, 52, 58, 59, and 68. In some embodiments, the at least one additional HPV type includes HPV 6, 11, 16, 18, 31, 33, 35, 39, 45, 51, 52, 56, 58, and 59. In some embodiments, the at least one additional HPV type includes HPV 6, 11, 16, 18, 26, 31, 33, 35, 45, 51, 52, 58, 59, and 69. In some embodiments, the at least one additional HPV type includes HPV 6, 11, 16, 18, 26, 31, 33, 35, 39, 45, 51, 52, 58, 59, 68, 69, and 70. In some embodiments, the at least one additional HPV type includes HPV 6, 11, 16, 18, 26, 31, 33, 35, 39, 45, 51, 52, 53, 56, 58, 59, 66, 68, 69, and 70.

The pharmaceutical compositions of the present invention comprise HPV VLPs comprised of recombinant L1 or recombinant L1+L2 proteins of HPV. HPV L1 or L1+L2 protein can be expressed recombinantly by molecular cloning of L1 or L1+L2 DNA into an expression vector containing a suitable promoter and other appropriate transcription regulatory elements, and transferred into prokaryotic or eukaryotic host cells to produce recombinant protein. Techniques for such manipulations are fully described by Sambrook et al. (Molecular Cloning: A Laboratory Manual; Cold Spring Harbor Laboratory, Cold Spring Harbor, New York, (1989)), which is hereby incorporated by reference. VLPs can self-assemble when L1 protein is recombinantly expressed in a host cell.

The recombinant HPV L1 proteins of the present invention may be any full-length L1 protein sequence that can be found in nature or any mutated or truncated L1 protein that is capable of self-assembling into VLPs. In particular embodiments of the invention, the pharmaceutical compositions and vaccines described herein comprise HPV VLPs comprised of recombinant HPV L1 protein and do not contain HPV L2 protein. In certain embodiments, the vaccine compositions or pharmaceutical compositions described herein comprise HPV VLPs comprised of a full-length recombinant HPV L1 protein. In other embodiments, the HPV VLPs are comprised of truncated HPV L1 protein, e.g., L1 protein that are truncated at the C-terminal end. L1 protein sequences for use in the present invention can be determined by isolating DNA from one or more clinical samples containing an HPV type of choice, determining the sequence of the HPV L1 DNA sequence, and translating the DNA sequence into an amino acid sequence using the genetic code. Many exemplary L1 sequences suitable for use in the present invention can be found in the literature. See, e.g., U.S. Pat. Nos. 5,820,870; 7,250,170; 7,276,243; 7,482,428; 7,976,848; 7,498,036; 7,700,103; 7,744,892; and 5,437,951; Kirii et al. (Virology 185(1): 424-427 (1991)). Further L1 proteins that are useful in the compositions and formulations of the present invention include biologically active fragments and/or mutants of an HPV L1 sequence, including but not necessarily limited to amino acid substitutions, deletions, additions, amino terminal truncations and carboxy-terminal truncations, such that these mutations provide for L1 proteins or protein fragments that are capable of forming a VLP. See, e.g., International Publication WO 2006/114312 and U.S. Pat. No. 6,599,508. Appropriate host cells for the expression of recombinant HPV L1 or recombinant L1+L2 and subsequent self-assembly of VLPs include, but are not limited to yeast cells, insect cells, mammalian cells or bacteria. In exemplary embodiments of the invention, the VLPs are produced in yeast cells such as a yeast selected from the group consisting of: *Saccharomyces cerevisiae, Hansenula polymorpha, Pichia pastoris, Kluyvermyces fragilis, Kluveromyces lactis*, and *Schizosaccharomyces pombe*. In particular embodiments, the HPV VLPs are produced in *Saccharomyces cerevisiae* cells.

Expression of HPV VLPs in yeast cells offers the advantages of being cost-effective and easily adapted to large-scale growth in fermenters.

The present invention also includes pharmaceutical compositions comprising mutant forms of HPV VLPs, such as HPV VLPs that comprise biologically active fragments and/or mutants of an HPV L1 or L2 protein, including but not necessarily limited to amino acid substitutions, deletions, additions, amino terminal truncations and carboxy-terminal truncations such that these mutations provide for proteins or protein fragments of therapeutic or prophylactic use and would be useful for HPV VLP vaccine development. Any such mutant form of an HPV L1 protein should be capable of forming VLPs and of provoking an immune response against the desired HPV type when administered to a human.

Additionally, one of skill in the art will recognize that the HPV L1 or L1+L2 proteins, which are used to self-assemble VLPs for inclusion in the compositions disclosed herein, may be encoded by a full-length wild-type HPV L1 or L2 polynucleotide, or may be encoded by a fragment or mutant of the known wild-type sequence. Wild-type polynucleotide sequences that encode mRNA expressing HPV L1 or L2 protein are available in the art. Any mutant polynucleotide will encode either a protein or protein fragment which at least substantially mimics the pharmacological properties of an HPV L1 or L1+L2 protein, including the ability to form VLPs that are able to provoke an immune response against the HPV type of interest when administered to a human. Any such polynucleotide includes but is not necessarily limited to: nucleotide substitutions, deletions, additions, amino-terminal truncations and carboxy-terminal truncations.

The amount of virus-like particles of each HPV type to be included in the formulations and compositions of the present invention will depend on the immunogenicity of the expressed gene product. In general, a therapeutically effective dose of VLPs of any of the at least one HPV type is about 1 μg to about 300 μg. In some embodiments, a therapeutically effective dose of VLPs of any of the at least one HPV type is about 1 μg to 200 μg. In some embodiments, a therapeutically effective dose of VLPs of any of the at least one HPV type is about 1 μg to 100 μg. In some embodiments, a therapeutically effective dose of VLPs of any of the at least one HPV type is about 10 μg to 200 μg. In some embodiments, a therapeutically effective dose of VLPs of any of the at least one HPV type is about 10 μg to 100 μg. In some embodiments, a therapeutically effective dose of VLPs of any of the at least one HPV type is about 10 μg to 80 μg. In some embodiments, a therapeutically effective dose of VLPs of any of the at least one HPV type is about preferably about 20 μg to 60 μg.

In some embodiments, a dose of a composition or vaccine including VLPs of the at least one HPV type includes:

15-160 μg of VLPs of HPV Type 6 L1 protein, 20-200 μg of VLPs of HPV Type 11 L1 protein, 30-280 μg of VLPs of HPV Type 16 L1 protein, 20-200 μg of VLPs of HPV Type 18 L1 protein,
10-120 μg of VLPs of HPV Type 31 L1 protein,
10-120 μg of VLPs of HPV Type 33 L1 protein,
10-120 μg of VLPs of HPV Type 45 L1 protein,
10-120 μg of VLPs of HPV Type 52 L1 protein, and
10-120 μg of VLPs of HPV Type 58 L1 protein.

In some embodiments, a dose of a composition or vaccine including VLPs of the at least one HPV type includes:
15-120 μg of VLPs of HPV Type 6 L1 protein,
20-150 μg of VLPs of HPV Type 11 L1 protein,
30-210 μg of VLPs of HPV Type 16 L1 protein,
20-150 μg of VLPs of HPV Type 18 L1 protein,
10-90 μg of VLPs of HPV Type 31 L1 protein,
10-90 μg of VLPs of HPV Type 33 L1 protein,
10-90 μg of VLPs of HPV Type 45 L1 protein,
10-90 μg of VLPs of HPV Type 52 L1 protein, and
10-90 μg of VLPs of HPV Type 58 L1 protein.

In some embodiments, a dose of a composition or vaccine including VLPs of the at least one HPV type includes:
15-80 μg of VLPs of HPV Type 6 L1 protein,
20-100 μg of VLPs of HPV Type 11 L1 protein,
30-140 μg of VLPs of HPV Type 16 L1 protein,
20-100 μg of VLPs of HPV Type 18 L1 protein,
10-60 μg of VLPs of HPV Type 31 L1 protein,
10-60 μg of VLPs of HPV Type 33 L1 protein,
10-60 μg of VLPs of HPV Type 45 L1 protein,
10-60 μg of VLPs of HPV Type 52 L1 protein, and
10-60 μg of VLPs of HPV Type 58 L1 protein.

In some embodiments, a dose of a composition or vaccine including VLPs of the at least one HPV type includes:
15-40 μg of VLPs of HPV Type 6 L1 protein,
20-50 μg of VLPs of HPV Type 11 L1 protein,
30-70 μg of VLPs of HPV Type 16 L1 protein,
20-50 μg of VLPs of HPV Type 18 L1 protein,
10-30 μg of VLPs of HPV Type 31 L1 protein,
10-30 μg of VLPs of HPV Type 33 L1 protein,
10-30 μg of VLPs of HPV Type 45 L1 protein,
10-30 μg of VLPs of HPV Type 52 L1 protein, and
10-30 μg of VLPs of HPV Type 58 L1 protein.

In some embodiments, a dose of a composition or vaccine including VLPs of the at least one HPV type includes:
90 μg of VLPs of HPV Type 6 L1 protein,
120 μg of VLPs of HPV Type 11 L1 protein,
180 μg of VLPs of HPV Type 16 L1 protein,
120 μg of VLPs of HPV Type 18 L1 protein,
60 μg of VLPs of HPV Type 31 L1 protein,
60 μg of VLPs of HPV Type 33 L1 protein,
60 μg of VLPs of HPV Type 45 L1 protein,
60 μg of VLPs of HPV Type 52 L1 protein, and
60 μg of VLPs of HPV Type 58 L1 protein.

In some embodiments, a dose of a composition or vaccine including VLPs of the at least one HPV type includes:
60 μg of VLPs of HPV Type 6 L1 protein,
80 μg of VLPs of HPV Type 11 L1 protein,
120 μg of VLPs of HPV Type 16 L1 protein,
80 μg of VLPs of HPV Type 18 L1 protein,
40 μg of VLPs of HPV Type 31 L1 protein,
40 μg of VLPs of HPV Type 33 L1 protein,
40 μg of VLPs of HPV Type 45 L1 protein,
40 μg of VLPs of HPV Type 52 L1 protein, and
40 μg of VLPs of HPV Type 58 L1 protein.

In some embodiments, a dose of a composition or vaccine including VLPs of the at least one HPV type includes:
30 μg of VLPs of HPV Type 6 L1 protein,
40 μg of VLPs of HPV Type 11 L1 protein,
60 μg of VLPs of HPV Type 16 L1 protein,
40 μg of VLPs of HPV Type 18 L1 protein,
20 μg of VLPs of HPV Type 31 L1 protein,
20 μg of VLPs of HPV Type 33 L1 protein,
20 μg of VLPs of HPV Type 45 L1 protein,
20 μg of VLPs of HPV Type 52 L1 protein, and
20 μg of VLPs of HPV Type 58 L1 protein.

In some embodiments of the formulations and compositions of the invention, a dose of composition is formulated in a total volume of 0.5 mL. In some embodiments of the formulations and compositions of the invention, a dose of composition is formulated in a different volume (i.e., the volume of each dose is greater than or less than 0.5 mL), but contains the same amount of HPV VLPs of any of the embodiments described herein (e.g., a composition of the invention may be formulated as a 0.2, mL, 0.3 mL, 0.4 mL, 0.5 mL, 0.6 mL, or 0.7 mL dose containing 30 μg of VLPs of HPV Type 6 L1 protein, 40 μg of VLPs of HPV Type 11 L1 protein, 60 μg of VLPs of HPV Type 16 L1 protein, 40 μg of VLPs of HPV Type 18 L1 protein, 20 μg of VLPs of HPV Type 31 L1 protein, 20 μg of VLPs of HPV Type 33 L1 protein, 20 μg of VLPs of HPV Type 45 L1 protein, 20 μg of VLPs of HPV Type 52 L1 protein, 20 μg of VLPs of HPV Type 58 L1 protein).

The Aluminum Adjuvant

The aluminum adjuvant of the present invention may be in the form of aluminum hydroxide ($Al(OH)_3$), aluminum phosphate ($AlPO_4$), aluminum hydroxyphosphate, amorphous aluminum hydroxyphosphate sulfate (AAHS) or so-called "alum" ($KAl(SO_4)$-$12H_2O$) (see Klein et al., Analysis of aluminum hydroxyphosphate vaccine adjuvants by (27) Al MAS NMR., J Pharm. Sci. 89(3): 311-21 (2000)). In exemplary embodiments of the invention provided herein, the aluminum adjuvant is aluminum hydroxyphosphate or AAHS. The ratio of phosphate to aluminum in the aluminum adjuvant can range from 0 to 1.3. In some embodiments of this aspect of the invention, the phosphate to aluminum ratio is within the range of 0.1 to 0.70. In other embodiments, the phosphate to aluminum ratio is within the range of 0.2 to 0.50.

In some embodiments of the invention, the aluminum adjuvant is in the form of AAHS. AAHS carries zero charge at neutral pH, while $Al(OH)_3$ carries a net positive charge and $AlPO_4$ typically carries a net negative charge at neutral pH. AAHS has a higher capacity to bind HPV VLPs than $Al(OH)_3$. In addition, VLPs adsorbed to AAHS can induce a greater humoral immune response in mice than VLPs adsorbed to $Al(OH)_3$ (Caulfield et al., Human Vaccines 3: 139-146 (2007)). While not wishing to be bound by theory, it is possible that net charge of the aluminum adjuvant can affect its ability to bind the VLP antigen, with strongly charged adjuvants unable to bind antigen as strongly as neutral charged adjuvants. For this reason, it is preferred that the aluminum adjuvant of the pharmaceutical compositions of the present invention have zero point surface charge at neutral pH. One of skill in the art will be able to vary the buffer, salt concentration and/or percent of free phosphate in order to allow a zero point surface charge at neutral pH.

One of skill in the art will be able to determine an optimal dosage of aluminum adjuvant that is both safe and effective at increasing the immune response to the targeted HPV type(s). For a discussion of the safety profile of aluminum, as well as amounts of aluminum included in FDA-licensed vaccines, see Baylor et al., Vaccine 20: S18-S23 (2002). In some embodiments, the aluminum adjuvant is present in an amount of about 100 to 3600 μg/dose (200 to 7200 μg/mL concentration). In some embodiments, the aluminum adjuvant is present in an amount of about 100 to 2700 μg/dose (200 to 5400 μg/mL concentration). In some embodiments, the aluminum adjuvant is present in an amount of about 100 to 1800 μg/dose (200 to 3600 μg/mL concentration). In some embodiments, the aluminum adjuvant is present in an amount of about 100 to 900 μg/dose (200 to 1800 μg/mL concentration). In some embodiments of the formulations and compositions of the present invention, there is between 200 and 300 μg aluminum adjuvant per dose of vaccine. In alternative embodiments of the formulations and compositions of the present invention, there is between 300 and 500 μg aluminum adjuvant per dose of vaccine. In alternative embodiments of the formulations and compositions of the present invention, there is between 400 and 1200 μg aluminum adjuvant per dose of vaccine. In alternative embodiments of the formulations and compositions of the present invention, there is between 1200 and 2000 μg aluminum adjuvant per dose of vaccine. In some embodiments of the formulations and compositions of the present invention, there is less than 2000 μg aluminum adjuvant per dose of vaccine. In some embodiments of the formulations and compositions of the present invention, there is less than 1500 μg aluminum adjuvant per dose of vaccine. In some embodiments of the formulations and compositions of the present invention, there is less than 1000 μg aluminum adjuvant per dose of vaccine. In some embodiments of the formulations and compositions of the present invention, there is less than 500 μg aluminum adjuvant per dose of vaccine. In some embodiments of the formulations and compositions of the present invention, there is less than 400 μg aluminum adjuvant per dose of vaccine. In some embodiments of the formulations and compositions of the present invention, there is less than 300 μg aluminum adjuvant per dose of vaccine. In some embodiments of the formulations and compositions of the present invention, there is less than 200 μg aluminum adjuvant per dose of vaccine. In some embodiments of the formulations and compositions of the present invention, there is less than 100 μg aluminum adjuvant per dose of vaccine.

The HPV VLP-Based Vaccine

Any HPV VLP-based vaccine, including known HPV VLP vaccines, can be modified to include both an aluminum adjuvant and an LNP adjuvant for use in the pharmaceutical compositions and methods of the present invention. In some embodiments, an HPV vaccine is modified to include an aluminum adjuvant and an LNP adjuvant that comprises a PEG-lipid having the structure set forth in Formula I (I)

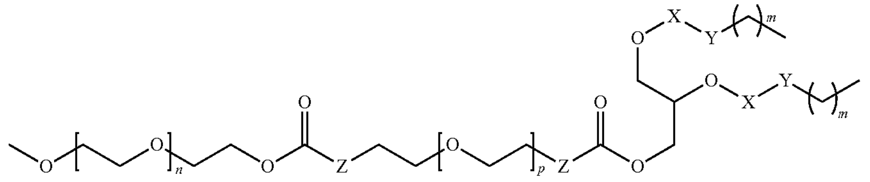

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl, and a diether-DSPC having a structure according to Formula (III)

(III)

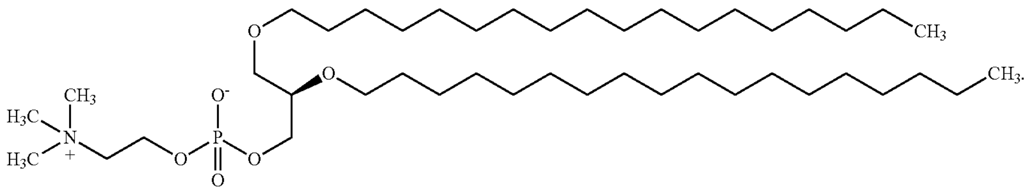

New vaccines can be developed according to the invention described herein that comprise antigens of at least one HPV type, optionally in the form of an HPV VLP adsorbed to an aluminum adjuvant, in combination with an LNP adjuvant comprising PEG-lipid having the structure set forth in Formula I (I)

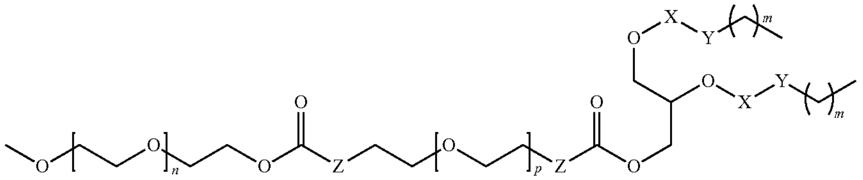

wherein:
each m is independently from 5-20;
n is from 20-60;
p is 0, 1, or 2;
each X is independently $CH_2$, CHR, $CR_2$, or C═O;
each Y is independently $CH_2$, CHR, $CR_2$, or NH;
each Z is independently absent, $CH_2$, or NH; and
each R is independently $C_1$-$C_6$ alkyl, $C_6$-$C_{10}$ aryl, $C_1$-$C_6$ heteroalkyl, or $C_6$-$C_{10}$ heteroaryl, and a diether-DSPC having a structure according to Formula III (III)

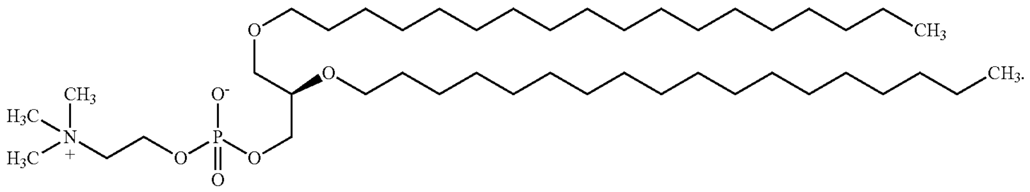

Additionally, new vaccines can be developed according to the invention described herein that comprise at least one HPV type in the form of an HPV VLP adsorbed to an aluminum adjuvant in combination with an LNP adjuvant comprising PEG-lipid having the structure set forth in Formula I (I)

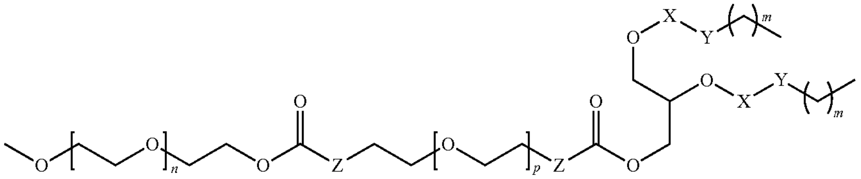

wherein:
each m is independently from 5-20;
n is from 20-60;
p is 0, 1, or 2;
each X is independently $CH_2$, CHR, $CR_2$, or C═O;
each Y is independently $CH_2$, CHR, $CR_2$, or NH;
each Z is independently absent, $CH_2$, or NH; and
each R is independently $C_1$-$C_6$ alkyl, $C_6$-$C_{10}$ aryl, $C_1$-$C_6$ heteroalkyl, or $C_6$-$C_{10}$ heteroaryl, and a diether-DSPC having a structure according to Formula (III)

(III)

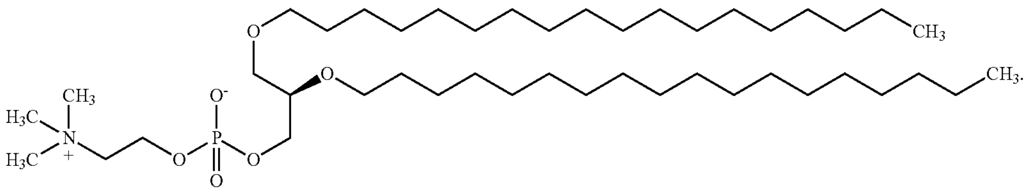

One exemplary HPV vaccine is a bivalent vaccine protective against HPV 16 and 18, which is known commercially as CERVARIX® (GlaxoSmithKline Biologicals, Rixensart, Belgium). Another exemplary HPV VLP vaccine is a non-infectious recombinant, quadrivalent vaccine prepared from highly purified VLPs of the major capsid (L1) protein of HPV types 6, 11, 16, and 18, and may be referred to herein by its proprietary name GARDASIL® (Merck & Co., Inc., Rahway, NJ, USA), see Bryan, J. T. Vaccine 25(16): 3001-6 (2007); Shi et al. Clinical Pharmacology and Therapeutics 81(2): 259-64 (2007). Another exemplary HPV VLP vaccine is the nine-valent vaccine marketed for prevention of HPV (that includes the capsid (L1) protein of HPV types 6, 11, 16, 18, 31, 33, 45, 52, and 58), which is referred to herein by its proprietary name GARDASIL®9 (Merck & Co., Inc., Rahway, NJ, USA).

In some embodiments, the vaccine dose includes, in addition to VLPs, an aluminum adjuvant (as amorphous aluminum hydroxyphosphate sulfate), sodium chloride, L-histidine, polysorbate 80, sodium borate, and water. In some embodiments, the HPV vaccine includes 100-3500 μg aluminum adjuvant, 1-50 mg sodium chloride, 0.05-10 mg L-histidine, 1-100 μg polysorbate, 1-100 μg sodium borate, and water. In some embodiments, the HPV vaccine includes about 500 μg aluminum adjuvant, about 9.56 mg sodium chloride, about 0.78 mg L-histidine, about 50 μg polysorbate 80, about 35 μg sodium borate, and water for injection.

Known HPV VLP vaccines can be modified to include both an aluminum adjuvant and an LNP adjuvant comprising PEG-lipid having the structure set forth in Formula I (I)

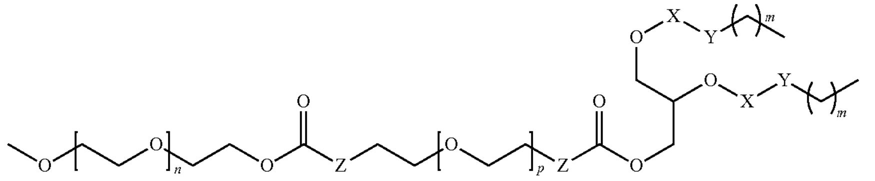

wherein:

each m is independently from 5-20;

n is from 20-60;

p is 0, 1, or 2;

each X is independently $CH_2$, CHR, $CR_2$, or C=O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl, and a diether-DSPC having a structure according to Formula III (III)

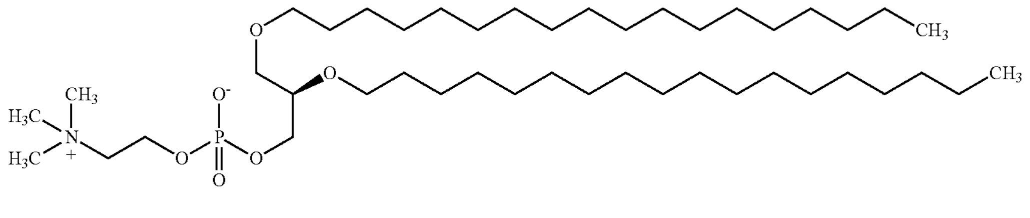

in accordance with the present invention.

In some embodiments of the invention, the pharmaceutical compositions and formulations comprise HPV VLP-based vaccines, or HPV VLPs as described herein, that are monovalent, bivalent, trivalent, quadrivalent, 5-valent, 6-valent, 7-valent, 8-valent or 9-valent. In particular embodiments, the pharmaceutical compositions and formulations are 9-valent. In some embodiments, the pharmaceutical compositions comprise HPV VLP-based vaccines, or HPV VLPs as described herein, with more than four different types of HPV VLPs. For example, the pharmaceutical compositions and formulations of the present invention may include HPV VLP-based vaccines, or HPV VLPs as described herein, that are 8-valent, 9-valent, 10-valent, and so forth. For example, pharmaceutical compositions comprising VLPs of HPV 16 and/or HPV 18, without the inclusion of other HPV VLP types, are included within the scope of the invention. Multi-valent vaccines comprising different HPV VLPs than the HPV types included in GARDASIL® or GARDASIL®9 are also contemplated herein.

In some embodiments, VLPs of HPV types 6 and 11 are included. In some embodiments, VLPs of HPV types 16, 31, and 35 are included. In some embodiments, VLPs of HPV types 18, 45, and 59 are included. In some embodiments, the VLPs of HPV types 26, 51, and 69 are included. In some embodiments, VLPs of HPV types 33, 52, and 58 are included. In some embodiments, VLPs of HPV types 39, 68, and 70 are included. In some embodiments, VLPs of HPV types 53, 56, and 66 are included.

In some embodiments, VLPs of HPV types 16 and 18 are included. In some embodiments, VLPs of HPV types 6, 11, 16, and 18 are included. In some embodiments, VLPs of HPV types 6, 18, 52, and 58 are included. In some embodiments, VLPs of HPV types 6, 11, 16, 18, 31, 45, 52, and 58 are included. In some embodiments, VLPs of HPV types 6, 11, 16, 18, 33, 45, 52, and 58 are included. In some embodiments, VLPs of HPV types 6, 11, 16, 18, 31, 33, 45, 52, and 58 are included. In some embodiments, VLPs of HPV types 6, 11, 16, 18, 31, 33, 45, 52, and 59 are included. In some embodiments, VLPs of HPV types 6, 11, 16, 18, 31, 33, 45, 53, and 58 are included. In some embodiments, VLPs of HPV types 6, 11, 16, 18, 31, 33, 45, 53, and 59 are included. In some embodiments, the VLPs of HPV types 6, 11, 16, 18, 31, 33, 35, 45, 52, and 58 are included. In some embodiments, VLPs of HPV types 6, 11, 16, 18, 31, 33, 35, 45, 52, 58, and 59 are included. In some embodiments, VLPs of HPV types 6, 11, 16, 18, 31, 33, 45, 52, 58, 59, and 68 are included. In some embodiments, VLPs of HPV types 6, 11, 16, 18, 31, 33, 35, 39, 45, 51, 52, 56, 58, and 59 are included. In some embodiments, VLPs of HPV types 6, 11, 16, 18, 26, 31, 33, 35, 45, 51, 52, 58, 59, and 69 are included. In some embodiments, VLPs of HPV types 6, 11, 16, 18, 26, 31, 33, 35, 39, 45, 51, 52, 58, 59, 68, 69, and 70 are included. In some embodiments, VLPs of HPV types 6, 11, 16, 18, 26, 31, 33, 35, 39, 45, 51, 52, 53, 56, 58, 59, 66, 68, 69, and 70 are included.

In some embodiments, the pharmaceutical compositions and formulations comprise HPV VLP-based vaccines and/or antigens as listed in Table I below:

TABLE 1

| Name | Antigen | Adjuvant | Party |
|---|---|---|---|
| CERVARIX ® (2vHPV vaccine) | L1 VLP of HPV-16 and HPV-18 | Aluminum hydroxide and MPL | GlaxoSmithKline Biologies (Rixensart, Belgium) |
| GARDASIL ® (4vHPV vaccine) | L1 VLP of HPV-6, HPV-11, HPV-16 and HPV-18 | AHSS | Merck & Co., Inc., Rahway NJ USA |
| GARDASIL ® 9 (9vHPV vaccine) | L1 VLP of HPV-6, HPV-11, HPV-16, HPV-18, HPV-31, HPV-33, HPV-45, HPV-52 and HPV-58 | AHSS | Merck & Co., Inc., Rahway NJ USA |
| CECOLIN ® | L1 VLP of HPV-16 and HPV-18 | Aluminum hydroxide | Xiamen Innovax |
| GEOCOLIN ® | L1 VLP of HPV-6 and HPV-11 | Aluminum hydroxide | Xiamen Innovax |
| L1 capsomers | L1 capsomers of HPV-16 | unknown | R. Garcea, University of Colorado-Boulder |
| RG1-VLP | HPV-16 L1-L2 (17-36) VLP | Aluminum hydroxide | R. Kirnbauer, NCl, Pathovax LLC |
| L2-AAV | L2 peptides of HPV-16 and HPV-31 displayed on AAV VLP | unknown | 2A Pharma |
| L2 multimer | Fusion protein of L2~11-88 of HPV-6, HPV-16, HPV-18, HPV-31 and HPV-39 | Alum | Sanofi, BravoVax |
| L2-thioredoxin | L2 peptide displayed on thioredoxin | unknown | M. Muller, DKFZ |
| AX03 | L2 peptide displayed on bacteriophage | unknown | Agilvax, NIAID |
| L1-E7 VLP | HPV-16 L1-E7 VLP | None | Medigene AG |
| TA-CIN | HPV-16 L2E7E6 fusion protein | None | Cantab Pharmaceuticals, Xenova |
| TA-GW | HPV-6 L2E7 fusion protein | Aluminum hydroxide or AS03 | Cantab Pharmaceuticals, GSK |

Single Dose Vaccine Compositions

In some embodiments, a single-dose vaccine composition is provided that is a pharmaceutical composition (i.e., includes a pharmaceutically acceptable carrier) and includes a PEG-lipid having the structure set forth in Formula I (I)

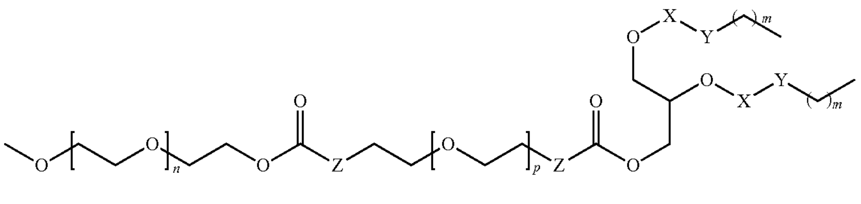

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and HPV VLPs of at least one HPV type.

In some embodiments, a single-dose vaccine composition is provided that includes a PEG-lipid having the structure set forth in Formula I

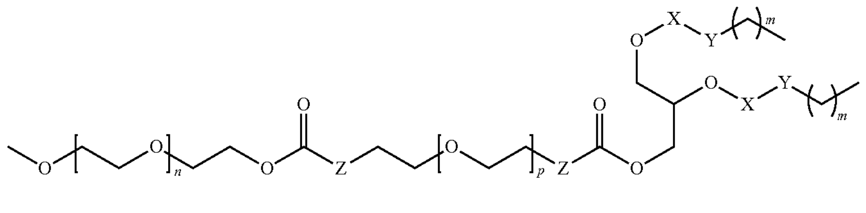

(I)

wherein:
each m is independently from 5-20;
n is from 20-60;
p is 0, 1, or 2;
each X is independently $CH_2$, CHR, $CR_2$, or C═O;
each Y is independently $CH_2$, CHR, $CR_2$, or NH;
each Z is independently absent, $CH_2$, or NH; and
each R is independently $C_1$-$C_6$ alkyl, $C_6$-$C_{10}$ aryl, $C_1$-$C_6$ heteroalkyl, or $C_6$-$C_{10}$ heteroaryl; and HPV VLPs of at least two HPV types.

In some embodiments, a single-dose vaccine composition is provided that includes PEG-lipid having the structure set forth in Formula I

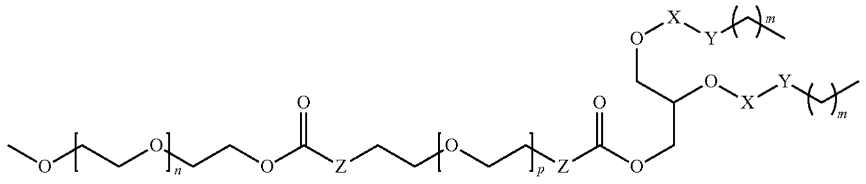

(I)

wherein:
each m is independently from 5-20;
n is from 20-60;
p is 0, 1, or 2;
each X is independently $CH_2$, CHR, $CR_2$, or C═O;
each Y is independently $CH_2$, CHR, $CR_2$, or NH;
each Z is independently absent, $CH_2$, or NH; and
each R is independently $C_1$-$C_6$ alkyl, $C_6$-$C_{10}$ aryl, $C_1$-$C_6$ heteroalkyl, or $C_6$-$C_{10}$ heteroaryl; and HPV VLPs of at least nine HPV types.

In some embodiments, a single-dose vaccine composition is provided that includes a PEG-lipid having the structure set forth in Formula I:

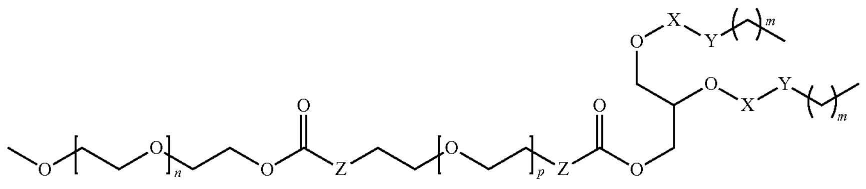

(I)

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently alkyl, aryl, heteroalkyl, or heteroaryl; and HPV VLPs of at least one HPV type and an aluminum adjuvant.

In some embodiments, a single-dose vaccine composition is provided that includes a PEG-lipid having the structure set forth in Formula I:

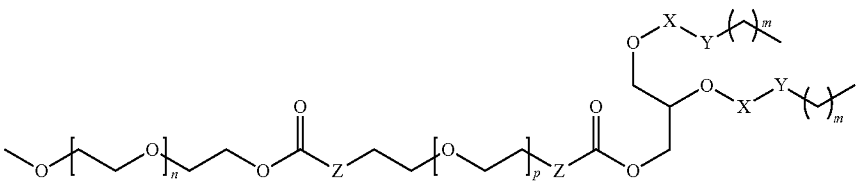

(I)

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently alkyl, aryl, heteroalkyl, or heteroaryl; and HPV VLPs of at least two HPV types and an aluminum adjuvant. In some embodiments, a single-dose vaccine composition is provided that includes a lipid nanoparticle adjuvant and HPV VLP particles of at least four HPV types and an aluminum adjuvant. In some embodiments, a vaccine composition is provided that includes PEG-lipid having the structure set forth in Formula I

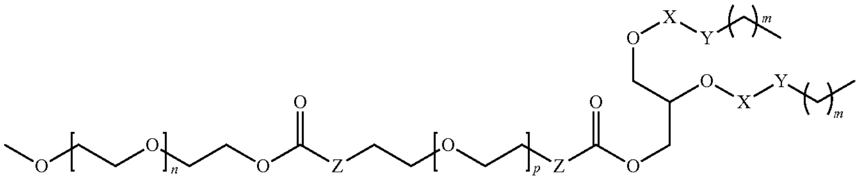

(I)

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl;

and HPV VLP particles of at least nine HPV types and an aluminum adjuvant.

In some embodiments, a single-dose vaccine composition is provided that includes (a) PEG-lipid having the structure set forth in Formula I (I)

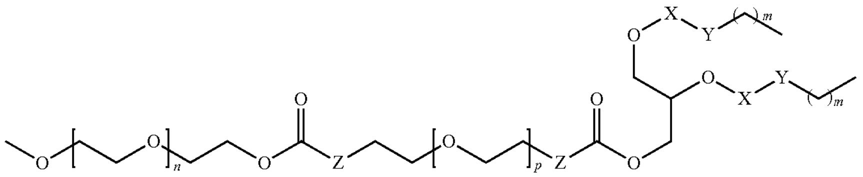

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and (b) HPV VLP particles of at least one HPV type, wherein each of the HPV VLPs, when present in the single dose vaccine composition, are present in a concentration of about 1 μg to about 300 μg per 0.5 mL of the single-dose vaccine composition and wherein the total VLP concentration is between about 10 μg to about 2000 μg per 0.5 mL of the single-dose vaccine composition. In some embodiments, a single-dose vaccine composition is provided that includes (a) about 0.1 μg to about 50 mg LNP adjuvant, (b) about 100 μg to about 3500 μg aluminum adjuvant, and (c) HPV VLP particles of at least one HPV type, wherein each of the HPV VLPs, when present in the single dose vaccine composition, are present in a concentration of about 1 μg to about 180 μg per 0.5 mL of the single-dose vaccine composition and wherein the total VLP concentration is between about 10 μg to about 2000 μg per 0.5 mL of the single-dose vaccine composition.

In some embodiments, a single-dose vaccine composition is provided that includes (a) about 0.1 μg to about 50 mg LNP, about 1 μg to about 2000 μg HPV VLP particles of at least two HPV types, and about 100 μg to about 2700 μg aluminum adjuvant. In some embodiments, a single-dose vaccine composition is provided that includes (a) about 0.1 μg to about 50 mg LNP, HPV VLP particles of at least four HPV types, and about 100 μg to about 3500 μg aluminum adjuvant.

In some embodiments, a single-dose vaccine composition is provided that includes 0.1 μg to about 50 mg LNP, and 1 μg to about 100 μg of each HPV VLP present in the single dose vaccine composition. In some embodiments, a single-dose vaccine composition is provided that includes 0.1 μg to about 50 mg LNP and 2 μg to about 600 μg of HPV VLPs of two HPV types (i.e., the single-dose vaccine is a bivalent VLP HPV vaccine). In some embodiments, a single-dose vaccine composition is provided that includes 0.1 μg to about 50 mg LNP and 4 μg to about 1200 μg of HPV VLPs of four HPV types (i.e., the single-dose vaccine is a quadrivalent VLP HPV vaccine). In some embodiments, a single dose vaccine composition is provided that includes 0.1 μg to about 50 mg LNP and 9 μg to about 2700 μg of HPV VLPs of nine (9) HPV types (i.e., the single-dose vaccine is 9-valent VLP HPV vaccine). In some embodiments, a single dose vaccine composition is provided that includes 0.1 μg to about 50 mg LNP and 20 μg to about 6000 μg of HPV VLPs of twenty (20) HPV types (i.e., the single-dose vaccine is a 20-valent VLP HPV vaccine). In some embodiments, the single-dose vaccine composition also includes about 100 μg to about 2700 μg aluminum adjuvant.

In some embodiments, a single-dose vaccine composition is provided that includes 0.1 μg to about 50 mg LNP, 1 μg to about 300 μg of a monovalent VLP HPV, and (c) 100 μg to about 2700 μg aluminum adjuvant. In some embodiments, a single-dose vaccine composition is provided that includes 0.1 μg to about 50 mg LNP, 1 μg to about 300 μg, per VLP, of a bivalent VLP HPV (i.e., HPV VLPs of two HPV types), and 100 μg to about 3500 μg aluminum adjuvant. In some embodiments, a single-dose vaccine composition is provided that includes (a) 0.1 μg to about 50 mg LNP, (b) 1 μg to about 300 μg, per VLP, of a quadrivalent VLP HPV (i.e., HPV VLPs of four HPV types), and (c) 100 μg to about 3500 μg aluminum adjuvant. In some embodiments, a single-dose vaccine composition is provided that (a) includes 0.1 μg to about 50 mg LNP, (b) 1 μg to about 300 μg, per VLP, of a 9-valent VLP HPV (i.e., HPV VLPs of 9 HPV types), and (c) 100 μg to about 3500 μg aluminum adjuvant. In some embodiments, a single-dose vaccine composition is provided that includes (a) includes 0.1 μg to about 50 mg LNP, (b) 1 μg to about 300 μg, per VLP, of a 20-valent VLP HPV (i.e., HPV VLPs of 20 HPV types), and (c) 100 μg to about 3500 μg aluminum adjuvant.

In some embodiments, the single-dose vaccine composition includes (a) 1 μg to about 300 μg, per VLP, of HPV VLPs (HPV types 16 and 18) and (b) 0.1 μg to about 50 mg LNP. In some embodiments, the single-dose vaccine composition includes (a) 1 μg to about 300 μg, per VLP, of HPV VLPs (HPV types 6, 11, 16, and 18,) and (b) 0.1 μg to about 50 mg LNP. In some embodiments, the single-dose vaccine composition includes (a) 1 μg to about 300 μg, per VLP, of HPV VLPs (HPV types 6, 11, 16, 18, 31, 33, 45, 52, and 58) and (b) 0.1 μg to about 50 mg LNP.

In some embodiments, the single-dose vaccine composition includes 1 μg to about 300 μg, per VLP, of HPV VLPs (HPV types 16 and 18), 100 μg to about 3500 μg of an aluminum adjuvant, and 0.1 μg to about 50 mg LNP. In some embodiments, the single-dose vaccine composition includes 1 μg to about 300 μg, per VLP, of HPV VLPs (HPV types 6, 11, 16, and 18), 100 μg to about 3500 μg of an aluminum adjuvant, and 0.1 μg to about 50 mg LNP. In some embodiments, the single-dose vaccine composition includes 1 μg to about 300 μg, per VLP, of HPV VLPs (HPV types 6, 11, 16, 18, 31, 33, 45, 52, and 58), 100 μg to about 3500 μg of an aluminum adjuvant, and 0.1 μg to about 50 mg LNP.

The vaccines of the invention comprise VLPs containing the antigenic determinants required to induce the generation of neutralizing antibodies in a subject. The vaccines are expected to be sufficiently safe to be administered without the risk of clinical infection, have no toxic side effects, are stable, compatible with conventional carriers and can be administered effectively. In some embodiments, an LNP adjuvant of the present invention may be combined with a Human Papillomavirus Bivalent (Types 16 and 18) Vaccine, Recombinant. In some embodiments, an LNP adjuvant of the present invention may be combined with CERVARIX®.

In some embodiments, an LNP adjuvant of the present invention may be combined with a Human Papillomavirus Quadrivalent (Types 6, 11, 16, 18) Vaccine, Recombinant. In some embodiments, an LNP adjuvant of the present invention may be combined with GARDASIL®. In some embodiments, an LNP adjuvant of the present invention may be combined with a Human Papillomavirus 9-valent Vaccine, Recombinant. In some embodiments, an LNP adjuvant of the present invention may be combined with GARDASIL® 9.

In some embodiments, the LNP adjuvant is present in the amount of about 0.1 μg to about 200 mg. In some embodiments, the LNP adjuvant is present in the amount of about 0.1 μg to about 100 mg. In some embodiments, the LNP adjuvant is present in the amount of about 0.1 μg to about 50 mg. In some embodiments, the LNP adjuvant is present in the amount of about 0.1 μg to about 25 mg. In some embodiments, the LNP adjuvant is present in the amount of about 0.1 μg to about 20 mg. In some embodiments, the LNP adjuvant is present in the amount of about 0.1 μg to about 10 mg. In some embodiments, the LNP adjuvant is present in the amount of about 0.1 μg to about 5 mg. In some embodiments, the LNP adjuvant is present in the amount of about 1 mg to about 20 mg. In some embodiments, the LNP adjuvant is present in the amount of about 1 mg to about 10 mg. In some embodiments, the LNP adjuvant is present in the amount of about 1 mg to about 5 mg. In some embodiments, the LNP adjuvant is present in the amount of about 1 mg to about 4 mg. In some embodiments, the LNP adjuvant is present in the amount of about 1 mg to about 3 mg. In some embodiments, the LNP adjuvant is present in the amount of about 1 mg to about 2 mg. In some embodiments, the LNP adjuvant is present in the amount of about 0.5 mg to about 20 mg. In some embodiments, the LNP adjuvant is present in the amount of about 0.5 mg to about 10 mg. In some embodiments, the LNP adjuvant is present in the amount of about 0.5 mg to about 5 mg. In some embodiments, the LNP adjuvant is present in the amount of about 0.5 mg to about 4 mg. In some embodiments, the LNP adjuvant is present in the amount of about 0.5 mg to about 3 mg. In some embodiments, the LNP adjuvant is present in the amount of about 0.5 mg to about 2 mg. In some embodiments, the LNP adjuvant is present in the amount of about 0.25 mg to about 20 mg. In some embodiments, the LNP adjuvant is present in the amount of about 0.25 mg to about 10 mg. In some embodiments, the LNP adjuvant is present in the amount of about 0.25 mg to about 5 mg. In some embodiments, the LNP adjuvant is present in the amount of about 0.25 mg to about 4 mg. In some embodiments, the LNP adjuvant is present in the amount of about 0.25 mg to about 3 mg. In some embodiments, the LNP adjuvant is present in the amount of about 0.25 mg to about 2 mg.

In some embodiments, compositions of the present invention include less than about 100 mg LNP. In some embodiments, compositions of the present invention include less than about 50 mg LNP. In some embodiments, compositions of the present invention include less than about 25 mg LNP. In some embodiments, compositions of the present invention include less than about 20 mg LNP. In some embodiments, compositions of the present invention include less than about 15 mg LNP. In some embodiments, compositions of the present invention include less than about 10 mg LNP. In some embodiments, compositions of the present invention include less than about 9 mg LNP. In some embodiments, compositions of the present invention include less than about 8 mg LNP. In some embodiments, compositions of the present invention include less than about 7 mg LNP. In some embodiments, compositions of the present invention include less than about 6 mg LNP. In some embodiments, compositions of the present invention include less than about 5 mg LNP. In some embodiments, compositions of the present invention include less than about 4 mg LNP. In some embodiments, compositions of the present invention include less than about 3 mg LNP. In some embodiments, compositions of the present invention include less than about 2 mg LNP. In some embodiments, compositions of the present invention include less than about 1 mg LNP. In some embodiments, compositions of the present invention include less than about 0.5 mg LNP.

In some embodiments, the LNP concentration is about 0.1 μg to about 200 mg per 0.5 mL of the pharmaceutical composition. In some embodiments, the LNP concentration is about 1 μg to about 100 mg per 0.5 mL of the pharmaceutical composition. In some embodiments, the LNP concentration is about 1 μg to about 50 mg per 0.5 mL of the pharmaceutical composition. In some embodiments, the LNP concentration is about 1 μg to about 25 mg per 0.5 mL of the pharmaceutical composition. In some embodiments, the LNP concentration is about 1 μg to about 10 mg per 0.5 mL of the pharmaceutical composition. In some embodiments, the LNP concentration is about 1 μg to about 5 mg per 0.5 mL of the pharmaceutical composition.

Pharmaceutical compositions, formulations, and single-dose vaccines of the present invention may be administered subcutaneously, topically, orally, on the mucosa, intravenously, or intramuscularly. The pharmaceutical compositions, formulations, and vaccines are administered in an amount sufficient to elicit a protective response. Vaccines, pharmaceutical compositions and formulations can be administered by various routes, for example, orally, parenterally, subcutaneously, on the mucosa, or intramuscularly. The dose administered may vary depending on the general condition, sex, weight and age of the patient, the route of administration and the type of HPV VLP in the vaccine. The vaccines, pharmaceutical compositions, and formulations of the invention may be in the form of a capsule, suspension, elixir or solution. It may be formulated with an immunologically acceptable carrier.

In some embodiments, formulations of the present invention exhibit physical stability, (e.g. particle size is maintained) and chemical stability (e.g. lipids do not undergo hydrolysis) when subjected to various times and temperatures. In some embodiments, formulations of the present invention exhibit physical stability for at least 1 month at 37° C. In some embodiments, formulations of the present invention exhibit chemical stability for at least 1 month at 37° C. In some embodiments, formulations of the present invention exhibit physical and chemical stability for at least 1 month at 37° C. In some embodiments, formulations of the present invention exhibit physical stability for at least 6 months at 25° C. In some embodiments, formulations of the present invention exhibit chemical stability for at least 6 months at 25° C. In some embodiments, formulations of the present invention exhibit physical and chemical stability for at least 6 months at 25° C. In some embodiments, formulations of the present invention exhibit physical stability for at least 3 years at 2-8° C. In some embodiments, formulations of the present invention exhibit chemical stability for at least 3 years at 2-8° C. In some embodiments, formulations of the present invention exhibit physical and chemical stability for at least 3 years at 2-8° C.

Kits of the Invention

Also provided herein are kits including any of the pharmaceutical compositions of single dose vaccines as described above and instructions for use.

Also provided herein are kits including (a) a pharmaceutical composition comprising HPV VLPs of at least one type of HPV, and (b) a lipid nanoparticle adjuvant.

In some embodiments of the kits, the pharmaceutical composition of (a) described above comprises HPV VLPs of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82. In some embodiment, the pharmaceutical composition of (a) is an HPV vaccine. In some embodiments, the HPV vaccine is a Human Papillomavirus Bivalent (Types 16 and 18) Vaccine, Recombinant. In some embodiments, the HPV vaccine is CERVARIX®. In some embodiments, the HPV vaccine is a Human Papillomavirus Quadrivalent (Types 6, 11, 16, 18) Vaccine, Recombinant. In some embodiments, the HPV vaccine is GARDASIL®. In some embodiments, the HPV vaccine is a Papillomavirus 9-valent Vaccine, Recombinant. In some embodiments, the HPV vaccine is GARDASIL® 9.

In some embodiments of the kits of the invention, the LNP adjuvant is any of the LNP adjuvants described herein above. In some embodiments, the kit includes 0.1 μg to 100 mg of LNP. In some embodiments, the kit includes a buffer. In some embodiments, the kit includes a tonicity modifier. In some embodiments, the kit includes a detergent.

In some embodiments of the kits of the invention, the kit includes a label or packaging insert that includes a description of the components and/or instructions for use in vivo of the components therein. In some embodiments, the kits include instructions for co-administering (or vaccinating) (a) the pharmaceutical composition or HPV Vaccine and (b) the LNP adjuvant. In some embodiments, the kits include instructions for admixing (a) the pharmaceutical composition or HPV vaccine and (b) the LNP adjuvant and subsequentially administering (or vaccinating) the admixture to a patient.

Methods of Treatment of the Invention

Also provided herein is a method of inducing an immune response to a human papillomavirus (HPV) in a human patient comprising administering to the patient a pharmaceutical composition including a lipid nanoparticle adjuvant and virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82.

Also provided herein is a method of inducing an immune response to a human papillomavirus (HPV) in a human patient including administering a lipid nanoparticle adjuvant and virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82. In some embodiments, the LNP adjuvant is formulated separately from the VLPs. In some embodiments, the LNP adjuvant is formulated with the VLPs (i.e., in the same composition). In some embodiments, the LNP adjuvant and VLPs are field-mixed to form a pharmaceutical composition prior to administration to the patient. In some embodiments, the LNP adjuvant and VLPs are administered sequentially to a patient.

Also provided herein is a method of inducing an immune response to a human papillomavirus (HPV) in a human patient including co-administering to the patient (a) a pharmaceutical composition comprising virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82 and (b) a lipid nanoparticle adjuvant.

Also provided herein is a method of preventing infection of or reducing the likelihood of infection of a human patient by a human papillomavirus (HPV) including administration to the patient a pharmaceutical composition including a lipid nanoparticle adjuvant and virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82.

Also provided herein is a method of delivering a pharmaceutical composition to a subject that induces a neutralizing titer against an HPV antigen in the subject that includes administering to the subject a pharmaceutical composition including a lipid nanoparticle adjuvant and virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82, whereby the administration of the pharmaceutical composition induces a neutralizing titer against the HPV antigen in the subject, and wherein a single dose of the pharmaceutical composition provides enhanced or comparable neutralizing titers for each HPV type in the pharmaceutical composition when compared to multiple doses of the same pharmaceutical composition when the same composition is formulated without a lipid nanoparticle adjuvant.

Also provided herein is a method for preventing cancer in a human patient that is caused by human papillomavirus (HPV) types 16, 18, 31, 33, 45, 52, and 58, the method comprising administering to the patient a pharmaceutical composition including a lipid nanoparticle adjuvant and virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82, wherein the cancer is cervical, vulvar, vaginal, anal, oropharyngeal, and other head and neck cancers.

Also provided herein is a method for preventing cancer in a human patient caused by HPV types 6, 11, 16, 18, 31, 33, 45, 52, and 58 including administering to the patient a pharmaceutical composition including a lipid nanoparticle adjuvant and virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82, wherein the cancer is cervical, vulvar, vaginal, and anal precancerous or dysplastic lesions.

Also provided herein is a method for preventing anogenital disease or condition in a human patient caused by HPV types 6 and 11 including administering to the patient a pharmaceutical composition including a lipid nanoparticle adjuvant and virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82, wherein the anogenital disease or condition is genital warts or condyloma *acuminata.*

Also provided herein is a method for preventing precancerous or dysplastic lesions in a human patient caused by HPV types 6, 11, 16, 18, 26, 31, 33, 35, 39, 45, 51, 52, 53, 55, 56, 58, 59, 66, 68, 73, and 82 including administering to the patient a pharmaceutical composition including a lipid nanoparticle adjuvant and virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82, wherein the lesions are selected from cervical intraepithelial neoplasia (CIN) grade 2/3, cervical adenocarcinoma in situ (AIS), cervical intraepithelial neoplasia (CIN) grade 1, vulvar intraepithelial neoplasia (VIN) grade 2 and grade 3, vaginal intraepithelial neoplasia (VaIN) grade 2 and grade 3, anal intraepithelial neoplasia (AIN) grades 1, 2, and 3. (1.1).

Also provided herein is a method for preventing HPV-related anogenital disease in a human patient caused by HPV types selected from the group consisting of HPV types: 6, 11, 16, 18, 26, 31, 33, 35, 39, 45, 51, 52, 53, 55, 56, 58, 59, 66, 68, 73, and 82 comprising administering to the patient a pharmaceutical composition including a lipid nanoparticle adjuvant and virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82.

Embodiments of the invention also include one or more of the pharmaceutical compositions described herein (i) for use in, (ii) for use as a medicament or composition for, or (iii) for use in the preparation of a medicament for: (a) therapy (e.g., of the human body); (b) medicine; (c) induction of an immune response against HPV types included in the vaccine (d) decreasing the likelihood of HPV infection in a patient; (e) prevention of infection with HPV types in the vaccine, (f) prevention or reduction of the likelihood of cervical cancer, (g) prevention or reduction of the likelihood of vulvar cancer, (h) prevention or reduction of the likelihood of vaginal cancer, (i) prevention or reduction of the likelihood of anal cancer, (j) prevention or reduction of the likelihood of oropharyngeal cancer, (k) prevention or reduction of the likelihood of other head and neck cancers, (k) prevention or reduction of the likelihood of precancerous or dysplastic anal lesions, (l) prevention or reduction of the likelihood of genital warts or condyloma *acuminata*, (m) prevention or reduction of the likelihood of Cervical intraepithelial neoplasia (CIN) grade 2/3 lesions, (n) prevention or reduction of the likelihood of cervical adenocarcinoma in situ (AIS) lesions, (o) prevention or reduction of the likelihood of Cervical intraepithelial neoplasia (CIN) grade 1 lesions, (p) prevention or reduction of the likelihood of Vulvar intraepithelial neoplasia (VIN) grade 2 and grade 3 lesions, (q) prevention or reduction of the likelihood of Vaginal intraepithelial neoplasia (VaIN) grade 2 and grade 3 lesions, (r) prevention or reduction of the likelihood of Anal intraepithelial neoplasia (AIN) grades 1, 2, and 3 lesions.

In embodiment 1, a PEG-lipid is provided having the structure set forth in Formula I (I)

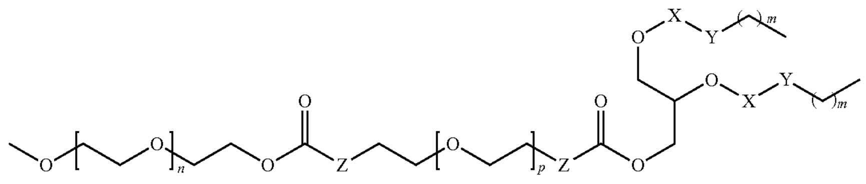

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl.

In embodiment 2, a lipid nanoparticle is provided comprising:

a PEG-lipid having the structure set forth in Formula I:

(I)

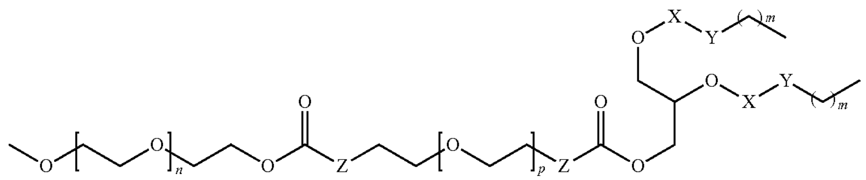

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and a phospholipid.

In embodiment 3, the lipid nanoparticle of embodiment 2 is provided, wherein the PEG-lipid is selected from:

In embodiment 9, the lipid nanoparticle of embodiment 7 is provided, wherein the lipid nanoparticle comprises 55-65 mole % cationic lipid, 5-15 mole % phospholipid, 25-35 mole % cholesterol, and 1-2.5 mole % PEG-lipid.

In embodiment 10, the lipid nanoparticle of embodiment 7 is provided, wherein the LNP adjuvant comprises 5-15 mole % phospholipid, 25-35 mole % cholesterol, 1-2.5 mole % PEG-lipid, and 55-65 mole % (13Z, 16Z)—N, N-dimethyl-3-nonyldocosa 13, 16-dien-1-amine.

In embodiment 11, the PEG lipid of embodiment 1 or the lipid nanoparticle of any of embodiments 2-10 is provided, (I)

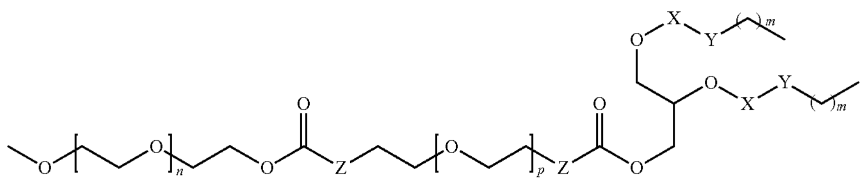

In embodiment 4, the lipid nanoparticle of embodiment 3 is provided, wherein the phospholipid has the structure set forth in Formula III:

wherein m is from 8-18; p is 1, or 2; X is $CH_2$, CHR, $CR_2$; Y is $CH_2$, CHR, $CR_2$; and R is alkyl, aryl, heteroalkyl, or heteroaryl.

(III)

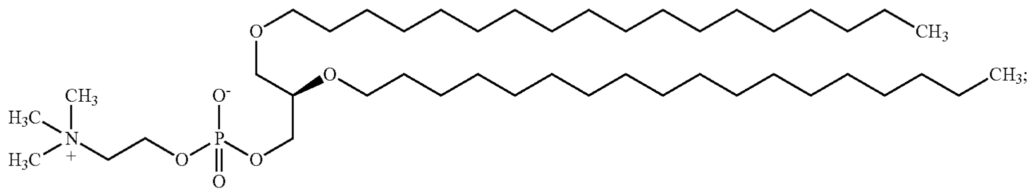

or the structure set forth in Formula III(a)

(IIIa)

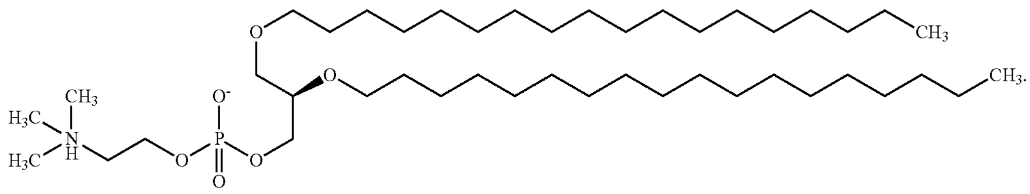

In embodiment 5, the lipid nanoparticle of any of embodiment 2-4 is provided, further comprising a cationic lipid.

In embodiment 6, the lipid nanoparticle of embodiment 5 is provided, wherein the cationic lipid is (13Z, 16Z)—N, N-dimethyl-3-nonyldocosa 13, 16-dien-1-amine.

In embodiment 7, the lipid nanoparticle of any of embodiment 2-6 is provided, further comprising cholesterol.

In embodiment 8, lipid nanoparticle of embodiment 7 is provided, wherein the lipid nanoparticle comprises 30-65 mole % cationic lipid, 5-30 mole % phospholipid, 10-40 mole % cholesterol, and 0.5-4 mole % PEG-lipid.

In embodiment 12, the PEG lipid of embodiment 1 or the lipid nanoparticle of any of embodiments 2-11 is provided, wherein n is from 25-55; and Z is NH.

In embodiment 13, the PEG lipid of embodiment 1 or the lipid nanoparticle of any of embodiments 2-12 is provided, wherein m is from 8-18; n is from 30-50; p is 1, or 2; X is $CH_2$, CHR, $CR_2$; Y is $CH_2$, CHR, $CR_2$; Z is NH; and R is alkyl, aryl, heteroalkyl, or heteroaryl.

In embodiment 14, the PEG lipid of embodiment 1 or the lipid nanoparticle of any of embodiments 2-13 is provided, wherein the PEG lipid has the structure of Formula II:

(II)

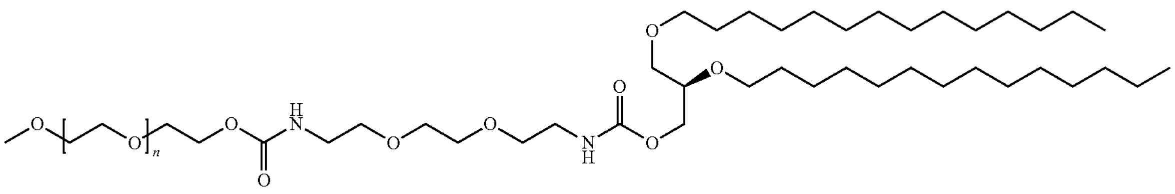

wherein n is from 30-50.

In embodiment 15, the PEG lipid of embodiment 1 or the lipid nanoparticle of any of embodiment 2-14 is provided, wherein the PEG lipid has the structure of Formula II:

(II)

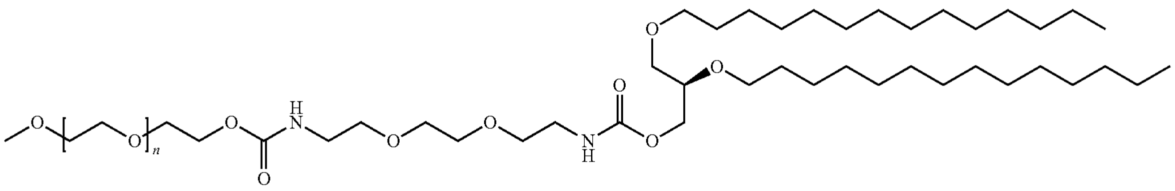

wherein n is from 40-50.

In embodiment 16, lipid nanoparticle of embodiment 7 is provided, wherein the LNP adjuvant comprises 55-65 mole % (13Z, 16Z)—N, N-dimethyl-3-nonyldocosa 13, 16-dien-1-amine, 25-35 mole % cholesterol, 5-15 mole % phospholipid, wherein the phospholipid has the structure set forth in Formula III (III)

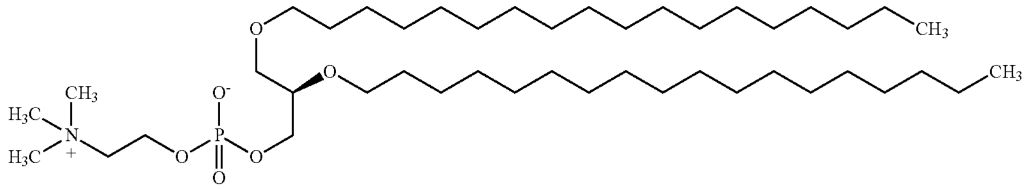

and 1-2.5 mole % PEG-lipid, wherein the PEG lipid has the structure of Formula II:

(II)

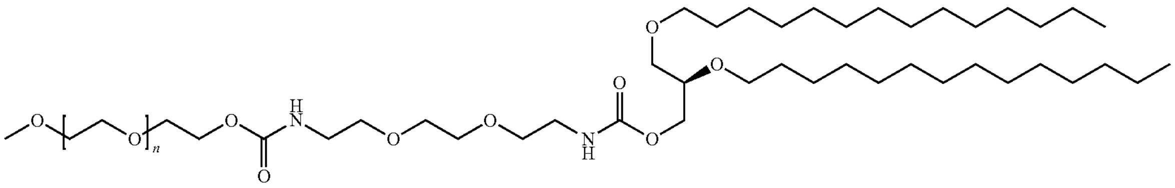

wherein n is from 30-50.

In embodiment 17, a formulation comprising the PEG lipid of embodiment 1 or the lipid nanoparticle of any of embodiments 2-16 is provided, wherein the formulations are stable for 1 month at 37° C.

In embodiment 18, a formulation comprising the PEG lipid of embodiment 1 or the lipid nanoparticle of any of embodiments 2-16 is provided, wherein the formulations are stable for 6 months at 25° C.

In embodiment 19, a formulation comprising the PEG lipid of embodiment 1 or the lipid nanoparticle of any of embodiments 2-16 is provided, wherein the formulations are stable for 3 years at 2-8° C.

In embodiment 20, pharmaceutical composition is provided comprising:

virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 69, 70, 73, and 82, a PEG-lipid having the structure set forth in Formula I:

(I)

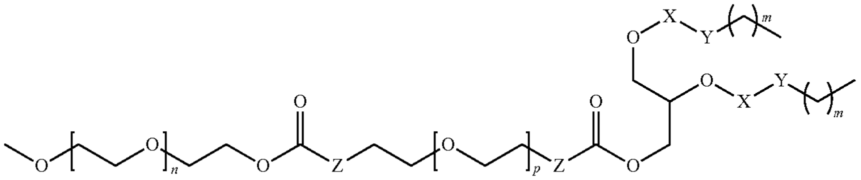

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and a pharmaceutically acceptable carrier.

In embodiment 21, a pharmaceutical composition is provided comprising:

virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 69, 70, 73, and 82, a phospholipid having the structure set forth in Formula III:

(III)

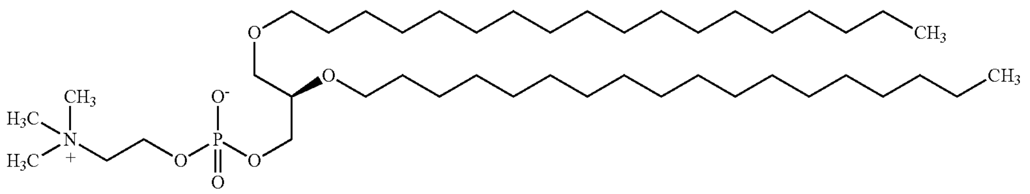

and, a pharmaceutically acceptable carrier.

In embodiment 22, a pharmaceutical composition is provided comprising:

virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 69, 70, 73, and 82, a PEG-lipid having the structure set forth in Formula I:

(I)

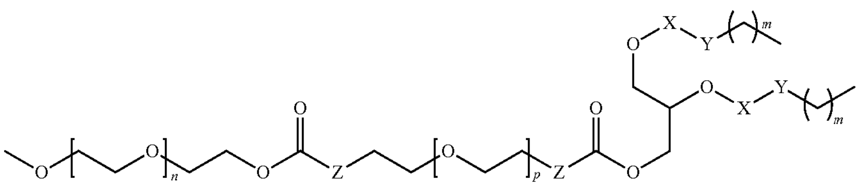

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and a phospholipid having the structure set forth in Formula III:

(III)

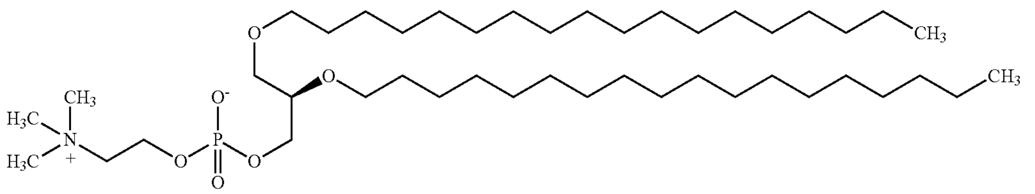

and a pharmaceutically acceptable carrier.

In embodiment 23, the pharmaceutical composition of any of embodiments 20-22 is provided, wherein the composition comprises VLPs of HPV types 16 and 18.

In embodiment 24, the pharmaceutical composition of any of embodiments 20-23 is provided, wherein the composition comprises VLPs of HPV types 6, 11, 16, and 18.

In embodiment 25, the pharmaceutical composition of any of embodiments 20-24 is provided, wherein the composition comprises VLPs of HPV types 31, 45, 52, and 58.

In embodiment 26, the pharmaceutical composition of any of embodiments 20-25 is provided, wherein the composition comprises VLPs of HPV types 6, 11, 16, 18, 31, 33, 45, 52, and 58.

In embodiment 27, the pharmaceutical composition of any of embodiments 20-26 is provided, wherein the pharmaceutical composition further comprises aluminum.

In embodiment 28, the pharmaceutical composition of any of embodiments 20-27 is provided, wherein the composition is made by mixing an HPV vaccine and an LNP adjuvant; wherein the HPV vaccine comprises HPV VLPs and a pharmaceutically acceptable carrier and an LNP adjuvant comprising:

a PEG-lipid having the structure set forth in Formula I:

(I)

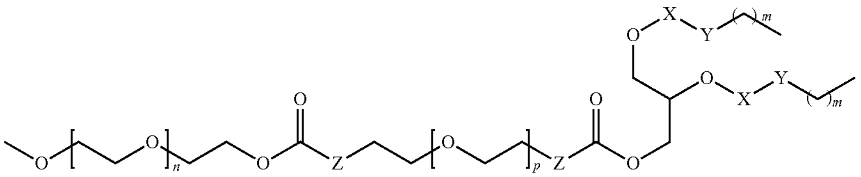

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and a phospholipid having the structure set forth in Formula III:

(III)

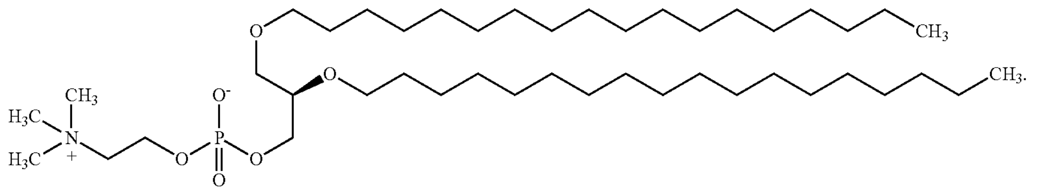

In embodiment 2, the pharmaceutical composition of any of embodiments 20-28 is provided, wherein the HPV VLPs comprise recombinant HPV L1 or recombinant HPV L1+L2 protein.

In embodiment 30, the pharmaceutical composition of any of embodiments 20-29 is provided, wherein the HPV VLPs of each of the at least one HPV types are present in a concentration of about 10 μg to about 300 μg per 0.5 mL of the pharmaceutical composition.

In embodiment 31, the pharmaceutical composition of any of embodiments 20-30 is provided, wherein the total VLP concentration is between 10 μg and 2000 μg per 0.5 mL of the pharmaceutical composition.

In embodiment 32, the pharmaceutical composition of any of embodiments 20-31 is provided, wherein the total LNP concentration is between 0.1 μg to about 200 mg per 0.5 mL of the pharmaceutical composition.

In embodiment 33, the pharmaceutical composition of any of embodiments 20-32 is provided, further comprising about 100 μg to about 3500 μg of an aluminum adjuvant.

In embodiment 34, the pharmaceutical composition of any of embodiments 20-33 is provided, wherein the HPV VLPs are adsorbed onto the aluminum adjuvant.

In embodiment 35, a single-dose vaccine composition is provided comprising:

virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82;

a PEG-lipid having the structure set forth in Formula I:

(I)

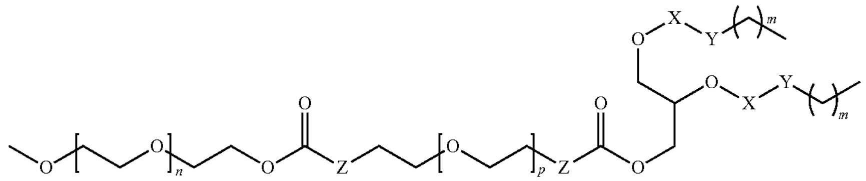

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and a phospholipid having the structure set forth in Formula III:

(III)

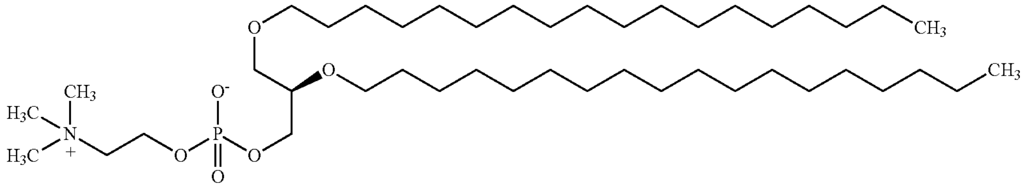

and a pharmaceutically acceptable carrier; wherein the single-dose vaccine composition provides an elevated or comparable anti-HPV immune response relative to multiple doses of the same composition formulated without a lipid nanoparticle adjuvant.

In embodiment 36, the single-dose vaccine composition of embodiment 35 is provided, wherein the vaccine further comprises an aluminum adjuvant.

In embodiment 37, the single-dose vaccine composition of embodiment 36 is provided, wherein the HPV VLPs are adsorbed onto the aluminum adjuvant.

In embodiment 38, the single-dose vaccine composition of any of embodiments 35-37 is provided, wherein each of the HPV VLPs are present in a concentration of about 10 μg to about 300 μg per 0.5 mL of the pharmaceutical composition and wherein the total HPV VLP concentration is between 10 μg and 2000 μg per 0.5 mL of the pharmaceutical composition.

In embodiment 39, the pharmaceutical composition of any of embodiments 20-34 or the single-dose vaccine composition of any of embodiments 35-38 is provided, wherein the HPV VLPs comprise HPV L1 protein and do not comprise HPV L2 protein.

In embodiment 40, the pharmaceutical composition of any of embodiments 20-34 or the single-dose vaccine composition of any of embodiments 35-38 is provided, wherein the HPV VLPs consist of HPV L1 protein.

In embodiment 41, a method of inducing an immune response to a human papillomavirus (HPV) in a human patient comprising administering to the patient the pharmaceutical composition of any of embodiments 20-34 or the single-dose vaccine composition of any of embodiments 35-38 is provided.

In embodiment 42, a method of inducing an immune response to a human papillomavirus (HPV) in a human patient is provided comprising co-administering to the patient (a) a pharmaceutical composition comprising virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82 and (b) a lipid nanoparticle comprising:

a PEG-lipid having the structure set forth in Formula I:

(I)

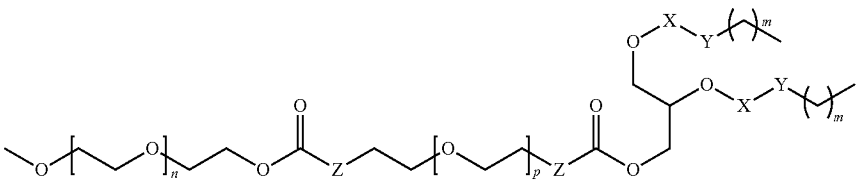

wherein:

each m is independently from 5-20;

n is from 20-60;

p is 0, 1, or 2;

each X is independently $CH_2$, CHR, $CR_2$, or C=O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl;

a phospholipid having the structure set forth in Formula III:

(III)

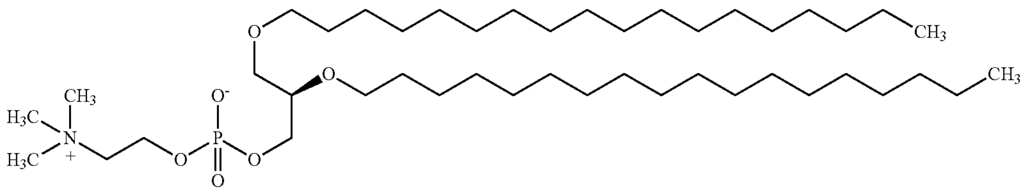

and a pharmaceutically acceptable carrier.

In embodiment 43, a method of preventing infection of or reducing the likelihood of infection of a human patient by a human papillomavirus (HPV) is provided comprising administration to the patient the pharmaceutical composition of any of embodiments 20-34 or the single-dose vaccine composition of any of embodiments 35-38.

In embodiment 44, a method of preventing infection of or reducing the likelihood of infection of a human patient by a human papillomavirus (HPV) is provided comprising co-administering to the patient (a) a pharmaceutical composition comprising virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82 and (b) a lipid nanoparticle comprising:

a PEG-lipid having the structure set forth in Formula I:

(I)

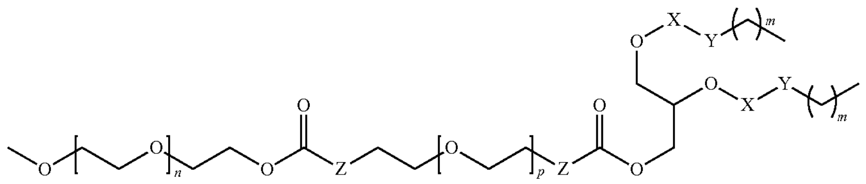

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl;

a phospholipid having the structure set forth in Formula III:

(III)

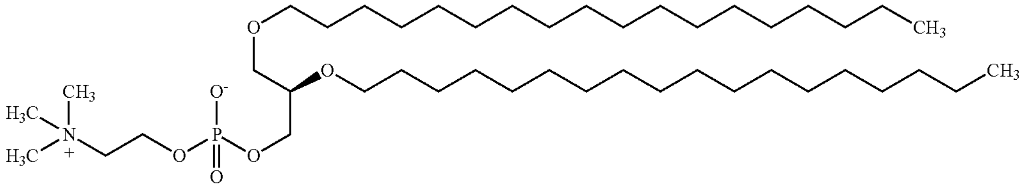

and a pharmaceutically acceptable carrier.

In embodiment 45, a kit is provided comprising:

(a) a human papilloma virus (HPV) vaccine; and (b) a lipid nanoparticle comprising:

(i) a PEG-lipid having the structure set forth in Formula I:

(I)

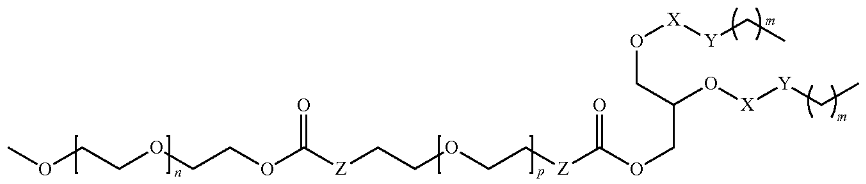

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and (ii) a phospholipid having the structure set forth in Formula III:

(III)

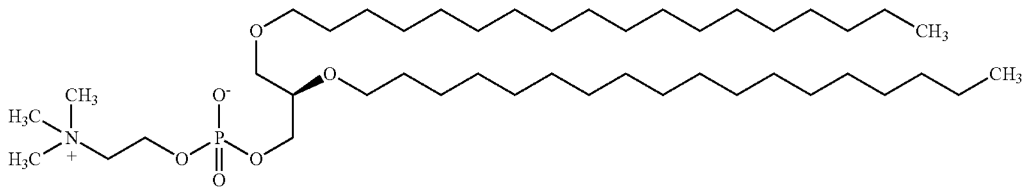

and (c) a pharmaceutically acceptable carrier.

In embodiment 46, the kit of embodiment 45 is provided, further comprising instructions for administering to a human patient the HPV vaccine and the lipid nanoparticle.

In embodiment 47, the kit of any of embodiments 45 and 46 is provided, wherein the HPV vaccine comprises virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82.

In embodiment 48, a method of delivering a pharmaceutical composition to a subject that induces a neutralizing titer against an HPV antigen in the subject is provided comprising:

administering to the subject a pharmaceutical composition comprising:

a lipid nanoparticle adjuvant comprising:

a PEG-lipid having the structure set forth in Formula I:

(I)

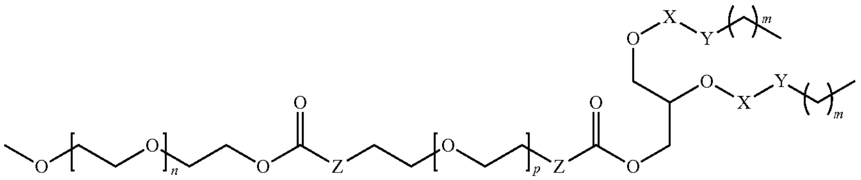

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl; and a phospholipid having the structure set forth in Formula III:

(III)

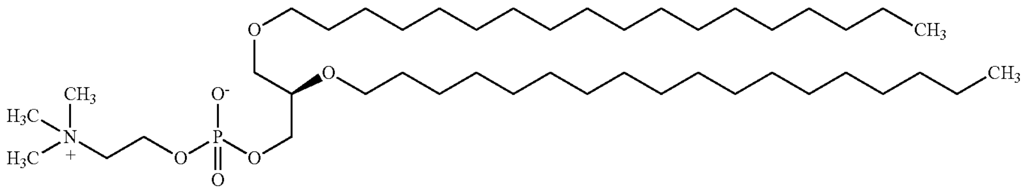

and a pharmaceutically acceptable carrier; and virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82, whereby the administration of the pharmaceutical composition induces a neutralizing titer against the HPV antigen in the subject, wherein a single dose of the pharmaceutical composition provides enhanced or comparable neutralizing titers when compared to multiple doses of the same pharmaceutical composition when the same composition is formulated without a lipid nanoparticle adjuvant.

In embodiment 49, the method of embodiment 48 is provided, wherein the pharmaceutical composition further comprises an aluminum adjuvant.

In embodiment 50, a formulation is provided comprising virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82; and a PEG-lipid having the structure set forth in Formula I:

(I)

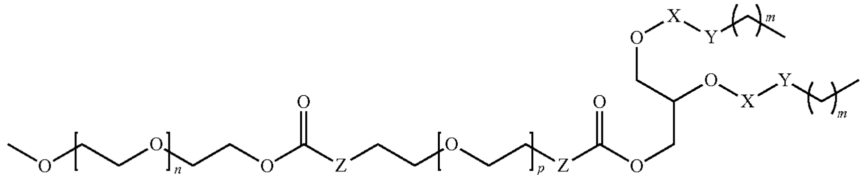

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl.

In embodiment 51, a formulation is provided comprising: virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82; and a phospholipid having the structure set forth in Formula III:

(III)

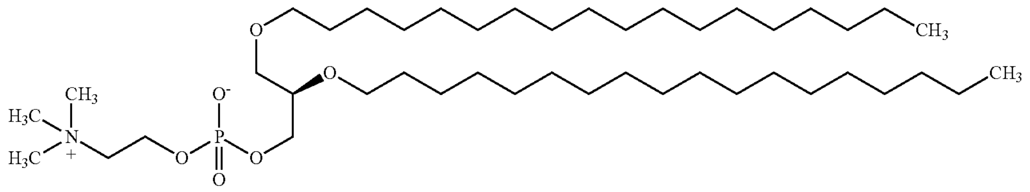

and a pharmaceutically acceptable carrier,

In embodiment 52, a formulation is provided comprising virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82; and a PEG-lipid having the structure set forth in Formula I:

(I)

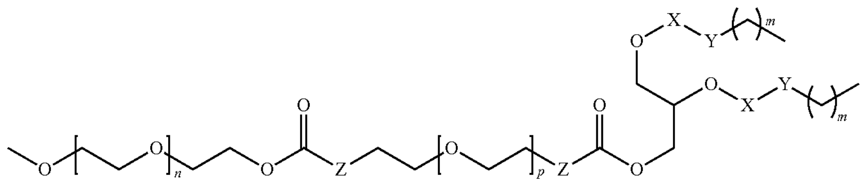

wherein:

each m is independently from 5-20;

n is from 20-60;

p is 0, 1, or 2;

each X is independently $CH_2$, CHR, $CR_2$, or C═O;

each Y is independently $CH_2$, CHR, $CR_2$, or NH;

each Z is independently absent, $CH_2$, or NH; and each R is independently $C_1$-$C_6$ alkyl, $C_6$-$C_{10}$ aryl, $C_1$-$C_6$ heteroalkyl, or $C_6$-$C_{10}$ heteroaryl;

a phospholipid having the structure set forth in Formula III:

(III)

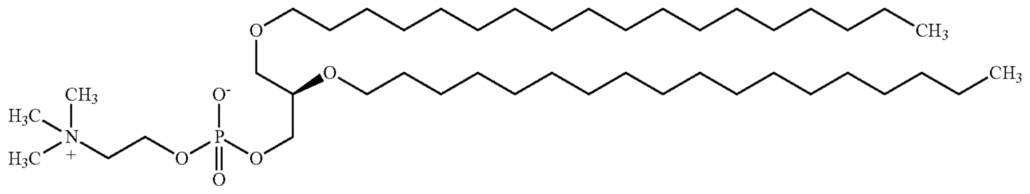

and a pharmaceutically acceptable carrier,

In embodiment 53, the formulation of any of embodiments 50-52 is provided, further comprising a salt.

In embodiment 54, the formulation of any of embodiments 50-53 is provided, further comprising a buffer.

In embodiment 55, the formulation of any of embodiments 50-54 is provided, further comprising a cryoprotectant.

In embodiment 56, the formulation of any of embodiments 50-55 is provided, wherein the formulation is a solution.

In embodiment 57, the formulation of any of embodiments 50-56 is provided, wherein the formulation is stable for 1 month at 37° C.

In embodiment 58, the formulation of any of embodiments 50-57 is provided, wherein the formulation is stable for 6 months at 25° C.

In embodiment 59, the formulation of any of embodiments 50-58 is provided, wherein the formulation is stable for 3 years at 2-8° C.

Intermediates and Examples

General Methods

Solvents, reagents, and intermediates that are commercially available were used as received. Reagents and intermediates that are not commercially available were prepared in the manner as described below. $^1$H NMR spectra are reported as ppm downfield from $Me_4Si$ with number of protons, multiplicities, and coupling constants in Hertz indicated parenthetically. Where LCMS data are presented, the observed parent ion is given. Flash column chromatography was performed using pre-packed normal phase silica or bulk silica, and using a gradient elution of hexanes/ethyl acetate, Pet. ether/ethyl acetate, or similar system, as indicated.

Example 1: Synthesis of 2,5-dioxopyrrolidin-1-yl (2-(2-methoxyethoxy)ethyl) carbonate (Intermediate 1)

Synthesis of Int-1

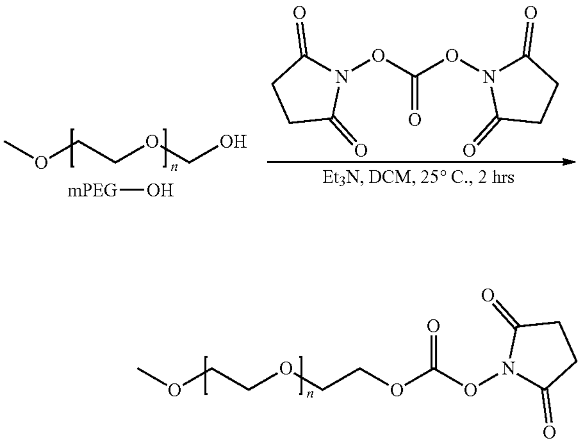

Int-1

To a solution of mPEG-OH (Mn~2000 Da, 48.0 g, 23.3 mmol), as supplied by Creative PEGWorks (Item #PJK-205), in $CH_2Cl_2$ (144 mL) was added a solution of DSC (29.9 g, 117 mmol) in $CH_2Cl_2$ (144 mL) with stirring at room temperature. The reaction mixture was stirred for 2 h. Next, TEA (11.8 g, 117 mmol, 16.2 mL) was added, and the reaction mixture stirred for 1 h. $H_2O$ (200 mL) was added, the organic phase was separated, and the mixture was extracted with additional $CH_2Cl_2$ (50 mL). The combined organics were dried, filtered, and concentrated in vacuo to provide unpurified 2,5-dioxopyrrolidin-1-yl (2-(2-methoxyethoxy)ethyl) carbonate (Intermediate 1) (48.0 g), which was used in subsequent steps without further analysis or purification.

Example 2: Synthesis of 2-bromoethyl phosphorodichloridate (Intermediate 2)

Synthesis of Int-2

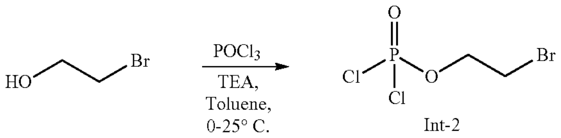

Int-2

Into a 3-L 4-necked round-bottom flask purged and maintained with an inert atmosphere of N2 was placed a solution of $POCl_3$ (432 g, 2.82 mol) in toluene (1.25 L). The reaction mixture was cooled to 0° C. with an EtOH/ice bath. A solution of 2-bromoethan-1-ol (50 g, 0.403 mol) and TEA (41 g, 0.403 mol) in toluene (250 mL) was added dropwise into the flask. The resulting mixture was stirred for 3 h at 25° C. The reaction mixture was filtered and the filtrate was concentrated in vacuo to afford unpurified 2-bromoethyl phosphorodichloridate (Intermediate 2) (90 g), which was used in subsequent chemistry without further purification. $^1H$ NMR (400 MHz, DMSO-d6) δ 4.48-4.30 (m, 2H), 3.87-3.27 (m, 2H) ppm.

Example 3: Synthesis of 1-isocyanatotridecane (Intermediate 3)

Synthesis of Int-3

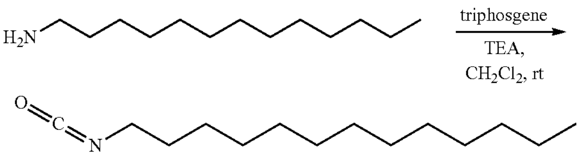

Int-3

Tridecan-1-amine (403 mg, 2.02 mmol) and TEA (0.617 ml, 4.42 mmol) in $CH_2Cl_2$ (10 mL) were added dropwise over 3 min to an ice cold solution of triphosgene (240 mg, 0.808 mmol) in $CH_2Cl_2$ (10 mL). After stirring at rt for 20 min, the mixture was heated to reflux for 20 min, cooled to rt, and stirred again for 16 h. The mixture was concentrated in vacuo, $H_2O$ (15 mL) was added, and extracted with EtOAc (3×15 mL). The combined organic fractions were washed with brine (15 mL), dried over $Na_2SO_4$, filtered, and concentrated in vacuo to provide 1-isocyanatotridecane (Intermediate 3) (450 mg, 1.997 mmol, 99% yield), which was used in the subsequent step without further analysis or purification.

Example 4: Synthesis of 2,2-dimethylpentadecanoyl chloride (Intermediate 4)

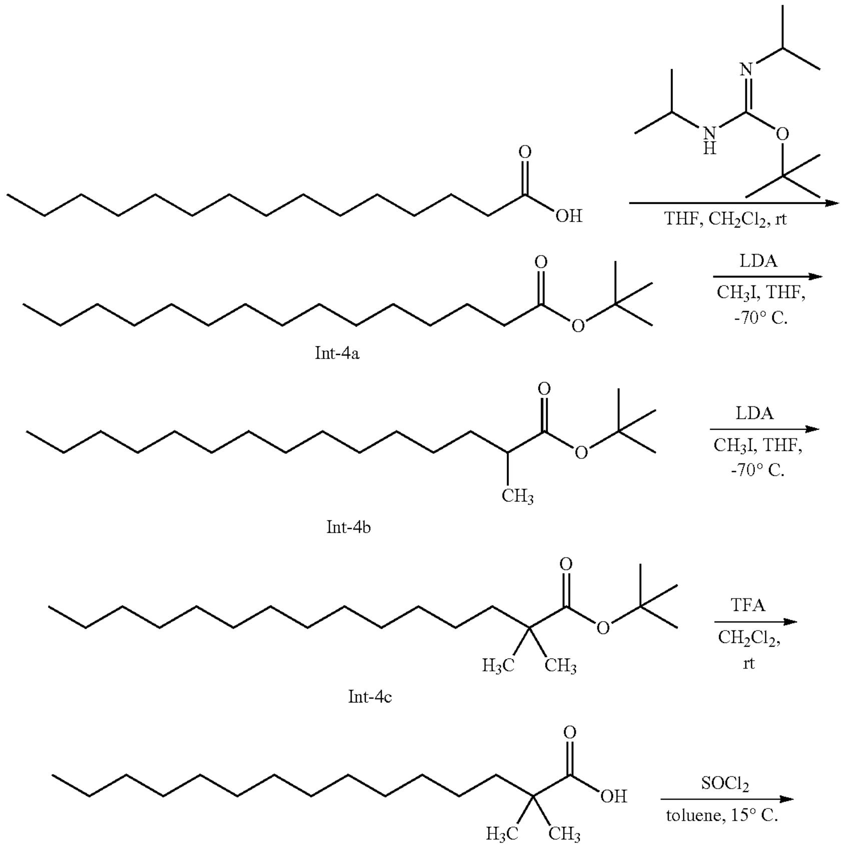

Int-4a

Int-4b

Int-4c

Int-4d

-continued

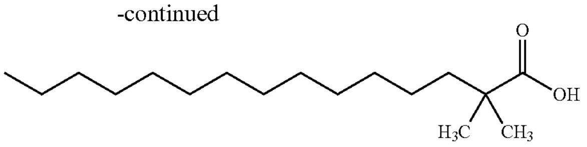

Int-4

Step 1: Synthesis of tert-butyl Pentadecanoate (Int-4a)

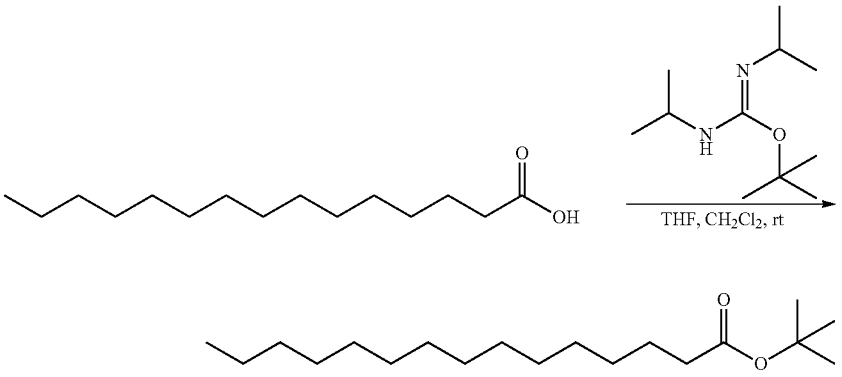

Int-4a tert-Butyl N,N'-diisopropylcarbamimidate (208 mL, 165 mmol, tBuOH solution) was added to a solution of pentadecanoic acid (4 g, 16.5 mmol) in THF (40 mL) and $CH_2Cl_2$ (20 mL) at rt and stirred for 16 h. The reaction mixture was filtered and $H_2O$ (100 mL) was added. The reaction mixture was extracted with EtOAc (2×100 mL), and the combined organic layers were washed with brine (2×200 mL), dried over anh. $Na_2SO_4$, filtered, and concentrated in vacuo. The residue was purified by column chromatography on $SiO_2$ (Pet. ether/EtOAc=20:1) to provide tert-butyl pentadecanoate (Int-4a) (1.3 g, 4.36 mmol, 26.4% yield). $^1$H NMR (400 MHz, $CDCl_3$) δ 2.20 (t, J=7.5 Hz, 2H), 1.45 (s, 9H), 1.26 (s, 24H), 0.89 (t, J=6.7 Hz, 3H) ppm.

Step 2: Synthesis of tert-butyl 2-methylpentadecanoate (Int-4b)

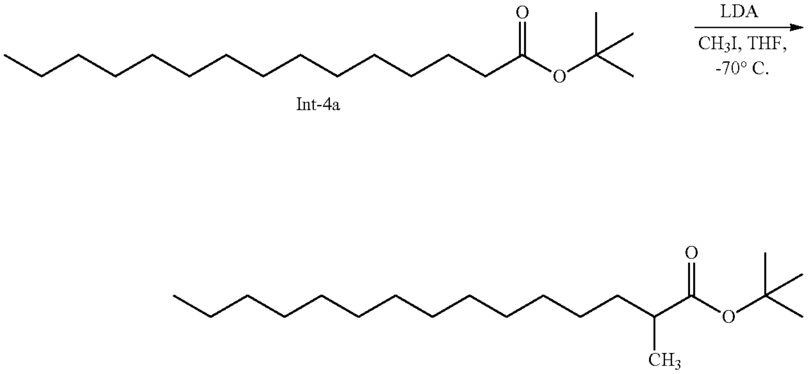

Int-4b

A solution of Int-4a (1.3 g, 4.36 mmol) in THF (20 mL) was cooled to −70° C. with a dry ice/acetone bath. A 2M THF solution of LDA (6.53 mL, 13.07 mmol) was added dropwise under inert atmosphere, and the mixture was slowly warmed to 0° C. for 30 min. The reaction was cooled to −70° C., and iodomethane (3.34 mL, 53.6 mmol) was added. The reaction mixture was again slowly warmed to 0° C. and stirred for 2 h. The reaction was quenched by the addition of $H_2O$ (50 mL), and the resulting mixture extracted with EtOAc (2×50 mL). The combined organic layers were washed with brine (2×20 mL), dried over anh. $Na_2SO_4$ filtered and concentrated in vacuo. The residue was purified by column chromatography on $SiO_2$ (Pet. ether/EtOAc=20:1) to provide tert-butyl 2-methylpentadecanoate (Int-4b) (1.3 g, 3.74 mmol, 86% yield). $^1$H NMR (500 MHz, $CDCl_3$) δ 2.30 (sxt, J=6.9 Hz, 1H), 1.45 (bs, 9H), 1.26 (bs, 24H), 1.11 (d, J=4.1 Hz, 3H), 0.89 (t, J=6.9 Hz, 3H) ppm.

Step 3: Synthesis of tert-butyl 2,2-dimethylpentadecanoate (Int-4c)

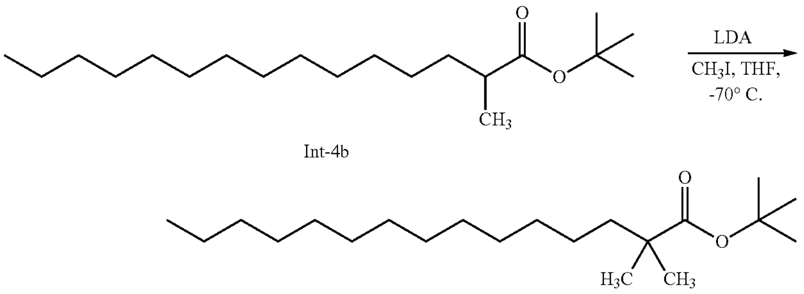

Int-4b
Int-4c

A solution of Int-4b (1.3 g, 4.16 mmol) in THF (20 mL) was cooled to −70° C. with a dry ice/acetone bath. A 2M THF solution of LDA (6.53 mL, 13.07 mmol) was added dropwise, and the mixture was slowly warmed to 0° C. for 30 min. The reaction was cooled to −70° C., and iodomethane (3.36 mL, 53.9 mmol) was added. The reaction mixture was again slowly warmed to 0° C. and stirred for 2 h. The reaction was quenched by the addition of $H_2O$ (50 mL), and the resulting mixture extracted with EtOAc (2×50 mL). The combined organic layers were washed with brine (2×100 mL), dried over anh. $Na_2SO_4$ filtered and concentrated in vacuo. The residue was purified by column chromatography on $SiO_2$ (Pet. ether/EtOAc=20:1) to provide tert-butyl 2,2-dimethylpentadecanoate (Int-4c) (1.1 g, 3.37 mmol, 81% yield). $^1$H NMR (400 MHz, $CDCl_3$) δ 1.44 (br s, 11H), 1.26 (m, 22H), 1.11 (s, 6H), 0.89 (t, J=6.8 Hz, 3H) ppm.

Step 4: Synthesis of 2,2-dimethylpentadecanoic acid (Int-4d)

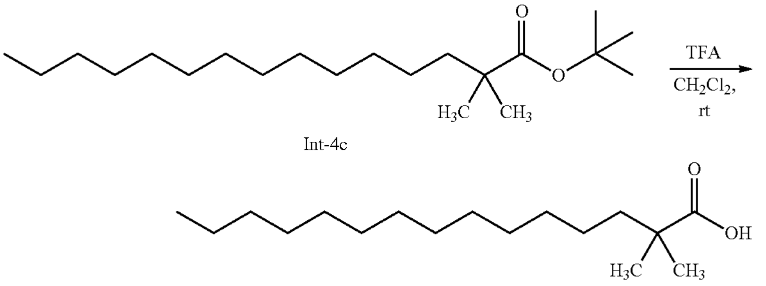

Int-4c
Int-4d

To solution of Int-4c (3 g, 9.19 mmol) in $CH_2Cl_2$ (46 mL) was added TFA (9 mL, 117 mmol) at 0° C. The mixture was stirred at rt for 24 h, and then concentrated in vacuo. The resulting residue was purified by column chromatography on $SiO_2$ (Pet. ether/EtOAc=40:1 to 5:1) to provide 2,2-dimethylpentadecanoic acid (Int-4d) (2.2 g, 7.32 mmol, 80% yield). $^1$H NMR (500 MHz, $CDCl_3$) δ=1.54 (m, 2H), 1.34-1.23 (m, 22H), 1.20 (s, 6H), 0.89 (t, J=6.9 Hz, 3H) ppm.

Step 5: Synthesis of 2,2-dimethylpentadecanoyl chloride (Int-4)

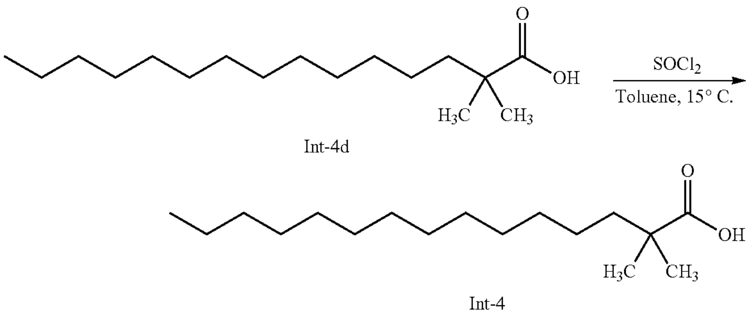

To a solution of 2,2-dimethylpentadecanoic acid (Int-4d) (600 mg, 2.219 mmol) in toluene (9 mL) under inert atmosphere was added $SOCl_2$ (0.6 mL, 8.27 mmol). The mixture was stirred at 15° C. for 3.5 h. The reaction mixture was concentrated in vacuo, additional toluene (~10 mL) was added, and the resulting mixture was concentrated in vacuo again to provide unpurified 2,2-dimethylpentadecanoyl chloride (Intermediate 4) (641 mg, 2.219 mmol, quantitative), which was used in the subsequent step without further analysis or purification.

Example 5: Synthesis of (R)-2-methylpentadecanoyl chloride (Intermediate 5)

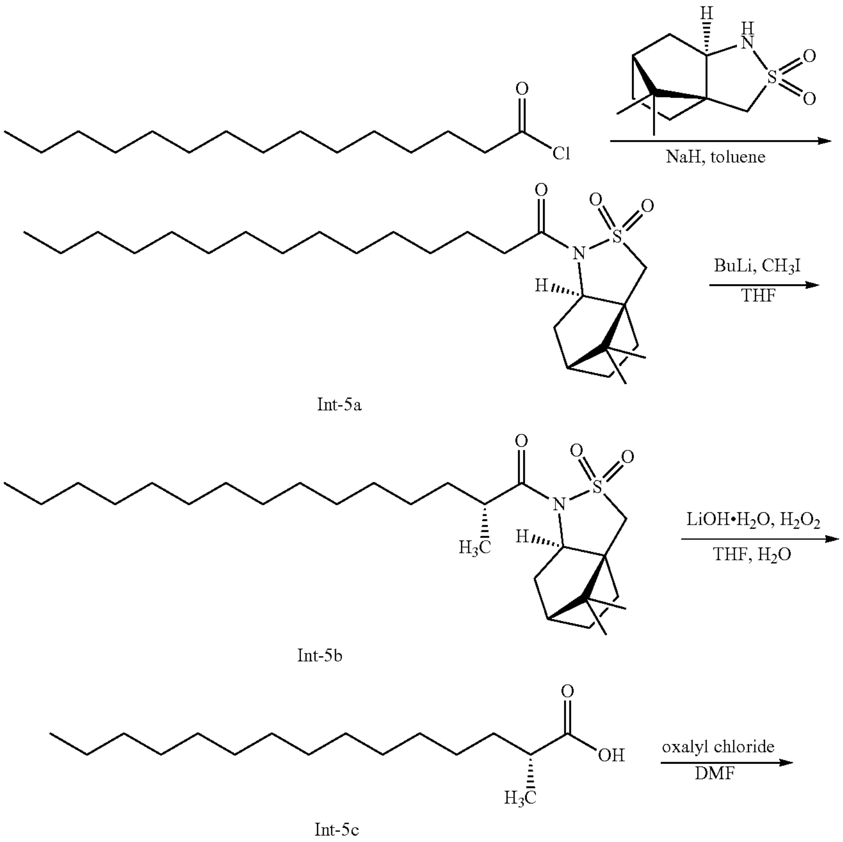

-continued

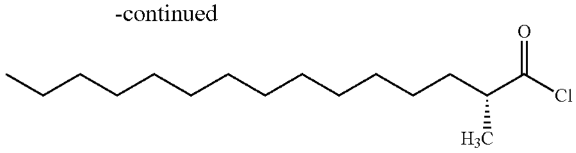

Int-5

Step 1: Synthesis of 1-((3aS,6R,7aR)-8,8-dimethyl-2,2-dioxidotetrahydro-3H-3a,6-methanobenzo[c]-isothiazol-1(4H)-yl)pentadecan-1-one (Int-5a)

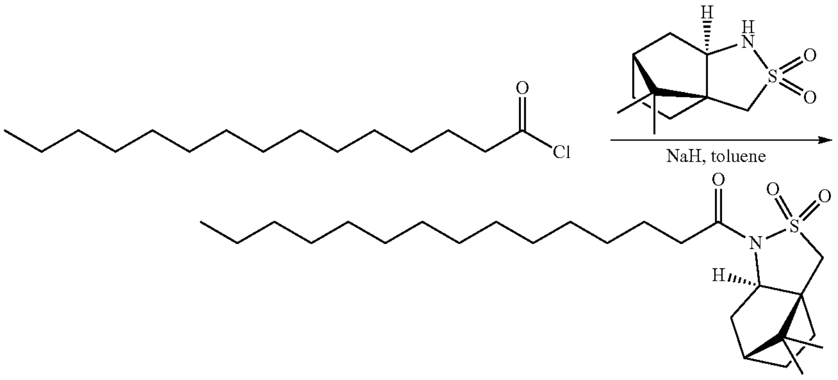

Int-5a (3aS,6R,7aR)-8,8-dimethylhexahydro-3H-3a,6-methanobenzo[c]isothiazole 2,2-dioxide (2.300 g, 10.68 mmol) was added to a stirring solution of NaH (90 mg, 3.75 mmol) in toluene (30 mL) at 0° C., and the mixture was stirred at 25° C. for 1 h. Next, pentadecanoyl chloride (3.228 g, 12.38 mmol) in toluene (30 ml) was added, the reaction mixture was warmed to rt, and stirring was continued for 18 h. Sat. aq. $NH_4Cl$ (40 mL) was added, and the mixture was extracted with EtOAc (3×20 mL). The combined organic phases were washed with brine (15 mL), dried over anh. $Na_2SO_4$, filtered, and concentrated in vacuo. The resulting residue was purified by column chromatography on $SiO_2$ (Pet. ether/EtOAc=10:1) to afford 1-((3aS,6R,7aR)-8,8-dimethyl-2,2-dioxidotetrahydro-3H-3a,6-methanobenzo[c]-isothiazol-1(4H)-yl)pentadecan-1-one (Int-5a) (4.0 g, 9.10 mmol, 85% yield). LCMS (ES, m/z)=440.3 [M+H]+.

Step 2: Synthesis of (R)-1-((3aS,6R,7aR)-8,8-dimethyl-2,2-dioxidotetrahydro-3H-3a,6-methanobenzo-[c]isothiazol-1(4H)-yl)-2-methylpentadecan-1-one (Int-5b)

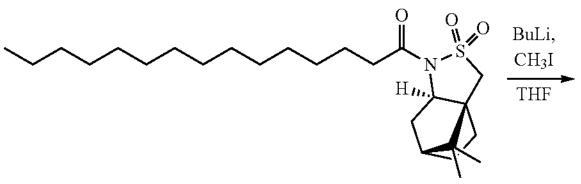

Int-5a

-continued

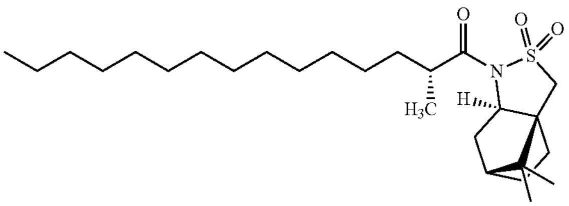

Int-5b

A 2.5M THF solution of n-BuLi (4.00 mL, 10.01 mmol) was added dropwise to a stirring solution of 1-((3aS,6R,7aR)-8,8-dimethyl-2,2-dioxidotetrahydro-3H-3a,6-methanobenzo[c]-isothiazol-1(4H)-yl)pentadecan-1-one (Int-5a) (4.0 g, 9.10 mmol) in THF (40 mL) at −78° C. and the mixture was stirred at −78° C. for 15 min. Next, a solution of iodomethane (1.706 mL, 27.3 mmol) in THF (1 mL) was added, the reaction was warmed to rt, and then stirred for 18 h. Sat. aq. $NH_4Cl$ (50 mL) was added, and the mixture was extracted with EtOAc (2×30 mL). The combined organic phases were washed with 1% aq. ammonia (20 mL) and brine (20 mL), dried over $Na_2SO_4$, filtered, and concentrated in vacuo. The resulting residue was purified by column chromatography on $SiO_2$ (Pet. ether/EtOAc=10:1) to afford (R)-1-((3aS,6R,7aR)-8,8-dimethyl-2,2-dioxidotetrahydro-3H-3a,6-methanobenzo-[c]isothiazol-1(4H)-yl)-2-methylpentadecan-1-one (Int-5b) (3.05 g, 6.72 mmol, 73.9% yield). LCMS (ES, m/z)=454.3 [M+H]+.

Step 3: Synthesis of (R)-2-methylpentadecanoic acid (Int-5c)

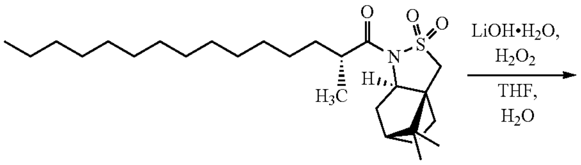

Int-5b

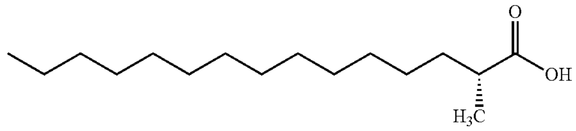

Int-5c

A 30% aqueous solution of $H_2O_2$ (4.60 ml, 45.0 mmol) was added to a stirring mixture of (R)-1-((3aS,6R,7aR)-8,8-dimethyl-2,2-dioxidotetrahydro-3H-3a,6-methanobenzo-[c]isothiazol-1(4H)-yl)-2-methylpentadecan-1-one (Int-5b) (2.05 g, 4.52 mmol) and LiOH.$H_2O$ (950 mg, 22.64 mmol) in THF (20 mL) and $H_2O$ (5 mL) at rt. The reaction mixture was stirred for 18 h. Once all starting material was consumed (by LCMS analysis), sat. aq. $NaHCO_3$ (20 mL) was added, and the mixture extracted with EtOAc (2×20 mL). The combined organic phases were washed with brine (15 mL), dried over $Na_2SO_4$, filtered, and concentrated in vacuo. The resulting residue was purified by column chromatography on $SiO_2$ (Pet. ether/EtOAc=4:1) to provide (R)-2-methylpentadecanoic acid (Int-5c).

Step 4: Synthesis of (R)-2-methylpentadecanoyl chloride (Int-5) oxalyl chloride

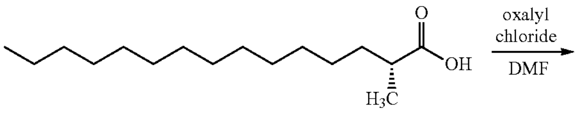

Int-5c

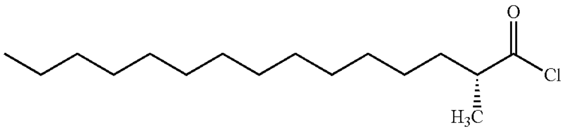

Int-5

Oxalyl chloride (3 mL, 35.5 mmol) was added to a solution of (R)-2-methylpentadecanoic acid (Int-5c) (1.200 g, 4.68 mmol) in $CH_2Cl_2$ (12 mL) and DMF (0.01 mL) at 25° C. and the mixture was stirred for 2 h. The reaction mixture was concentrated in vacuo to provide unpurified (R)-2-methylpentadecanoyl chloride (Int-5) (1.286, g, 4.68 mmol, quantitative), which was used in subsequent steps without further analysis or purification.

Example 6: Synthesis of α-[(15R)-1,12-Dioxo-15-(tetradecyloxy)-5,8,13,17-tetraoxa-2,11-diazahentriacont-1-yl]-ω-methoxypoly(oxyethane-1,2-diyl (Compound 1)

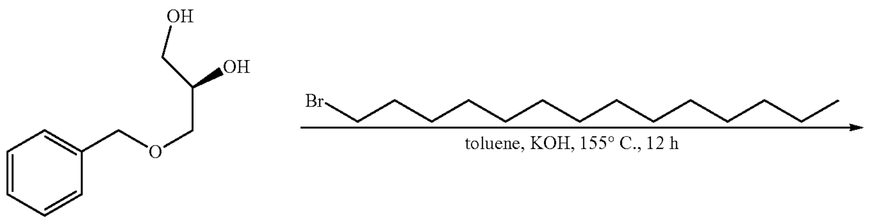

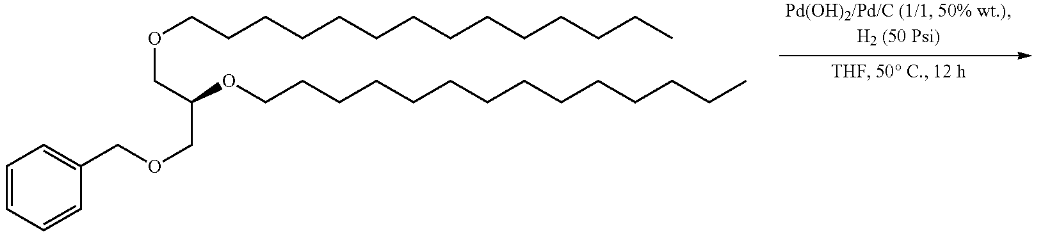

1a

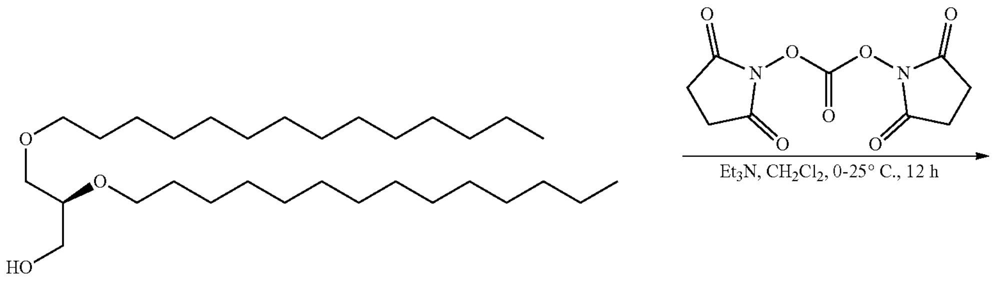

1b

-continued
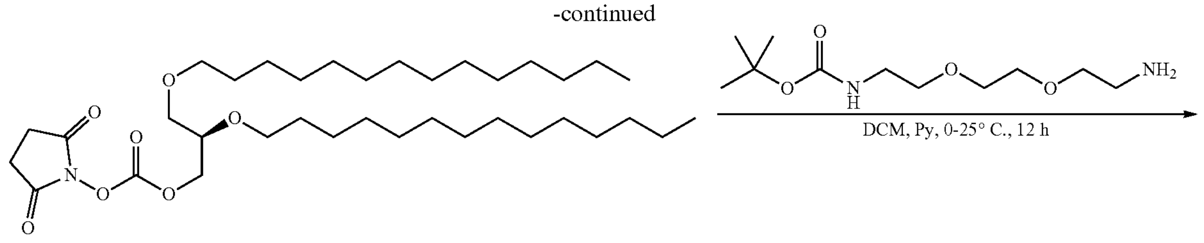
1c
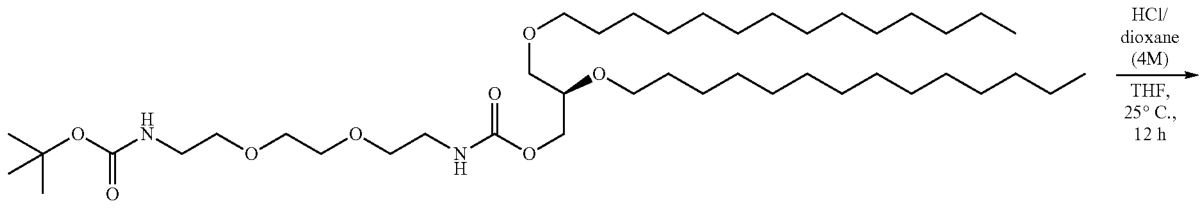
1d
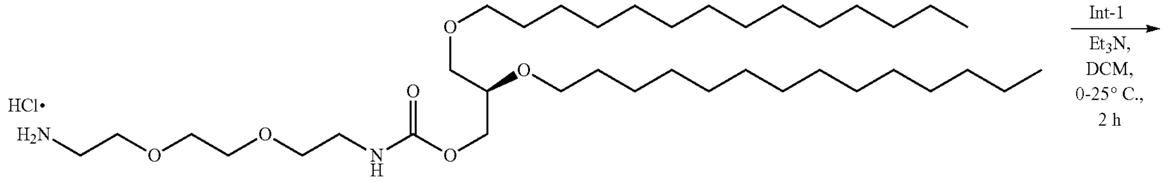
1e
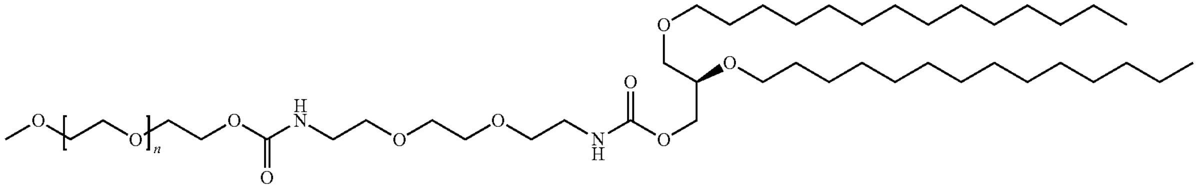
Compound 1
Step 1: Synthesis of (R)-((2,3-bis(tetradecyloxy) propoxy)methyl)benzene (Compound 1a)
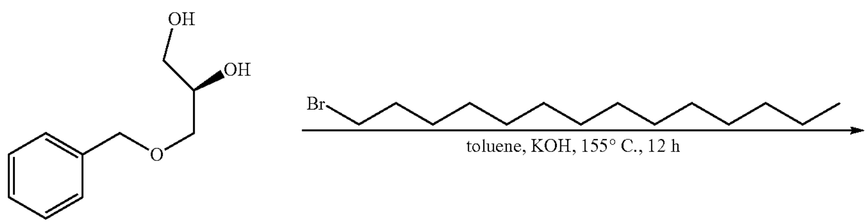
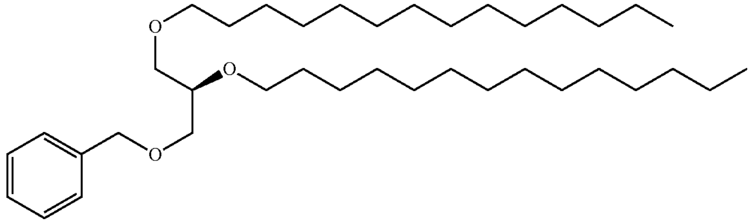
1a To a solution of (R)-3-(benzyloxy)propane-1,2-diol (10.0 g, 54.8 mmol) and 1-bromotetradecane (45.7 g, 165 mmol, 49.1 mL) in toluene (750 mL) was added KOH (12.3 g, 220 mmol) with rapid stirring. The reaction mixture was heated to 155° C. and stirred for 12 h. The reaction mixture was cooled, added to $H_2O$ (300 mL) and extracted with EtOAc (50.0 mL). The extracts were concentrated in vacuo. The resulting residue was purified by column chromatography on $SiO_2$ (Pet. ether/EtOAc=10:1) to afford (R)-((2,3-bis(tetradecyloxy)propoxy)methyl)benzene (Compound 1a) (22.0 g, 38.3 mmol, 69.7% yield). $^1H$ NMR (400 MHz, $CDCl_3$) δ 7.27-7.19 (m, 5H), 4.48 (s, 2H), 3.52-3.34 (m, 9H), 1.51-1.46 (m, 4H), 1.25-1.11 (m, 44H), 0.81 (t, J=8, 8 Hz, 6H) ppm.

Step 2: Synthesis of (S)-2,3-bis(tetradecyloxy)propan-1-ol (Compound 1b)

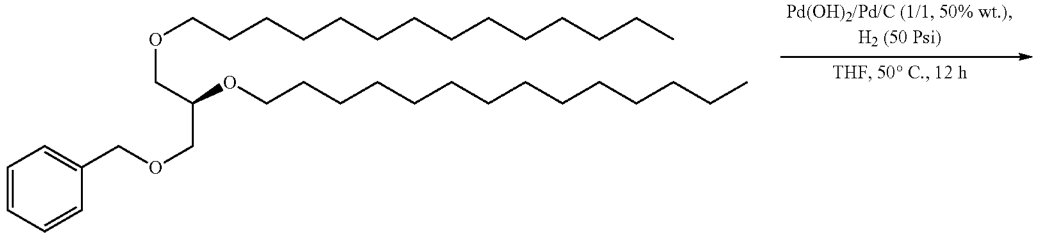

1a

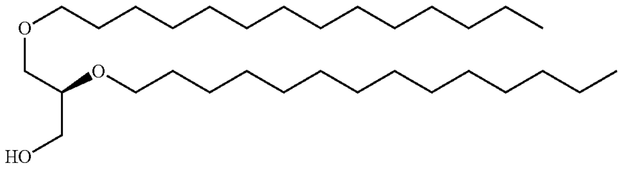

1b

To a solution of (R)-((2,3-bis(tetradecyloxy)propoxy) methyl)benzene (Compound 1a) (22.0 g, 38.3 mmol) in THF (600 mL) was slowly added $Pd(OH)_2$ (5.37 g, 3.83 mmol, 10%) and Pd/C (5.37 g, 3.83 mmol, 10%). The mixture was degassed, and then stirred under an atmosphere of H2 (50 psi) at 50° C. for 12 h. The reaction mixture was cooled, filtered, and concentrated in vacuo. The resulting residue was purified by column chromatography on $SiO_2$ (Pet. ether/EtOAc=5:1) to afford (S)-2,3-bis(tetradecyloxy)propan-1-ol (Compound 1b) (18.5 g, 38.2 mmol, 99.7% yield). $^1H$ NMR (400 MHz, $CDCl_3$) δ 3.75-3.44 (m, 9H), 2.19 (t, J=8, 4 Hz, 1H), 1.61-1.55 (m, 4H), 1.42-1.21 (m, 44H), 0.90 (t, J=8, 4 Hz, 6H) ppm.

Step 3: Synthesis of (R)-2,3-bis(tetradecyloxy)propyl (2,5-dioxopyrrolidin-1-yl) carbonate (Compound 1c)

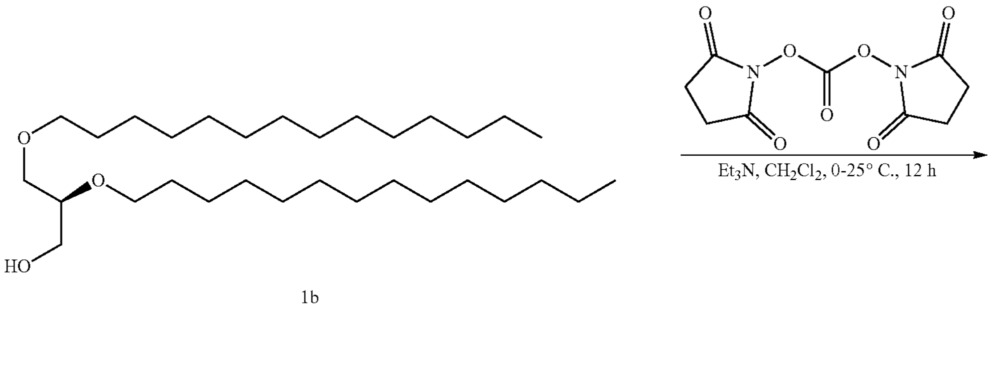

1b

-continued

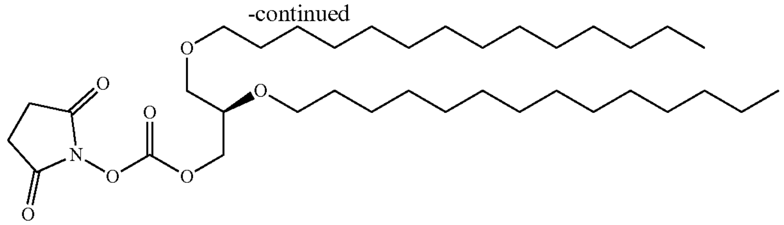

1c

To a solution of (S)-2,3-bis(tetradecyloxy)propan-1-ol (Compound 1b) (18.0 g, 37.1 mmol, 1.00 eq) in $CH_2Cl_2$ (240 mL) was added DSC (28.5 g, 111 mmol, 3.00 eq), and resulting reaction mixture was stirred at 25° C. $Et_3N$ (18.8 g, 186 mmol, 25.8 mL, 5.00 eq) was added to the reaction mixture at 0° C., which was then warmed to 25° C. and stirred for 5 h. $NaHCO_3$ (100 mL, sat. aq.) was added to the reaction mixture with stirring, and the organic phase was extracted and concentrated directly in vacuo to afford the unpurified (R)-2,3-bis(tetradecyloxy)propyl (2,5-dioxopyrrolidin-1-yl) carbonate (Compound 1c) (22.5 g), which was used in the subsequent step without further purification. $^1H$ NMR (400 MHz, $CDCl_3$) δ 4.50-4.37 (m, 2H), 3.59-3.44 (m, 7H), 2.85 (s, 4H), 1.62-1.54 (m, 4H), 1.34-1.18 (m, 44H), 0.90 (t, J=8, 8 Hz, 6H) ppm.

Step 4: Synthesis of (R)-2,3-bis(tetradecyloxy)propyl (2,2-dimethyl-4-oxo-3,8,11-trioxa-5-azatridecan-13-yl)carbamate (Compound 1d)

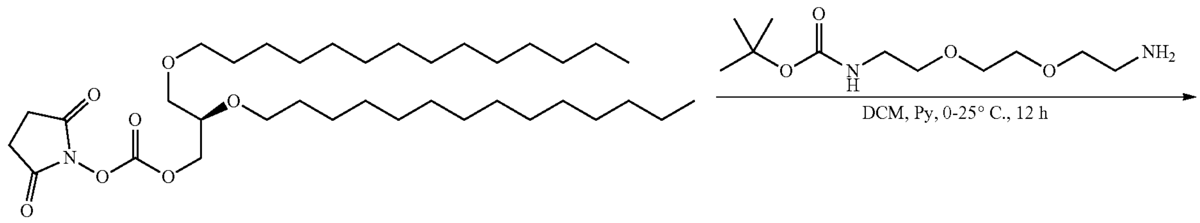

1c

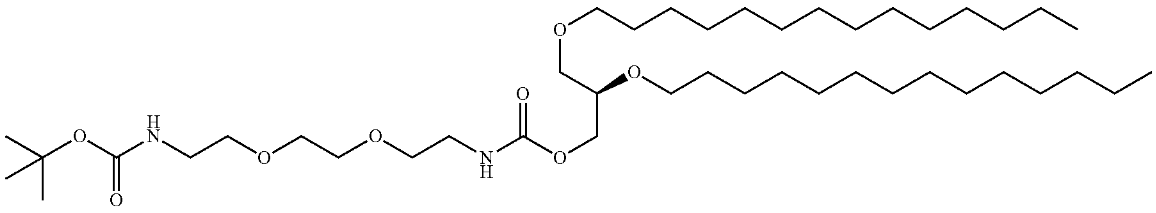

1d

To a solution of crude (R)-2,3-bis(tetradecyloxy)propyl (2,5-dioxopyrrolidin-1-yl) carbonate (Compound 1c) (22.0 g, 35.2 mmol) in $CH_2Cl_2$ at 0° C. was added tert-butyl (2-(2-(2-aminoethoxy)ethoxy)ethyl)carbamate (9.16 g, 36.9 mmol) and pyridine (58.4 g, 738 mmol, 59.6 mL). The reaction mixture was warmed to 25° C. and stirred for 12 h. The reaction mixture was added to a biphasic mixture of $NaHCO_3$ (50.0 mL, sat. aq.) and $CH_2Cl_2$ (50 mL). The organic phase was extracted and concentrated in vacuo. The resulting residue was purified by column chromatography on $SiO_2$ (Pet. ether/EtOAc=20:1 to 0:1) to afford (R)-2,3-bis (tetradecyloxy)propyl (2,2-dimethyl-4-oxo-3,8,11-trioxa-5-azatridecan-13-yl)carbamate (Compound 1d) (23.0 g, 30.3 mmol, 86.2% yield). $^1H$ NMR (400 MHz, $CDCl_3$) δ=5.41-5.00 (m, 2H), 4.26-4.14 (m, 1H), 4.14-4.06 (m, 1H), 3.62 (s, 5H), 3.59-3.53 (m, 6H), 3.49 (d, J=5.4 Hz, 2H), 3.47-3.32 (m, 6H), 1.74 (s, 1H), 1.63-1.54 (m, 4H), 1.46 (s, 9H), 1.32-1.23 (m, 43H), 0.94-0.86 (m, 6H) ppm.

Step 5: Synthesis of (R)-2,3-bis(tetradecyloxy)propyl (2-(2-(2-aminoethoxy)ethoxy)ethyl)carbamate hydrochloride (Compound 1e)

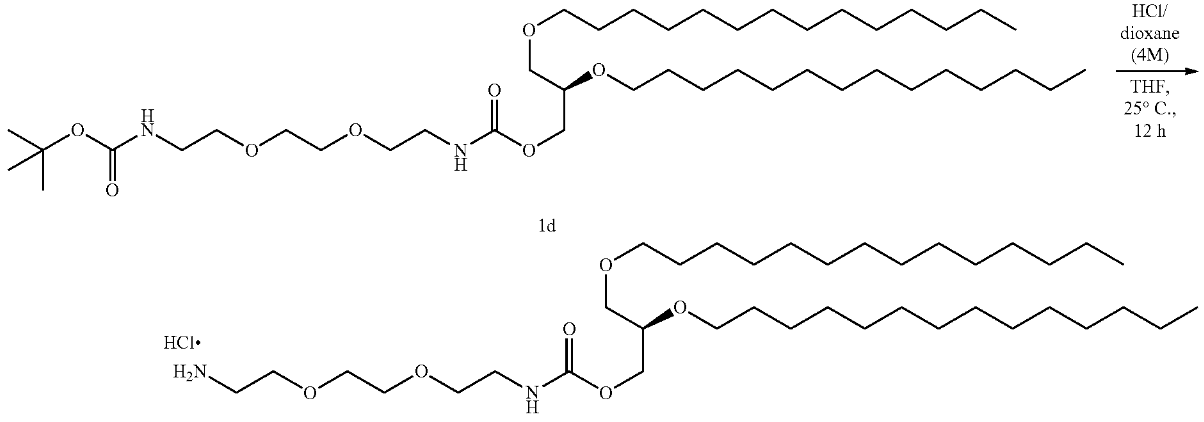

1d

1e

HCl in dioxane (4 M, 52.7 mL, 10.0 eq) was added to a stirring solution of (R)-2,3-bis(tetradecyloxy)propyl (2,2-dimethyl-4-oxo-3,8,11-trioxa-5-azatridecan-13-yl)carbamate (Compound 1d) (16.0 g, 21.1 mmol, 1.00 eq) in THF (80.0 mL) at 25° C. The reaction mixture was stirred for 12 h and then concentrated in vacuo to provide unpurified (R)-2,3-bis(tetradecyloxy)propyl (2-(2-(2-aminoethoxy)ethoxy)ethyl)carbamate hydrochloride (Compound 1e) (16.8 g), which was used in the subsequent step without further purification.

Step 6: Synthesis of α-[(15R)-1,12-Dioxo-15-(tetradecyloxy)-5,8,13,17-tetraoxa-2,11-diazahentriacont-1-yl]-ω-methoxypoly(oxyethane-1,2-diyl) (Compound 1)

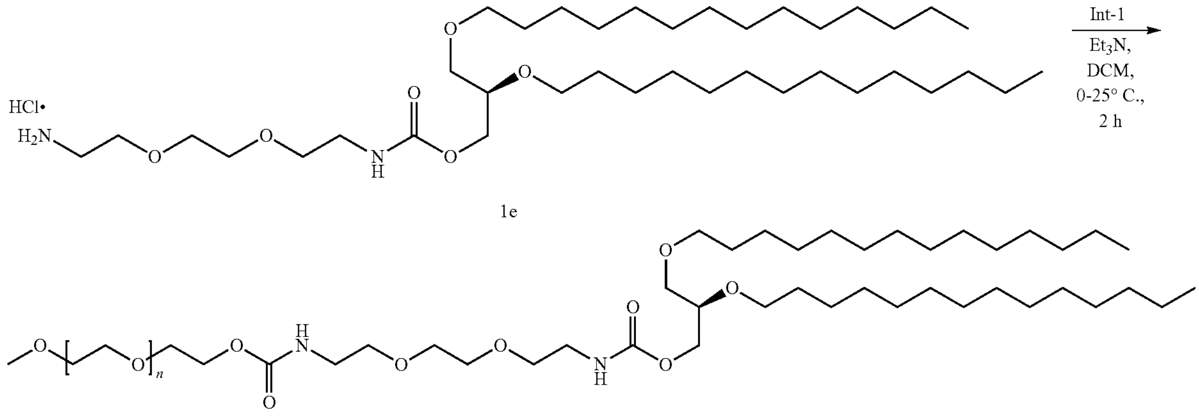

1e

Compound 1

(R)-2,3-bis(tetradecyloxy)propyl (2-(2-(2-aminoethoxy)ethoxy)ethyl)carbamate hydrochloride (Compound 1e) (19.2 g, 27.6 mmol) was added to a solution of unpurified 2,5-dioxopyrrolidin-1-yl (2-(2-methoxyethoxy)ethyl) carbonate (Intermediate 1) (48.0 g, 21.8 mmol) in $CH_2Cl_2$ (480 mL) at 0° C. with stirring. Next, pyridine (36.3 g, 458 mmol, 37.0 mL) was added and the reaction mixture was warmed to 25° C. and stirred for 2 h. The reaction mixture was added to $H_2O$ (200 mL) and the mixture acidified to pH=6 with 2M HCl (aq.). The biphasic mixture was extracted with additional $CH_2Cl_2$ (50 mL) and concentrated in vacuo. The resulting residue was purified by column chromatography on $SiO_2$ ($CH_2Cl_2$/MeOH=10:1) to afford α-[(15R)-1,12-Dioxo-15-(tetradecyloxy)-5,8,13,17-tetraoxa-2,11-diazahentriacont-1-yl]-ω-methoxypoly(oxyethane-1,2-diyl) (Compound 1) (22.6 g, 8.81 mmol, 31.9% yield). mp=49.99° C. (differential scanning calorimetry, 2.0230 mg). $^1$H NMR (400 MHz, $CDCl_3$) δ 5.28-5.36 (m, 1H), 5.25 (br s, 1H), 4.15-4.27 (m, 3H), 4.06-4.15 (m, 1H), 3.77-3.86 (m, 1H), 3.64 (s, 166H), 3.60 (s, 5H), 3.55 (br t, J=5.2 Hz, 8H), 3.33-3.49 (m, 12H), 1.73 (br s, 7H), 1.51-1.60 (m, 4H), 1.25 (s, 48H), 0.87 (t, J=6.8 Hz, 6H) ppm. Mn=2588.85 (n=42). pd=1.00741. Polymer distribution ranging from n=30 to n=55.

Example 6A: Synthesis of α-[(15S)-1,12-Dioxo-15-(tetradecyloxy)-5,8,13,17-tetraoxa-2,11-diazahentriacont-1-yl]-ω-methoxypoly(oxyethane-1,2-diyl) (Compound 2)

Compound 2 is prepared in a manner analogous to Compound 1, as described in Example 6 above. The (R)-3-(benzyloxy)propane-1,2-diol is substituted with (S)-3-(benzyloxy)propane-1,2-diol in Step 1. The remaining steps are similar to those of Example 6 to arrive at α-[(15S)-1,12-Dioxo-15-(tetradecyloxy)-5,8,13,17-tetraoxa-2,11-diazahentriacont-1-yl]-ω-methoxypoly(oxyethane-1,2-diyl) (Compound 2).

Example 6B: Synthesis of rac-α-[1,12-Dioxo-15-(tetradecyloxy)-5,8,13,17-tetraoxa-2,11-diazahentriacont-1-yl]-ω-methoxypoly(oxyethane-1,2-diyl) (Compound 3)

Compound 3 is prepared in a manner analogous to Compound 1, as described in Example 6 above. The (R)-3-(benzyloxy)propane-1,2-diol is substituted with rac-3-(benzyloxy)propane-1,2-diol in Step 1. The remaining steps are similar to those of Example 6 to arrive at α-[(15S)-1,12-Dioxo-15 rac-α-[1,12-Dioxo-15-(tetradecyloxy)-5,8,13,17-tetraoxa-2,11-diazahentriacont-1-yl]-ω-methoxypoly(oxyethane-1,2-diyl) (Compound 3).

Example 6C: Synthesis of α-[(15R)-1,12,18-Trioxo-15-[(1-oxo-2-aza-tetradecyl)oxy]-5,8,13,17-tetraoxa-2,11,19-triazahentriacont-1-yl]-ω-methoxypoly-(oxyethane-1,2-diyl)(Compound 4)

Compound 4 was prepared in a manner analogous to Compound 1, as described in Example 6 above. The 1-bromotetradecane was substituted with 1-isocyanatotridecane (Intermediate 3) in Step 1. The remaining steps were similar to those of Example 6 to arrive at α-[(15R)-1,12,18-Trioxo-15-[(1-oxo-2-aza-tetradecyl)oxy]-5,8,13,17-tetraoxa-2,11,19-triazahentriacont-1-yl]-ω-methoxypoly-(oxyethane-1,2-diyl) (Compound 4).

Example 6D: Synthesis of α-[(15R)-1,12,18-Trioxo-19,19-dimethyl-15-[(1-oxo-2,2-dimethyl-tetradecyl)oxy]-5,8,13,17-tetraoxa-2,11-diazahentriacont-1-yl]-ω-methoxypoly-(oxyethane-1,2-diyl) (Compound 5)

Compound 5 was prepared in a manner analogous to Compound 1, as described in Example 6 above. The 1-bromotetradecane was substituted with 2,2-dimethylpentadecanoyl chloride (Intermediate 4) in Step 1. The remaining steps were similar to those of Example 6 to arrive at α-[(15R)-1,12,18-Trioxo-19,19-dimethyl-15-[(1-oxo-2,2-dimethyl-tetradecyl)oxy]-5,8,13,17-tetraoxa-2,11-diazahentriacont-1-yl]-ω-methoxypoly-(oxyethane-1,2-diyl).

Example 6E: Synthesis of α-[(15R)-1,12,18-Trioxo-19R-methyl-15-[(1-oxo-2R-methyl-tetradecyl)oxy]-5,8,13,17-tetraoxa-2,11-diazahentriacont-1-yl]-ω-methoxypoly-(oxyethane-1,2-diyl) (Compound 6)

Compound 6 was prepared in a manner analogous to Compound 1, as described in Example 6 above. The 1-bromotetradecane was substituted with (R)-2-methylpentadecanoyl chloride (Int-5) in Step 1. The remaining steps were similar to those of Example 6 to arrive at α-[(15R)-1,12,18-Trioxo-19,19-dimethyl-15-[(1-oxo-2,2-dimethyl-tetradecyl)oxy]-5,8,13,17-tetraoxa-2,11-diazahentriacont-1-yl]-ω-methoxypoly-(oxyethane-1,2-diyl).

Example 7: Synthesis of (2R)-2,3-bis(octadecyloxy)propyl 2-(trimethylazaniumyl)ethyl phosphate (Compound 7)

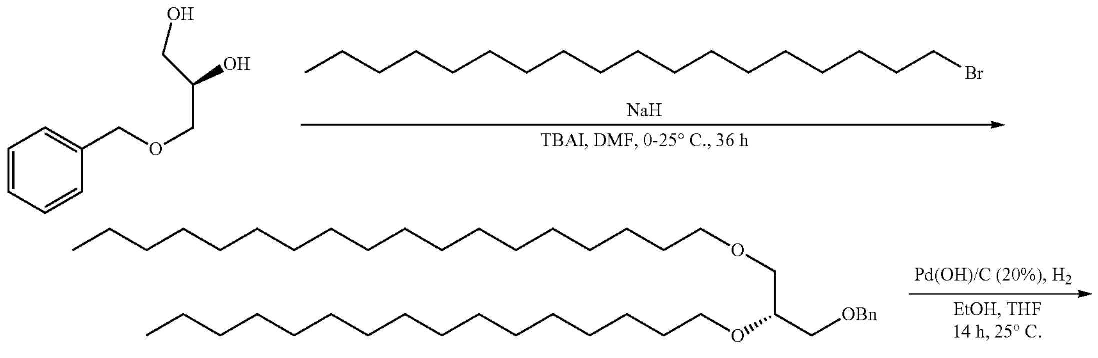

7a

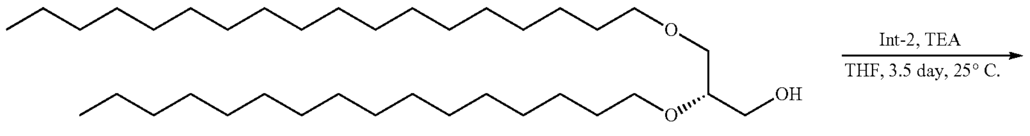

7b

-continued

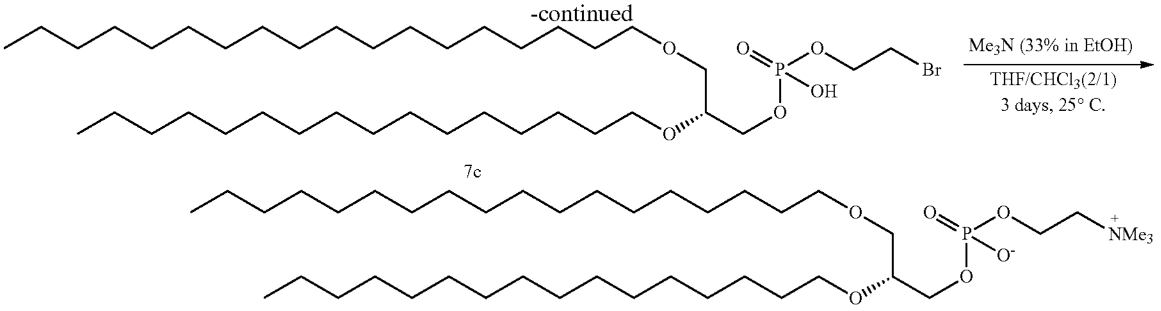

7c

Compound 7

Step 1: Synthesis of (R)-((2,3-bis(octadecyloxy) propoxy)methyl)benzene (Compound 7a)

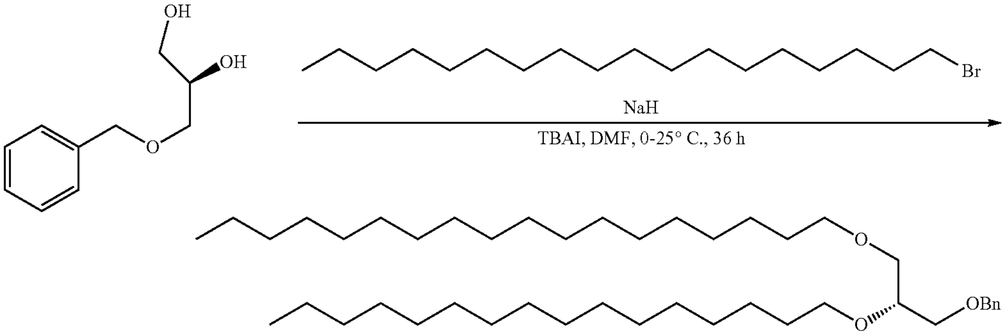

Into a 1-L 3-necked round-bottom flask purged and maintained with an inert atmosphere of nitrogen was placed a solution of NaH (22 g, 60% wt, in mineral oil, 5.00 equiv.) in DMF (500 mL). The reaction mixture was cooled to 0° C. with an EtOH/ice bath. (R)-3-(benzyloxy)propane-1,2-diol (20 g, 0.11 mmol, 1.00 equiv.) was added into the flask in batches. The mixture was stirred for 60 min at room temperature. Next, octadecyl bromide (110 g, 0.33 mmol, 3.0 equiv.) and TBAI (8.26 g, 0.022 mmol, 0.2 equiv.) were added, and the resulting reaction mixture was warmed to 25° C. and stirred for 36 h. The reaction was quenched by pouring into $NH_4Cl$ (500 mL, sat. aq.). The mixture was stirred for 10 min, extracted with $Et_{20}$ (2×1 L) and washed with water (3×300 mL). The organic phase was dried over anhydrous $Na_2SO_4$, filtrated, and the filtrate was concentrated in vacuo. The resulting residue was purified by column chromatography on SiO2 (Pet. ether/EtOAc=1/50 to 1/10) to afford (R)-((2,3-bis(octadecyloxy)propoxy)methyl) benzene (Compound 7a) (59 g, 0.086 mmol, 78%). $^1$H NMR (400 MHz, $CDCl_3$) δ 7.24-7.21 (m, 3H), 7.19 (t, J=4, 4 Hz, 2H), 4.48 (s, 2H), 3.52-3.34 (m, 9H), 1.51-1.46 (m, 4H), 1.25-1.11 (m, 60H), 0.83-0.77 (m, 6H) ppm.

Step 2: Synthesis of (S)-2,3-bis(octadecyloxy)propan-1-ol (Compound 7b)

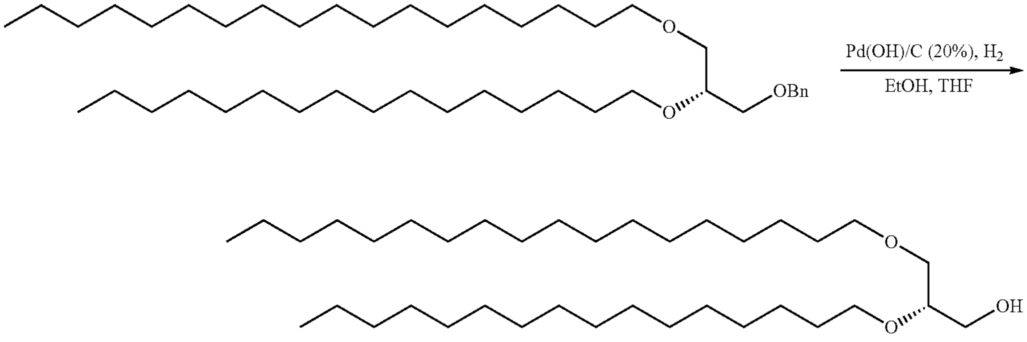

Into 3-L 1-necked round-bottom flask was placed a solution of (R)-((2,3-bis(octadecyloxy)propoxy)methyl)benzene (Compound 7a) (59 g, 0.086 mmol) in EtOH/THF (600 mL/600 mL). The flask was evacuated and back-filled with N2 (5×). $Pd(OH)_2/C$ (11.8 g, 20% wt) was added slowly into the solution. The flask was evacuated and back-filled with N2 (3×). The resulting mixture was stirred for 14 h at 25° C. under hydrogen balloon. The catalyst was removed by filtration through a pad of celite to afford (S)-2,3-bis(octadecyloxy)propan-1-ol (Compound 7b) (44 g, 0.073 mmol, 85%), which was used in the subsequent step without further purification. $^1H$ NMR (400 MHz, $CDCl_3$) δ 3.71-3.36 (m, 9H), 2.17 (d, J=28 Hz, 1H), 1.62-1.53 (m, 4H), 1.48-1.12 (m, 6H), 0.89 (t, J=8, 8 Hz, 6H) ppm.

Step 3: Synthesis of (R)-2,3-bis(octadecyloxy)propyl (2-bromoethyl) phosphate (Compound 7c)

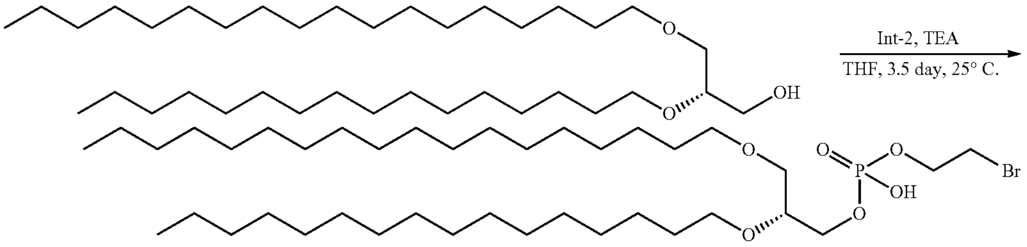

Into a 1-L 3-necked round-bottom flask purged and maintained with an inert atmosphere of N2 was placed a solution of 2-bromoethyl phosphorodichloridate (Intermediate 2) (72 g, 0.3 mmol) in THF (420 mL). A solution of (S)-2,3-bis(octadecyloxy)propan-1-ol (Compound 7b) (42 g, 0.07 mmol, 1.00 equiv.) and $Et_3N$ (42 g, 0.42 mmol) in THF (420 mL) was added dropwise into the flask. The resulting mixture was stirred in the dark at 25° C. for 3.5 days. Toluene (1.0 L) was added, and the resulting reaction mixture was filtered through a pad of celite, and the filtrate concentrated in vacuo. The resulting residue was dissolved in a 1/5 mixture of THF/$NaHCO_3$ (1.0 L, sat. aq.) and the mixture was stirred for an additional 12 h at 25° C. THF was removed in vacuo and the resulting aqueous solution was acidified to pH=1 with 1 M HCl (aq.) and extracted with 4/1 $CH_2Cl_2$/MeOH (2×500 mL). The organic phase was washed with $H_2O$ (2×100 mL), and the combined organic phases were dried over $Mg_2SO_4$ and concentrated in vacuo to afford unpurified (R)-2,3-bis(octadecyloxy)propyl (2-bromoethyl) phosphate (Compound 7c) (45 g, 0.057 mmol, 82% yield), which was used in the subsequent step without further purification. LCMS: (ES, m/z)=783.5, 785.5 [M+H]+.

Step 4: Synthesis of (2R)-2,3-bis(octadecyloxy)propyl 2-(trimethylazaniumyl)ethyl phosphate (Compound 7)

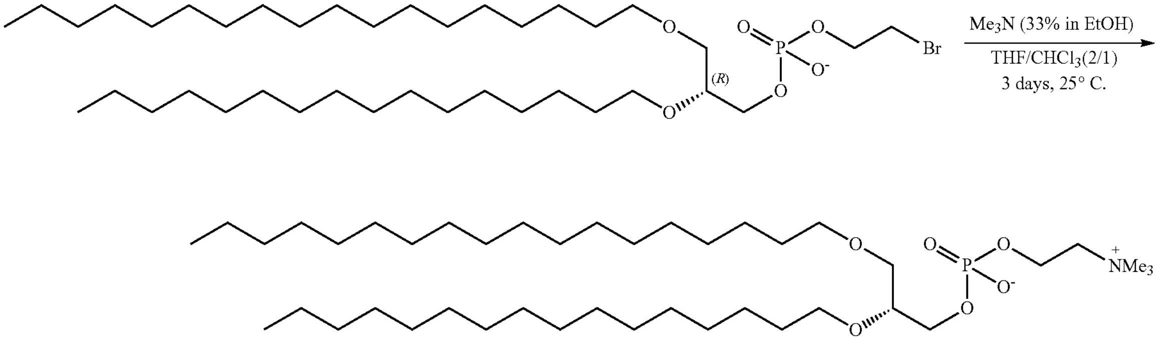

Into a 3-L 4-necked round-bottom flask purged and maintained with an inert atmosphere of nitrogen was placed a solution of unpurified (R)-2,3-bis(octadecyloxy)propyl (2-bromoethyl) phosphate (Compound 7c) (45 g, 0.057 mmol) in 2/1 THF/CHCl3 (1125 mL), and trimethylamine (33% in EtOH) (1350 mL) was added. The reaction mixture was stirred at 25° C. for 3 days. The reaction mixture was concentrated directly in vacuo to afford the unpurified title compound. The resulting residue was slurried in MeCN (1.02 L), and the mixture was filtered. The filter cake was collected to afford an unpurified solid, which was purified by column chromatography on SiO2 (CHCl3/aq. MeOH (12% water)=100:0 to 70:30) The isolated pure material was then recrystallized from EtOAc (440 mL) to afford (2R)-2,3-bis (octadecyloxy)propyl 2-(trimethylazaniumyl)ethyl phosphate (Compound 7) (21.6 g, 0.028 mmol, 49% yield). 1H NMR (400 MHz, $CDCl_3$) δ 4.35 (s, 2H), 3.89 (t, J=4, 4 Hz, 4H), 3.59-3.53 (m, 4H), 3.43 (t, J=12, 12 Hz, 12H), 1.53 (t, J=4, 8 Hz, 4H), 1.31 (d, J=16 Hz, 60H), 0.89 (t, J=8, 8 Hz, 6H) ppm. LCMS: (ES, m/z)=762.7 [M+H]+.

Example 8: Preparation of Lipid Nanoparticle Adjuvant 1 (LNP 1)

Compositions that include an LNP adjuvant of the present invention were made according to the following method. First, the lipid components (DSPC, cholesterol, ePEG2000-DMG, and (13Z, 16Z)—N, N-dimethyl-3-nonyldocosa 13, 16-dien-1-amine) were dissolved in ethanol to form an organic solution. The lipid/ethanol composition was then exposed to a rapid precipitation process, whereby the lipid/ethanol solution was micro-mixed with an aqueous solution of a sodium citrate buffered salt solution having a pH of about 2-6 using a confined volume T-mixer apparatus. The aqueous and organic solutions were combined in a confined-volume mixer with a ratio in the range of about 1:1 to 4:1 vol:vol, with a total flow rate from 10 mL/min-600 L/minute, to form the LNP adjuvant. The resulting LNP adjuvant was diluted with a citrate buffer having a pH of about 6-8.

The LNP adjuvant was then concentrated and filtered via an ultrafiltration process where the alcohol was removed, and the buffer was exchanged for phosphate buffered saline having a pH between 6-8. The ultrafiltration process, having a tangential flow filtration format ("TFF"), used a hollow fiber membrane nominal molecular weight cutoff range from 30-500 KD, targeting 100 KD. The TFF retained the LNP in the retentate and the filtrate or permeate contained the alcohol and final buffer wastes. The TFF provided an initial LNP concentration to a lipid concentration of 1-100 mg/mL. Following concentration, the LNP adjuvant was diafiltered against the final buffer (for example, phosphate buffered saline ("PBS") to remove the alcohol and perform buffer exchange. The material was then concentrated via ultrafiltration.

The concentrated LNP adjuvant was then sterile filtered into a suitable container under aseptic conditions. Sterile filtration was accomplished by passing the LNP suspension through a pre-filter (Acropak 500 PES 0.45/0.8μιη capsule) and a bioburden reduction filter (Acropak 500 PES 0.2/0.8μιη capsule). Following filtration, the vialed LNP adjuvant was stored under suitable conditions.

Example 9: Preparation of Lipid Nanoparticle Adjuvant 2

Compositions that include an LNP adjuvant of the present invention were made according to the following method. First, the lipid components (diether-DSPC, cholesterol, ePEG2000-DMG, and (13Z, 16Z)—N, N-dimethyl-3-nonyldocosa 13, 16-dien-1-amine) were dissolved in ethanol to form an organic solution. The lipid/ethanol composition was then exposed to a rapid precipitation process, whereby the lipid/ethanol solution was micro-mixed with an aqueous solution of a sodium citrate buffered salt solution having a pH of about 2-6 using a confined volume T-mixer apparatus. The aqueous and organic solutions were combined in a confined-volume mixer with a ratio in the range of about 1:1 to 4:1 vol:vol, with a total flow rate from 10 mL/min-600 L/minute, to form the LNP adjuvant. The resulting LNP adjuvant was diluted with a citrate buffer having a pH of about 6-8 followed by a final dilution with phosphate buffered saline having a pH between 6-8.

The LNP adjuvant was then concentrated and filtered via an ultrafiltration process where the alcohol was removed, and the buffer was exchanged for phosphate buffered saline having a pH between 6-8. The ultrafiltration process, having a tangential flow filtration format ("TFF"), used a hollow fiber membrane nominal molecular weight cutoff range from 30-500 KD, targeting 500 KD. The TFF retained the LNP in the retentate and the filtrate or permeate contained the alcohol and final buffer wastes. The TFF provided an initial LNP concentration to a lipid concentration of 1-100 mg/mL. Following initial concentration, the LNP adjuvant was diafiltered against the final buffer (for example, phosphate buffered saline ("PBS") to remove the alcohol and perform buffer exchange. The material was then concentrated via ultrafiltration.

The concentrated LNP adjuvant was then filtered to reduce bioburden into a suitable container under aseptic conditions. Bioburden reduced filtration (BRF) was accomplished by passing the LNP suspension through a pre-filter (Sartobran P 0.45μιη capsule) and a bioburden reduction filter (Sartobran P 0.2μιη capsule). Following filtration, the LNP adjuvant bulk intermediate (ABI) was stored under suitable conditions.

Example 10: Preparation of Lipid Nanoparticle Adjuvant 3

Compositions that include an LNP adjuvant of the present invention were made according to the following method. First, the lipid components (DSPC, cholesterol, ether-ePEG2000-DMG, and (13Z, 16Z)—N, N-dimethyl-3-nonyldocosa 13, 16-dien-1-amine) were dissolved in ethanol to form an organic solution. The lipid/ethanol composition was then exposed to a rapid precipitation process, whereby the lipid/ethanol solution was micro-mixed with an aqueous solution of a sodium citrate buffered salt solution having a pH of about 2-6 using a confined volume T-mixer apparatus. The aqueous and organic solutions were combined in a confined-volume mixer with a ratio in the range of about 1:1 to 4:1 vol:vol, with a total flow rate from 10 mL/min-600 L/minute, to form the LNP adjuvant. The resulting LNP adjuvant was diluted with a citrate buffer having a pH of about 6-8 followed by a final dilution with phosphate buffered saline having a pH between 6-8.

The LNP adjuvant was then concentrated and filtered via an ultrafiltration process where the alcohol was removed, and the buffer was exchanged for phosphate buffered saline having a pH between 6-8. The ultrafiltration process, having a tangential flow filtration format ("TFF"), used a hollow fiber membrane nominal molecular weight cutoff range from 30-500 KD, targeting 500 KD. The TFF retained the LNP in the retentate and the filtrate or permeate contained the alcohol and final buffer wastes. The TFF provided an initial LNP concentration to a lipid concentration of 1-100 mg/mL. Following initial concentration, the LNP adjuvant was diafiltered against the final buffer (for example, phosphate buffered saline ("PBS") to remove the alcohol and perform buffer exchange. The material was then concentrated via ultrafiltration.

The concentrated LNP adjuvant was then filtered to reduce bioburden into a suitable container under aseptic conditions. Bioburden reduced filtration (BRF) was accomplished by passing the LNP suspension through a pre-filter (Sartobran P 0.45μιη capsule) and a bioburden reduction filter (Sartobran P 0.2μιη capsule). Following filtration, the LNP adjuvant bulk intermediate (ABI) was stored under suitable conditions.

Example 11: Preparation of Lipid Nanoparticle Adjuvant 4

Compositions that include an LNP adjuvant of the present invention were made according to the following method. First, the lipid components (diether-DSPC, cholesterol, ether-ePEG2000-DMG, and (13Z, 16Z)—N, N-dimethyl-3-nonyldocosa 13, 16-dien-1-amine) were dissolved in ethanol to form an organic solution. The lipid/ethanol composition was then exposed to a rapid precipitation process, whereby the lipid/ethanol solution was micro-mixed with an aqueous solution of a sodium citrate buffered salt solution having a pH of about 2-6 using a confined volume T-mixer apparatus. The aqueous and organic solutions were combined in a confined-volume mixer with a ratio in the range of about 1:1 to 4:1 vol:vol, with a total flow rate from 10 mL/min-600 L/minute, to form the LNP adjuvant. The resulting LNP adjuvant was diluted with a citrate buffer having a pH of about 6-8 followed by a final dilution with phosphate buffered saline having a pH between 6-8.

The LNP adjuvant was then concentrated and filtered via an ultrafiltration process where the alcohol was removed, and the buffer was exchanged for phosphate buffered saline having a pH between 6-8. The ultrafiltration process, having a tangential flow filtration format ("TFF"), used a hollow fiber membrane nominal molecular weight cutoff range from 30-500 KD, targeting 500 KD. The TFF retained the LNP in the retentate and the filtrate or permeate contained the alcohol and final buffer wastes. The TFF provided an initial LNP concentration of 1-100 mg/mL. Following initial concentration, the LNP adjuvant was diafiltered against the final buffer (for example, phosphate buffered saline ("PBS") to remove the alcohol and perform buffer exchange. The material was then concentrated via ultrafiltration.

The concentrated LNP adjuvant was then filtered to reduce bioburden into a suitable container under aseptic conditions. Bioburden reduced filtration (BRF) was accomplished by passing the LNP suspension through a pre-filter (Sartobran P 0.45μιη capsule) and a bioburden reduction filter (Sartobran P 0.2μιη capsule). Following filtration, the LNP adjuvant bulk intermediate (ABI) was stored under suitable conditions.

Example 12: Preparation of Lipid Nanoparticle Adjuvant 5

Compositions that include an LNP adjuvant of the present invention were made according to the following method. First, the lipid components (diether-DSPC, cholesterol, ether-ePEG2000-DMG (a-[(15R)-1,12,18-Trioxo-15-[(1-oxo-2-aza-tetradecyl)oxy]-5,8,13,17-tetraoxa-2,11,19-triazahentriacont-1-yl]-ω-methoxypoly-(oxyethane-1,2-diyl)), and (13Z, 16Z)—N, N-dimethyl-3-nonyldocosa 13, 16-dien-1-amine) were dissolved in ethanol to form an organic solution. The lipid/ethanol composition was then exposed to a rapid precipitation process, whereby the lipid/ethanol solution was micro-mixed with an aqueous solution of a sodium citrate buffered salt solution having a pH of about 2-6 using a confined volume T-mixer apparatus. The aqueous and organic solutions were combined in a confined-volume mixer with a ratio in the range of about 1:1 to 4:1 vol:vol, with a total flow rate from 10 mL/min-600 L/minute, to form the LNP adjuvant. The resulting LNP adjuvant was diluted with a citrate buffer having a pH of about 6-8 followed by a final dilution with phosphate buffered saline having a pH between 6-8.

The LNP adjuvant was then concentrated and filtered via an ultrafiltration process where the alcohol was removed, and the buffer was exchanged for phosphate buffered saline having a pH between 6-8. The ultrafiltration process, having a tangential flow filtration format ("TFF"), used a hollow fiber membrane nominal molecular weight cutoff range from 30-500 KD, targeting 500 KD. The TFF retained the LNP in the retentate and the filtrate or permeate contained the alcohol and final buffer wastes. The TFF provided an initial LNP concentration of 1-100 mg/mL. Following initial concentration, the LNP adjuvant was diafiltered against the final buffer (for example, phosphate buffered saline ("PBS") to remove the alcohol and perform buffer exchange. The material was then concentrated via ultrafiltration.

The concentrated LNP adjuvant was then filtered to reduce bioburden into a suitable container under aseptic conditions. Bioburden reduced filtration (BRF) was accomplished by passing the LNP suspension through a pre-filter (Sartobran P 0.45μιη capsule) and a bioburden reduction filter (Sartobran P 0.2μιη capsule). Following filtration, the LNP adjuvant bulk intermediate (ABI) was stored under suitable conditions.

Example 13: Preparation of Lipid Nanoparticle Adjuvant 6

Compositions that include an LNP adjuvant of the present invention were made according to the following method. First, the lipid components (diether-DSPC, cholesterol, ether-ePEG2000-DMG (a-[(15R)-1,12,18-Trioxo-19,19-dimethyl-15-[(1-oxo-2,2-dimethyl-tetradecyl)oxy]-5,8,13,17-tetraoxa-2,11-diazahentriacont-1-yl]-ω-methoxypoly-(oxyethane-1,2-diyl)), and (13Z, 16Z)—N, N-dimethyl-3-nonyldocosa 13, 16-dien-1-amine) were dissolved in ethanol to form an organic solution. The lipid/ethanol composition was then exposed to a rapid precipitation process, whereby the lipid/ethanol solution was micro-mixed with an aqueous solution of a sodium citrate buffered salt solution having a pH of about 2-6 using a confined volume T-mixer apparatus. The aqueous and organic solutions were combined in a confined-volume mixer with a ratio in the range of about 1:1 to 4:1 vol:vol, with a total flow rate from 10 mL/min-600 L/minute, to form the LNP adjuvant. The resulting LNP adjuvant was diluted with a citrate buffer having a pH of about 6-8 followed by a final dilution with phosphate buffered saline having a pH between 6-8.

The LNP adjuvant was then concentrated and filtered via an ultrafiltration process where the alcohol was removed, and the buffer was exchanged for phosphate buffered saline having a pH between 6-8. The ultrafiltration process, having a tangential flow filtration format ("TFF"), used a hollow fiber membrane nominal molecular weight cutoff range from 30-500 KD, targeting 500 KD. The TFF retained the LNP in the retentate and the filtrate or permeate contained the alcohol and final buffer wastes. The TFF provided an initial LNP concentration to a lipid concentration of 1-100 mg/mL. Following initial concentration, the LNP adjuvant was diafiltered against the final buffer (for example, phosphate buffered saline ("PBS") to remove the alcohol and perform buffer exchange. The material was then concentrated via ultrafiltration.

The concentrated LNP adjuvant was then filtered to reduce bioburden into a suitable container under aseptic conditions. Bioburden reduced filtration (BRF) was accomplished by passing the LNP suspension through a pre-filter (Sartobran P 0.45μιη capsule) and a bioburden reduction filter (Sartobran P 0.2μιη capsule). Following filtration, the LNP adjuvant bulk intermediate (ABI) was stored under suitable conditions.

Example 14: Preparation of Refrigerator-Stable Lipid Nanoparticle

LNPs were formulated at 5 mg/mL total lipids in 20 mM Tris 10% Sucrose pH 7.5, and placed on stability in 2R glass vials with a fill volume of 0.7 mL. A formulation including the LNP adjuvant described in Example 8 (hereinafter "LNP Adjuvant 1") or LNP versions where Ether-ePEG-DMG or Diether-DSPC were singly substituted (i.e., a formulation including the LNP adjuvant described in Example 9 (hereinafter "LNP Adjuvant 2") and a formulation including the LNP adjuvant described in Example 10 (hereinafter "LNP Adjuvant 3")) into LNP for accelerated stability evaluation at 37 C.

Figure 1B:
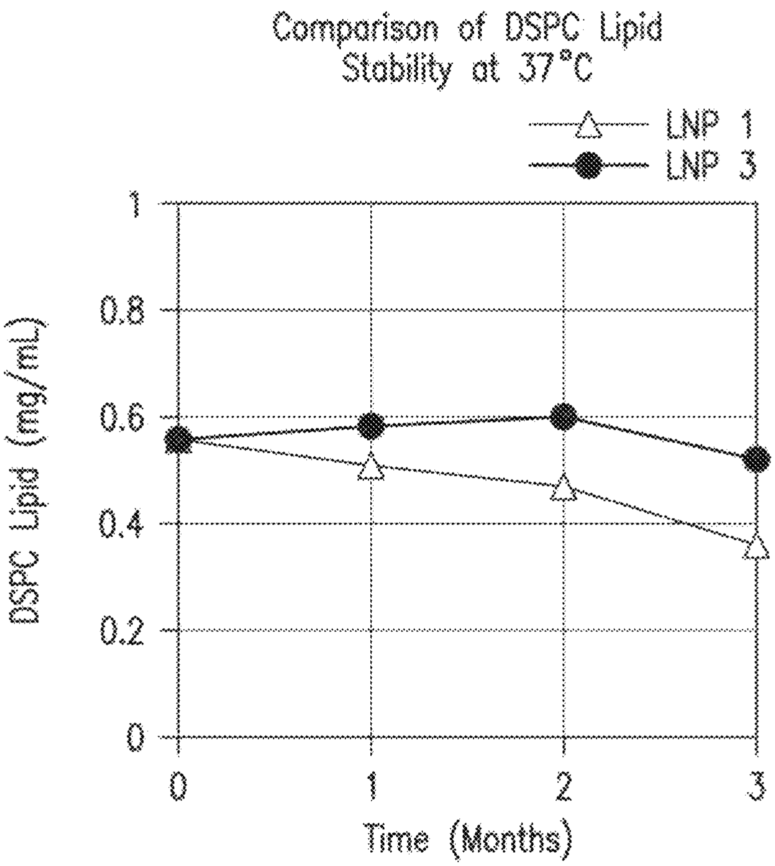
Figure 2A:
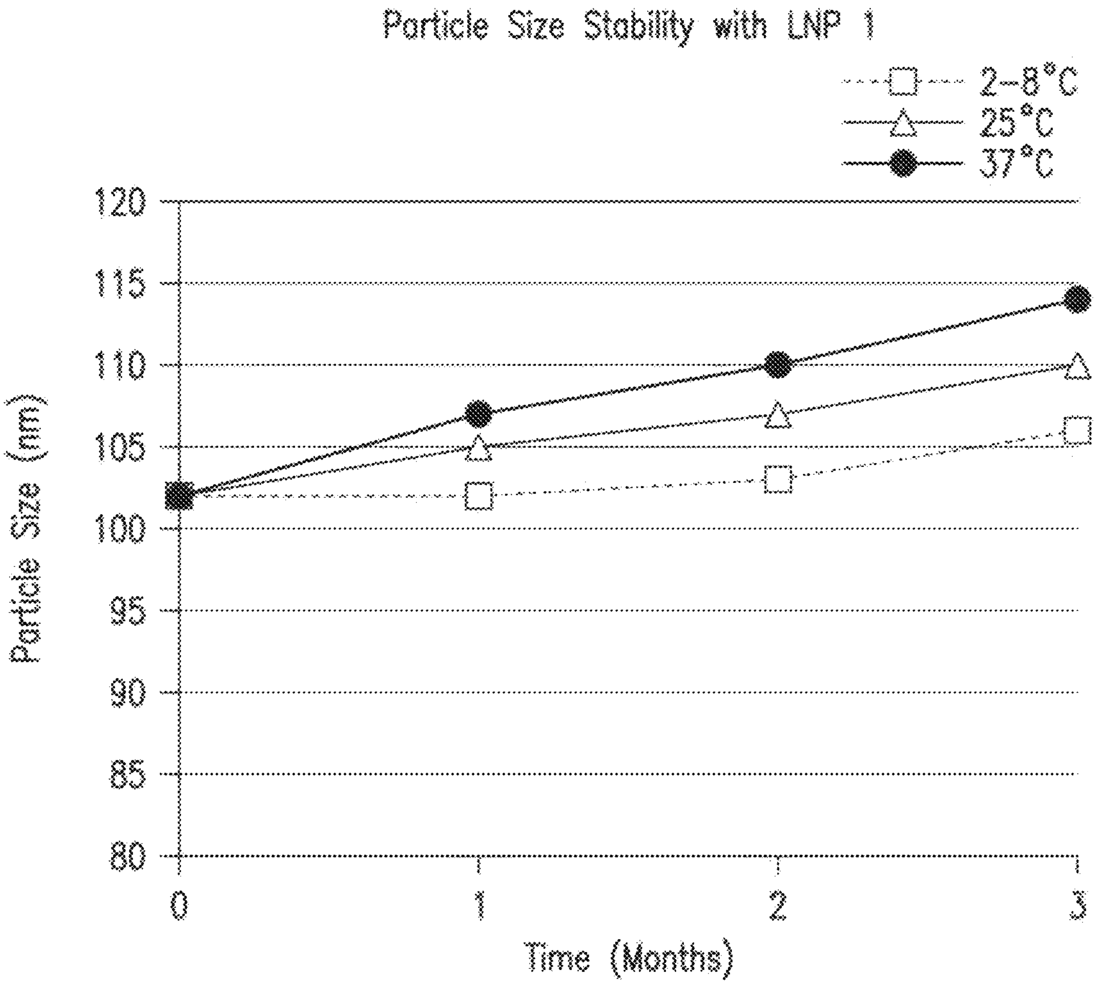
FIGS. 2A-2D depict graphical comparison of stability of particle size and various (PEG, DSPC, and DSPC/PEG) components of a lipid nanoparticle over 3 months.
Figure 2B:
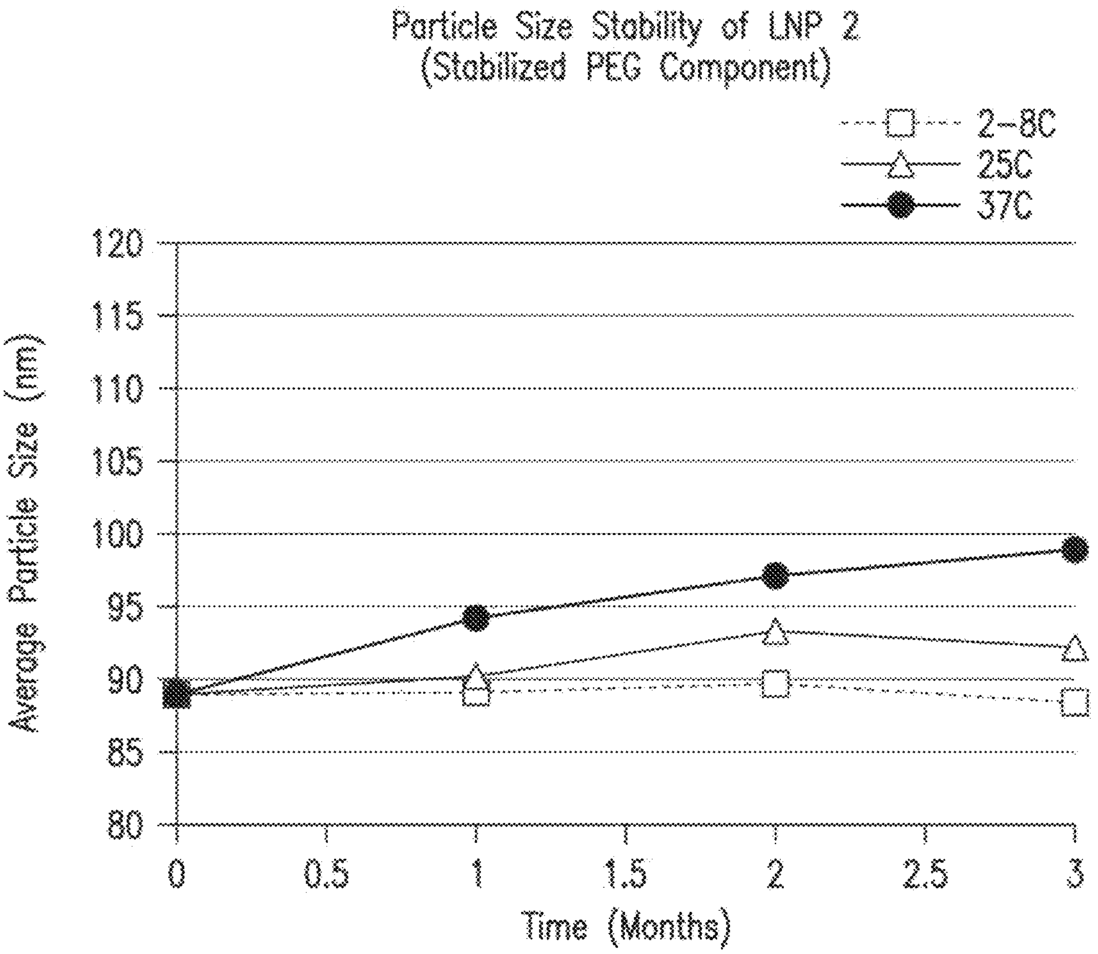
Figure 2C:
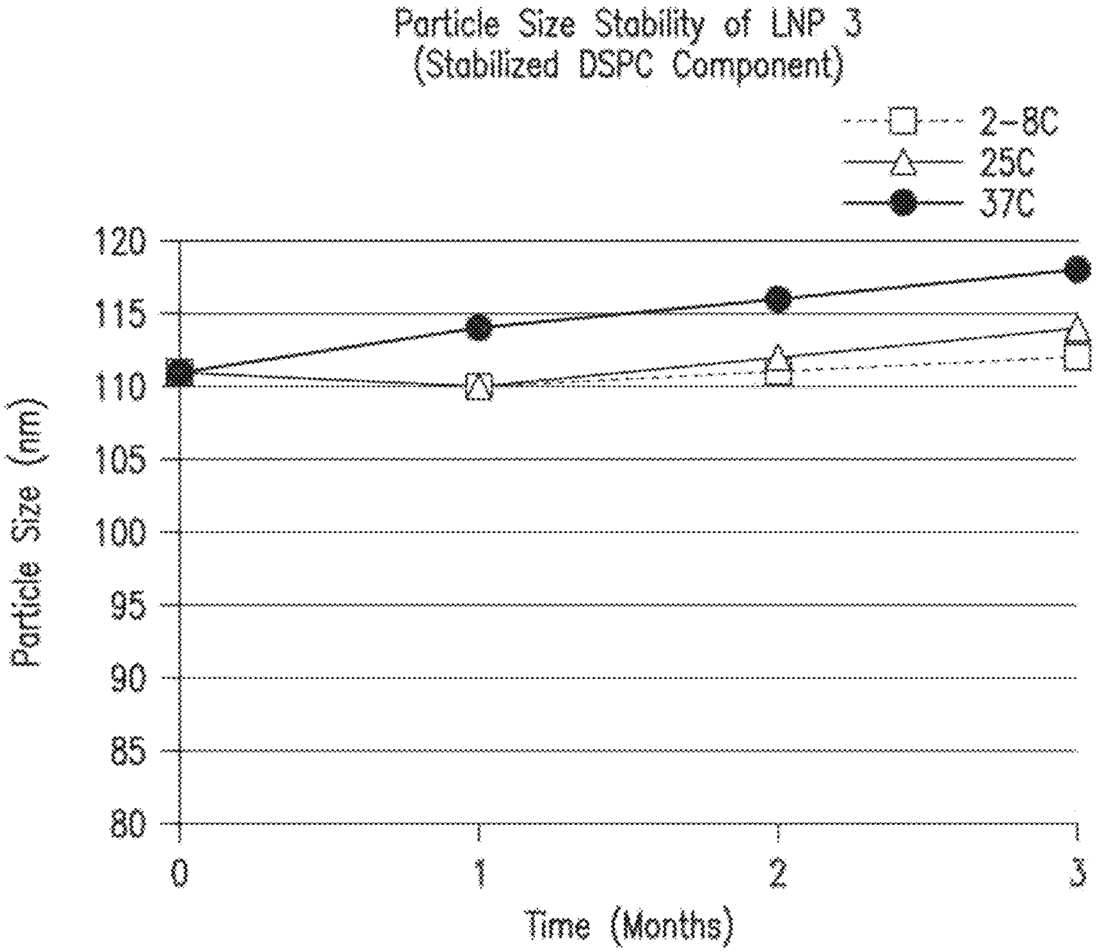
Figure 2D:
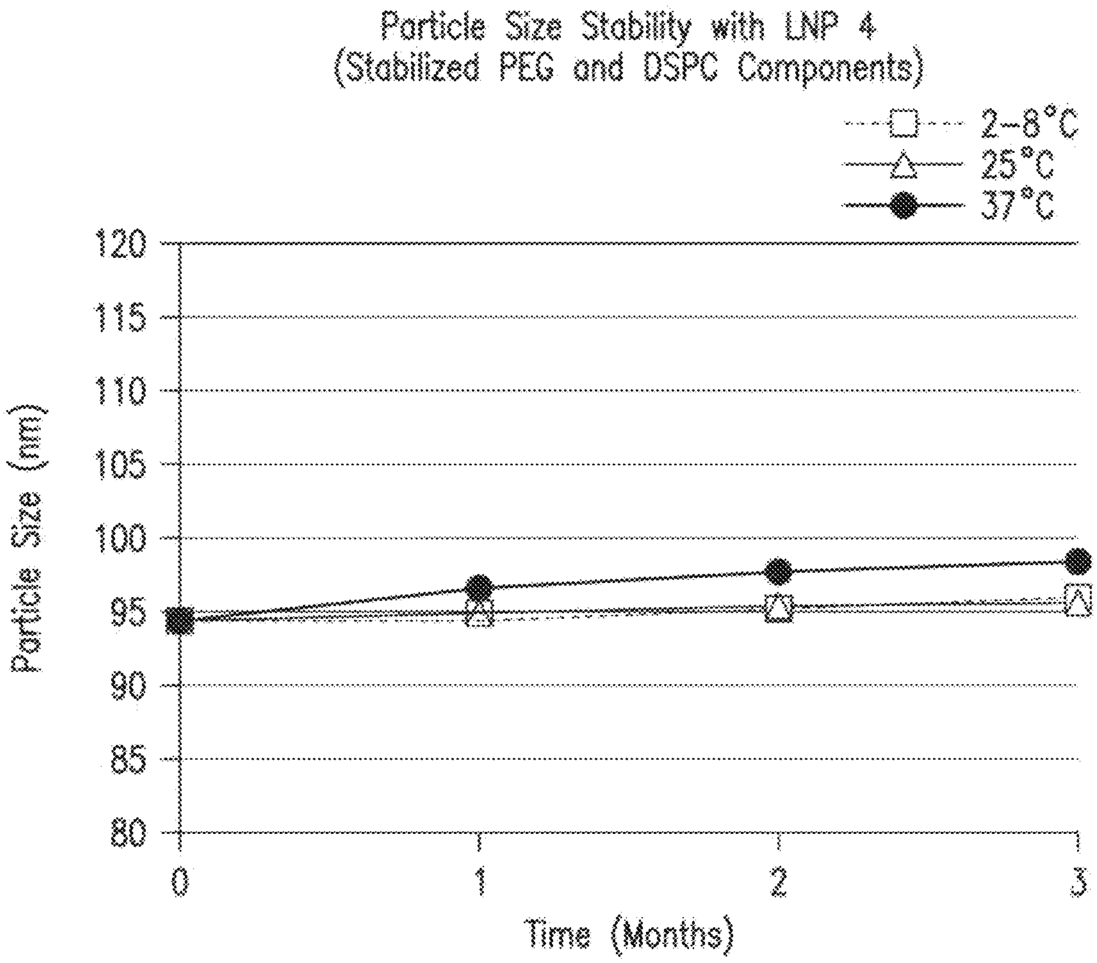

Lipid identities were confirmed by a UPLC-CAD assay (e.g. An assay that utilizes Ultra Performance Liquid Chromatography (UPLC)/Charged Aerosol Detector (CAD) method with an Agilent Zorbax Eclipse 2.1 ID×100 mm C18 UPLC reversed-phase column using a gradient of water and methanol with 16.2 mM triethylamine and 19.2 mM glacial acetic acid (pH 5.4)) to assess the integrity of the ePEG-DMG or DSPC moieties in the LNPS. As shown in FIGS. 1A and 1B, incorporation of individual ether lipids in LNP dramatically improved solution stability under accelerated condition.

Example 15: Analysis of Particle Size of LNP Adjuvants 1-4 after Accelerated Stability Bulk ABI or LNP is diluted to the target total lipid concentration in the same buffer system it is prepared in and aliquoted into 2R glass vials (0.7 mL per vial) and stoppered with a serum stopper. Vials were then incubated at their intended temperature for the pre-determined time.

Dynamic Light Scattering (DLS) is used to estimate the average particle size of samples. DLS uses a laser to illuminate particles in a solution, and then examines the changes in intensity of the scattered light over time as a result of Brownian motion of illuminated particles. The correlation of the scattered light intensity over time to the intensity at time zero results in an exponential decay curve, or correlation function. The rate of decay correlation function, with respect to time, is much faster for smaller particles than larger particles. Therefore, this correlation function along with the Stokes-Einstein equation can be used to calculate the mean particle size.

LNPs as described in Examples 8-11 above were formulated at 5 mg/mL total lipids in 20 mM Tris 10% Sucrose pH 7.5 and placed on stability in 2R glass vials with a fill volume of 0.7 mL. LNP Adjuvant 1, LNP Adjuvant 2, LNP Adjuvant 3, and a formulation including the LNP adjuvant described in Example 11 (hereinafter "LNP Adjuvant 4") were evaluated for accelerated stability at multiple temperatures. Particle size of the LNPs were measured using dynamic light scattering. As shown in FIGS. 2A-2D, incorporation of individual ether lipids in LNP dramatically improved solution stability under accelerated condition.

Example 16: Analysis of Accelerated Stability of LNP Adjuvants 1, 5, and 6

Figure 3A:
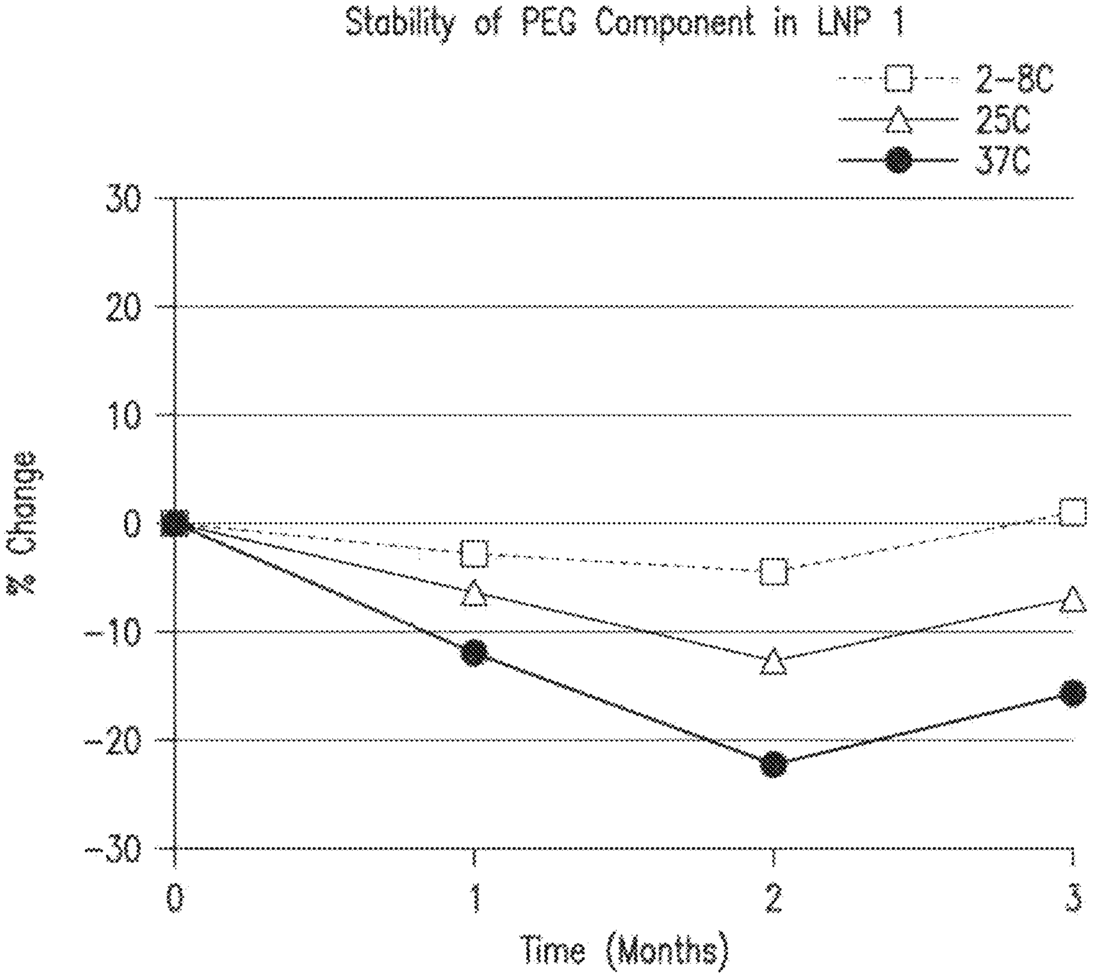
FIGS. 3A-3C depict graphical comparison of stability of particle size and various PEG components in lipid nanoparticles over 3 months.
Figure 3B:
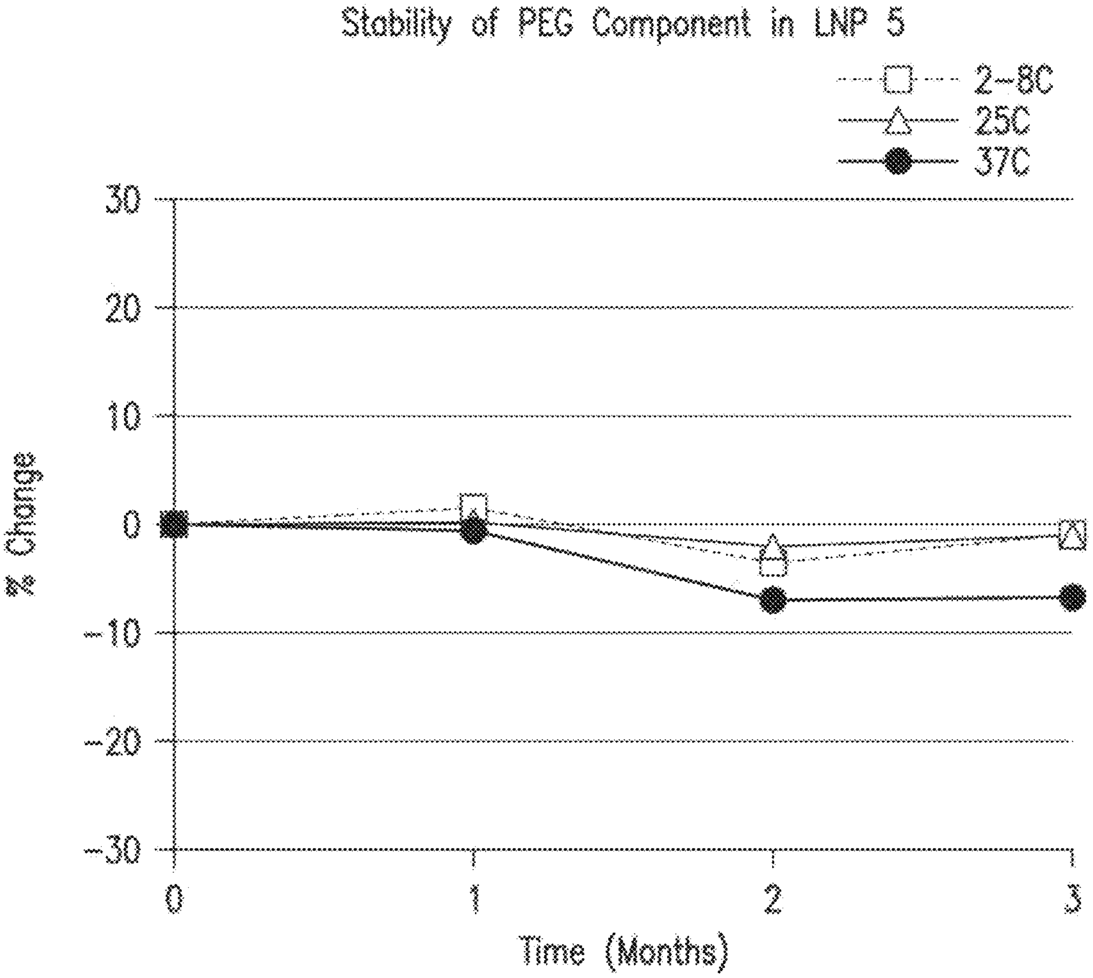
Figure 3C:
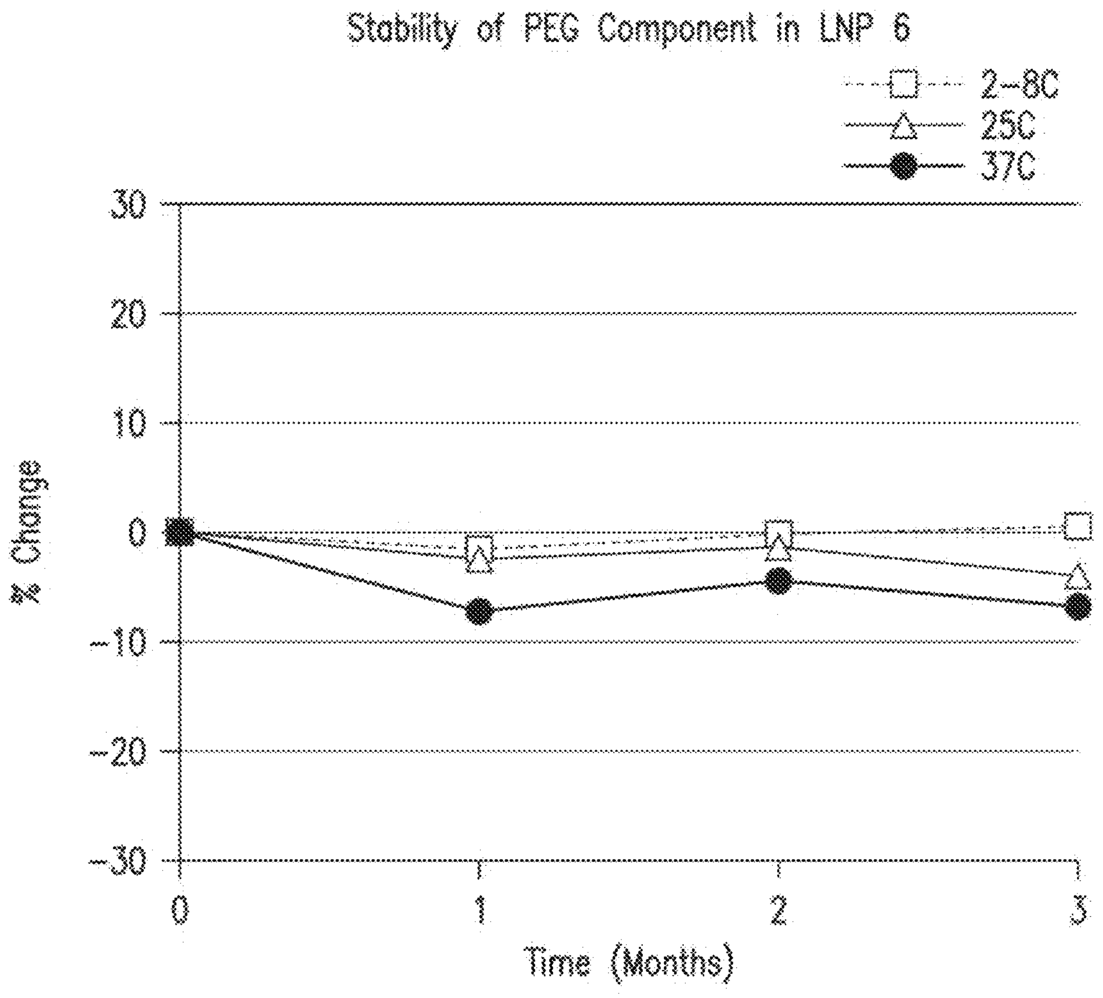

LNPs as described in Examples 8, 12 and 13 above were formulated at 5 mg/mL total lipids in 20 mM Tris 10% Sucrose pH 7.5, and placed on stability in 2R glass vials with a fill volume of 0.7 mL. LNP Adjuvant 1, a formulation including the LNP adjuvant described in Example 12 (hereinafter "LNP Adjuvant 5"), and a formulation including the LNP adjuvant described in Example 13 (hereinafter "LNP Adjuvant 6") were prepared for stability evaluation. The Lipids UPLC-CAD assay was used to assess the integrity of the ePEG-DMG or DSPC moieties in the LNPS. As shown in FIGS. 3A-3C, incorporation of alternate PEG-DMG molecules into the LNP dramatically improved solution stability under accelerated conditions.

Example 17: Analysis of Stability of LNP Adjuvant 1 and 4 Components

Figure 4A:
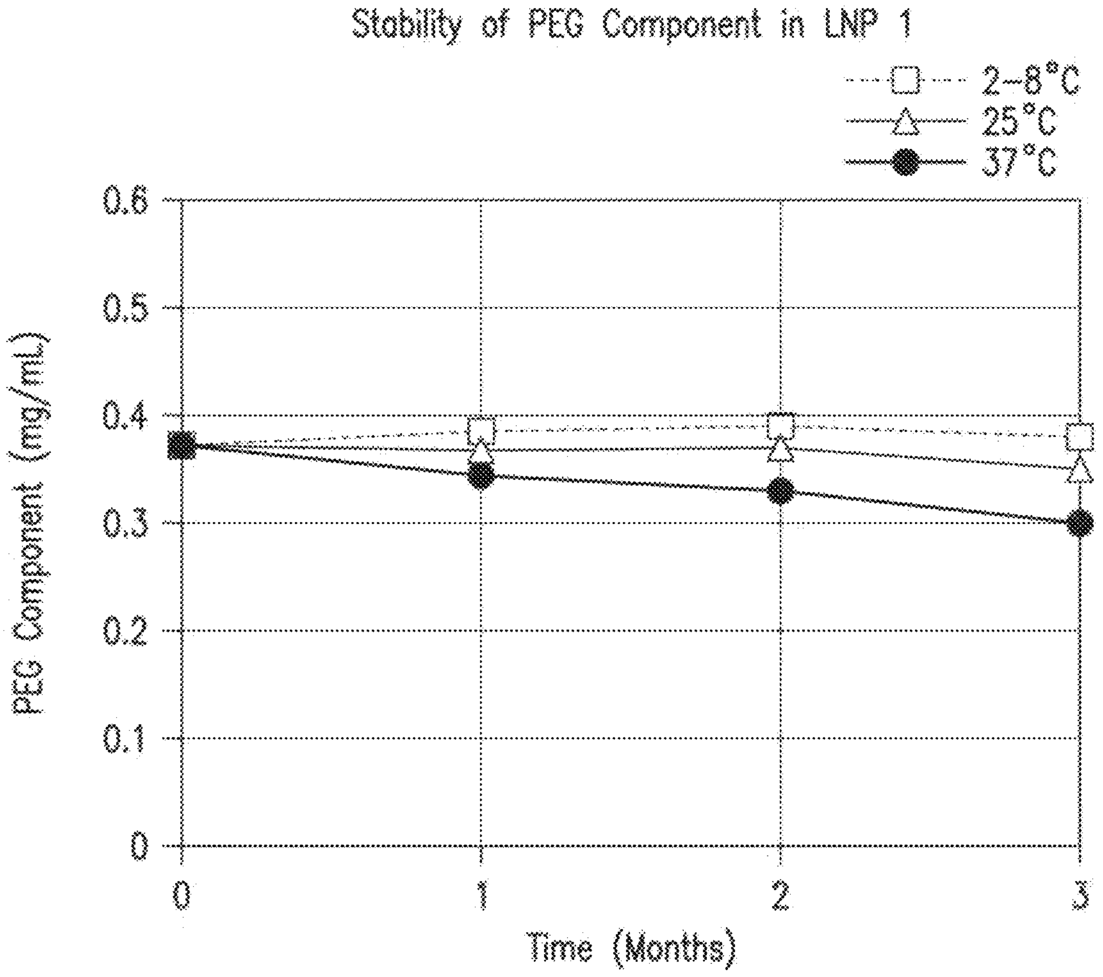
FIGS. 4A-4B depict graphical comparison of the stability of the PEG component in lipid nanoparticle 1 and lipid nanoparticle 4 at various temperatures over 3 months.
Figure 4B:
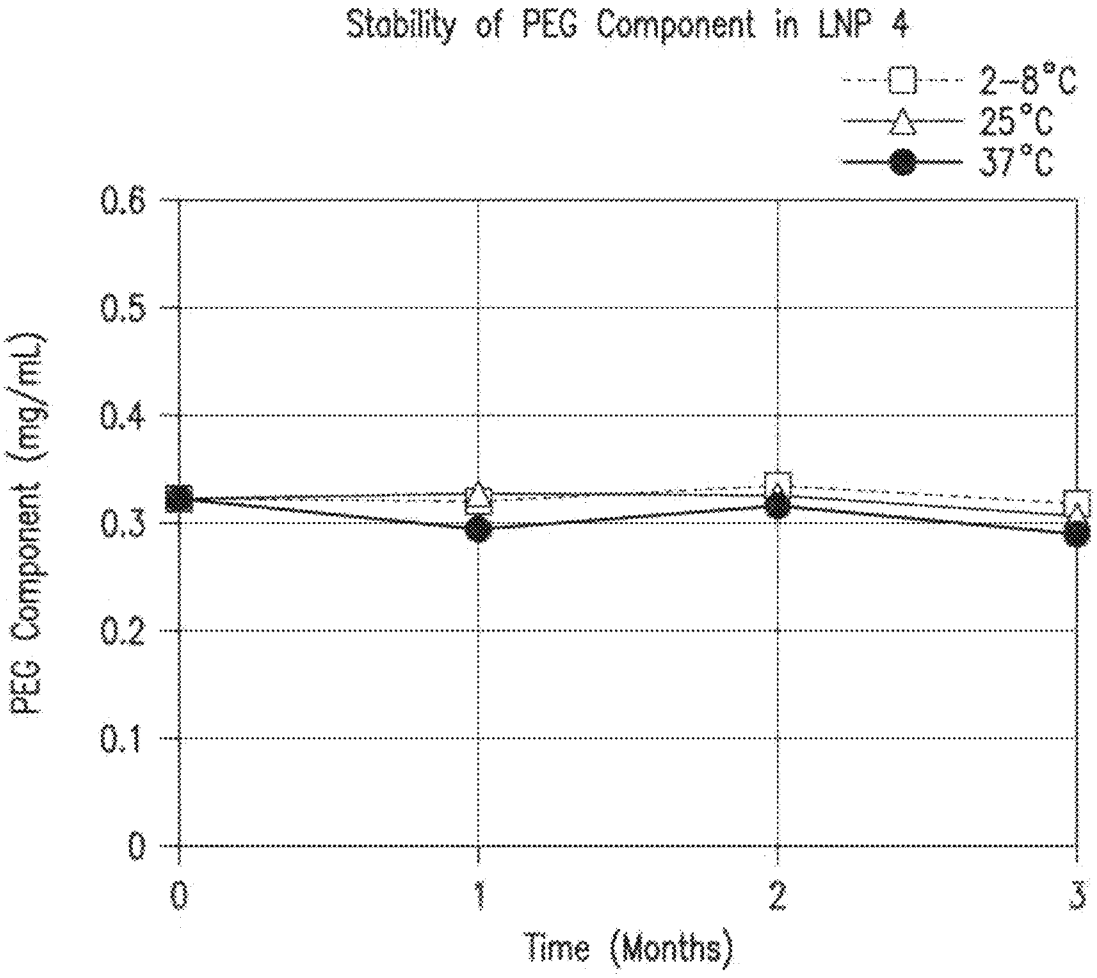
Figure 5A:
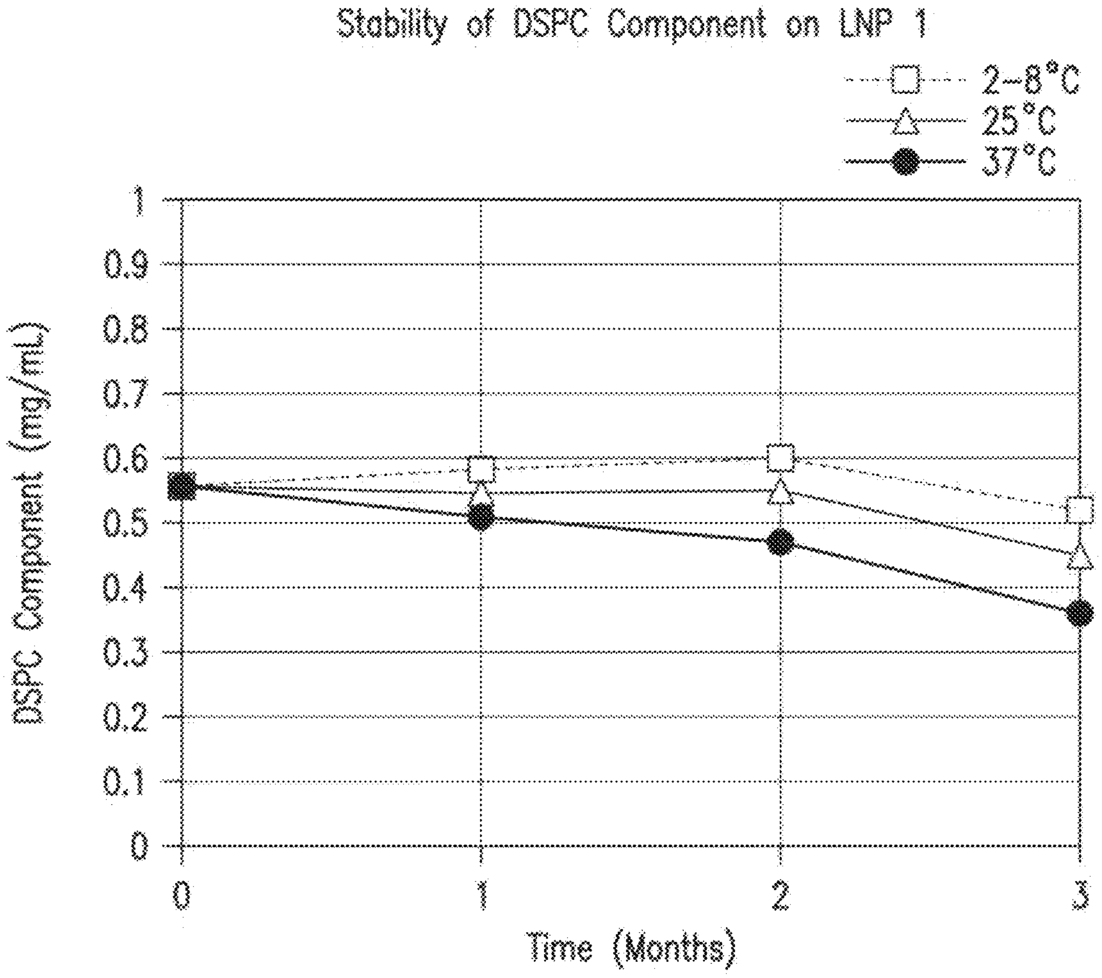
FIGS. 5A-5B depict graphical comparison of the stability of the DSPC component in lipid nanoparticle 1 and lipid nanoparticle 4 at various temperatures over 3 months.
Figure 5B:
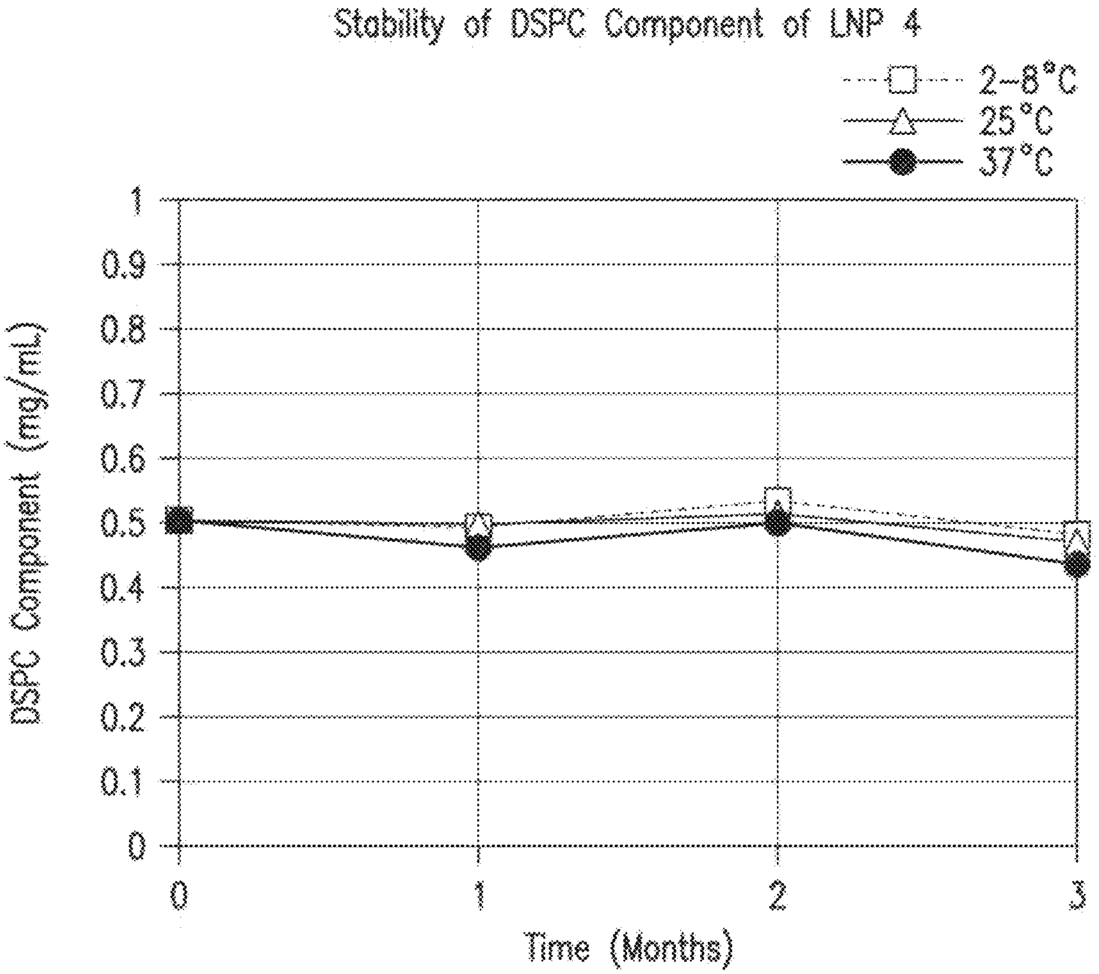
Figure 6A:
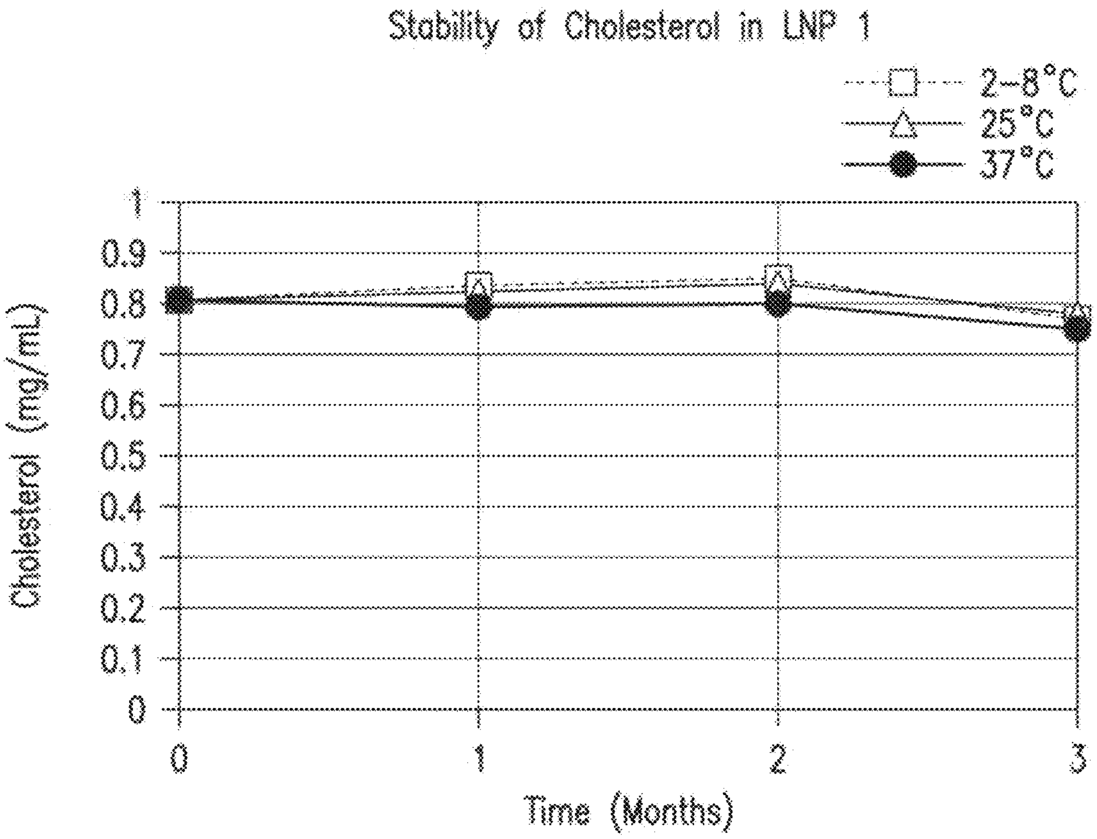
FIGS. 6A-6B depict graphical comparison of the stability of the cholesterol component in lipid nanoparticle 1 and lipid nanoparticle 4 at various temperatures over 3 months.
Figure 6B:
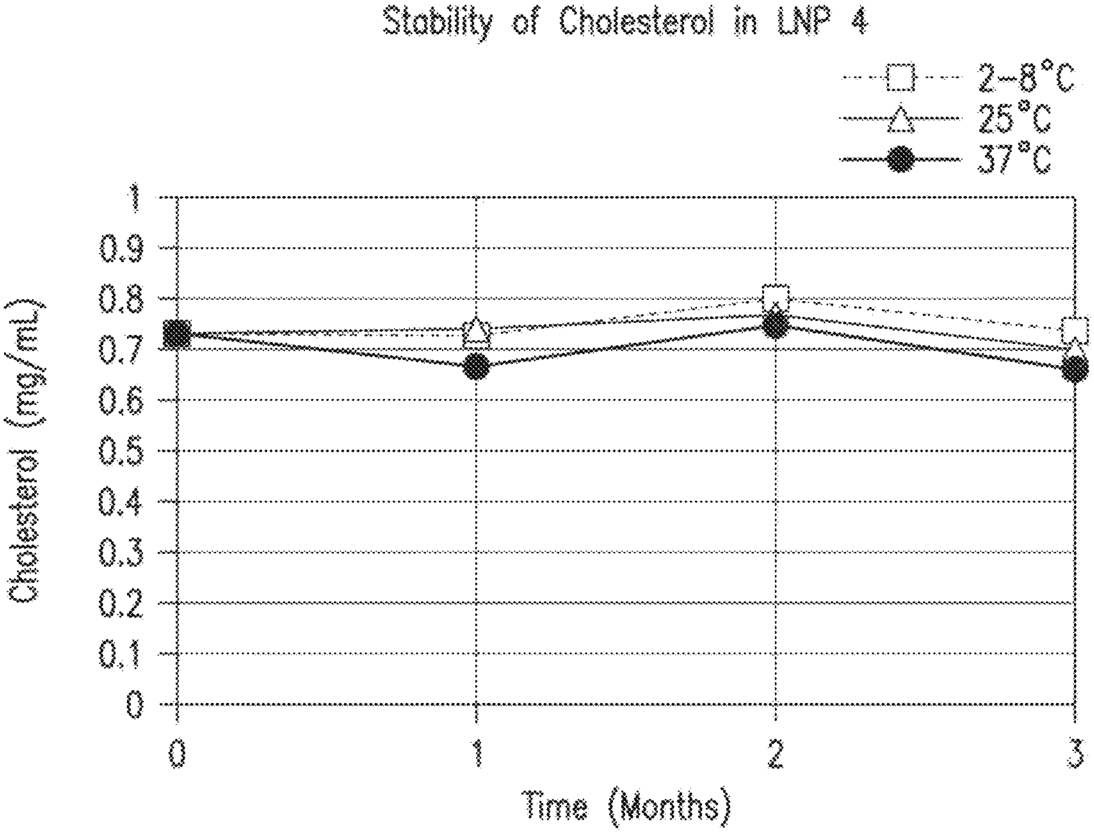
Figure 7A:
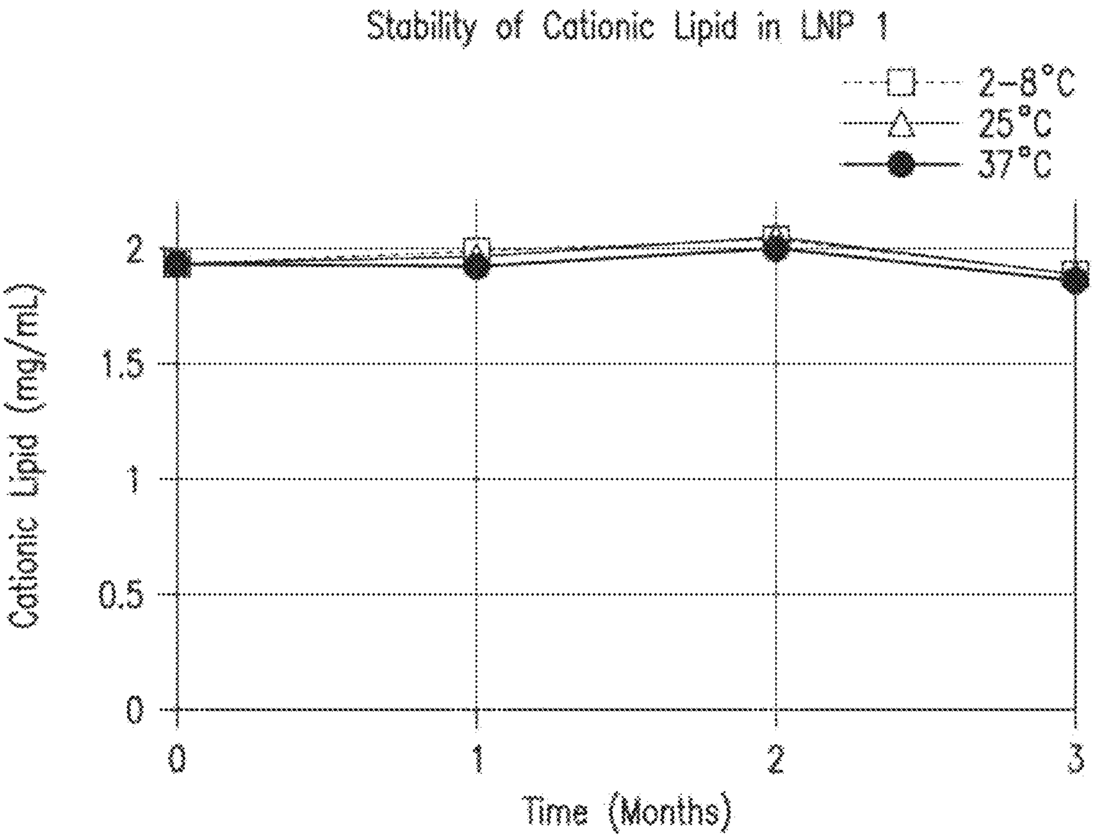
FIGS. 7A-7B depict graphical comparison of the stability of the cationic lipid component in lipid nanoparticle 1 and lipid nanoparticle 4 at various temperatures over 3 months.
Figure 7B:
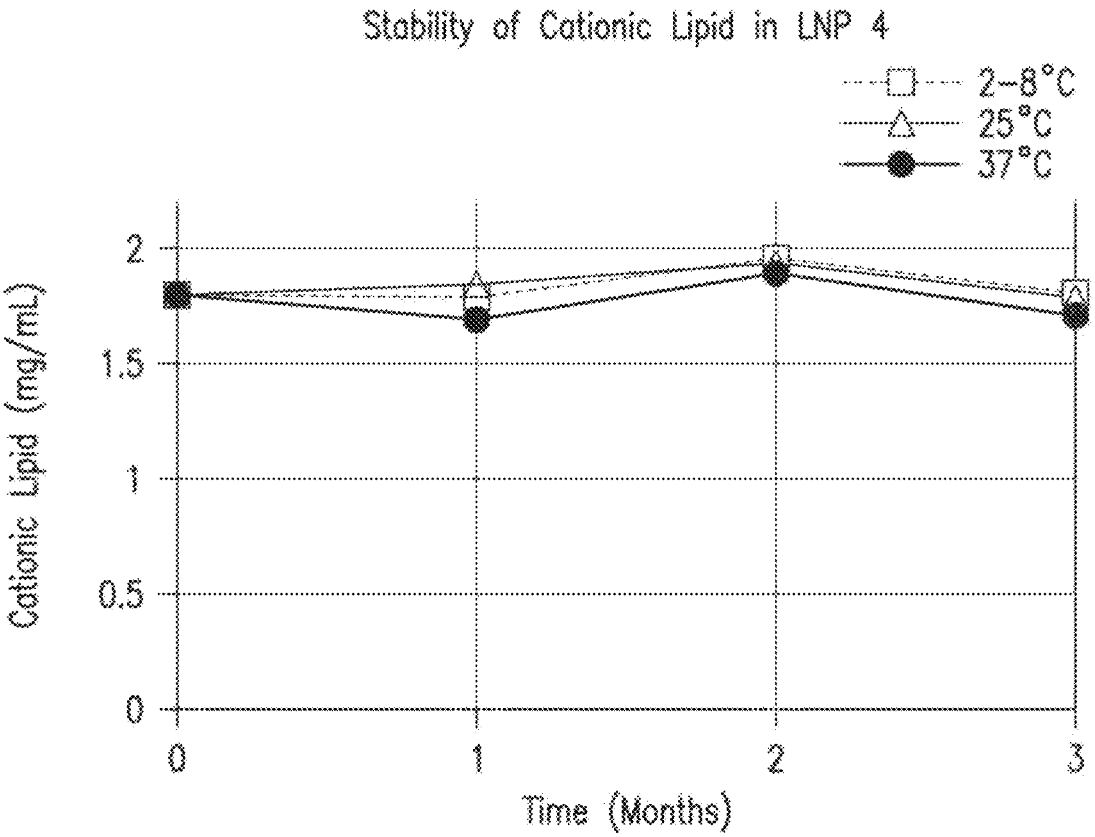
Figure 8A:
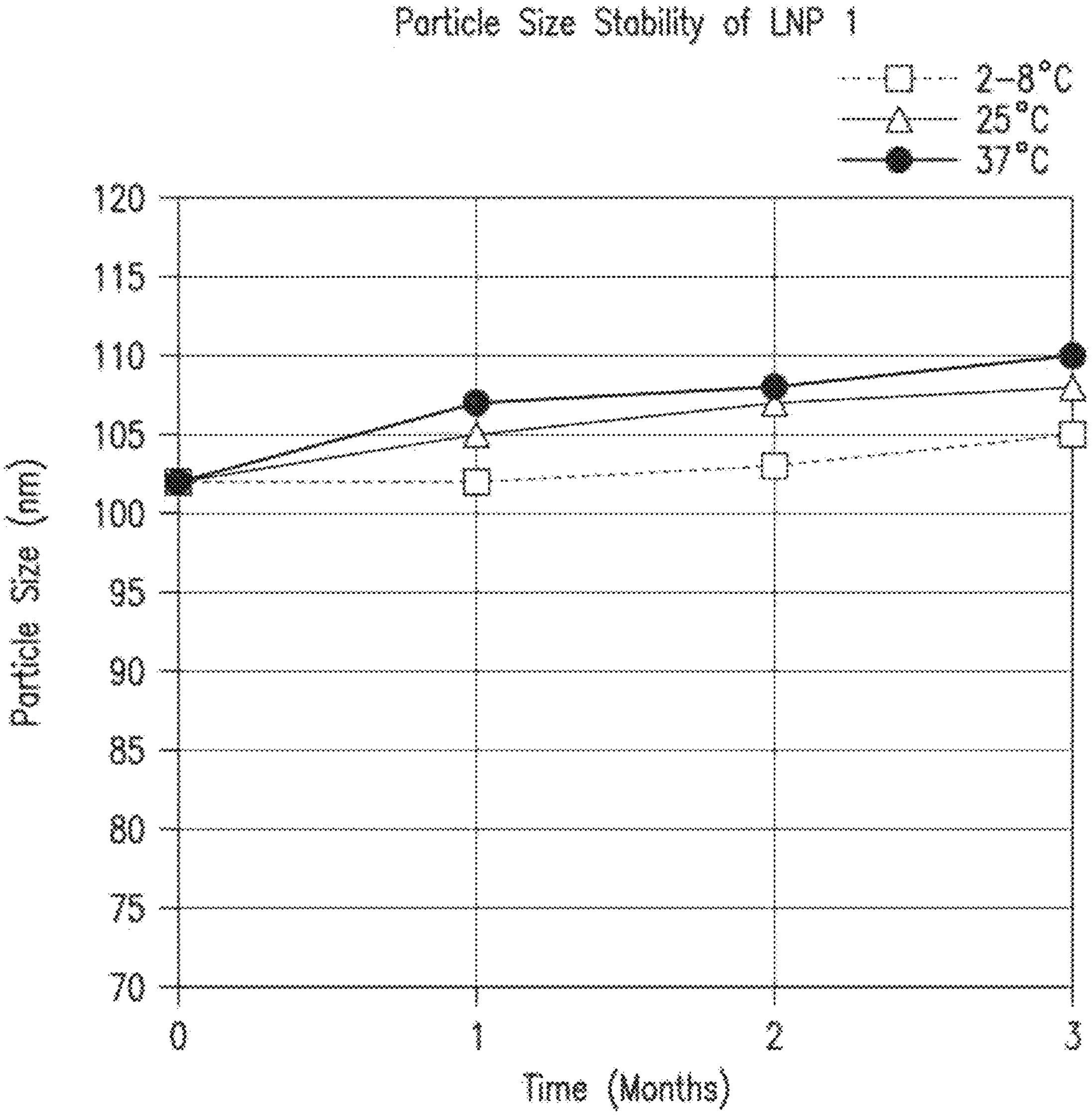
FIGS. 8A-8B depict graphical comparison of the particle size stability of lipid nanoparticle 1 and lipid nanoparticle 4 at various temperatures over 3 months.
Figure 8B:
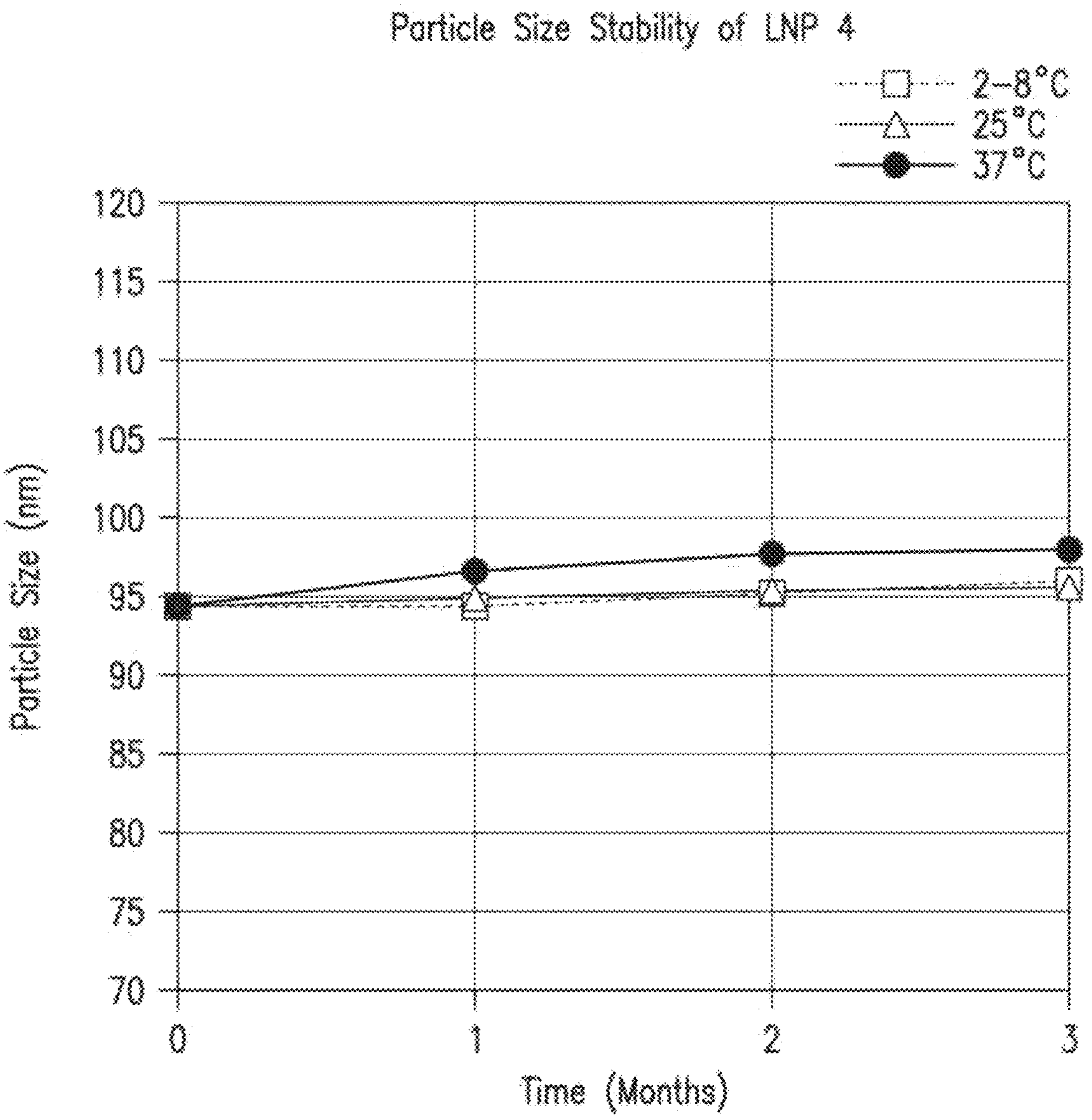

LNP Adjuvant 1 and LNP Adjuvant 4 at a total lipid concentration of 4 mg/mL were formulated in 325 mM NaCl+10 mM Histidine+0.01% (w/v) PS-80, pH 6.2. Stability was assessed through 3 months at 2-8 C, 25 C and 37 C. Analysis included DLS to monitor particle size and UPLC-CAD to monitor lipid degradation. Stability of PEG component in LNP Adjuvant 1 and LNP Adjuvant 4 is shown in FIGS. 4A and 4B. Stability of DSPC component in LNP Adjuvant 1 and LNP Adjuvant 4 is shown in FIGS. 5A and 5B. Stability of cholesterol component in LNP Adjuvant 1 and LNP Adjuvant 4 is shown in FIGS. 6A and 6B. Stability of cationic lipid component in LNP Adjuvant 1 and LNP Adjuvant 4 is shown in FIGS. 7A and 7B. Particle size stability of LNP Adjuvant 1 and LNP Adjuvant 4 is shown in FIGS. 8A and 8B.

Example 18: Preparation of HPV Vaccine Compositions

A formulation including the LNP adjuvant described in Example 9 (hereinafter "LNP Adjuvant 2") was combined with a dose of a 9 valent HPV/aluminum adjuvant vaccine prepared from the purified virus-like particles (VLPs) of the major capsid (L1) protein of HPV Types 6, 11, 16, 18, 31, 33, 45, 52, and 58, adsorbed on preformed aluminum-containing adjuvant (Amorphous Aluminum Hydroxyphosphate Sulfate) (hereinafter "9vHPV Vaccine" or "Gardasil®9") to make a single-dose vaccine composition.

Example 19: Preparation of HPV Vaccine Compositions

A formulation including the LNP adjuvant described in Example 10 (hereinafter "LNP Adjuvant 3") was combined with a dose of 9vHPV Vaccine to make a single-dose vaccine composition.

Example 20: Preparation of HPV Vaccine Compositions

A formulation including the LNP adjuvant described in Example 11 (hereinafter "LNP Adjuvant 4") was combined with a dose of 9VHPV Vaccine to make a single-dose vaccine composition.

Example 21: Analysis of Co-Formulation of LNP Adjuvant 4 and Gardasil©9

Separation of the lipids: cationic lipid, cholesterol, DSPC, and ePEG-DMG, was performed on an Ultra Performance Liquid Chromatography (UPLC) system with a C18 UPLC column. The method used a gradient of water and methanol with 16.2 mM trimethylamine and 19.2 mM glacial acetic acid (pH 5.4) and monitored signal with a Corona Charged Aerosol Detector (CAD). The determination of lipids content was done by first constructing a standard curve from each individual lipid reference standard. The concentration of each lipid was determined by calculating the sample peak area against the lipid standards peak areas. Lipid identity was confirmed by a spiking experiment with lipid standards.

Prior to Analysis of the LNP, samples were subjected to a low speed centrifugation (3000 rpm for 2 minutes) to remove the AAHS and HPV VLPS. Alternatively, samples may be subject to dissolution of the AAHS by mixing 1:1 with 50 mmol adipic acid and 100 mMol EDTA at pH 6.8. UPLC-CAD and DLS analysis produced the same as LNP alone samples.

Figure 9A:
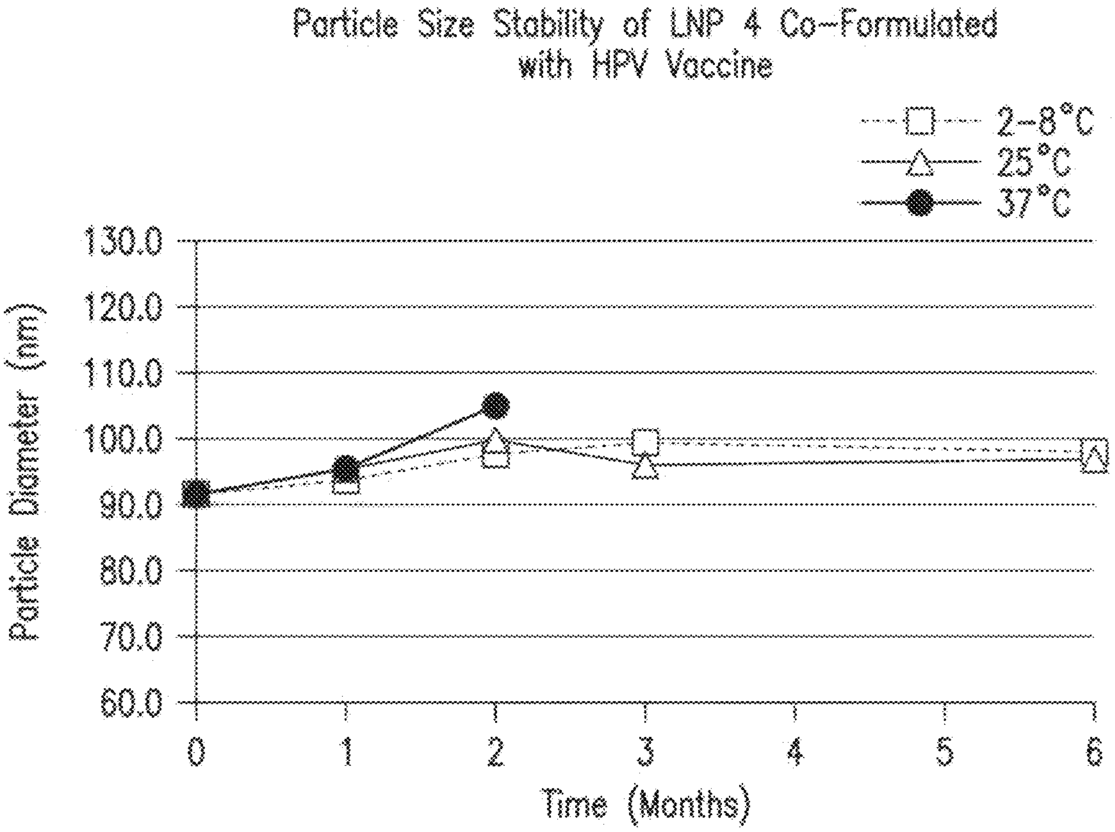
FIGS. 9A-9F depict graphical comparison of the stability of various LNP components when LNP Adjuvant 4 is co-formulated with an HPV vaccine.
Figure 9B:
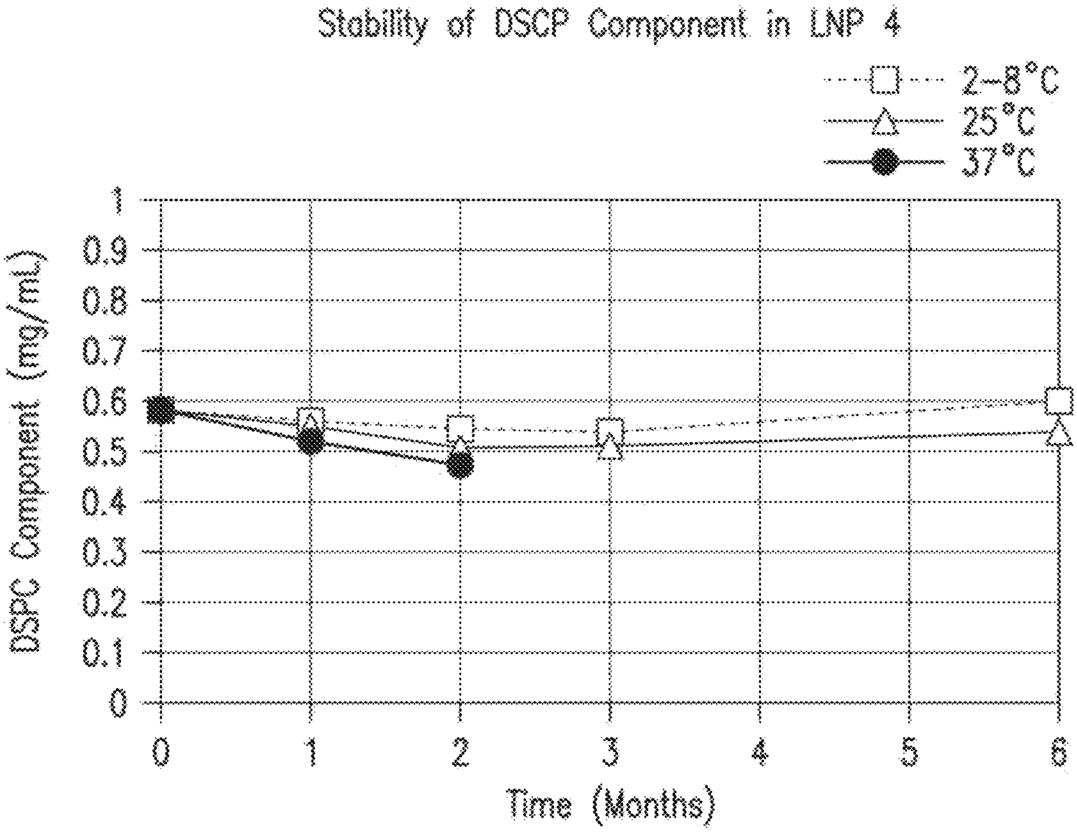
Figure 9C:
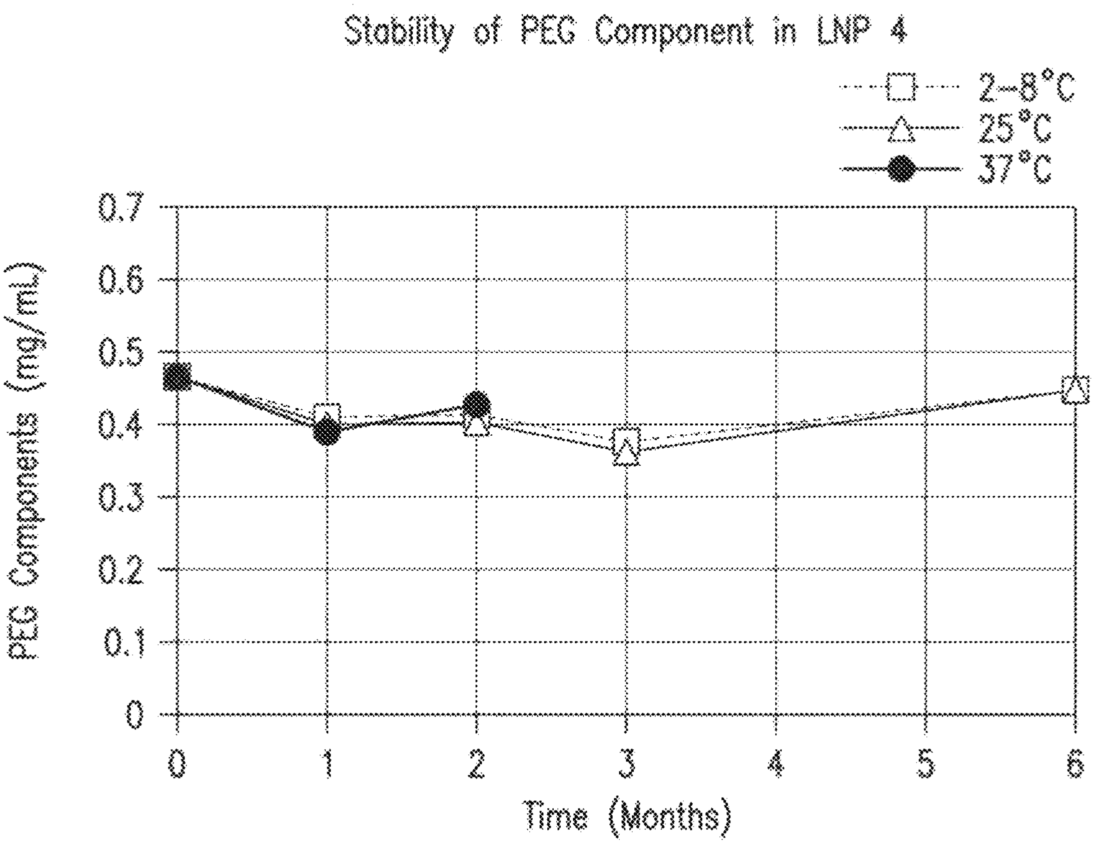
Figure 9D:
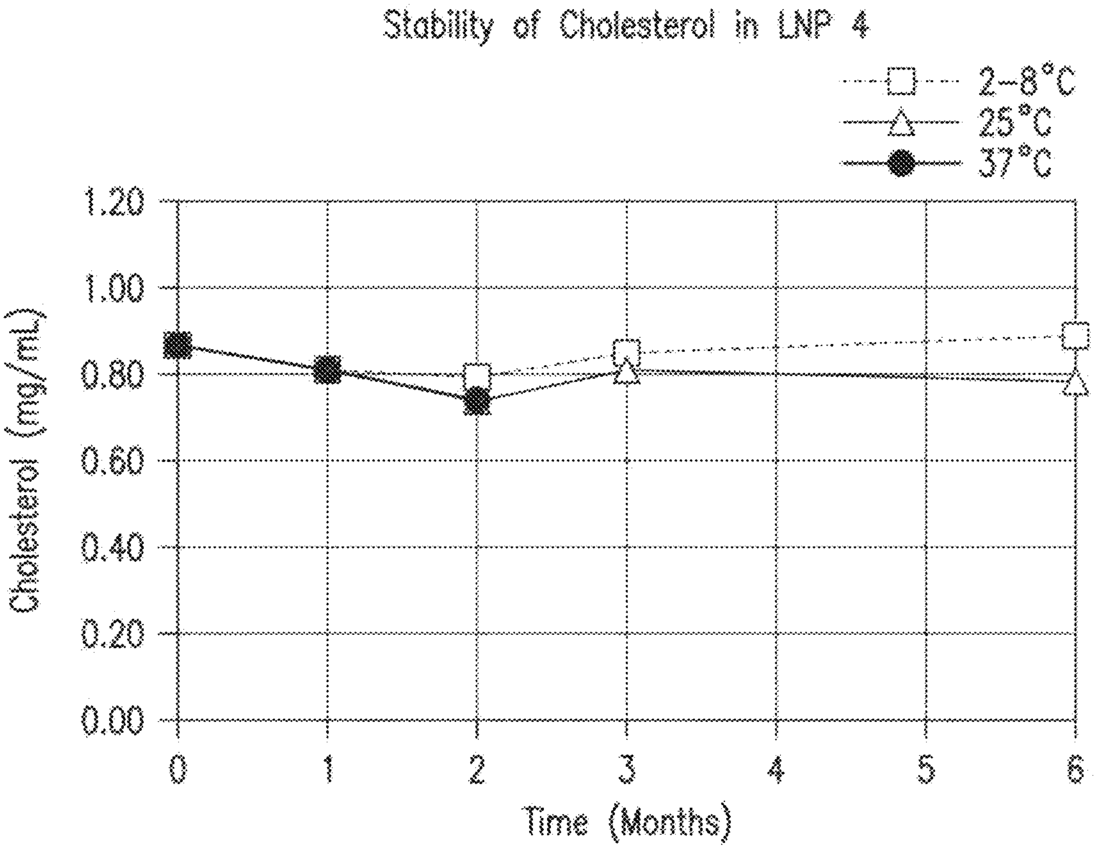
Figure 9E:
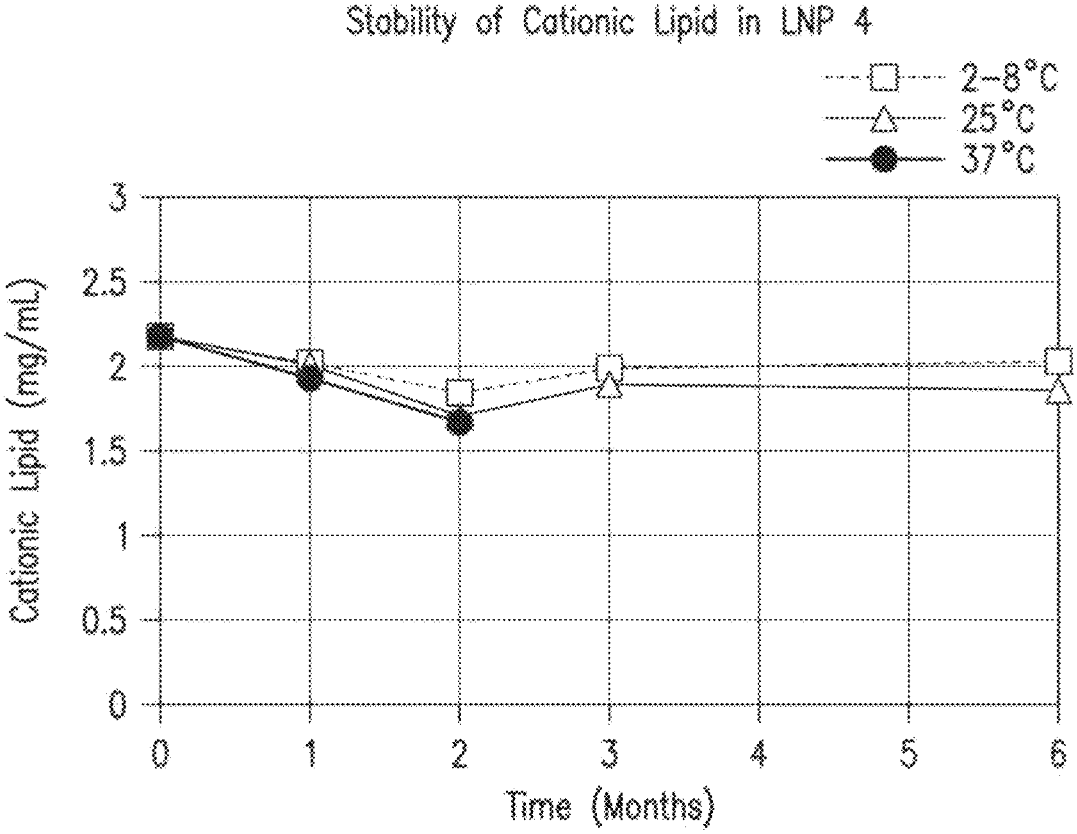
Figure 9F:
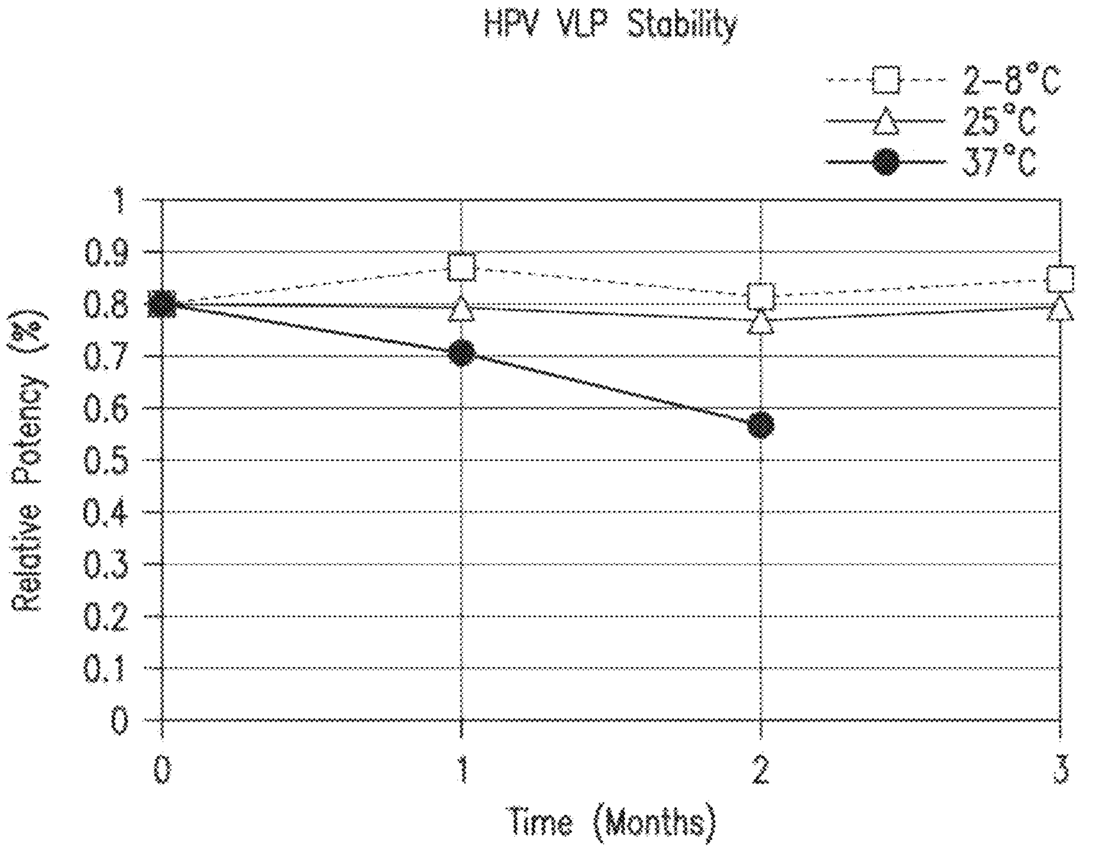

LNP Adjuvant 4 at a total lipid concentration of 4 mg/mL was co-formulated with Gardasil® 9 in a 325 mM NaCl+10 mM Histidine+0.01% (w/v) PS-80, pH 6.2 formulation. Stability was assessed through 6 months at 2-8 C, 25° C. and 37° C. Analysis included DLS to monitor particle size and UPLC-CAD to monitor lipid degradation. In-Vitro Relative Potency (IVRP) was used to assess the stability of Gardasil®9 HPV VLP components. The IVRP assay is a sandwich ELISA that employs antibodies against neutralizing epitopes specific for each of the 9 HPV VLP types to determine potency relative to a reference standard for each strain contained in the vaccine. Evaluation of the stability of the LNP components was done using a combination of lipid concentration analysis to look for degradation of the lipid components and dynamic light scattering to confirm LNP of still assembled. Particle size stability of LNP Adjuvant 4 co-formulated with Gardasil 9 is shown in FIG. 9A. Stability of the DSPC component in Adjuvant 4, when co-formulated with Gardasil 9, is shown in FIG. 9B. Stability of the PEG component in LNP Adjuvant 4 co-formulated with Gardasil 9 is shown in FIG. 9C. Stability of the cholesterol component in LNP Adjuvant 4 co-formulated with Gardasil 9 is shown in FIG. 9D. Stability of the cationic lipid component in LNP Adjuvant 4, when co-formulated with Gardasil 9, is shown in FIG. 9E. Stability of the VLP component of the co-formulation is shown in FIG. 9F.

Figure 10A:
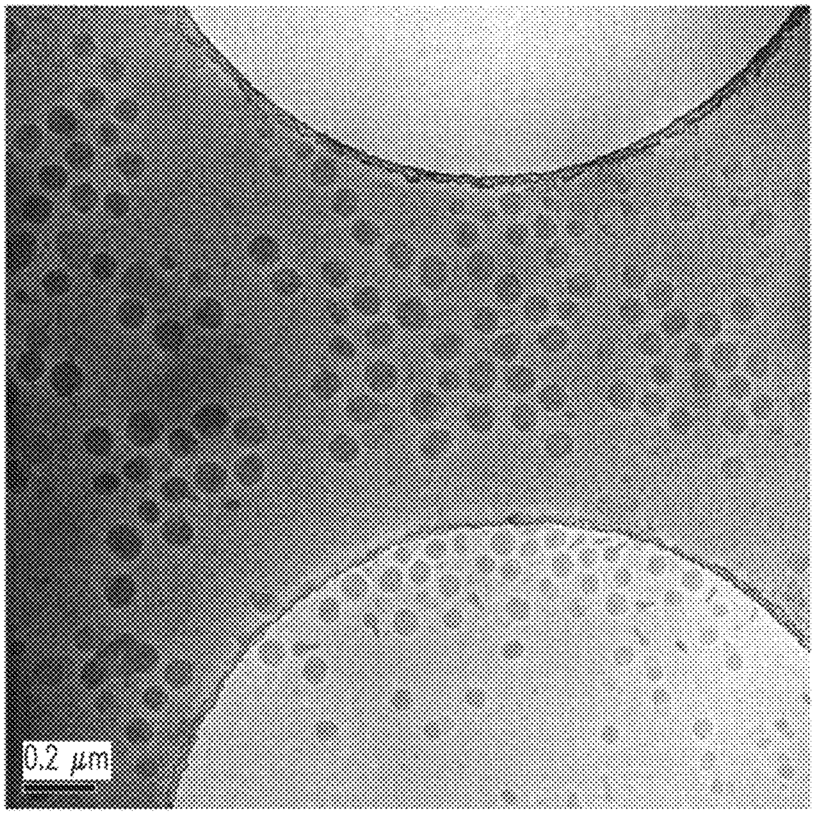
FIGS. 10A-10B depict imaging of freshly mixed coformulations of LNP Adjuvant 4 and an HPV Vaccine and after 7.5 months of storage, respectively.
Figure 10B:
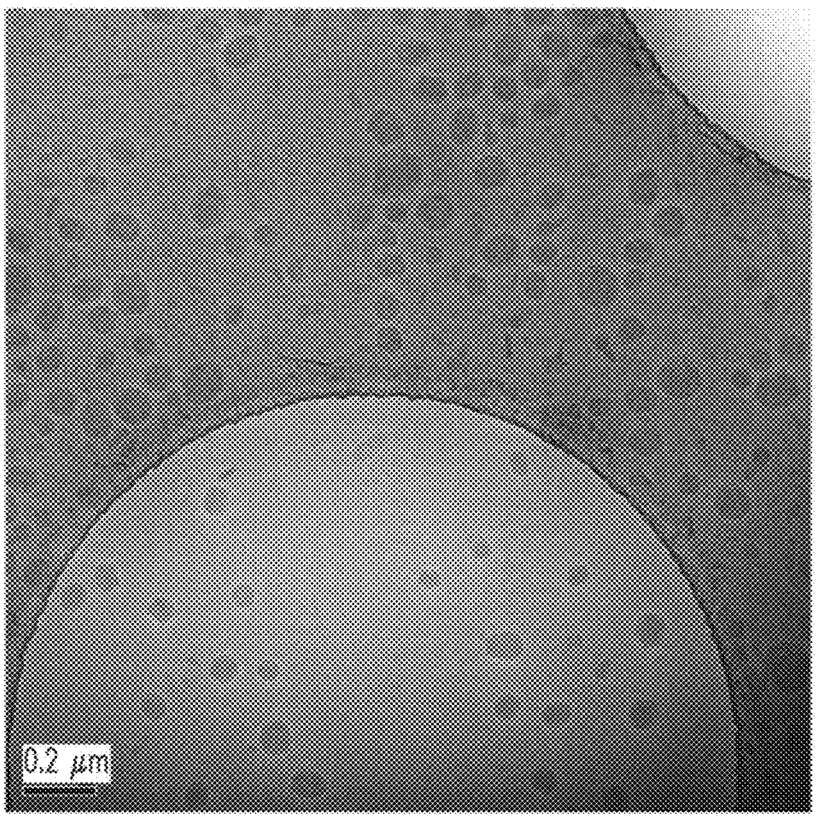

FIG. 10A shows CryoTEM analysis imaging of freshly mixed co-formulation of LNP Adjuvant 4 and Gardasil 9. FIG. 10B shows CryoTEM analysis co-formulation of LNP Adjuvant 4 and Gardasil 9 after 7.5 months of storage at 2-8 C.

Figure 11A:
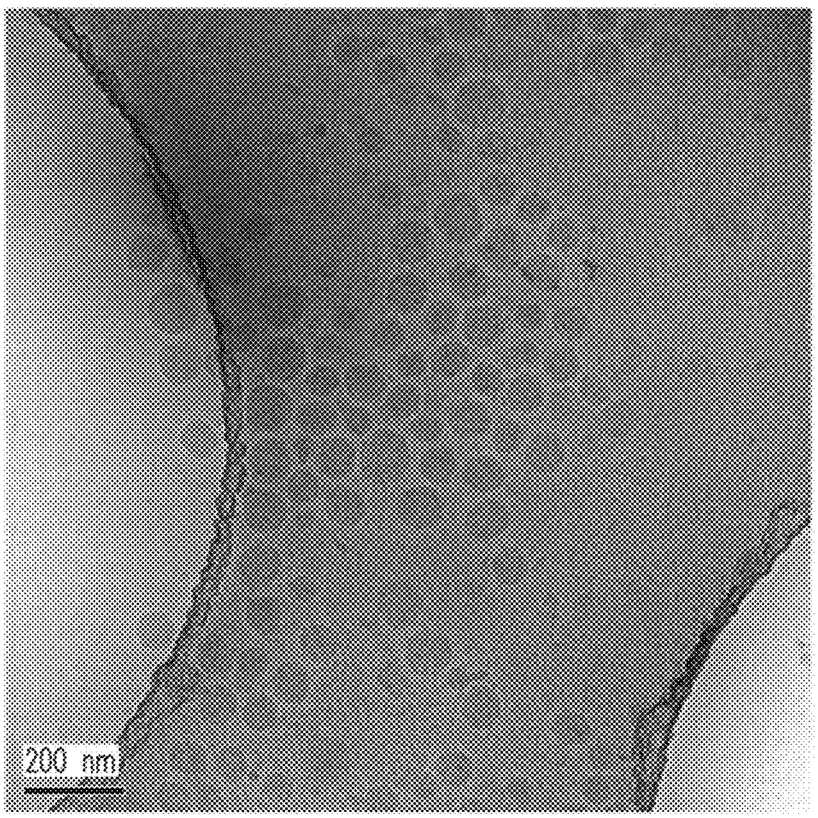
FIGS. 11A-11B depict imaging of freshly mixed coformulations of LNP Adjuvant 4 and an HPV Vaccine and after 7.5 months of storage, respectively.
Figure 11B:
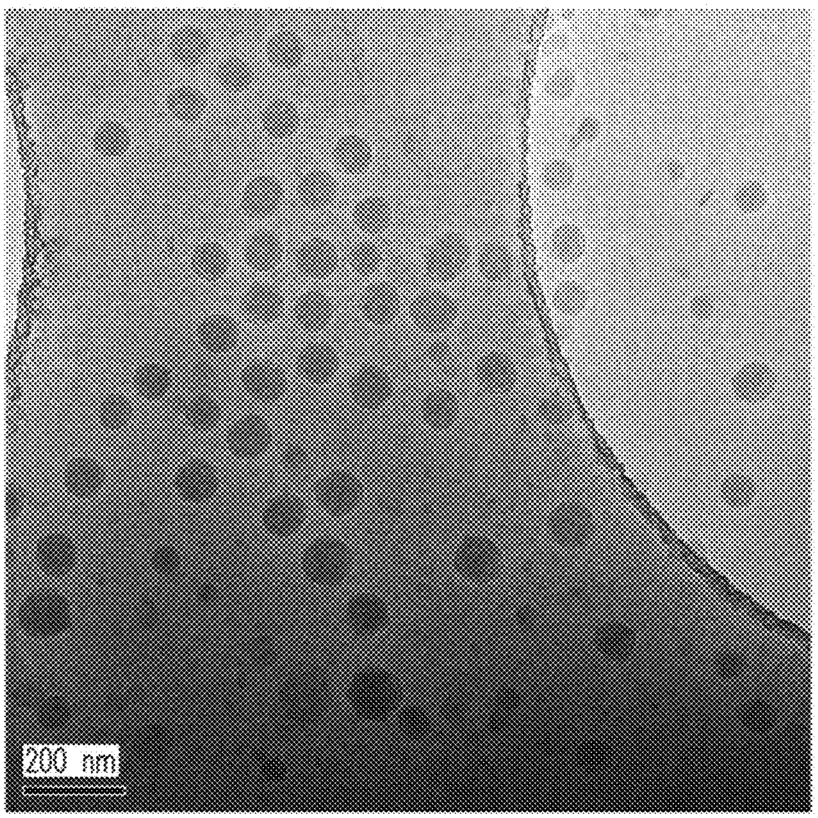

FIG. 11A shows CryoTEM analysis of freshly mixed co-formulation of LNP Adjuvant 4 and Gardasil 9. FIG. 11B shows CryoTEM analysis of LNP Adjuvant 4 in co-formulation after 6 months at 25 C and 1.5 months at 2-8 C.

Example 22: Buffer Concentration Impact on Stability of LNP Adjuvant 4 Components LNP Adjuvant 4 at a total lipid concentration of 3 mg/mL was formulated in 325 mM NaCl+10 mM Histidine pH 6.2. with varying concentrations of PS-80. Stability was assessed through 2 months at 2-8° C., 25° C. and 37° C. Analysis included DLS to monitor particle size and UPLC-CAD to monitor lipid degradation. IVRP was used to monitor HPV VLP stability Buffers:

0×PS-80: 325 mM NaCl+10 mM Histidine, pH 6.2

0.25×PS-80: 325 mM NaCl+10 mM Histidine+0.0025% (w/v) PS-80, pH 6.2

0.75×PS-80: 325 mM NaCl+10 mM Histidine+0.0075% (w/v) PS-80, pH 6.2

1×PS-80: 325 mM NaCl+10 mM Histidine+0.01% (w/v) PS-80, pH 6.2

Figure 12A:
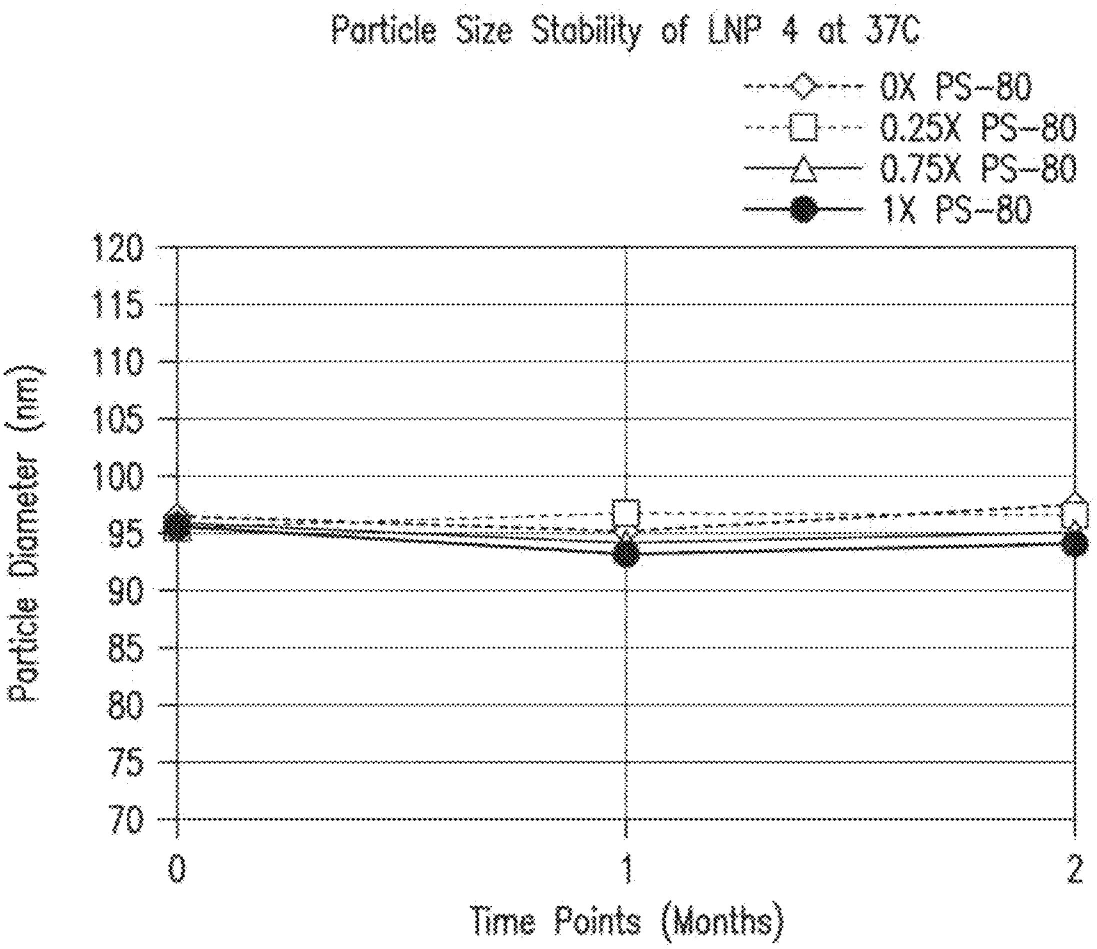
FIGS. 12A-12E depict graphical comparison of the stability of various LNP components of LNP 4.
Figure 12B:
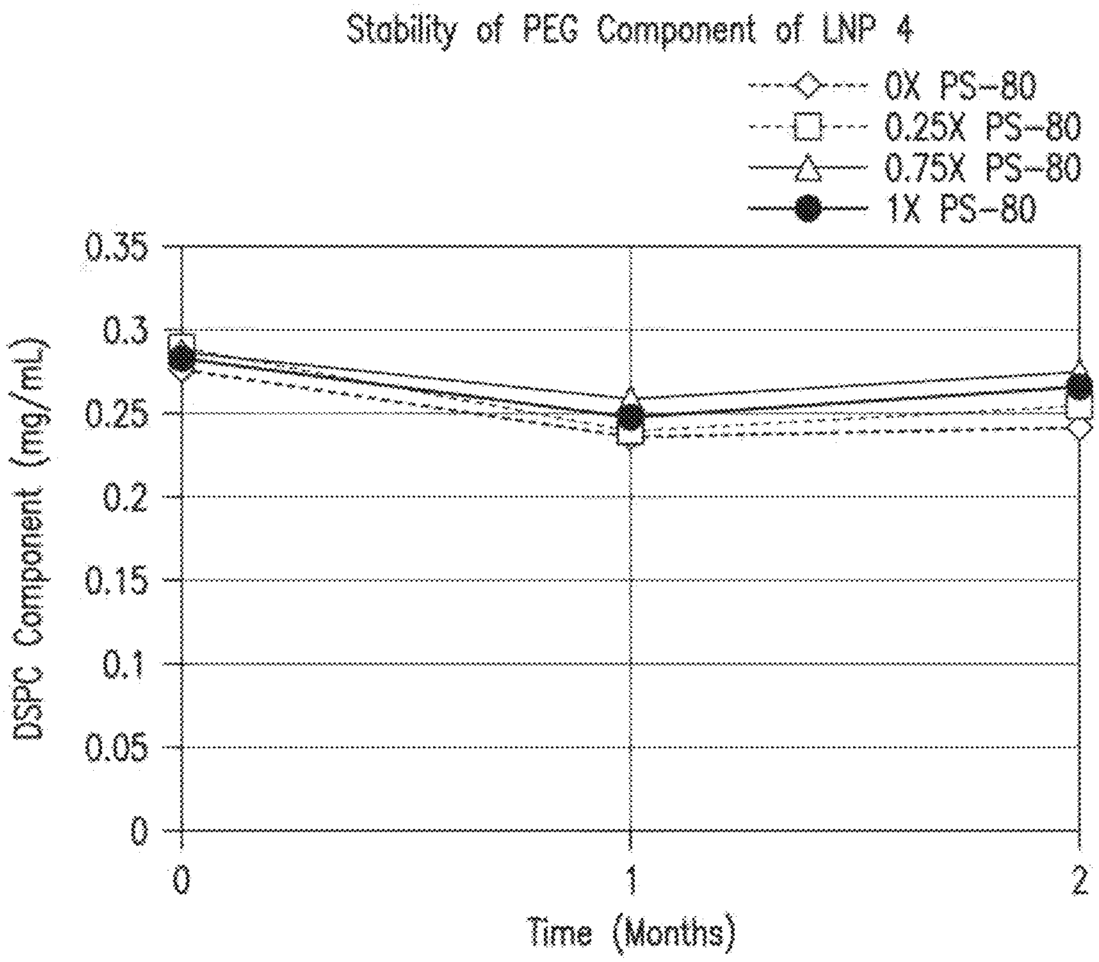
Figure 12C:
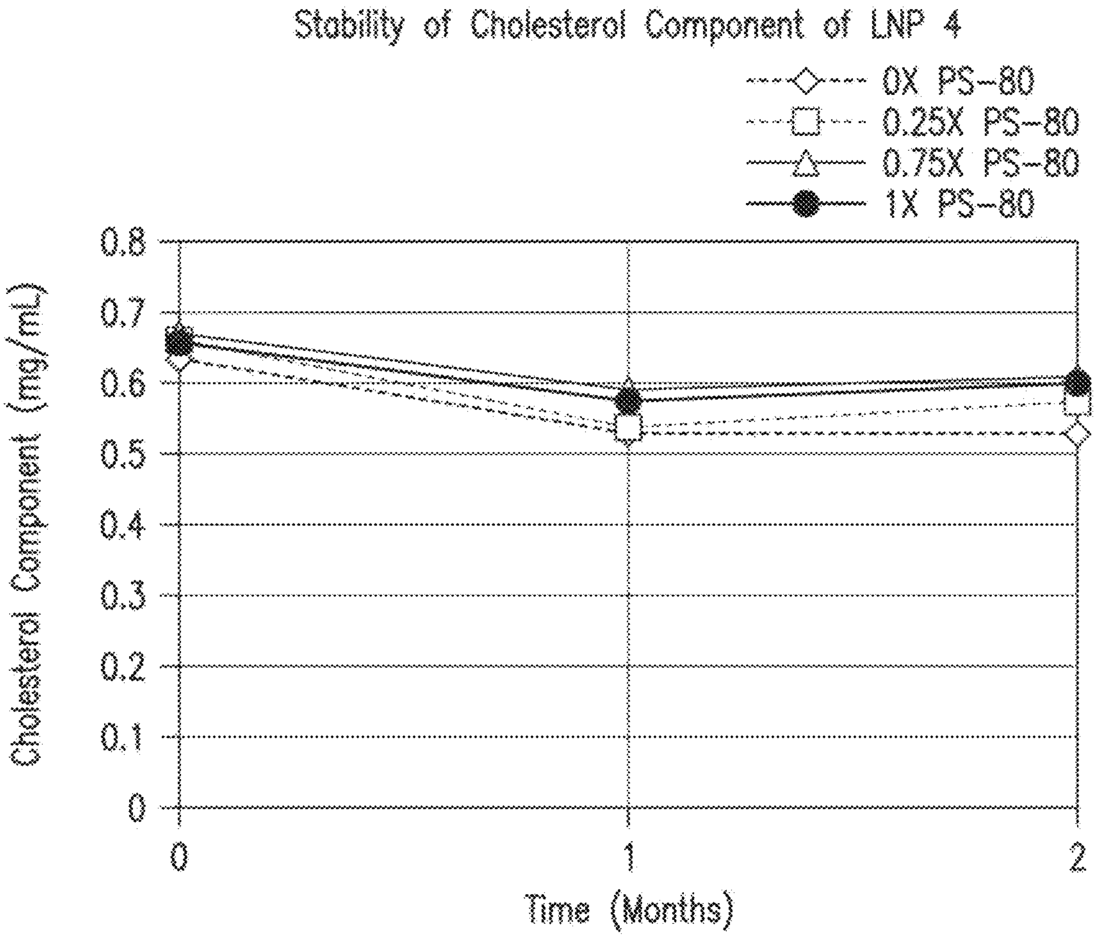
Figure 12D:
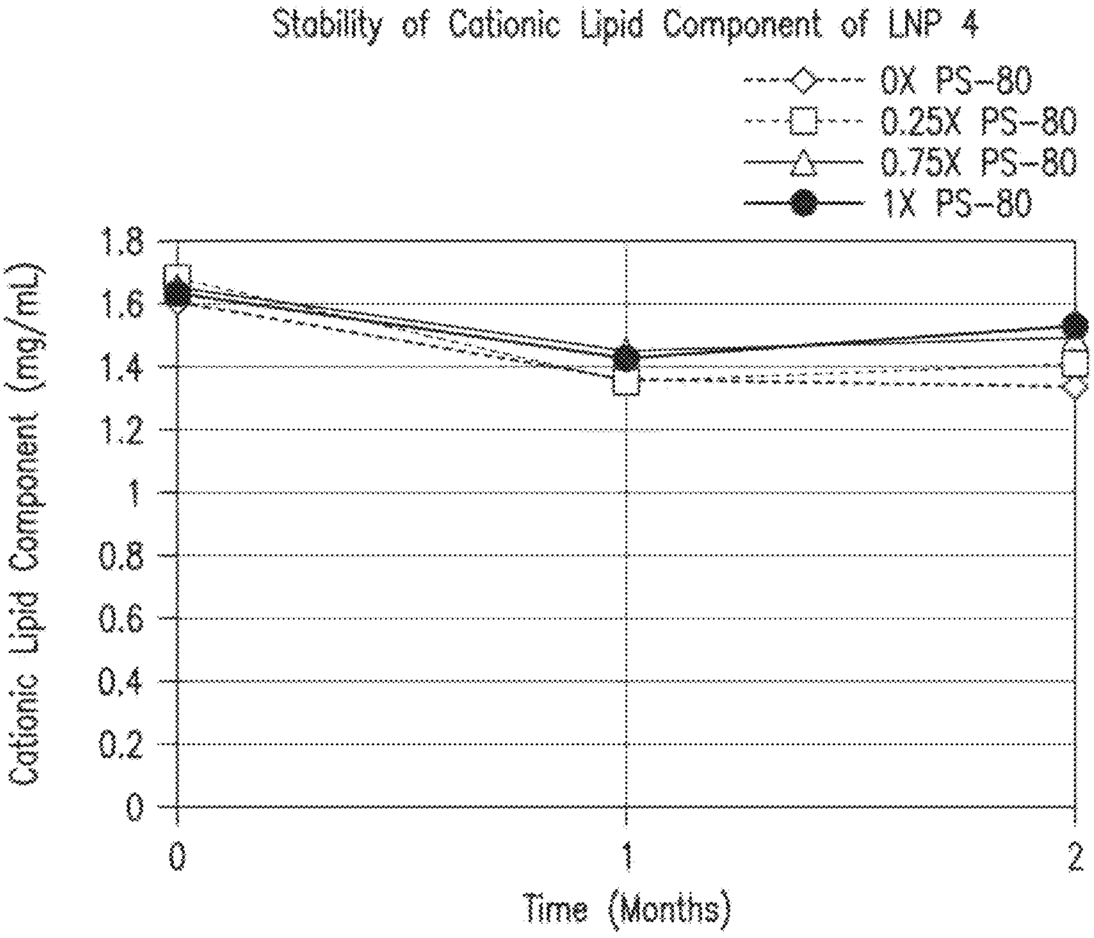
Figure 12E:
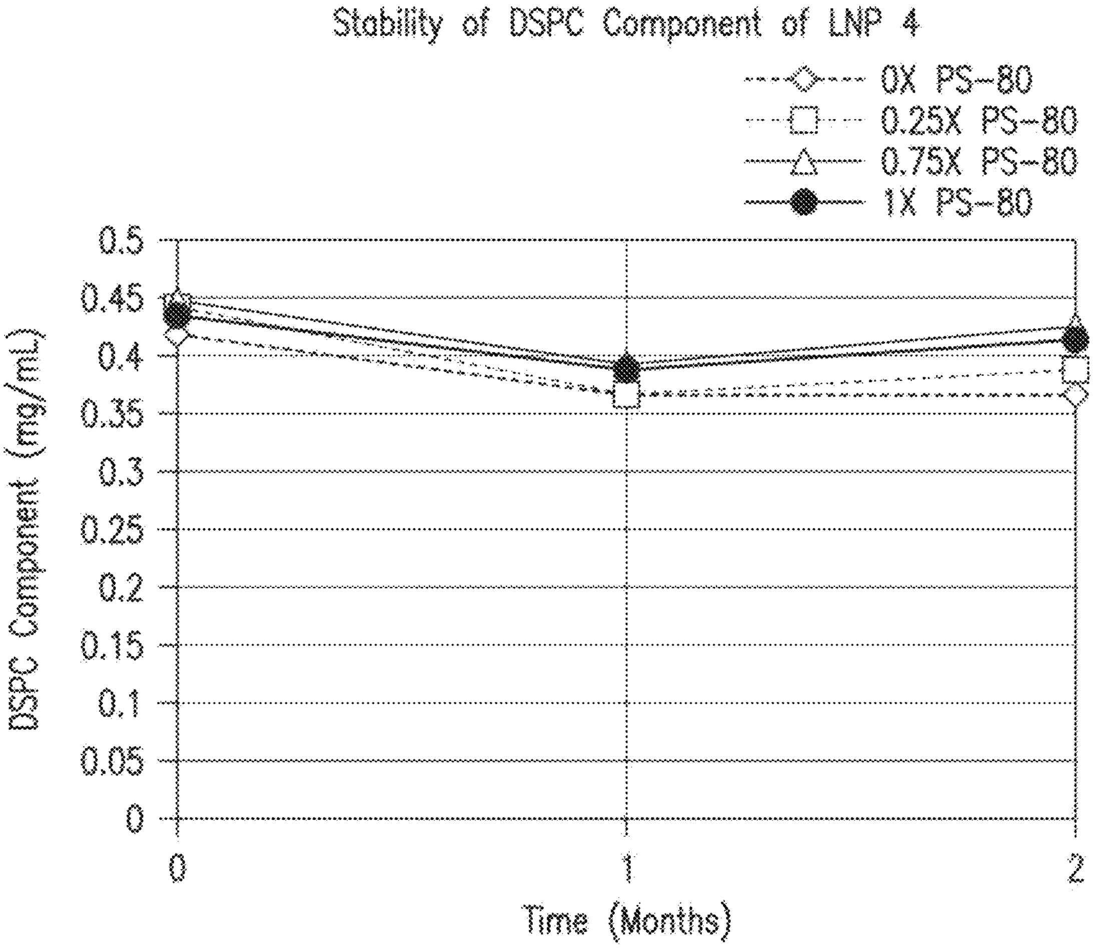
Figure 13A:
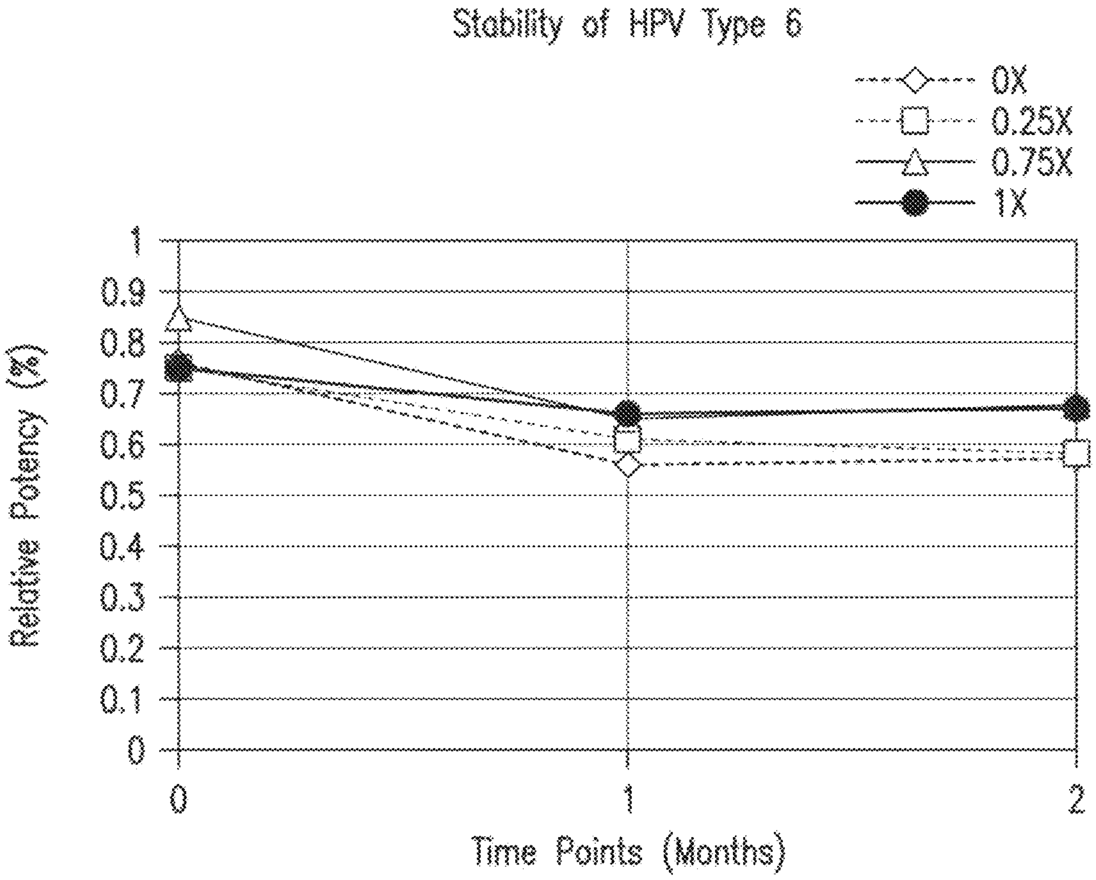
FIGS. 13A-13D depict graphical comparison of the stability of HPV Types 6, 11, 16, and 18.
Figure 13B:
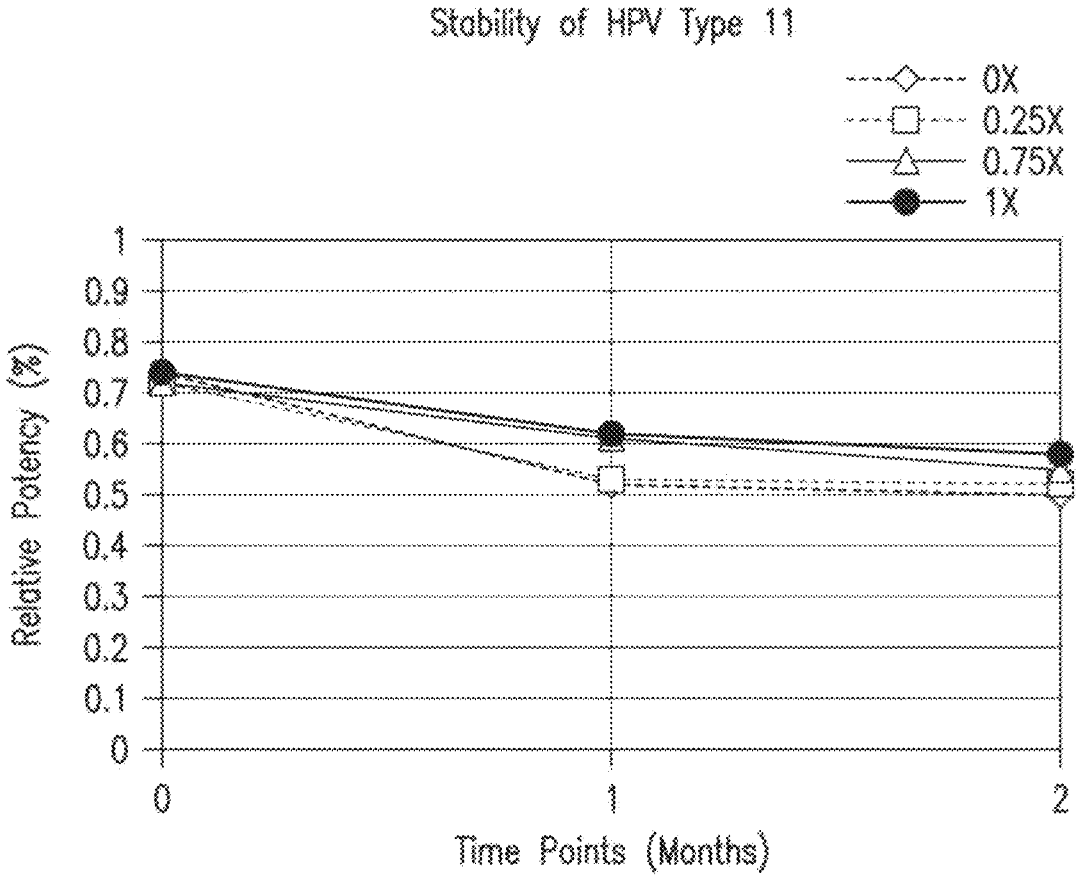
Figure 13C:
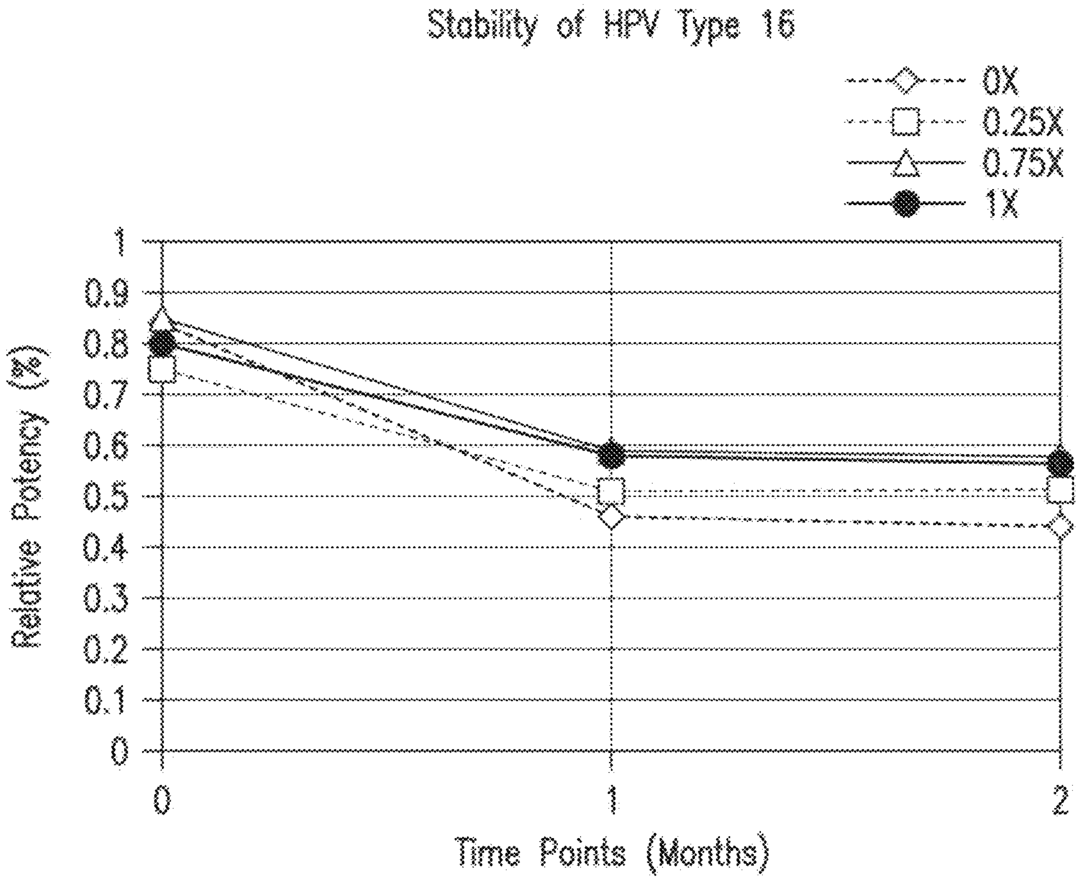
Figure 13D:
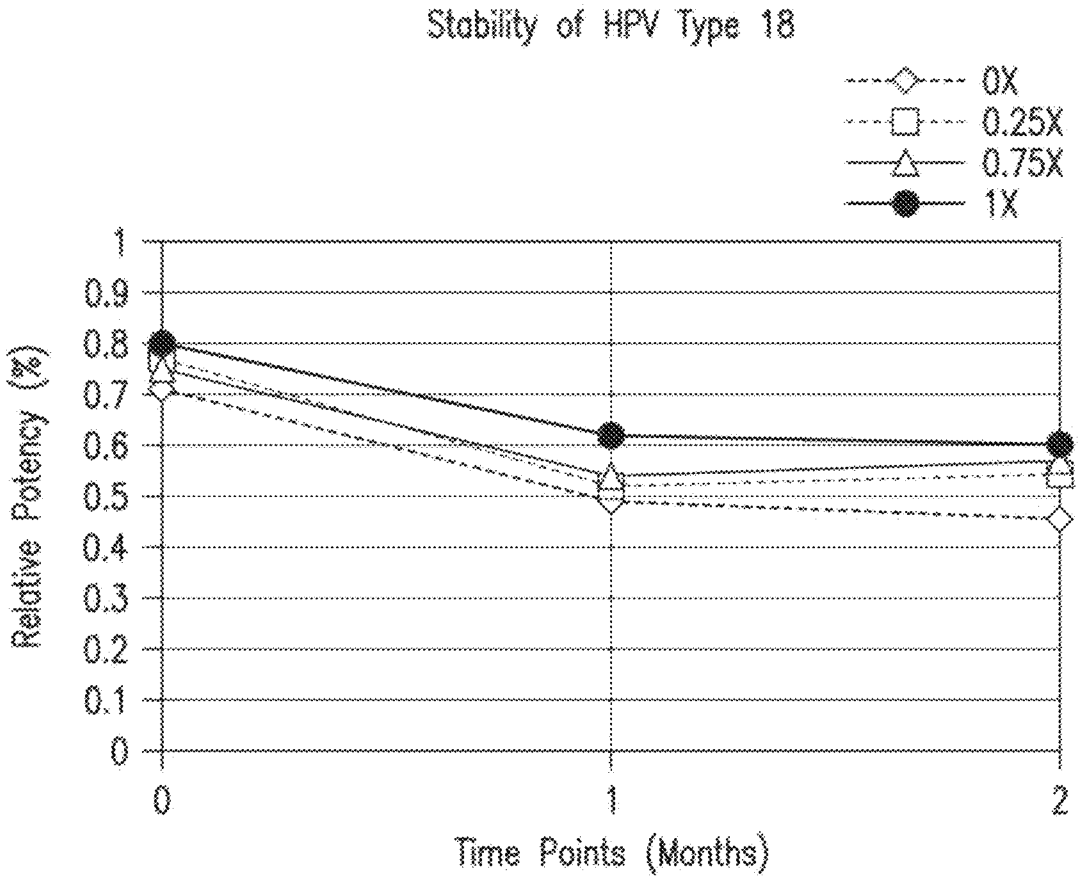

Stability of particle size of LNP Adjuvant 4 at 37° C. is shown in FIG. 12A. Stability of the PEG component of LNP Adjuvant 4 at 37° C. is shown in FIG. 12B. Stability of the cholesterol of LNP Adjuvant 4 at 37° C. is shown in FIG. 12C. Stability of the cationic lipid of LNP Adjuvant 4 at 37° C. is shown in FIG. 12D. Stability of the DSPC component of LNP Adjuvant 4 at 37° C. is shown in FIG. 12E.

Stability of HPV Types 6, 11, 16, and 18 are shown in FIGS. 13A-13D, respectively.

Example 23: Immunogenicity and Durability of a Single Dose of Gardasil®9+LNP Adjuvant 1 in Rhesus Macaques (Study SD-HPV-009)

The immunogenicity of Gardasil®9 when combined with increasing doses of LNP Adjuvant 1 (1, 3, or 6 mg) as evaluated in rhesus macaques. The group designations are described in Table 2. In brief, five groups of 6 rhesus macaques each were inoculated at week 0 with either Gardasil©9 only or with Gardasil®9 mixed with 1, 3, or 6 mg of LNP Adjuvant 1. At week 4, the animals in group 1 were given a second dose of Gardasil©9 (two-dose G9) while none of the other groups were boosted. The 1.0 mL inoculums were prepared by admixing Gardasil®9 and LNP Adjuvant 1 and administering into the rhesus macaque quadricep within 4 hours of formulation.

TABLE 2

Groups, Dose Levels, and Dosing Schedule in Non-Human Primates for Study SD-HPV-009

| Group | No. of Rhesus Macaques | Inoculum | LNP Adjuvant 1 Dose | ROA[a] | Dosing Schedule |
|---|---|---|---|---|---|
| 1 | 6 | Gardasil ® 9[b] | NA | IM | 0, 4 weeks |
| 2 | 6 | Gardasil ® 9 | NA | IM | week 0 |
| 3 | 6 | Gardasil ® 9 + LNP Adjuvant 1 | 1 mg | IM | week 0 |
| 4 | 6 | Gardasil ® 9 + LNP Adjuvant 1 | 3 mg | IM | week 0 |
| 5 | 6 | Gardasil ® 9 + LNP Adjuvant 1 | 6 mg | IM | week 0 |

[a]All doses were delivered in 1 mL to single quaericeps

[b]Rhesus monkey dose of Gardasil ® 9 is equivalent to a 1/20 human dose

IM = intramuscular;

NA = not applicable;

ROA = route of administration

Figure 14A:
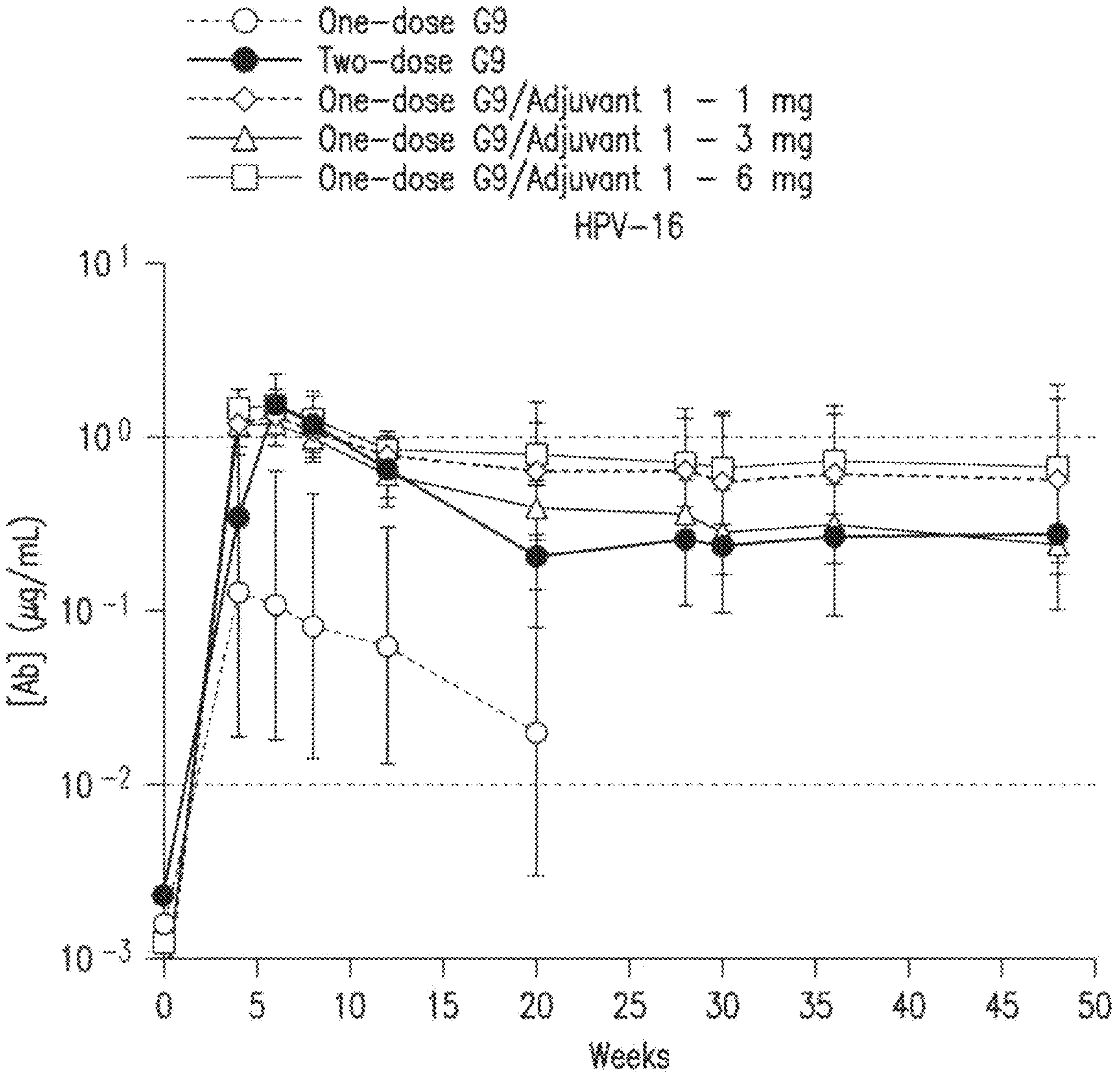
FIGS. 14A-14B depicts graphical comparison of HPV 16 and 18 antibody levels in rhesus macaques after one-dose or two-dose immunization with Gardasil®9 (G9) alone or combined with LNP Adjuvant 1.
Figure 14B:
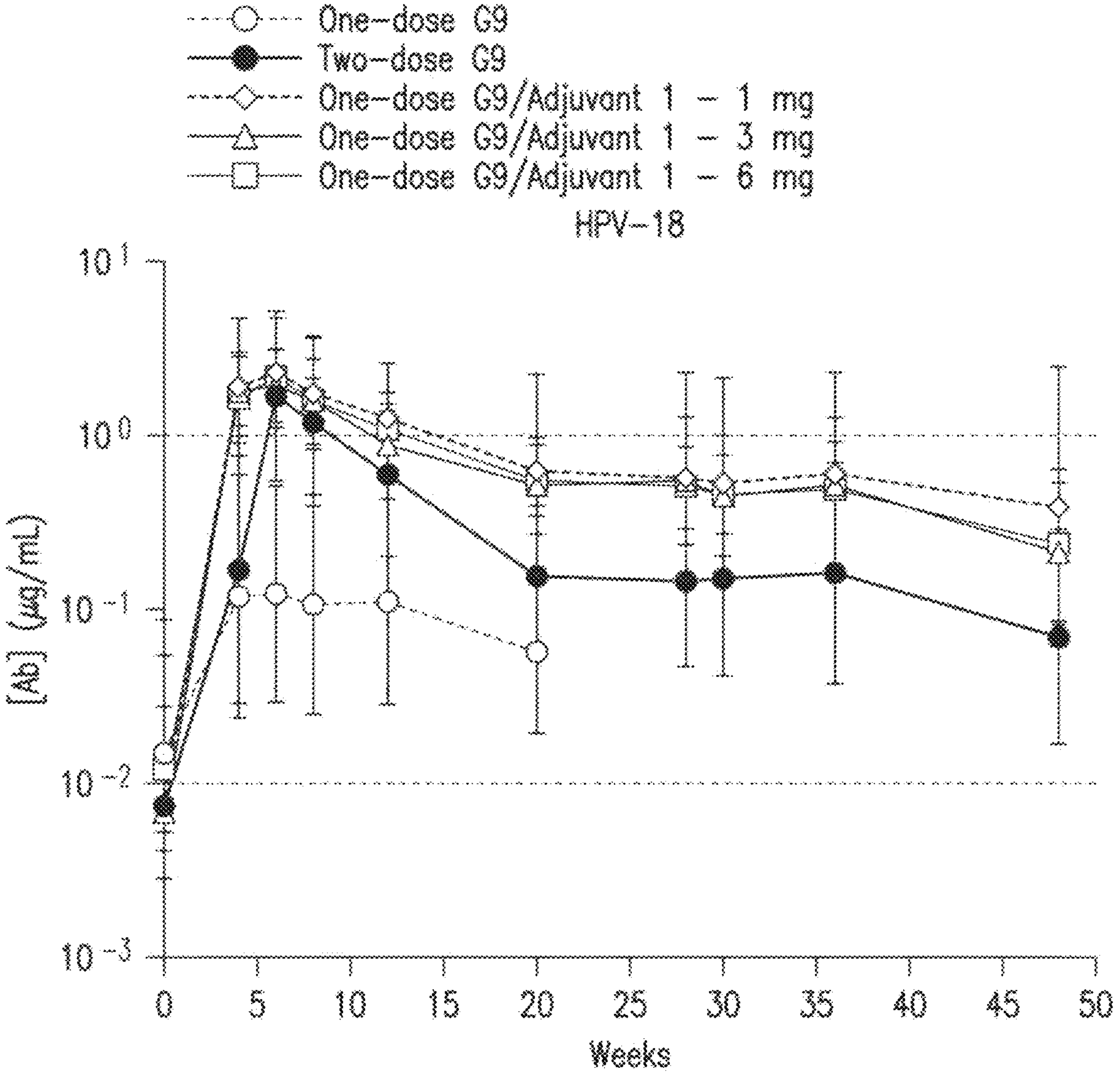
Figure 15:
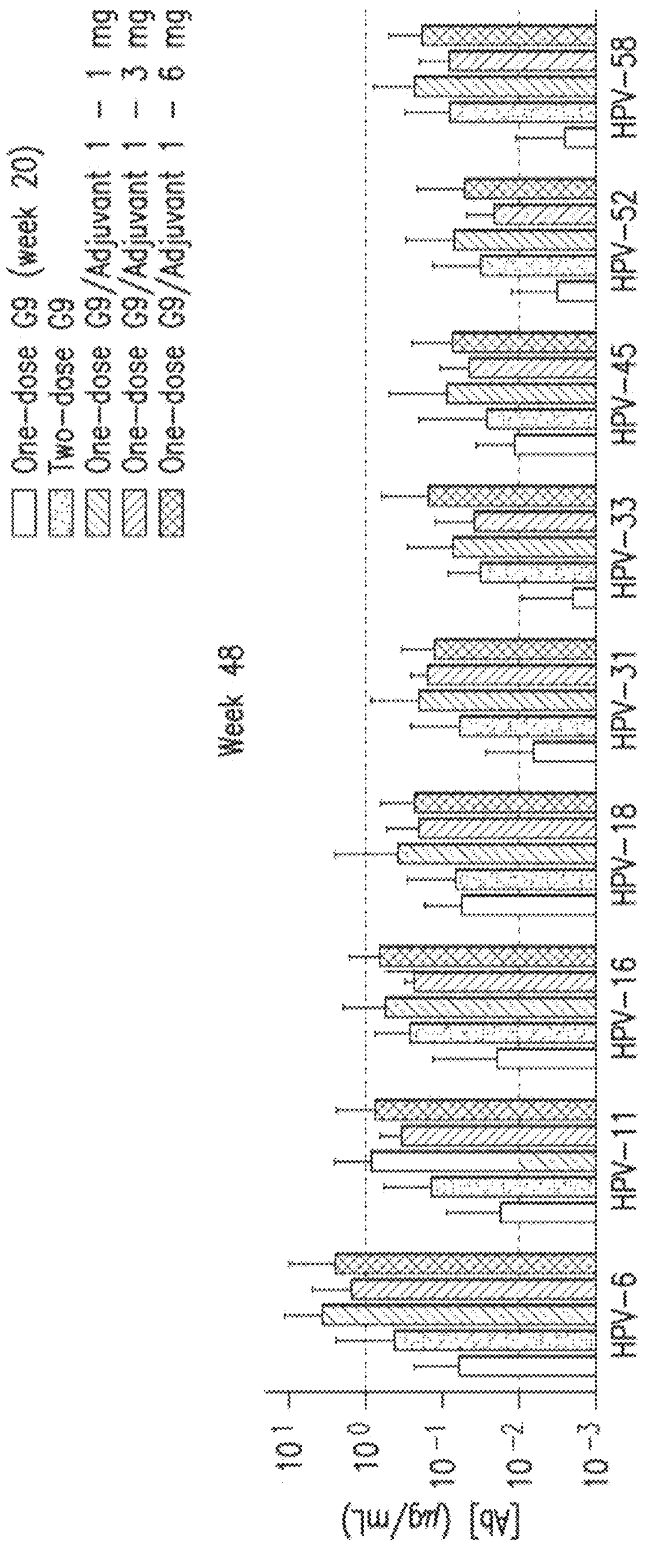
FIG. 15 depicts graphical comparison of serotype-specific HPV antibody levels in rhesus macaques 48 weeks after one-dose or two-dose immunization with Gardasil®9 (G9) alone or combined with LNP Adjuvant 1.

To assess immunogenicity, sera from individual animals were evaluated using a multiplex assay for antibody levels to all 9 HPV types in Gardasil®9. VLP-specific HPV antibody concentrations were determined at study week 0, 4, 6, 8, 12, 20, 28, 30, 36 and 48. Representative titers to HPV VLP-16 and HPV VLP-18 are shown in FIGS. 14A and 14B. A single inoculation of Gardasil©9 combined with LNP Adjuvant 1 induced similar peak antibody concentrations as two doses of Gardasil©9 injected 4 weeks apart for all doses of LNP Adjuvant 1 evaluated. Antibody levels were significantly higher in the animals that received LNP Adjuvant 1 and Gardasil®9 compared to those receiving a single dose of Gardasil®9 alone. Furthermore, the decline in long term antibody titers was more pronounced in animals that received two doses of Gardasil®9 than in the LNP Adjuvant 1-adjuvanted groups. Immune responses observed for all 9 VLP types at week 48 are presented in FIG. 15. In the animals immunized with Gardasil®9+LNP Adjuvant 1, antibody levels against each VLP serotype were similar to, or higher than, the two-dose Gardasil©9 group.

Example 24: Comparison of the Immunogenicity of LNP Adjuvant 1 or LNP Adjuvant 4 Admixed with Gardasil®9 in Rhesus Macaques (Study SD-HPV-044)

The immunogenicity of Gardasil®9 when combined with LNP Adjuvant 4 was evaluated in rhesus macaques. The group designations are described in Table 3. In brief, 4 groups of 5 rhesus macaques each were inoculated at week 0 with either Gardasil®9 only or with Gardasil®9 mixed with 0.3 or 1 mg of LNP Adjuvant 4 or 1 mg of LNP Adjuvant 1. The 1.0 mL inoculums were prepared by admixing Gardasil©9 and the LNP adjuvant (LNP Adjuvant 1 or LNP Adjuvant 4) and administering into the rhesus macaque quadriceps within 4 hours of formulation.

TABLE 3

Groups, Dose Levels, and Dosing Schedule in Non-Human Primates for Study SD-HPV-044

| Group | No. of Rhesus Macaques | Inoculum | LNP Dose | ROA[a] | Dosing Schedule |
|---|---|---|---|---|---|
| 1 | 5 | Gardasil ® 9[b] | NA | IM | week 0 |
| 2 | 5 | Gardasil ® 9 + LNP Adjuvant 1 | 1 mg | IM | week 0 |
| 3 | 5 | Gardasil ® 9 + LNP Adjuvant 4 | 1 mg | IM | week 0 |
| 4 | 5 | Gardasil ® 9 + LNP Adjuvant 4 | 0.3 mg | IM | week 0 |

Figure 16A:
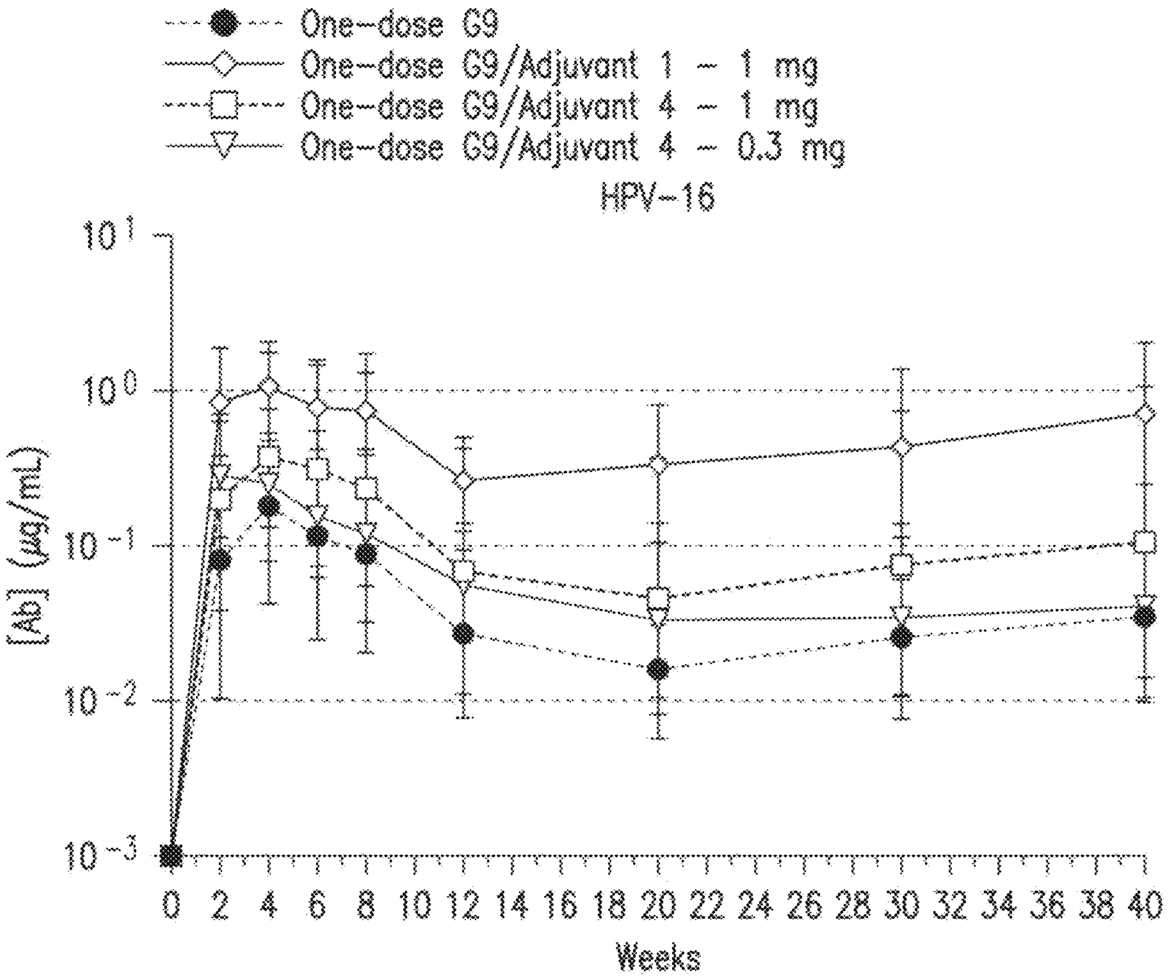
FIGS. 16A-16B depicts graphical comparison of HPV 16 and 18 antibody levels in rhesus macaques after one-dose immunization with Gardasil®9 (G9) alone or one-dose G9 combined with LNP Adjuvant 1 or LNP Adjuvant 4.
Figure 16B:
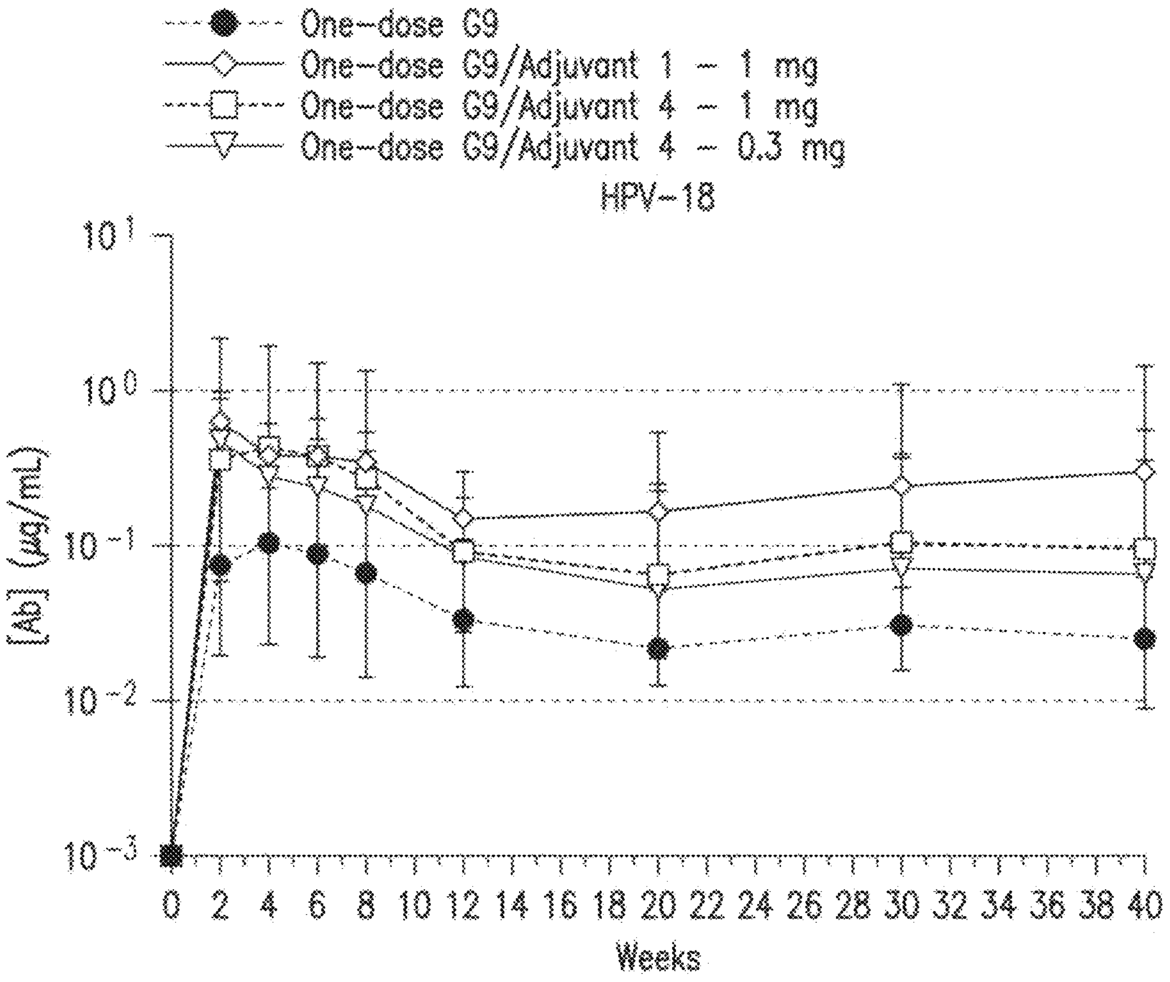
Figure 17:
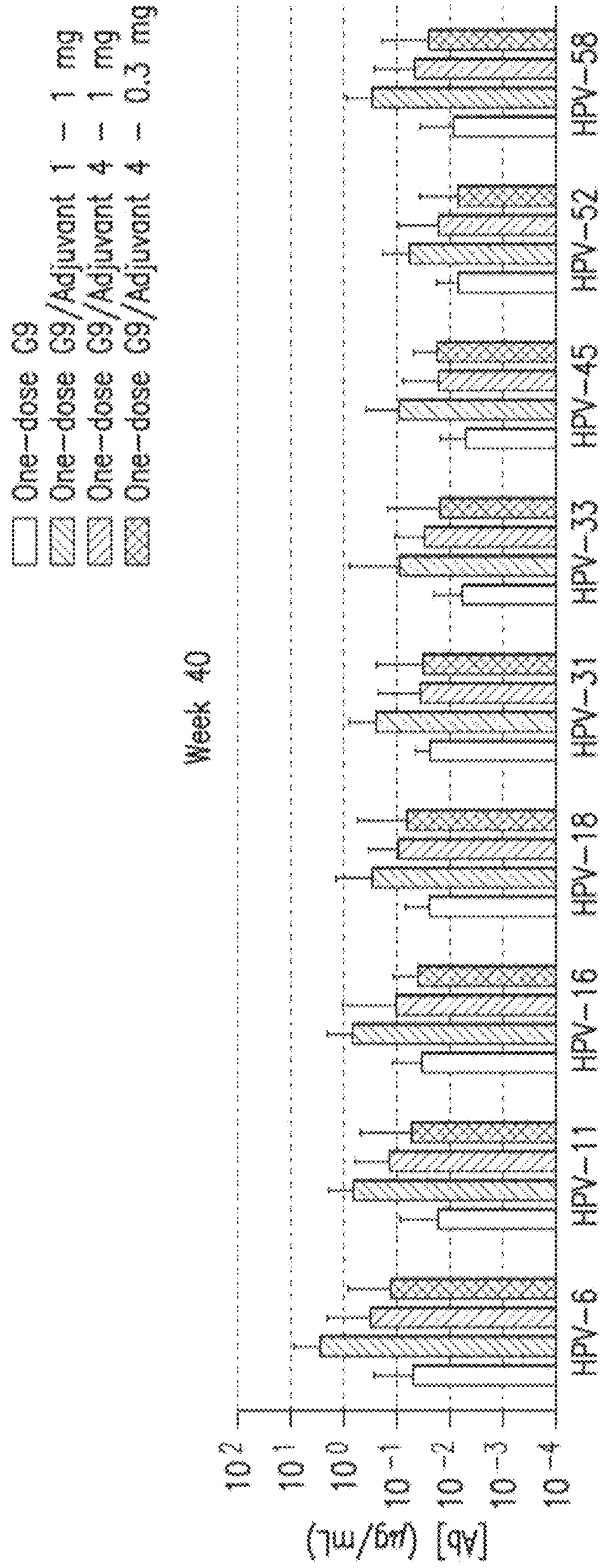
FIG. 17 depicts graphical comparison of serotype-specific HPV antibody levels in rhesus macaques 30 weeks after one-dose immunization with Gardasil®9 (G9) alone or one-dose G9 combined with LNP Adjuvant 1 or LNP Adjuvant 4.

[a]All doses were delivered in 1 mL to single quadriceps
[b]Rhesus monkey dose of Gardasil ® 9 is equivalent to a 1/20 human dose
IM = intramuscular;
NA = not applicable;
ROA = route of administration To assess immunogenicity, sera from individual animals are being evaluated using a multiplex assay for antibody levels to all 9 HPV types in Gardasil®9. To date VLP-specific HPV antibody concentrations have been determined at study week 0, 2, 4, 6, 8, 12, 20, 30 and 40. Representative titers to HPV VLP-16 and HPV VLP-18 are shown in FIGS. 16A and 16B for the animals that received LNP Adjuvant 4 or LNP Adjuvant 1 mixed with Gardasil©9. Although the titers in animals that received Gardasil©9 mixed with either LNP Adjuvant 4 or LNP Adjuvant 1 were higher than in the animals that received just Gardasil©9, the geometric mean responses in the animals immunized with Adjuvant 4 (1 mg) trended lower than in the animals that received Adjuvant 1 (1 mg). This trend was seen throughout the duration of the study. Immune responses observed for all 9 VLP types at week 40 are presented in FIG. 17. Since LNP Adjuvant 1 and LNP Adjuvant 4 had performed comparably at equivalent dose levels (in previous small animal studies, data not shown), and because in this study the responses in the animals immunized with LNP Adjuvant 4 (1 mg) trended lower (95% confidence intervals overlap) than in animals that received LNP Adjuvant 1 (1 mg), a more comprehensive evaluation of the adjuvant potential of LNP Adjuvant 4 in NHP was conducted. Study SD-HPV-053 (described below) was initiated to evaluate the immunogenicity of GARDASIL®9 when combined with increasing doses of Adjuvant 4 (1, 3, or 6 mg). An evaluation of these dose levels allowed a more complete comparison to LNP Adjuvant 1 as they match the dose levels evaluated for LNP Adjuvant 1 in the SD-HPV-009 study described above.

Example 25: Immunogenicity and Durability of a Single Dose of Gardasil®9+LNP Adjuvant 4 in Rhesus Macaques (Study SD-HPV-053)

The immunogenicity of Gardasil®9 when combined with increasing doses of LNP Adjuvant 4 (1, 3, or 6 mg) was evaluated in rhesus macaques. The dose levels selected matched the doses evaluated for LNP Adjuvant 1 described in Example 23 above. The group designations are described in Table 4. Four groups of 4 or 5 rhesus macaques each were inoculated at week 0 with either Gardasil©9 only or with Gardasil©9 mixed with 1, 3, or 6 mg of LNP Adjuvant 4. At week 4, the animals in group 1 were given a second dose of Gardasil®9 (two-dose G9) while none of the other groups were boosted. The 1.0 mL inoculums were prepared by admixing Gardasil®9 with LNP Adjuvant 4 and administering into the rhesus macaque quadricep within 4 hours of formulation.

TABLE 4

Groups, Dose Levels, and Dosing Schedule in Non-Human Primates for Study SD-HPV-053

| Group | No. of Rhesus Macaques | Inoculum | LNP Dose | ROA[a] | Dosing Schedule |
|---|---|---|---|---|---|
| 1 | 4 | Gardasil ® 9[b] | NA | IM | 0, 4 weeks |
| 2 | 5 | Gardasil ® 9 + LNP Adjuvant 4 | 6 mg | IM | week 0 |
| 3 | 5 | Gardasil ® 9 + LNP Adjuvant 4 | 3 mg | IM | week 0 |
| 4 | 5 | Gardasil ® 9 + LNP Adjuvant 4 | 1 mg | IM | week 0 |

Figure 18A:
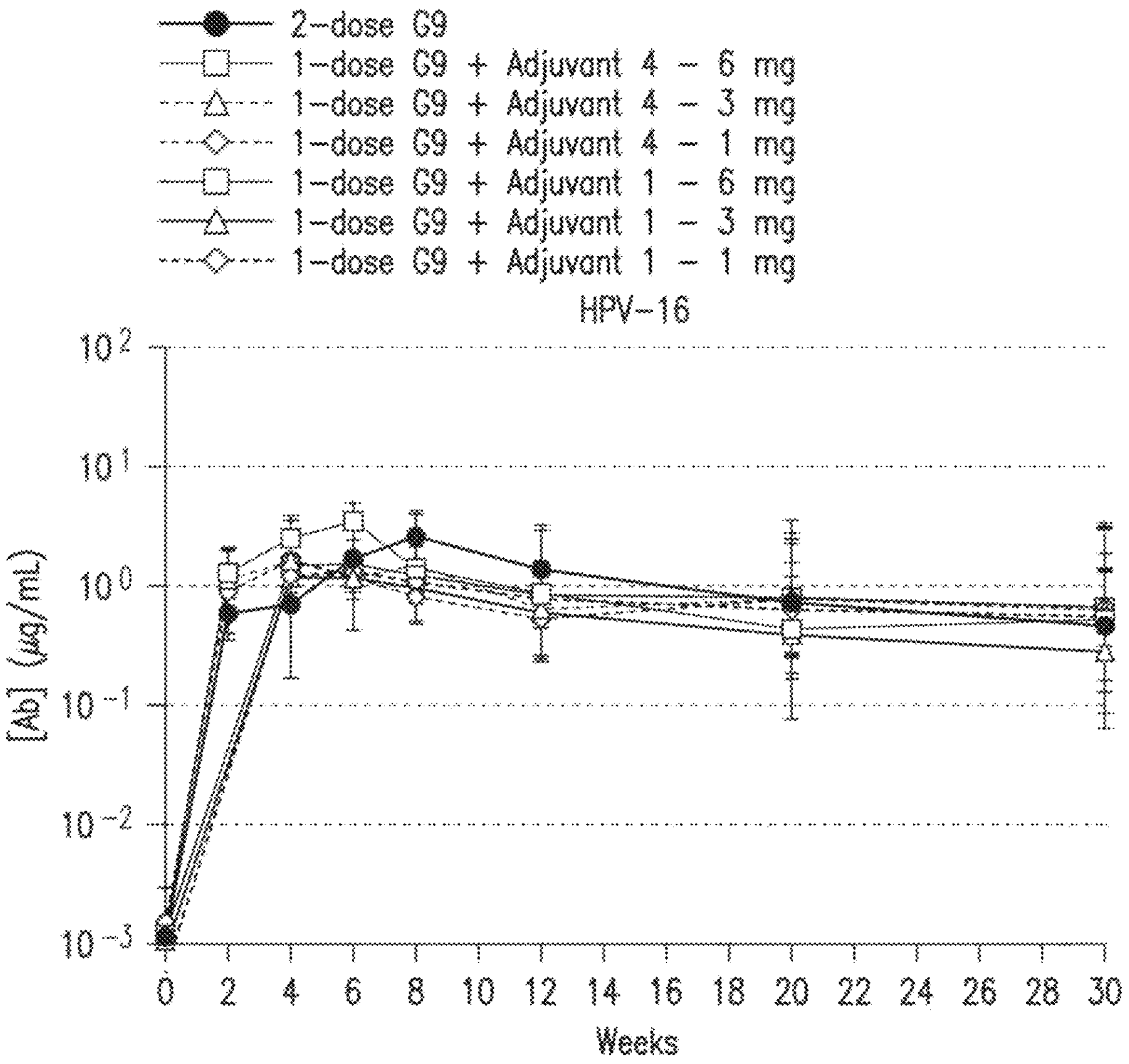
FIGS. 18A-18B depicts graphical comparison of HPV 16 and 18 antibody levels in rhesus macaques after two-dose immunization with Gardasil®9 (G9) alone or one-dose G9 combined with LNP Adjuvant 1 or LNP Adjuvant 4.
Figure 18B:
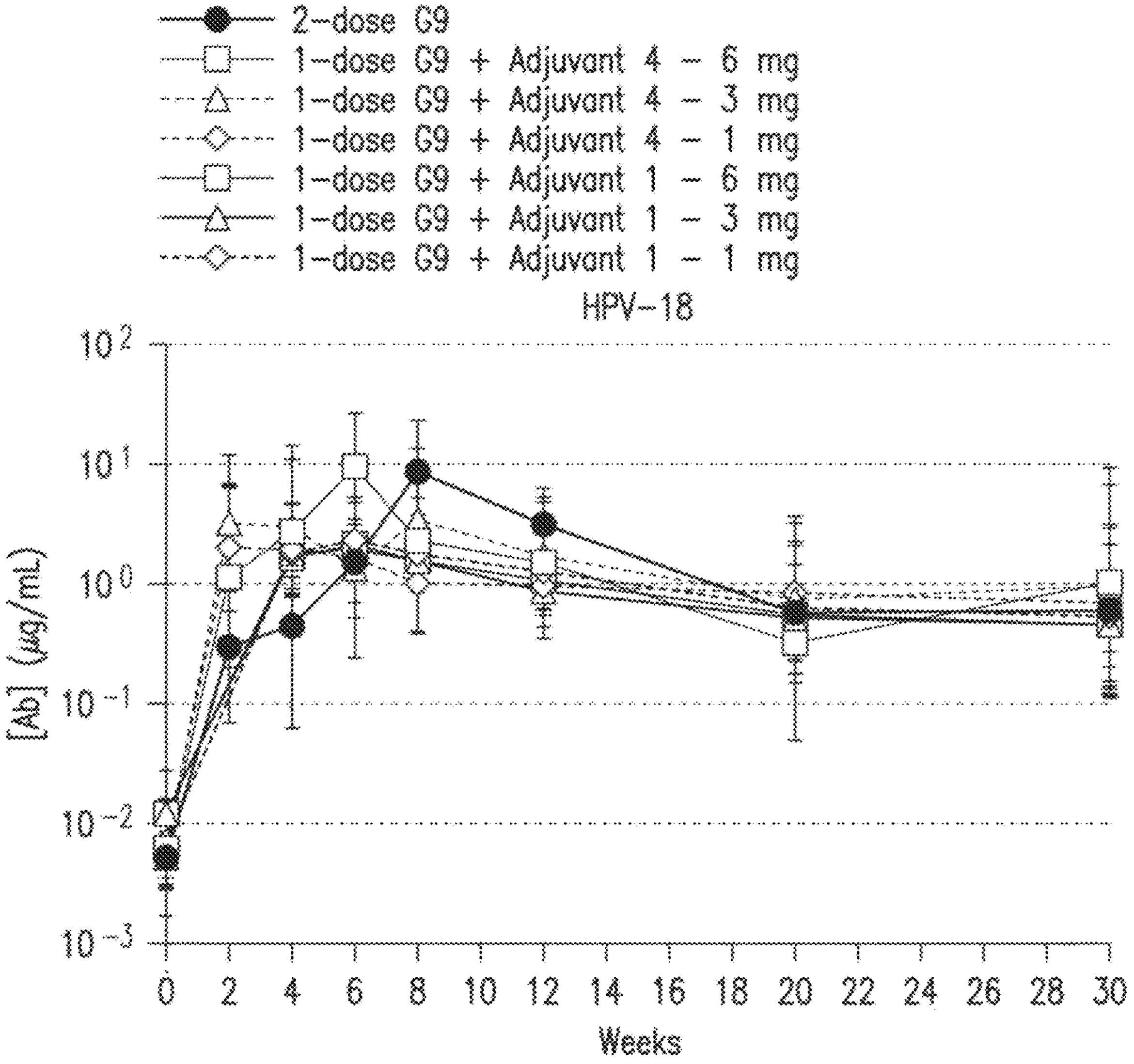

[a]All doses were delivered in 1 mL to single quadriceps
[b]Rhesus monkey dose of Gardasil ® 9 is equivalent to a 1/20 human dose
IM = intramuscular;
NA = not applicable;
ROA = route of administration To assess immunogenicity, sera from individual animals are being evaluated using a multiplex assay for antibody levels to all 9 HPV types in Gardasil®9. To date VLP-specific HPV antibody concentrations have been determined at study week 0, 2, 4, 6, 8,12, 20 and 30. Representative titers to HPV VLP-16 and HPV VLP-18 are shown in FIGS. 18A and 18B. A single inoculation of Gardasil©9 combined with LNP Adjuvant 4 induced similar peak antibody concentrations as two doses of Gardasil©9 injected 4 weeks apart for all doses of LNP Adjuvant 4 evaluated. Data for Gardasil®9+LNP Adjuvant 1 from Example 25 (described above) are shown for comparison. LNP Adjuvant 4 and LNP Adjuvant 1 elicit comparable titers at the dose levels tested.

Figure 19:
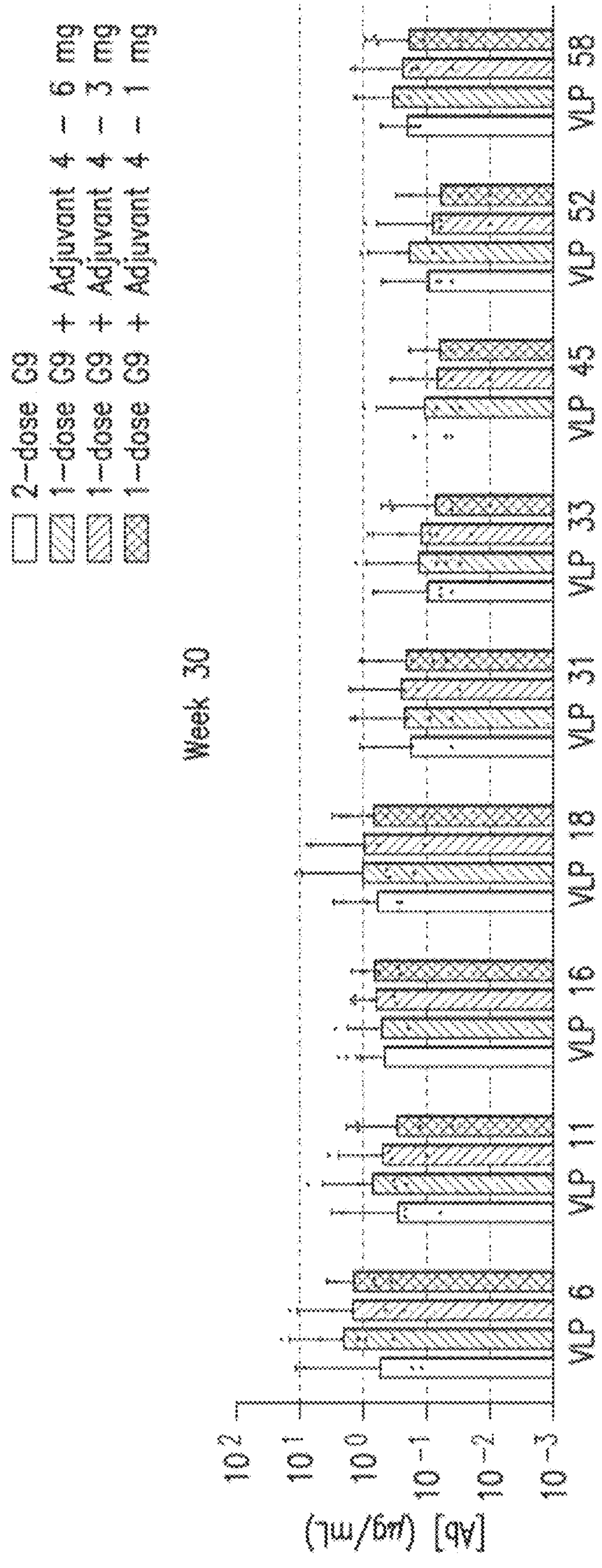
FIG. 19 depicts graphical comparison of serotype-specific HPV antibody levels in rhesus macques 12 weeks after two-dose immunization with Gardasil®9 (G9) alone or one-dose G9 combined with LNP Adjuvant 4.

Immune responses observed for all 9 VLP types at week 30 are presented in FIG. 19. In the animals immunized with Gardasil®9+LNP Adjuvant 4, antibody levels against each VLP serotype were similar to the two-dose Gardasil®9 group. These data are consistent with our previous data (mentioned above), thus suggesting that the lower trend for LNP Adjuvant 4 (1 mg) measured in the SD-HPV-044 study (described above) may reflect between-animal variability. Taken together these data indicate that the LNP Adjuvant 4 has similar adjuvant potential to LNP Adjuvant 1.

What is claimed:

1. A lipid nanoparticle comprising:

(1) a PEG-lipid having the structure set forth in Formula II, wherein n is from 30-50;

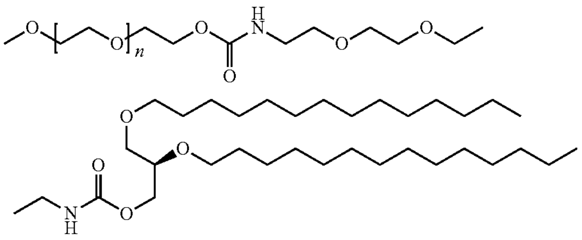

(2) a phospholipid having the structure set forth in Formula III or Formula IIIa;

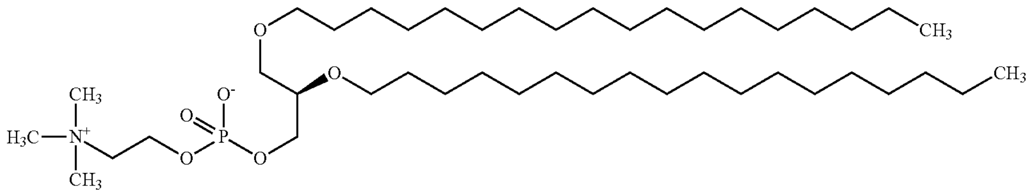

(III)

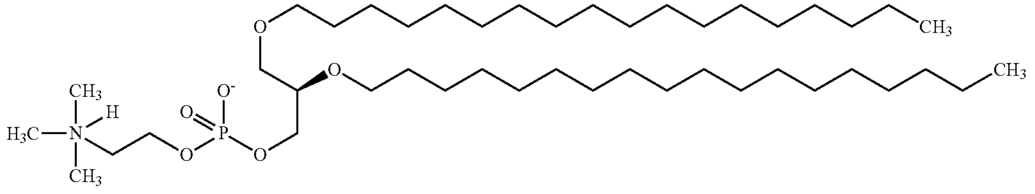

(IIIa)

(3) the following cationic lipid: (13Z, 16Z)—N, N-dimethyl-3-nonyldocosa 13, 16-dien-1-amine; and (4) cholesterol.

2. The lipid nanoparticle of claim 1, wherein the lipid nanoparticle comprises 5-15 mole % phospholipid, 25-35 mole % cholesterol, 1-2.5 mole % PEG-lipid, and 55-65 mole % (13Z, 16Z)—N, N-dimethyl-3-nonyldocosa 13, 16-dien-1-amine.

* * * * *